(12) United States Patent
Pavco et al.

(10) Patent No.: US 6,346,398 B1
(45) Date of Patent: Feb. 12, 2002

(54) METHOD AND REAGENT FOR THE TREATMENT OF DISEASES OR CONDITIONS RELATED TO LEVELS OF VASCULAR ENDOTHELIAL GROWTH FACTOR RECEPTOR

(75) Inventors: Pamela Pavco, Lafayette; James McSwiggen; Daniel Stinchcomb, both of Boulder, all of CO (US); Jaime Escobedo, Alamo, CA (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 08/584,040

(22) Filed: Jan. 11, 1996

Related U.S. Application Data

(60) Provisional application No. 60/005,974, filed on Oct. 26, 1995.

(51) Int. Cl.$^7$ .............................. C12Q 1/68; C12P 19/34; C07H 21/04; C12N 15/85; C12N 15/86

(52) U.S. Cl. ....................... 435/91.31; 435/6; 435/91.1; 435/325; 435/375; 514/44; 536/23.1; 536/24.5; 536/23.2

(58) Field of Search .......................... 514/44; 435/325, 435/320.1, 6, 91.31, 91.1, 440, 366, 375; 536/24.5, 23.1, 23.2, 24.3

(56) References Cited

U.S. PATENT DOCUMENTS

| | | | | |
|---|---|---|---|---|
| 4,987,071 | A | | 1/1991 | Cech et al. ..................... 435/91 |
| 5,334,711 | A | | 8/1994 | Sproat et al. ............... 536/24.5 |
| 5,359,051 | A | | 10/1994 | Cook et al. ................. 536/26.7 |
| 5,496,698 | A | * | 3/1996 | Draper et al. .................... 435/6 |
| 5,525,468 | A | * | 6/1996 | McSwiggen .................... 435/6 |
| 5,712,380 | A | * | 1/1998 | Kendal et al. .............. 536/23.5 |

FOREIGN PATENT DOCUMENTS

| | | |
|---|---|---|
| EP | 0360257 | 3/1990 |
| WO | 9103162 | 3/1991 |
| WO | 9207065 | 9/1991 |
| WO | 9323569 | 4/1993 |
| WO | 9315187 | 8/1993 |
| WO | 9323057 | 11/1993 |
| WO | 9402595 | 2/1994 |
| WO | 9411499 | 5/1994 |
| WO | 9421679 | 9/1994 |
| WO | 9504142 | 2/1995 |
| WO | 9504818 | 2/1995 |
| WO | 9513380 | 5/1995 |
| WO | 9521868 | 8/1995 |
| WO | 9523225 | 8/1995 |

OTHER PUBLICATIONS

Beigelman et al., Beigelman et al., "Chemical Modification of Hammerhead Ribozymes," *J. Biol. Chem.* 270:25702–25708 (1995).

Carter, "Adeno–Associated Virus Vectors," *Curr Opi. Biotech.* 3:533–539 (1992).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Chowrira and Burke, "Extensive Phosphorothioate Substitution Yields Highly Active and Nuclease–Resistant Hairpin Ribozymes," *Nucleic Acids Res.* 20:2835–2840 (1992).

Collins and Olive, "Reaction Conditions and Kinetics of Self–Cleavage of a Ribozyme Derived From Neurospora VS RNA," *Biochemistry* 32:2795–2799 (1993).

Dropulic et al., "Functional Characterization of a U5 Ribozyme: Intracellular Suppression of Human Immunodeficiency Virus Type I Expression," *Journal of Virology* 66:1432–1441 (1992).

Duval–Valentin, "Specific inhibition of transcription by triple helix–forming oligonucleotides," *Proc. Natl. Acad. Sci. USA* 89:504 (1992).

Egholm et al., "PNA hybridizes to complementary oligonucleotides obeying the Watson–Crick hydrogen–bonding rules," *Nature* 365:566–568 (1993).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Folkman and Shing, "Angiogenesis," *J. Biol. Chem.* 267:10931–10934 (1992).

Folkman, "What is the Evidence that Tumors are Angiogenesis Dependent?" *Journal of the National Cancer Institute* 82:4–6 (1990).

Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).

Guerrier–Takada et al., "The RNA Moiety of Ribonuclease P Is the Catalytic Subunit of the Enzyme," *Cell* 35:849–857 (1983).

Hampel et al., "'Hairpin' Catalytic RNA Model: Evidence for Helices and Sequence Requirement for Substrate RNA," *Nucleic Acids Research* 18:299–304 (1990).

Hampel and Tritz, "RNA Catalytic Properties of the Minimum a(–)sTRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

(List continued on next page.)

*Primary Examiner*—George C. Elliott
*Assistant Examiner*—Janet Epps

(57) ABSTRACT

Nucleic acid molecule which modulates the synthesis, expression and/or stability of an mRNA encoding one or more receptors of vascular endothelial growth factor.

23 Claims, 20 Drawing Sheets

OTHER PUBLICATIONS

Hertel et al., "Numbering System for the Hammerhead," *Nucleic Acids Res.* 20:3252 (1992).

Izant and Weintraub, "Constitutive and Conditional Suppression of Exogenous and Endogeneous Genes by Anti-Sense RNA," *Science* 229:345–352 (1985).

Jaeger et al., "Improved Predictions of Secondary Structures for RNA," *Proc. Natl. Acad. Sci. USA* 86:7706–7710 (1989).

Jeffries and Symons, "A Catalytic 13–mer Ribozyme," *Nucleic Acids Research* 17:1371–1377 (1989).

Jellinek et al., "Inhibition of Receptor Binding by High–Affinity RNA Ligands to Vascular Endothelial Growth Factor," *Biochemistry* 33:10450–10456 (1994).

Kashani–Sabet et al., "Reversal of the Malignant Phenotype by an Anti–ras Ribozyme," *Antisense Research & Development* 2:3–15 (1992).

Kim et al., "Inhibition of vascular endothelial growth factor–induced angiogenesis suppresses tumour growth in vivo," *Nature* 362:841–844 (1993).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

McGarry and Lindquist, "Inhibition of heat shock protein synthesis by heat–inducible antisense RNA," *Proc. Natl. Acad. Sci. USA* 83:399–403 (1986).

Millauer, "High Affintiy VEGF Binding and Developmental Expression Suggest Flk–1 as a Major Regulator of Vasculogenesis and Angiogenesis," *Cell* 72:835–846 (1993).

Milligan and Uhlenbeck, "Synthesis of Small RNAs Using T7 RNA Polymerase," *Methods Enzymol.* 180:51–62 (1989).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Perreault et al., "Mixed Deoxyribo– and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Plate, "Vascular endothelial growth factor is potential tumor angiogenesis factor in human gilomas in vivo," *Nature* 359:845–848 (1992).

Rossi et al, "Ribozymes as Anti–HIV–1 Therapeutic Agents: Principles, Applications, and Problems," *Aids Research and Human Retroviruses* 8:183–189 (1992).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self––Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl. Acids Res.* 18:5433–5441 (1990).

Stein and Cheng, "Antisense Oligonucleotides as Therapeutic Agenst—Is the Bullet Really Magical?" *Science* 261:1004–1288 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Thompson et al., "Improved accumulation and activity of ribozymes expressed from a tRNA–based RNA polymerase III promoter," *Nucleic Acids Research* 23:2259–2268 (1995).

Torrence et al., "Targeting RNA for degradation with a (2'–5') oligoadenylate–antisense chimera," *Proc. Natl. Acad. Sci. USA* 90:1300–1304 (1993).

Uhlenbeck, "A Small Catalytic Oligoribonucleotide," *Nature* 328:596–600 (1987).

Usman et al.,"Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman and Cedergren, "Exploiting the chemical synthesis of RNA," *TIBS* 17:334–339 (1992).

Usman et al., "Chemical modification of hammerhead ribozymes: activity and nuclease resistance," *Nucleic Acids Symposium Series* 31:163–164 (1994).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994).

Wincott et al., "Synthesis, deprotection, analysis and purification of RNA and ribozymes," *Nucleic Acids Research* 23:2677–2684 (1995).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.* 10:4529–4537 (1990).

Andrea D. Branch, A good antisense molecule is hard to find, TIBS, 47–48, Feb. 1998.*

Eugene Uhlmann and Anusch Peyman, Antisense Oligonucleotides: A new Therapeutic Principle, Chemical Reviews, pp. 545–546, Jun. 1990.*

Shibuya, M. et al., Nucleotide sequence and expression of a novel human receptor–type tyrosine kinase gene (flt) closely related to the fms family, Oncogene, 5, pp. 519–524, 1990.*

Stanley T. Crooke, Basic Principles of Antisense Therapeutics, Springer–Verlag, NY, p. 3, Jul. 1998.*

* cited by examiner

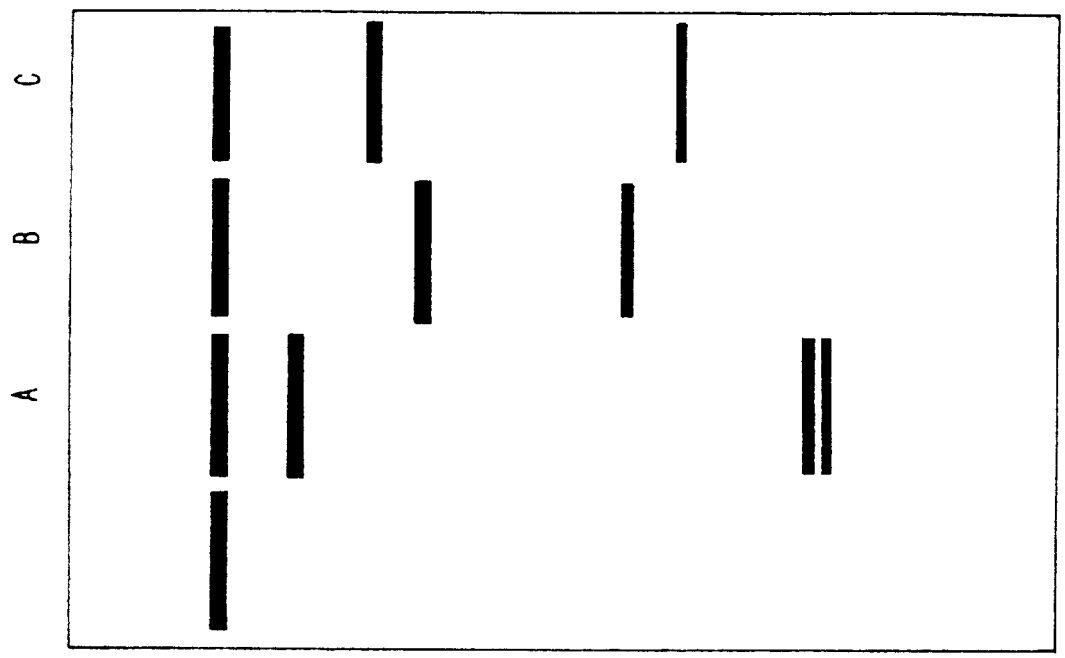
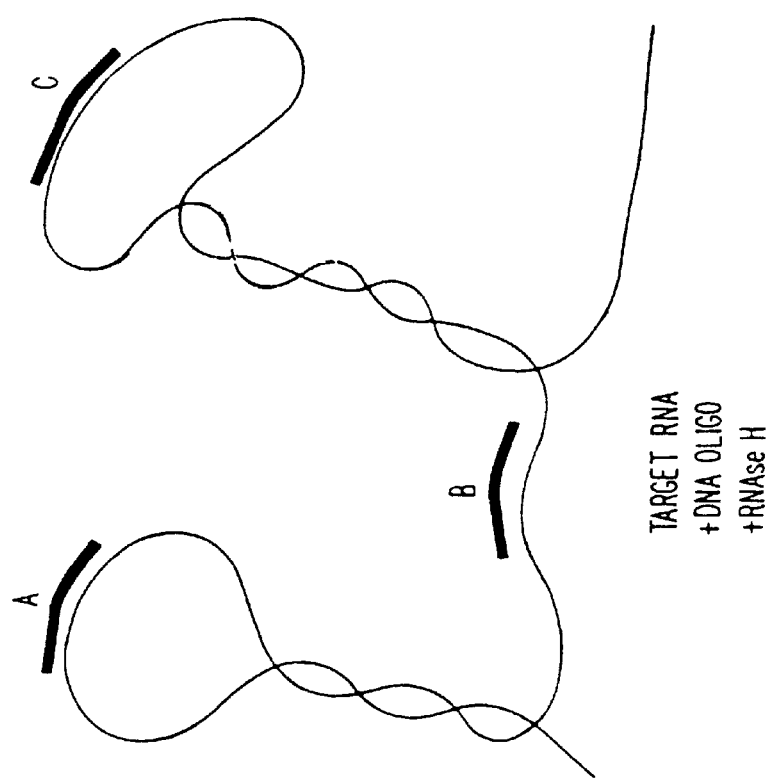
FIG. 6.

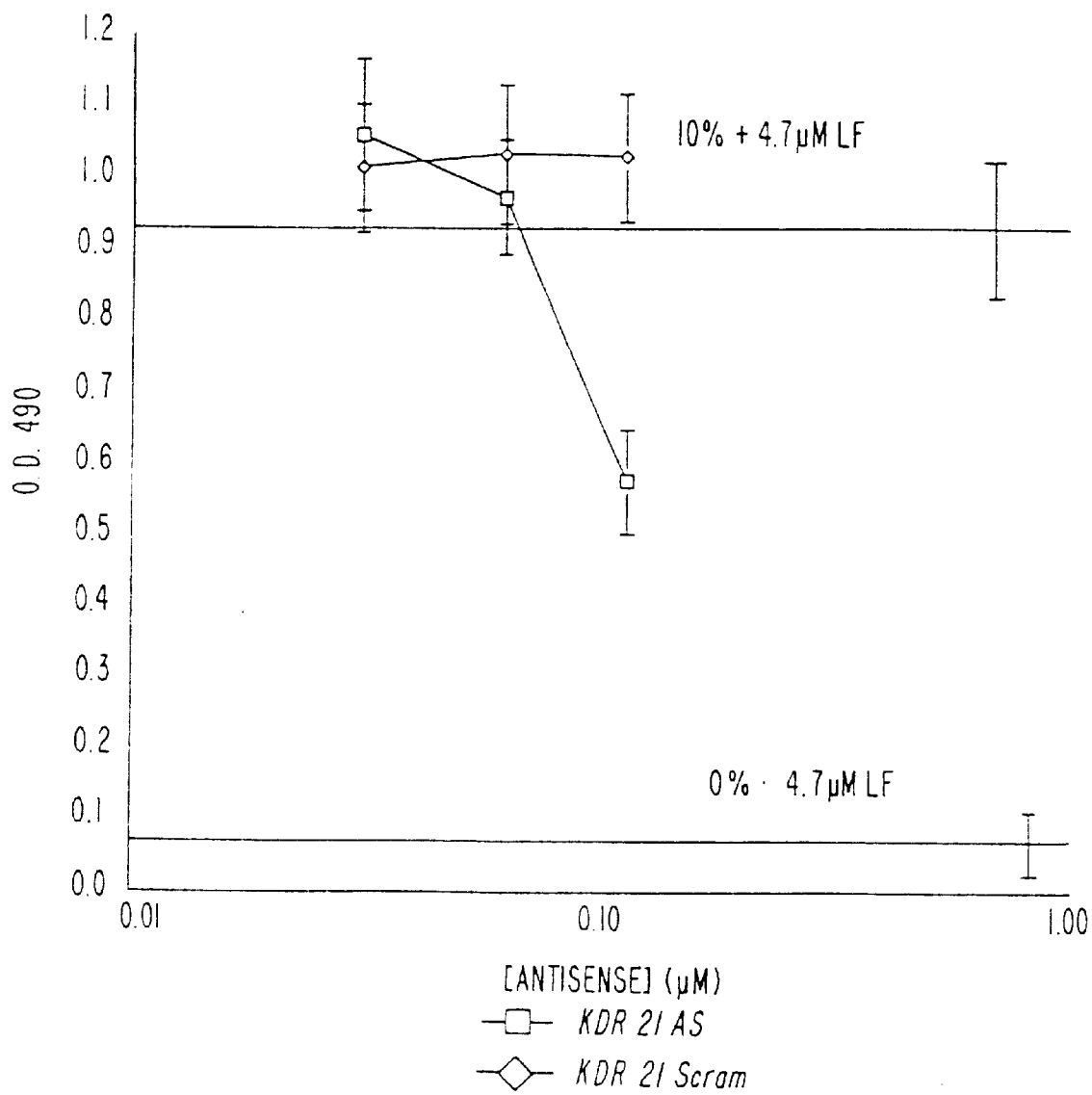

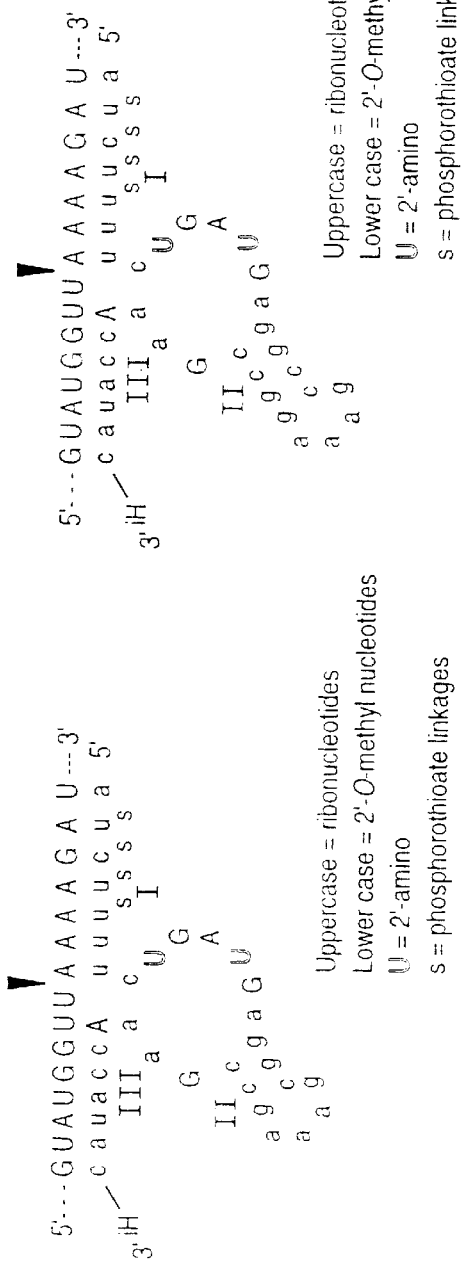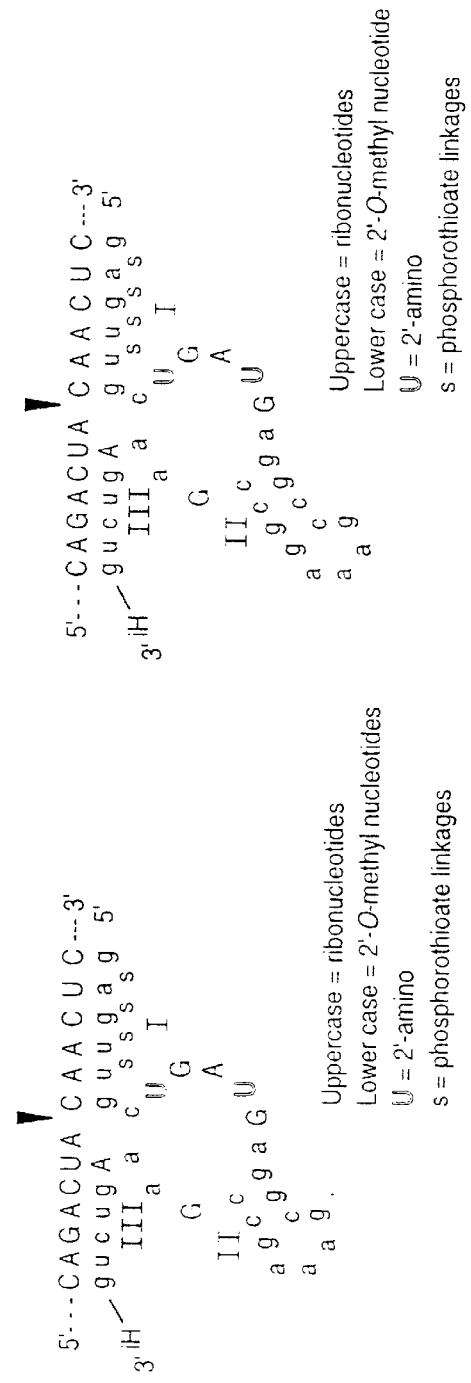
FIG. 11A.

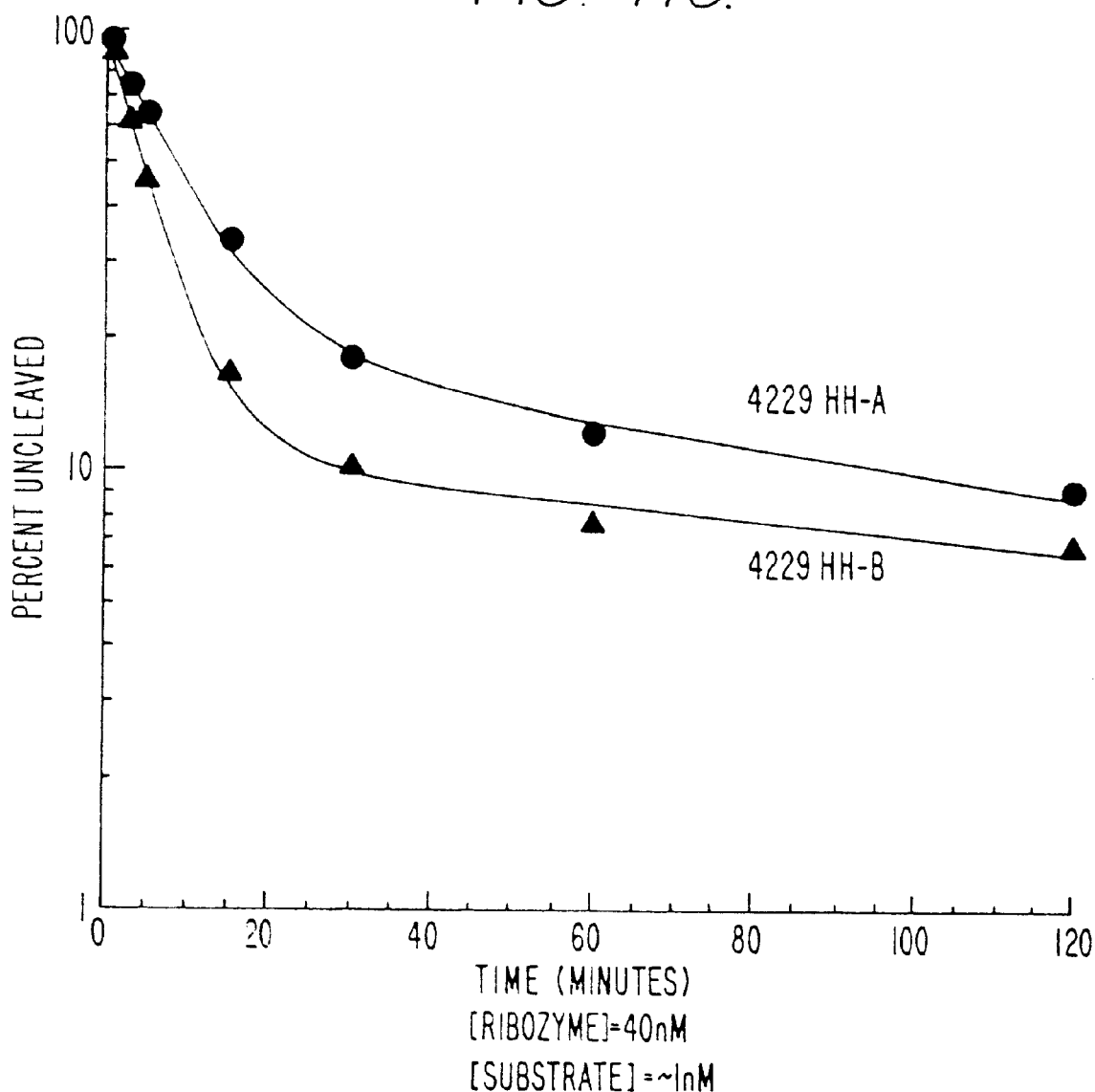

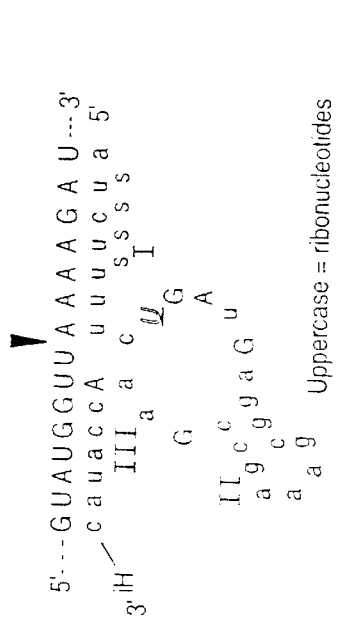
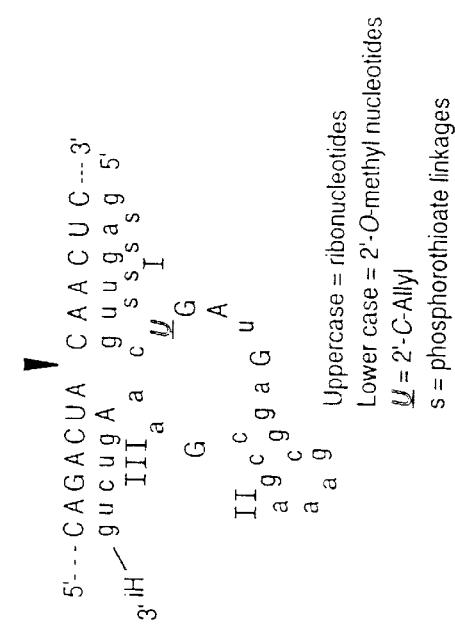
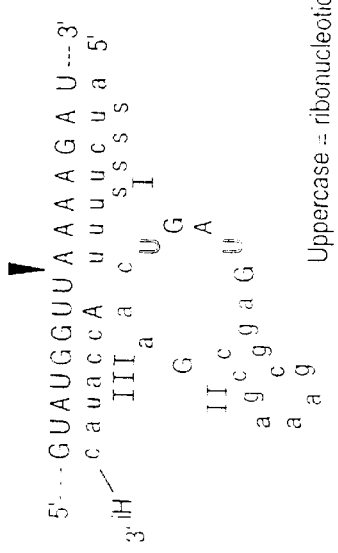
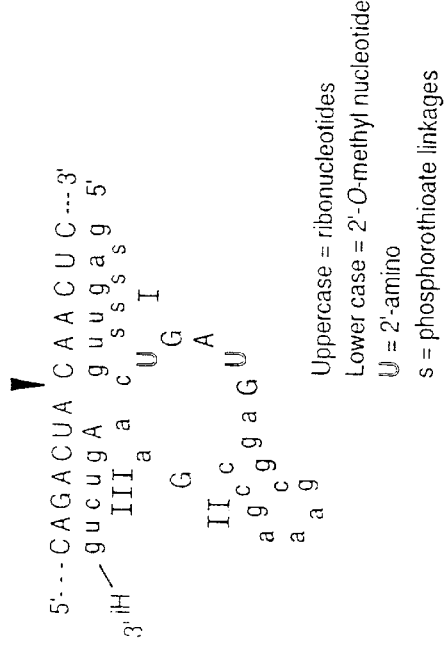
FIG. 12A.

METHOD AND REAGENT FOR THE TREATMENT OF DISEASES OR CONDITIONS RELATED TO LEVELS OF VASCULAR ENDOTHELIAL GROWTH FACTOR RECEPTOR

RELATED APPLICATIONS

This application claims the benefit of Pavco et al., U.S. Ser. No. 60/005,974, entitled Method and Reagent for the Treatment of Diseases or Conditions Related to Levels of Vascular Endothelial Growth Factor Receptor, filed Oct. 26, 1995, which is incorporated by reference herein in its entirety, including drawings.

BACKGROUND OF THE INVENTION

This invention relates to methods and reagents for the treatment of diseases or conditions relating to the levels of expression of vascular endothelial growth factor (VEGF) receptor(s).

The following is a discussion of relevant art, none of which is admitted to be prior art to the present invention.

VEGF, also referred to as vascular permeability factor (VPF) and vasculotropin, is a potent and highly specific mitogen of vascular endothelial cells (for a review see Ferrara, 1993 *Trends Cardiovas. Med.* 3, 244; Neufeld et al., 1994 *Prog. Growth Factor Res.* 5, 89). VEGF induced neovascularization is implicated in various pathological conditions such as tumor angiogenesis, proliferative diabetic retinopathy, hypoxia-induced angiogenesis, rheumatoid arthritis, psoriasis, wound healing and others.

VEGF, an endothelial cell-specific mitogen, is a 34–45 kDa glycoprotein with a wide range of activities that include promotion of angiogenesis, enhancement of vascular-permeability and others. VEGF belongs to the platelet-derived growth factor (PDGF) family of growth factors with approximately 18% homology with the A and B chain of PDGF at the amino acid level. Additionally, VEGF contains the eight conserved cysteine residues common to all growth factors belonging to the PDGF family (Neufeld et al., supra). VEGF protein is believed to exist predominantly as disulfide-linked homodimers; monomers of VEGF have been shown to be inactive (Plouet et al., 1989 *EMBO J.* 8, 3801).

VEGF exerts its influence on vascular endothelial cells by binding to specific high-affinity cell surface receptors. Covalent cross-linking experiments with $^{125}$I-labeled VEGF protein have led to the identification of three high molecular weight complexes of 225, 195 and 175 kDa presumed to be VEGF and VEGF receptor complexes (Vaisman et al., 1990 *J. Biol. Chem.* 265, 19461). Based on these studies VEGF-specific receptors of 180, 150 and 130 kDa molecular mass were predicted. In endothelial cells, receptors of 150 and the 130 kDa have been identified. The VEGF receptors belong to the superfamily of receptor tyrosine kinases (RTKs) characterized by a conserved cytoplasmic catalytic kinase domain and a hydrophylic kinase sequence. The extracellular domains of the VEGF receptors consist of seven immunoglobulin-like domains that are thought to be involved in VEGF binding functions.

The two most abundant and high-affinity receptors of VEGF are flt-1 (fms-like tyrosine kinase) cloned by Shibuya et al., 1990 *Oncogene* 5, 519 and KDR (kinase-insert-domain-containing receptor) cloned by Terman et al., 1991 *Oncogene* 6, 1677. The murine homolog of KDR, cloned by Mathews et al., 1991, *Proc. Natl. Acad. Sci.,* USA, 88, 9026, shares 85% amino acid homology with KDR and is termed as flk-1 (fetal liver kinase-1). Recently it has been shown that the high-affinity binding of VEGF to its receptors is modulated by cell surface-associated heparin and heparin-like molecules (Gitay-Goren et al, 1992 *J. Biol. Chem.* 267, 6093).

VEGF expression has been associated with several pathological states such as tumor angiogenesis, several forms of blindness, rheumatoid arthritis, psoriasis and others. Following is a brief summary of evidence supporting the involvement of VEGF in various diseases:

1) Tumor angiogenesis: Increased levels of VEGF gene expression have been reported in vascularized and edema-associated brain tumors (Berkman et al., 1993 *J. Clini. Invest.* 91, 153). A more direct demostration of the role of VEGF in tumor angiogenesis was demonstrated by Jim Kim et al., 1993 *Nature* 362,841 wherein, monoclonal antibodies against VEGF were successfully used to inhibit the growth of rhabdomyosarcoma, glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576).

2) Ocular diseses: Aiello et al., 1994 *New Engl. J. Med.* 331, 1480, showed that the ocular fluid, of a majority of patients suffering from diabetic retinopathy and other retinal disorders, contains a high concentration of VEGF. Miller et al., 1994 *Am. J. Pathol.* 145, 574, reported elevated levels of VEGF mRNA in patients suffering from retinal ischemia. These observations support a direct role for VEGF in ocular diseases.

3) Psoriasis: Detmar et al., 1994 *J. Exp. Med.* 180, 1141 reported that VEGF and its receptors were over-expressed in psoriatic skin and psoriatic dermal microvessels, suggesting that VEGF plays a significant role in psoriasis.

4) Rheumatoid arthritis: Immunohistochemistry and in situ hybridization studies on tissues from the joints of patients suffering from rheumatoid arthritis show an increased level of VEGF and its receptors (Fava et al., 1994 *J. Exp. Med.* 180, 341). Additionally, Koch et al., 1994 *J. Immunol.* 152, 4149, found that VEGF-specific antibodies were able to significantly reduce the mitogenic activity of synovial tissues from patients suffering from rheumatoid arthritis. These observations support a direct role for VEGF in rheumatoid arthritis.

In addition to the above data on pathological conditions involving excessive angiogenesis, a number of studies have demonstrated that VEGF is both necessary and sufficient for neovascularization. Takashita et al., 1995 *J. Clin. Invest.* 93, 662, demonstrated that a single injection of VEGF augmented collateral vessel development in a rabbit model of ischemia. VEGF also can induce neovascularization when injected into the cornea. Expression of the VEGF gene in CHO cells is sufficient to confer tumorigenic potential to the cells. Kim et al., supra and Millauer et al., supra used monoclonal antibodies against VEGF or a dominant negative form of flk-1 receptor to inhibit tumor-induced neovascularization.

During development, VEGF and its receptors are associated with regions of new vascular growth (Millauer et al., 1993 *Cell* 72, 835; Shalaby et al., 1993 *J. Clin. Invest.* 91, 2235). Furthermore, transgenic mice lacking either of the VEGF receptors are defective in blood vessel formation, infact these mouse do not survive; flk-1 appears to be required for differentiation of endothelial cells, while flt-1 appears to be required at later stages of vessel formation (Shalaby et al., 1995 Nature 376, 62; Fung et al., 1995 Nature 376, 66). Thus, these receptors must be present to properly signal endothelial cells or their precursors to respond to vascularization-promoting stimuli.

All of the conditions listed above, involve extensive vascularization. This hyper-stimulation of endothelial cells may be alleviated by VEGF antagonists. Thus most of the therapeutic efforts for the above conditions have concentrated on finding inhibitors of the VEGF protein.

Kim et al., 1993 Nature 362, 841 have been successful in inhibiting VEGF-induced tumor growth and angiogenesis in nude mice by treating the mice with VEGF-specific monoclonal antibody.

Koch et al., 1994 J. Immunol. 152, 4149 showed that the mitogenic activity of microvascular endothelial cells found in rheumatoid arthritis (RA) synovial tissue explants and the chemotactic property of endothelial cells from RA synovial fluid can be neutralized significantly by treatment with VEGF-specific antibodies.

Ullrich et al., International PCT Publication No. WO 94/11499 and Millauer et al., 1994 Nature 367, 576 used a soluble form of flk-1 receptor (dominant-negative mutant) to prevent VEGF-mediated tumor angiogenesis in immunodeficient mice.

Kendall and Thomas, International PCT Publication No. WO 94/21679 describe the use of naturally occuring or recombinantly-engineered soluble forms of VEGF receptors to inhibit VEGF activity.

Robinson, International PCT Publication No. WO 95/04142 describes the use of antisense oligonucleotides targeted against VEGF RNA to inhibit VEGF expression.

Jellinek et al., 1994 Biochemistry 33, 10450 describe the use of VEGF-specific high-affinity RNA aptamers to inhibit the binding of VEGF to its receptors.

Rockwell and Goldstein, International PCT Publication No. WO 95/21868, describe the use of anti-VEGF receptor monoclonal antibodies to neutralize the the effect of VEGF on endothelial cells.

SUMMARY OF THE INVENTION

The invention features novel nucleic acid-based techniques [e.g., enzymatic nucleic acid molecules (ribozymes), antisense nucleic acids, 2–5A antisense chimeras, triplex DNA, antisense nucleic acids containing RNA cleaving chemical groups (Cook et al., U.S. Pat. No. 5,359,051)] and methods for their use to down regulate or inhibit the expression of receptors of VEGF (VEGF-R).

In a preferred embodiment, the invention features use of one or more of the nucleic acid-based techniques to inhibit the expression of flt-1 and/or flk-1 /KDR receptors.

By "inhibit" it is meant that the activity of VEGF-R or level of mRNAs or equivalent RNAs encoding VEGF-R is reduced below that observed in the absence of the nucleic acid. In one embodiment, inhibition with ribozymes preferably is below that level observed in the presence of an enzymatically inactive RNA molecule that is able to bind to the same site on the mRNA, but is unable to cleave that RNA. In another embodiment, inhibition with antisense oligonucleotides is preferably below that level observed in the presence of for example, an oligonucleotide with scrambled sequence or with mismatches.

By "enzymatic nucleic acid molecule" it is meant an RNA molecule which has complementarity in a substrate binding region to a specified gene target, and also has an enzymatic activity which is active to specifically cleave target RNA. That is, the enzymatic RNA molecule is able to intermolecularly cleave RNA and thereby inactivate a target RNA molecule. This complementary regions allow sufficient hybridization of the enzymatic RNA molecule to the target RNA and thus permit cleavage. One hundred percent complementarity is preferred, but complementarity as low as 50–75% may also be useful in this invention. By "equivalent" RNA to VEGF-R is meant to include those naturally occurring RNA molecules in various animals, including human, mice, rats, rabbits, primates and pigs.

By "antisense nucleic acid" it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review see Stein and Cheng, 1993 Science 261, 1004).

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A-dependent ribonuclease which, in turn, cleaves the target RNA (Torrence et al., 1993 Proc. Natl. Acad. Sci. USA 90, 1300).

By "triplex DNA" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504).

By "gene" it is meant a nucleic acid that encodes an RNA.

By "complementarity" it is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in VEGF-R mRNAs represent a novel therapeutic approach to treat tumor angiogenesis, ocular diseases, rhuematoid arthritis, psoriasis and others. Applicant indicates that ribozymes are able to inhibit the activity of VEGF-R (specifically flt-1 and flk-1/KDR) and that the catalytic activity of the ribozymes is required for their inhibitory effect. Those of ordinary skill in the art will find that it is clear from the examples described that other ribozymes that cleave VEGF-R mRNAs may be readily designed and are within the invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *AIDS Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of target mRNAs encoding VEGF-R proteins (specifically flt-1 and flk-1/KDR) such that specific treatment of a disease or condition can be provided with either one or several enzymatic nucleic acids. Such enzymatic nucleic acid molecules can be delivered exogenously to specific tissue or cellular targets as required. Alternatively, the ribozymes can be expressed from DNA and/or RNA vectors that are delivered to specific cells.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; SullengerScanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225; Thompson et al., 1995 *Nucleic Acids Res.* 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO93/23569, and Sullivan et al., PCT WO94/02595, both hereby incorporated in their totality by reference herein; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856).

Such nucleic acids are useful for the prevention of the diseases and conditions discussed above, and any other diseases or conditions that are related to the levels of VEGF-R (specifically flt-1 and flk-1/KDR) in a cell or tissue.

By "related" is meant that the reduction of VEGF-R (specifically flt-1 and flk-1/KDR) RNA levels and thus reduction in the level of the respective protein will relieve, to some extent, the symptoms of the disease or condition.

Ribozymes are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II to IX. Examples of such ribozymes also are shown in Tables II to IX. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target RNA molecules and inhibit VEGF-R (specifically flt-1 and flk-1/KDR) activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

Other features and advantages of the invention will be apparent from the following description of the preferred embodiments thereof, and from the claims.

DESCRIPTION OF THE PREFERRED EMBODIMENTS

First the drawings will be described briefly.

DRAWINGS

FIG. 1 is a diagrammatic representation of the hammerhead ribozyme domain known in the art. Stem II can be $\geq 2$ base-pair long.

FIGS. 2a–2d: is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a diagramatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H refers to bases A, U, or C. Y refers to pyrimidine bases. "_" refers to a covalent bond.

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
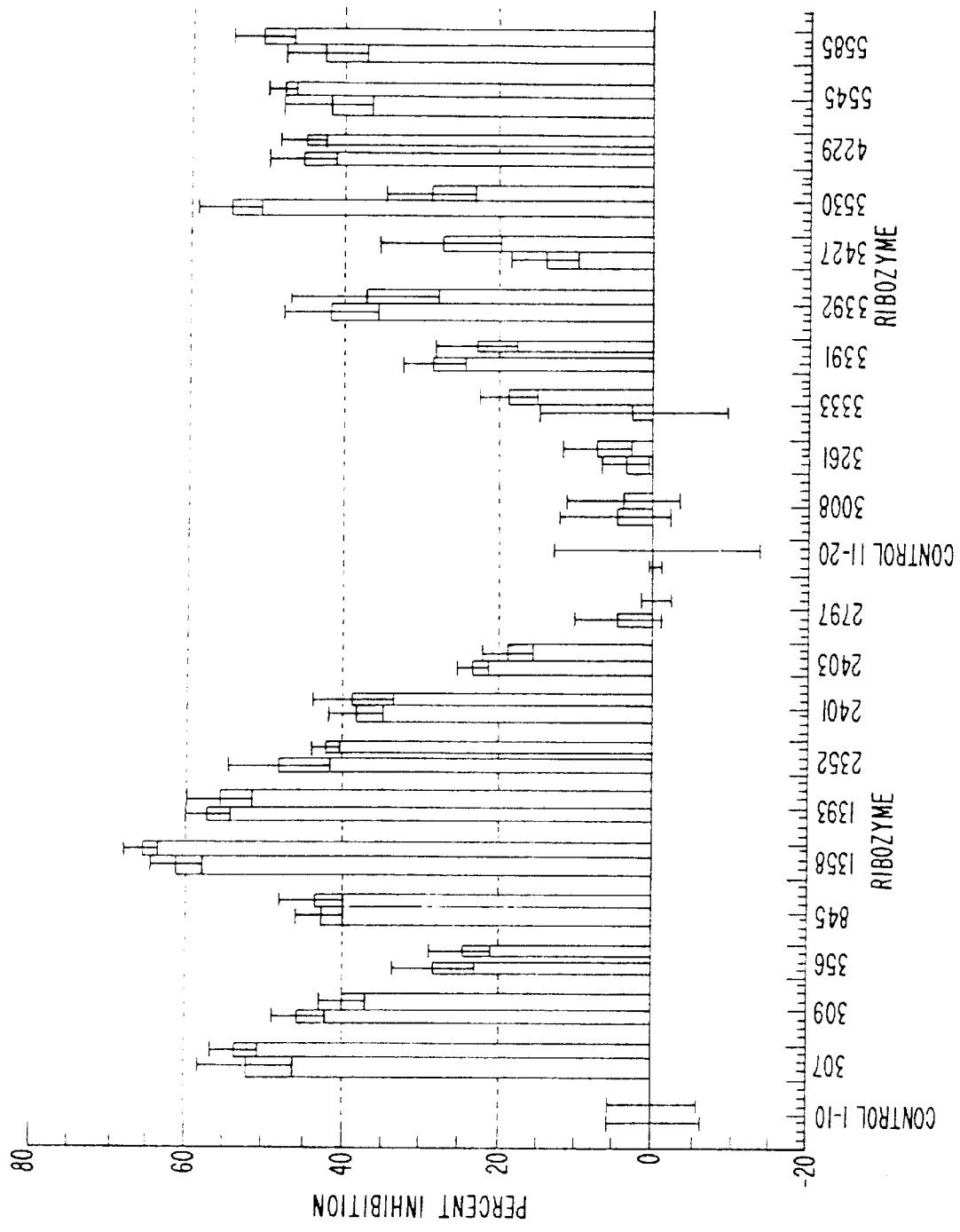

FIG. 7 shows the effect of hammerhead ribozymes targeted against flt-1 receptor on the binding of VEGF to the surface of human microvascular endothelial cells. Sequences of the ribozymes used are shown in Table II; the length of stem II region is 3 bp. The hammerhead ribozymes were chemically modified such that the ribozyme consists of ribose residues at five positions (see FIG. 11); U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The results of two separate experiments are shown as separate bars for each set. Each bar represents the average of triplicate samples. The standard deviation is shown with error bars. For the flt-1 data, 500 nM ribozyme (3:1 charge ratio with LipofectAMINE®) was used. Control 1–10 is the control for ribozymes 307–2797, control 11–20 is the control for ribozymes 3008–5585. The Control 1–10 and Control 11–20 represent the treatment of cells with LipofectAMINE® alone without any ribozymes.

Figure 8:
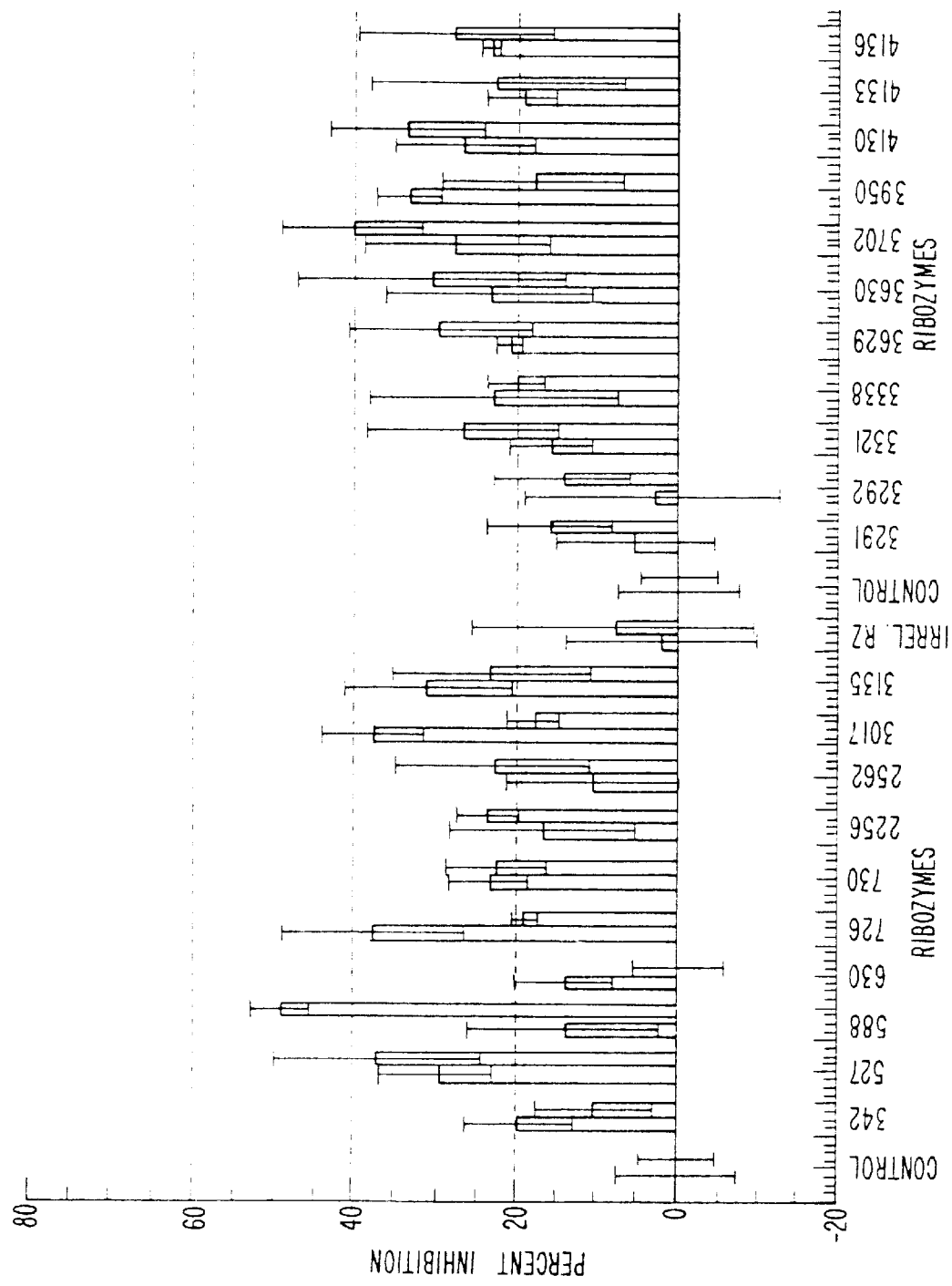

FIG. 8 shows the effect of hammerhead ribozymes targeted against KDR receptor on the binding of VEGF to KDR on the surface of human microvascular endothelial cells. Sequences of the ribozymes used are shown in Table IV; the length of stem II region is 3 bp. The hammerhead ribozymes were chemically modified such that the ribozyme consists of ribose residues at five positions (see FIG. 11); U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The Control 1–10 and Control 11–20 represent the treatment of cells with LipofectAMINE® alone without any ribozymes. Irrel. RZ, is a control experiment wherein the cells are treated with a non-KDR-targeted ribozyme complexed with Lipofectamine®. 200 nM ribozyme (3:1 charge ratio with LipofectAMINE(®) was used. In addition to the KDR-targeted ribozymes, the effect on VEGF binding of a ribozyme targeted to an irrelevant mRNA (irrel. RZ) is also shown. Because the affinity of KDR for VEGF is about 10-fold lower than the affinity of flt-1 for VEGF, a higher concentration of VEGF was used in the binding assay.

Figure 9:
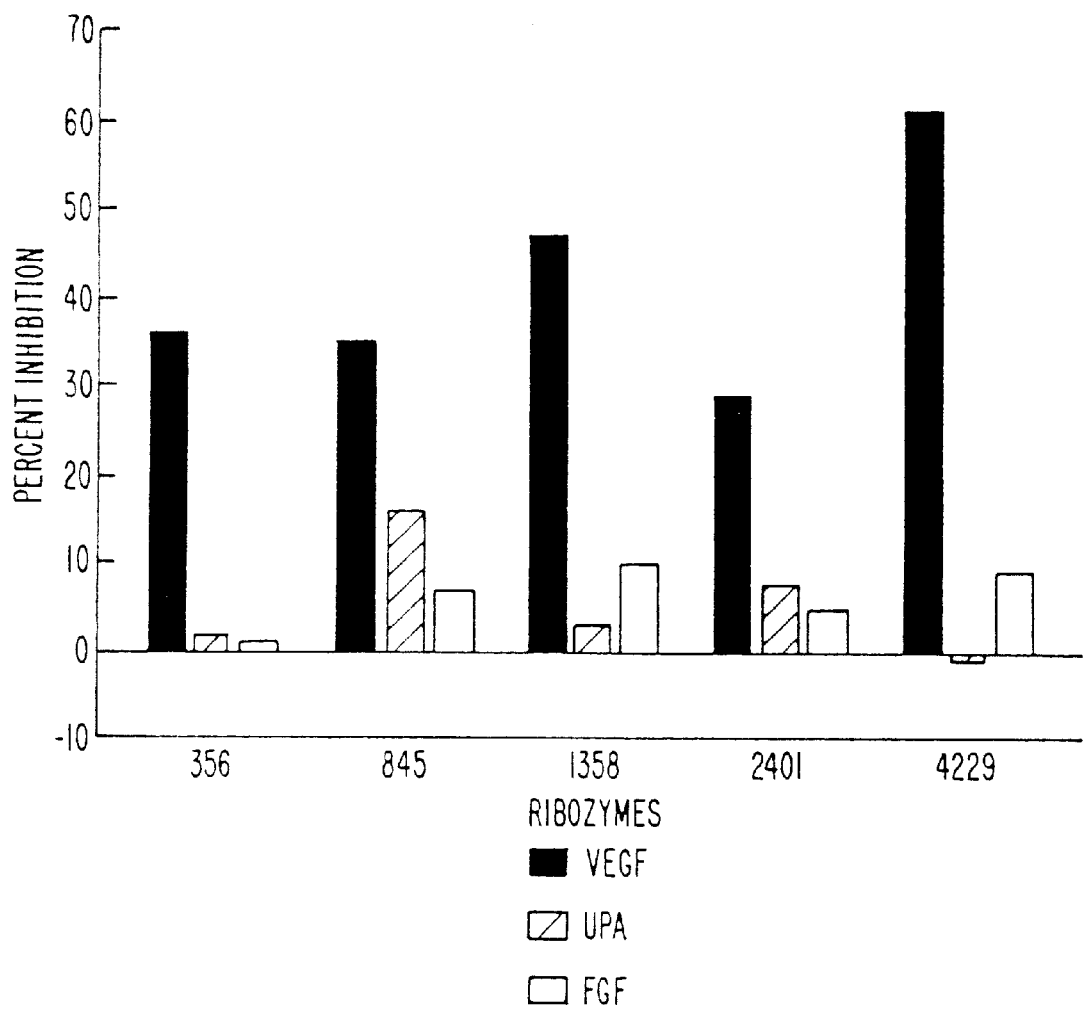

FIG. 9 shows the specificity of hammerhead ribozymes targeted against flt-1 receptor. Inhibition of the binding of VEGF, urokinase plasminogen activator (UPA) and fibroblast growth factor (FGF) to their corresponding receptors as a function of anti-FLT ribozymes is shown. The sequence and description of the ribozymes used are as described under FIG. 7 above. The average of triplicate samples is given; percent inhibition as calculated below.

FIG. 10 shows the inhibition of the proliferation of Human aortic endothelial cells (HAEC) mediated by phosphorothioate antisense oligodeoxynucleotides targeted against human KDR receptor RNA. Cell proliferation (O.D. 490) as a function of antisense oligodeoxynucleotide concentration is shown. KDR 21AS represents a 21 nt phosphorothioate antisense oligodeoxynucleotide targeted against KDR RNA. KDR 21 Scram represents a 21 nt phosphorothioate oligodeoxynucleotide having a scrambled sequence. LF represents the lipid carrier Lipofectin.

FIGS. 11 A–C show in vitro cleavage of flt-1 RNA by hammerhead ribozymes. A) diagrammatic representation of hammerhead ribozymes targeted against flt-1 RNA. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose (designated as 3'-iH). 1358 HH-A and 4229 HH-A contain 3 base-paired stem 11 region. 1358 HH-B and 4229 HH-B contain 4 base-paired stem II region. B) and C) shows in vitro cleavage kinetics of HH ribozymes targeted against sites 1358 and 4229 within the flt-1 RNA.

FIGS. 12 A–B show inhibition of human microvascular endothelial cell proliferation mediated by anti-flt-1 hammerhead ribozymes. A) Diagrammatic representation of hammerhead (HH) ribozymes targeted against sites 1358 and 4229 within the the flt-1 RNA. B) Graphical representation of the inhibition of cell proliferation mediated by 1358HH and 4229HH ribozymes.

Figure 13:
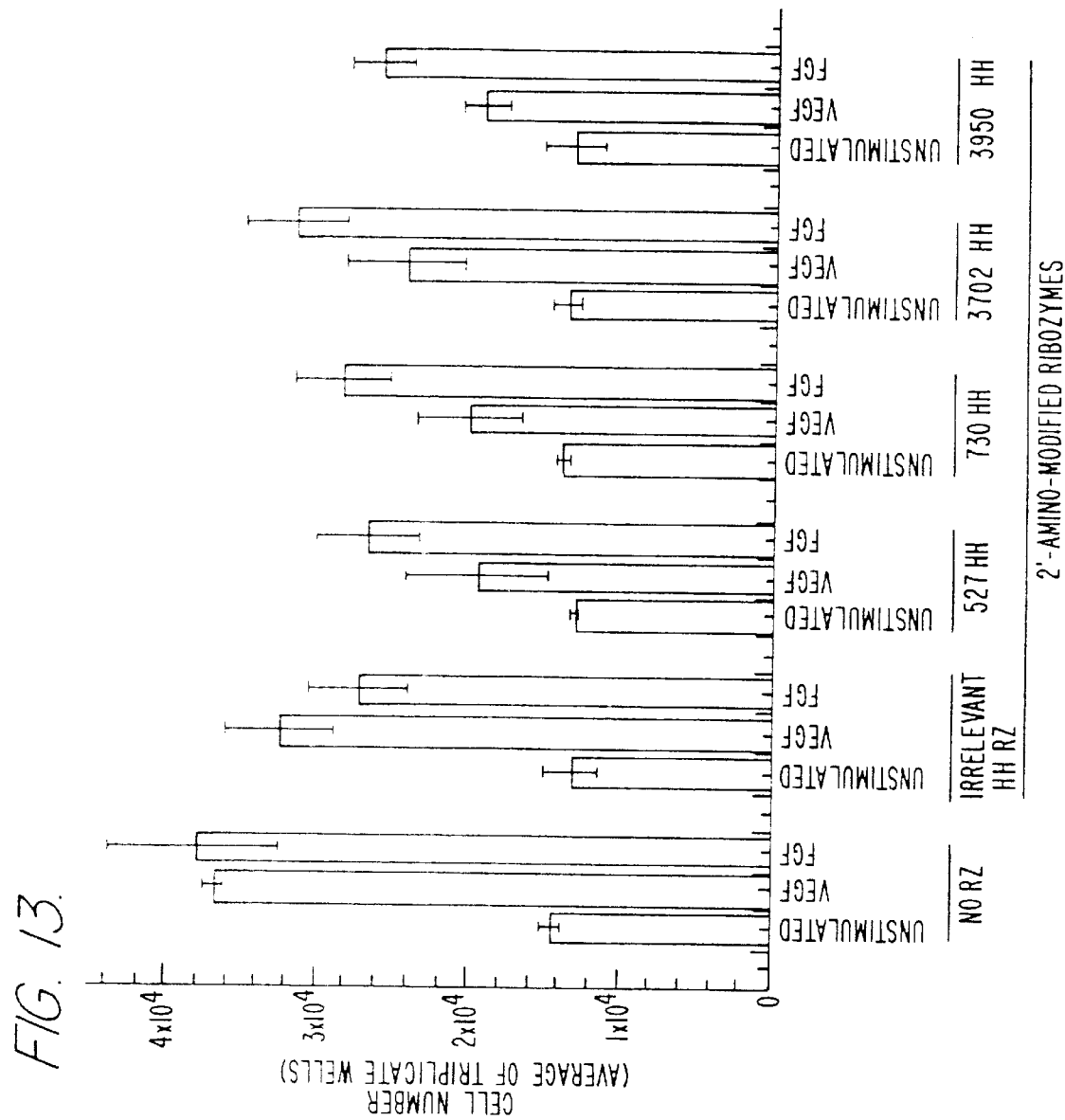

FIG. 13 shows inhibition of human microvascular endothelial cell proliferation mediated by anti-KDR hammerhead ribozymes. The figure is a graphical representation of the inhibition of cell proliferation mediated by hammerhead ribozymes targeted against sites 527, 730, 3702 and 3950 within the KDR RNA. Irrelevant HH RZ is a hammerhead ribozyme targeted to an irrelevant target. All of these ribozymes, including the Irrelevant HH RZ, were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

Figure 14:
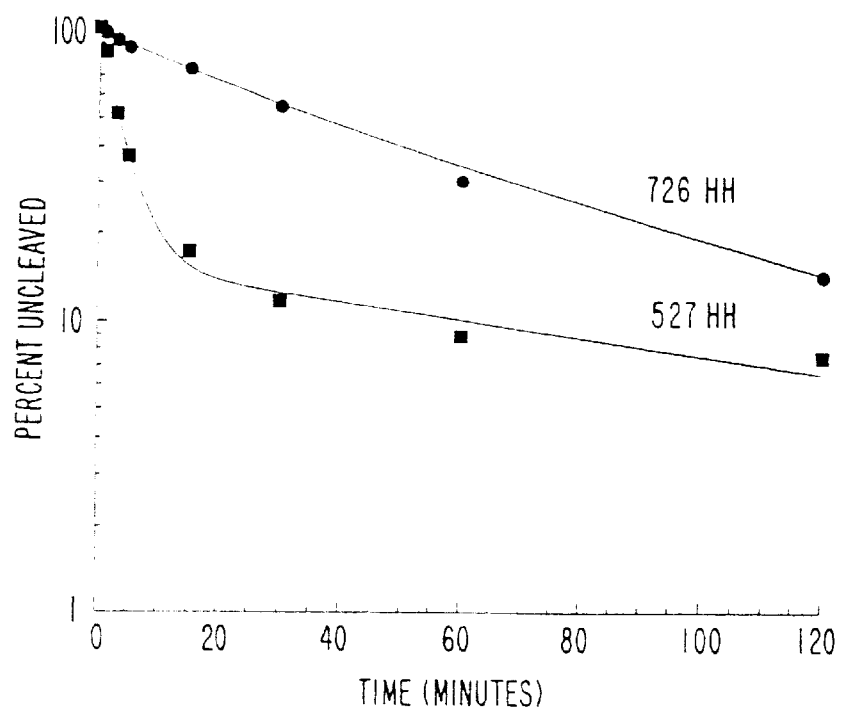

FIG. 14 shows in vitro cleavage of KDR RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). 726 HH and 527 HH contain 4 base-paired stem II region. Percentin vitro cleavage kinetics as a function of time of HH ribozymes targeted against sites 527 and 726 within the KDR RNA is shown.

Figure 15:
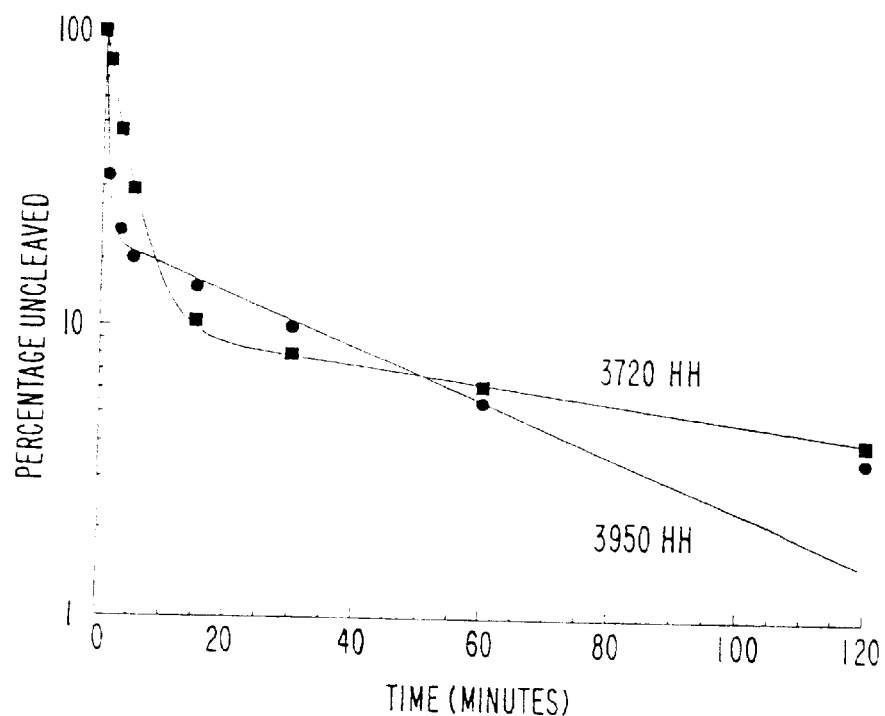

FIG. 15 shows in vitro cleavage of KDR RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). 3702 HH and 3950 HH contain 4 base-paired stem II region. Percentin vitro cleavage kinetics as a function of time of HH ribozymes targeted against sites 3702 and 3950 within the KDR RNA is shown.

Figure 16:
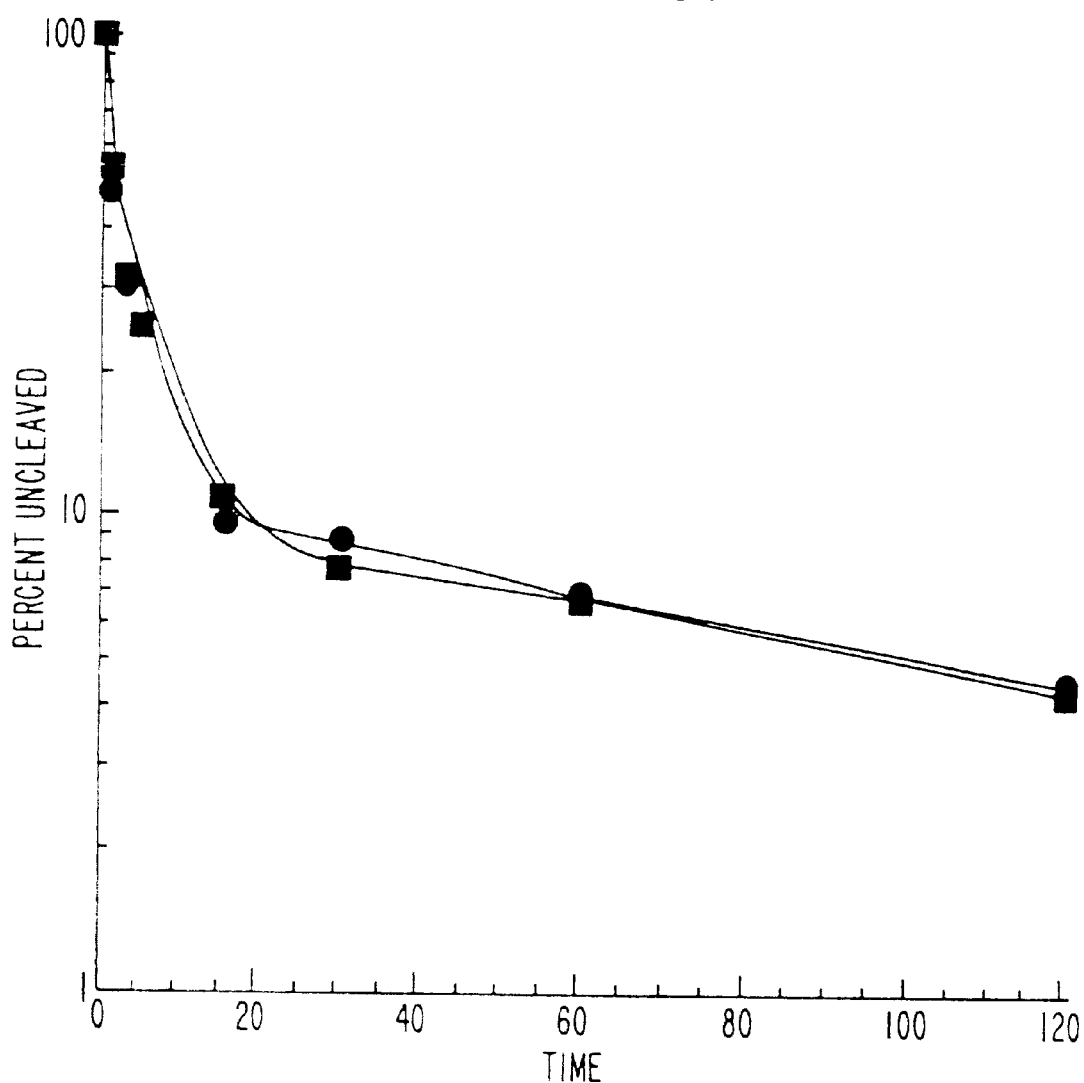

FIG. 16 shows in vitro cleavage of RNA by hammerhead ribozymes that are targeted to sites that are conserved between flt-1 and KDR RNA. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3'end of the ribozyme contains a 3'-3' linked inverted abasic deoxyribose (designated as 3'-iH). FLT/KDR-I HH ribozyme was synthesized with either a 4 base-paired or a 3 base-paired stem II region. FLT/KDR-I HH can cleave site 3388 within flt-1 RNA and site 3151 within KDR RNA. Percentin vitro cleavage kinetics as a function of time of HH ribozymes targeted against sites 3702 and 3950 within the KDR RNA is shown.

Figure 17:
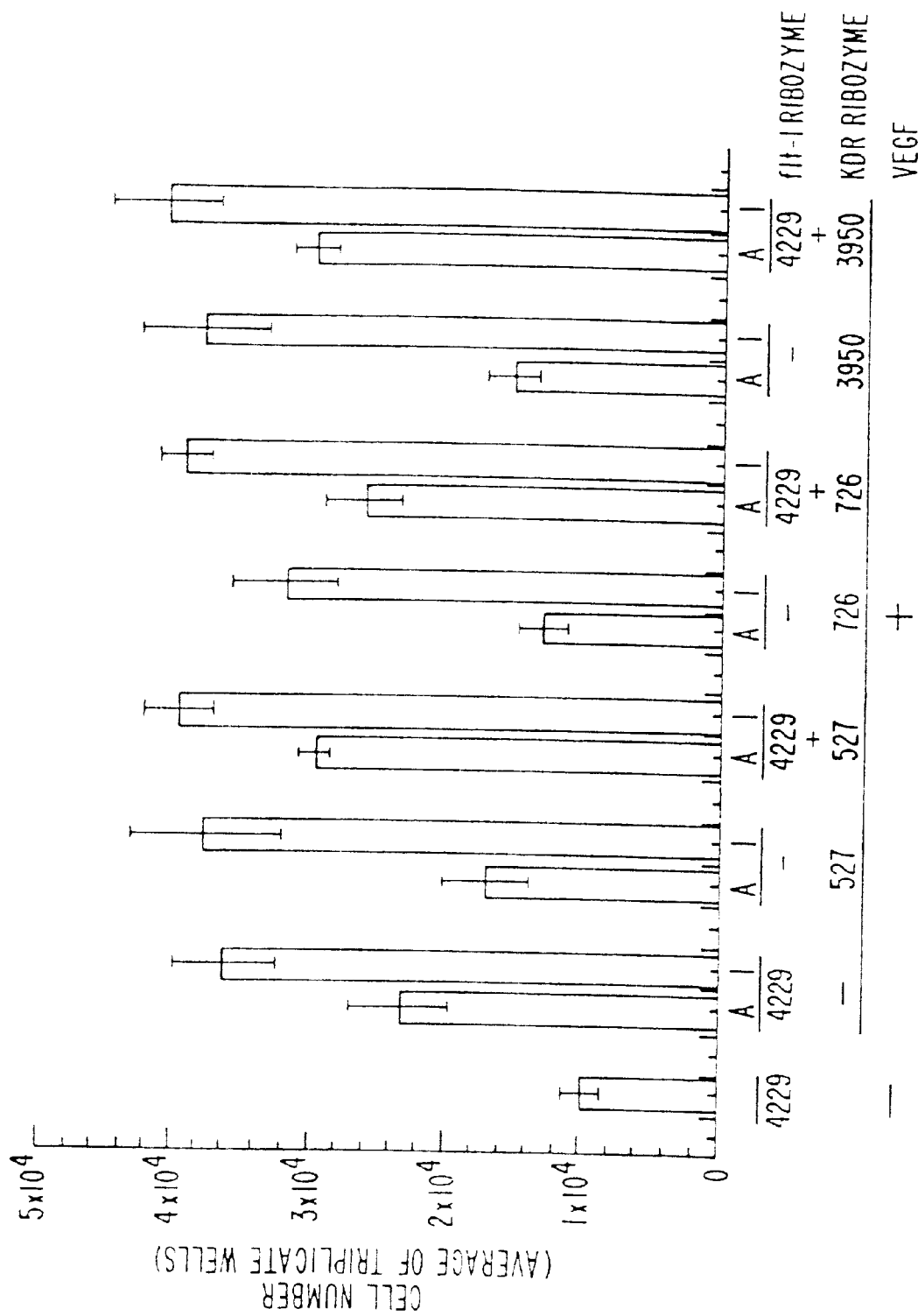

FIG. 17 shows inhibition of human microvascular endothelial cell proliferation mediated by anti-KDR and anti-flt-1 hammerhead ribozymes. The figure is a graphical representation of the inhibition of cell proliferation mediated by hammerhead ribozymes targeted against sites KDR sites-527, 726 or 3950 or flt-1 site 4229. The figure also shows enhanced inhibition of cell proliferation by a combination of flt-1 and KDR hammerhead ribozymes. 4229+527, indicates the treatment of cells with both the flt 4229 and the KDR 527 ribozymes. 4229+726, indicates the treatment of cells with both the flt 4229 and the KDR 726 ribozymes. 4229+3950, indicates the treatment of cells with both the flt 4229 and the KDR 3950 ribozymes. VEGF –, indicates the basal level of cell proliferation in the absence of VEGF. A, indicates catalytically active ribozyme; I, indicates catalytically inactive ribozyme. All of these ribozymes were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

Figure 18:
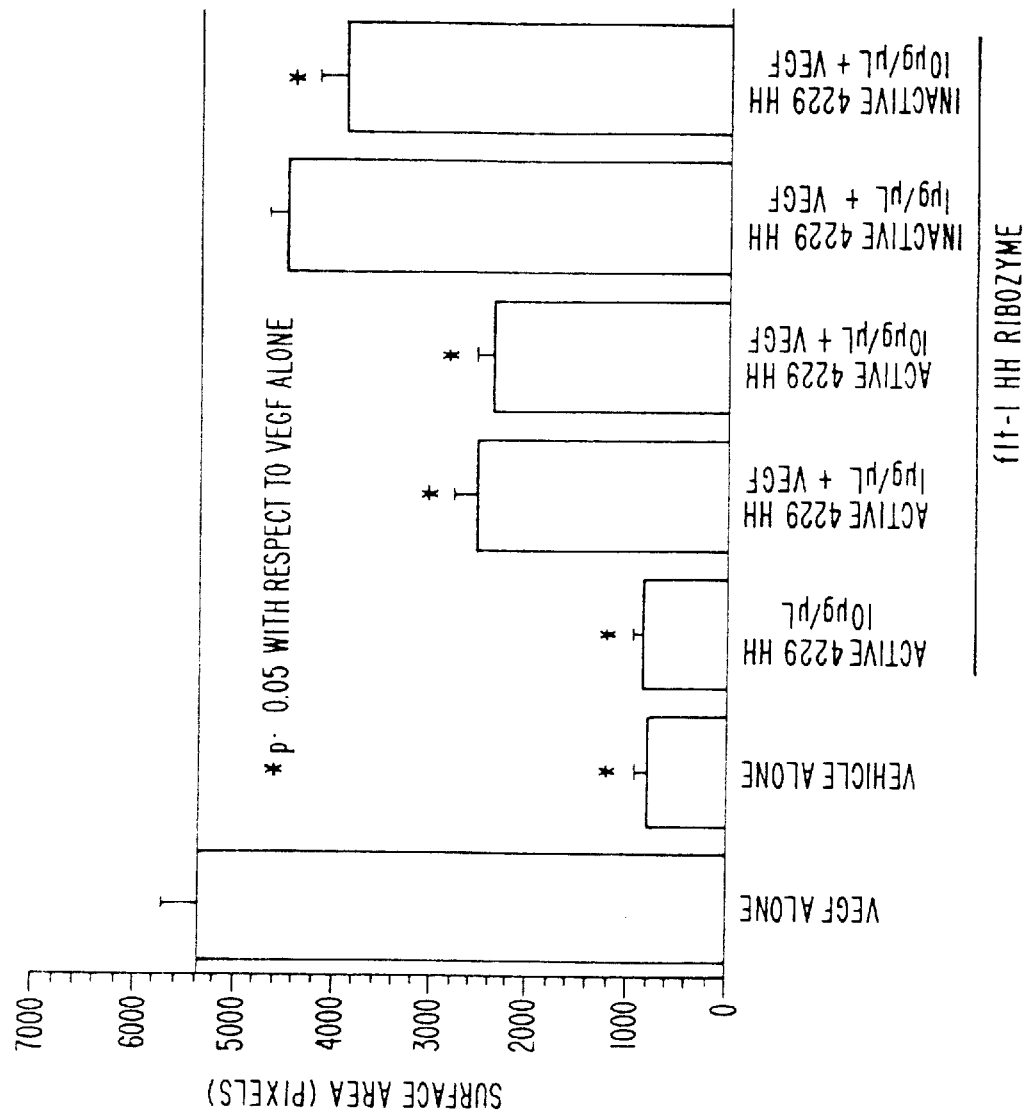

FIG. 18 shows the inhibition of VEGF-induced angiogenesis in rat cornea mediated by anti-flt-1 hammerhead ribozyme. All of these ribozymes were chemically modified such that the ribozyme consists of ribose residues at five positions; U4 position contains 2'-C-allyl modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH). A decrease in the Surface Area corresponds to a reduction in angiogenesis. VEGF alone, corresponds to treatment of the cornea with VEGF and no ribozymes. Vehicle alone, corresponds to the treatment of the cornea with the carrier alone and no VEGF. This control gives a basal level of Surface Area. Active 4229 HH, corresponds to the treatment of cornea with the flt-1 4229 HH ribozyme in the absence of any VEGF. This control also gives a basal level of Surface Area. Active 4229 HH+VEGF, corresponds to the co-treatment of cornea with the flt-1 4229 HH ribozyme and VEGF. Inactive 4229 HH+VEGF, corresponds to the co-treatment of cornea with a catalytically inactive version of 4229 HH ribozyme and VEGF.

Ribozymes

Ribozymes of this invention block to some extent VEGF-R (specifically flt-1 and flk-1/KDR) production and can be used to treat disease or diagnose such disease. Ribozymes will be delivered to cells in culture, to cells or tissues in animal models of angiogenesis and/or RA and to human cells or tissues ex vivo or in vivo. Ribozyme cleavage of VEGF-R RNAs (specifically RNAs that encode flt-1 and flk-1/KDR) in these systems may alleviate disease symptoms.

Target Sites

Targets for useful ribozymes can be determined as disclosed in Draper et al., International PCT Publication No. WO 95/13380, and hereby incorporated by reference herein in totality. Other examples include the following PCT applications which concern inactivation of expression of disease-related genes: WO 95/23225, WO 95/13380, WO 94/02595, incorporated by reference herein. Rather than repeat the guidance provided in those documents here, below are provided specific examples of such methods, not limiting to those in the art. Ribozymes to such targets are designed as described in those applications and synthesized to be tested in vitro and in vivo, as also described.

The sequence of human and mouse flt-1, KDR and/or flk-1 mRNAs were screened for optimal ribozyme target sites using a computer folding algorithm. Hammerhead or hairpin ribozyme cleavage sites were identified. These sites are shown in Tables II to IX (all sequences are 5' to 3' in the tables; X can be any base-paired sequence, the actual sequence is not relevant here). The nucleotide base position is noted in the Tables as that site to be cleaved by the designated type of ribozyme. While mouse and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, mouse targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and cleave target RNA in a sequence-specific manner. The ribozymes were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity.

Referring to FIG. 6, mRNA is screened for accessible cleavage sites by the method described generally in Draper et al., PCT WO93/23569, hereby incorporated by reference herein. Briefly, DNA oligonucleotides complementary to potential hammerhead or hairpin ribozyme cleavage sites were synthesized. A polymerase chain reaction is used to generate substrates for T7 RNA polymerase transcription from human and mouse flt-1, KDR and/or flk-1 cDNA clones. Labeled RNA transcripts are synthesized in vitro from the templates. The oligonucleotides and the labeled transcripts were annealed, RNAseH was added and the mixtures were incubated for the designated times at 37° C. Reactions are stopped and RNA separated on sequencing polyacrylamide gels. The percentage of the substrate cleaved is determined by autoradiographic quantitation using a PhosphorImaging system. From these data, hammerhead or hairpin ribozyme sites are chosen as the most accessible.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table XI outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4mL glass screw top vial and suspended in a solution of methylamine (MA) at 65° C. for 10 min. After cooling to −20° C., the supernatant was removed from the polymer support. The support was washed three times with 1.0 mL of $EtOH:MeCN:H_2O/3:1:1$, vortexed and the supernatant was then added to the first supernatant. The combined supernatants, containing the oligoribonucleotide, were dried to a white powder.

The base-deprotected oligoribonucleotide was resuspended in anhydrous TEA.HF/NMP solution (250 μL of a solution of 1.5 mL N-methyl-pyrrolidinone, 750 μL TEA and 1.0 mL TEA.3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U Hertel, K. J., et al., 1992, *Nucleic Acids Res.* 20, 3252).

The average stepwise coupling yields were >98% (Wincott et al., 1995 *Nucleic Acids Res.* 23, 2677–2684).

Hairpin ribozymes are synthesized in two parts and annealed to reconstruct the active ribozyme (Chowrira and Burke, 1992 *Nucleic Acids Res.*, 20, 2835–2840). Ribozymes are also synthesized from DNA templates using bacteriophage T7 RNA polymerase (Milligan and Uhlenbeck, 1989, *Methods Enzymol.* 180, 51).

All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34; Usman et al., 1994 *Nucleic Acids Symp. Ser.* 31, 163). Ribozymes are purified by gel electrophoresis using general methods or are purified by high pressure liquid chromatography (HPLC; See Usman et al., PCT Publication No. WO95/23225, the totality of which is hereby incorporated herein by reference) and are resuspended in water.

The sequences of the ribozymes that are chemically synthesized, useful in this study, are shown in Tables II to IX. Those in the art will recognize that these sequences are representative only of many more such sequences where the enzymatic portion of the ribozyme (all but the binding arms) is altered to affect activity. Stem-loop IV sequence of hairpin ribozymes listed in for example Table III (5'-CACGUUGUG-3') can be altered (substitution, deletion, and/or insertion) to contain any sequence, provided a minimum of two base-paired stem structure can form. The sequences listed in Tables II to IX may be formed of ribonucleotides or other nucleotides or non-nucleotides. Such ribozymes are equivalent to the ribozymes described specifically in the Tables.

Optimizing Ribozyme Activity

Figure 2A:
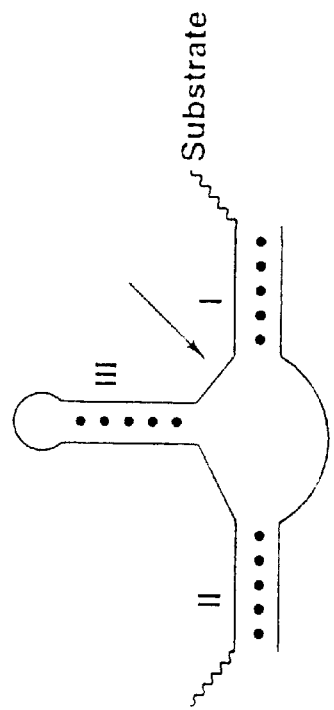
Figure 2B:
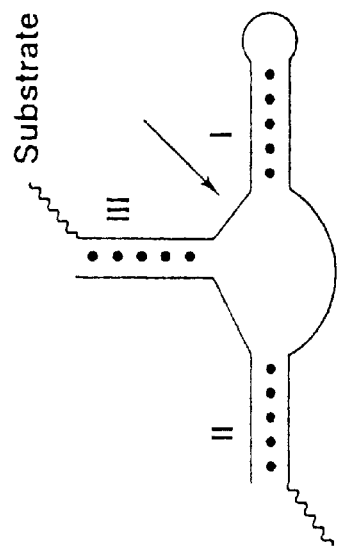
Figure 2C:
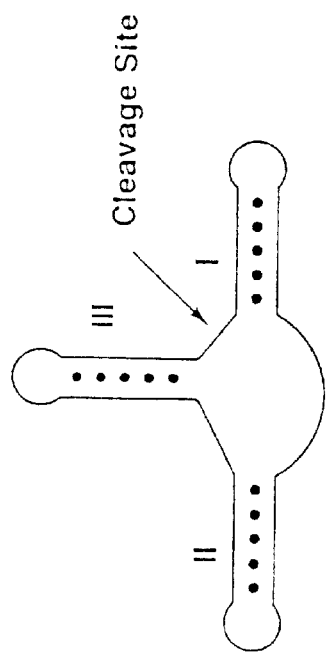
Figure 2D:
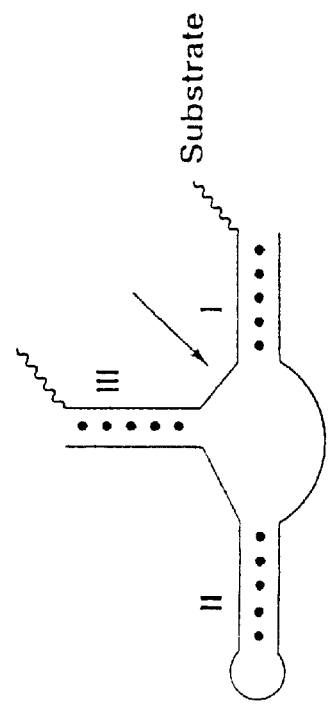

Ribozyme activity can be optimized as described by Stinchcomb et al., supra. The details will not be repeated here, but include altering the length of the ribozyme binding arms (stems I and II, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; Rossi et al., International Publication No. WO 91/03162; Beigelman et al., 1995 *J Biol Chem.* in press; as well as Sproat, U.S. Pat. No. 5,334,711 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein).

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U.S.A.,* 87, 6743–7; Gao and Huang 1993 *Nucleic Acids Res.,* 21, 2867–72; Lieber et al., 1993 *Methods Enzymol.,* 217, 47–66; Zhou et al., 1990 *Mol. Cell. Biol.,* 10, 4529≧37; Thompson et al., 1995 supra). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad. Sci. U.S.A.,* 89,10802–6; Chen et al., 1992 *Nucleic Acids Res.,* 20, 4581–9; Yu et al., 1993 *Proc. Natl. Acad. Sci. U.S.A,* 90, 6340–4; L'Huillier et al., 1992 *EMBO J.* 11, 4411–8; Lisziewicz et al., 1993 *Proc. Natl. Acad. Sci. U.S.A.,* 90, 8000–4; Thompson et al., 1995 *Nucleic Acids Res.* 23, 2259). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves RNAs that encode flt-1, KDR and/or flk-1 are inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 Cell 75, 207; Carter, 1992 *Curr. Opi. Biotech.* 3, 533). The adenovirus, AAV or retroviral vector is delivered as recombinant viral particles. The DNA may be delivered alone or complexed with vehicles (as described for RNA above). The recombinant adenovirus or AAV or retroviral particles are locally administered to the site of treatment, e.g., through incubation or inhalation in vivo or by direct application to cells or tissues ex vivo. Retroviral vectors have also been used to express ribozymes in mammalian cells (Ojwang et al., 1992 supra; Thompson et al., 1995 supra).

flt-1, KDR and/or flk-1 are attractive nucleic acid-based therapeutic targets by several criteria. The interaction between VEGF and VEGF-R is well-established. Efficacy can be tested in well-defined and predictive animal models. Finally, the disease conditions are serious and current therapies are inadequate. Whereas protein-based therapies would inhibit VEGF activity nucleic acid-based therapy provides a direct and elegant approach to directly modulate flt-1, KDR and/or flk-1 expression.

Because flt-1 and KDR mRNAs are highly homologous in certain regions, some ribozyme target sites are also homologous (see Table X). In this case, a single ribozyme will target both flt-1 and KDR mRNAs. At partially homologous sites, a single ribozyme can sometimes be designed to accomodate a site on both mRNAs by including G/U basepairing. For example, if there is a G present in a ribozyme target site in KDR mRNA at the same position there is an A in the flt-1 ribozyme target site, the ribozyme can be synthesized with a U at the complementary position and it will bind both to sites. The advantage of one ribozyme that targets both VEGF-R mRNAs is clear, especially in cases where both VEGF receptors may contribute to the progression of angiogenesis in the disease state.

"Angiogenesis" refers to formation of new blood vessels which is an essential process in reproduction, development and wound repair. "Tumor ngiogenesis" refers to the induction of the growth of blood vessels from surrounding tissue into a solid tumor. Tumor growth and tumor metastasis are dependent on angiogenesis (for a review see Folkman, 1985 supra; Folkman 1990 *J. Natl. Cancer Inst.,* 82, 4; Folkman and Shing, 1992 *J Biol. Chem.* 267, 10931).

Angiogenesis plays an important role in other diseases such as arthritis wherein new blood vessels have been shown to invade the joints and degrade cartilage (Folkman and Shing, supra).

"Retinopathy" refers to inflammation of the retina and/or degenerative condition of the retina which may lead to occlusion of the retina and eventual blindness. In "diabetic retinopathy" angiogenesis causes the capillaries in the retina to invade the vitreous resulting in bleeding and blindness which is also seen in neonatal retinopathy (for a review see Folkman, 1985 supra; Folkman 1990 supra; Folkman and Shing, 1992 supra).

EXAMPLE 1 flt-1. KDR and/or flk-1 Ribozymes

By engineering ribozyme motifs applicant has designed several ribozymes directed against flt-1, KDR and/or flk-1 encoded mRNA sequences. These ribozymes were synthesized with modifications that improve their nuclease resistance (Beigelman et al., 1995 *J Biol. Chem.* 270, 25702) and enhance their activity in cells. The ability of ribozymes to cleave target sequences in vitro was evaluated essentially as described in Thompson et al., PCT Publication No. WO 93/23057; Draper et al., PCT Publication No. WO 95/04818.

EXAMPLE 2
Effect of Ribozymes on the Binding of VEGF to flt-1. KDR and/or flk-1 Receptors Several common human cell lines are available that express endogenous flt-1, KDR and/or flk-1. flt-1, KDR and/or flk-1 can be detected easily with monoclonal antibodies. Use of appropriate fluorescent reagents and fluorescence-activated cell-sorting (FACS) will permit direct quantitation of surface flt-1, KDR and/or flk-1 on a cell-by-cell basis. Active ribozymes are expected to directly reduce flt-1, KDR and/or flk-1 expression and thereby reduce VEGF binding to the cells. In this example, human umbelical cord microvascular endothelial cells were used.

Cell Preparation

Plates are coated with 1.5% gelatin and allowed to stand for one hour. Cells (e.g., microvascular endothelial cells derived from human umbilical cord vein) are plated at 20,000 cells/well (24 well plate) in 200 µl growth media and incubated overnight (~1 doubling) to yield ~40,000 cells (75–80% confluent).

Ribozyme Treatment

Media is removed from cells and the cells are washed two times with 300 µl 1× PBS: $Ca^{2+}$: $Mg^{2+}$ mixture. A complex of 200–500 nM ribozyme and LipofectAMINE® (3:1 lipid:phosphate ratio) in 200 µl OptiMEM® (5% FBS) was added to the cells. The cells are incubated for 6 hr (equivalent to 2–3 VEGF-R turnovers).

$^{125}$I VEGF Binding Assay

The assay is carried out on ice to inhibit internalization of VEGF during the experiment. The media containing the ribozyme is removed from the cells and the cells are washed twice with with 300 µl 1× PBS: $Ca^{2+}$: $Mg^{2+}$ mixture containing 1% BSA. Appropriate $^{125}$I VEGF solution (100,000 cpm/well, +/−10× cold 1× PBS, 1% BSA) was applied to the cells. The cells are incubated on ice for 1 h. $^{125}$I VEGF-containing solution is removed and the cells are washed three times with with 300 µl 1× PBS: $Ca^{2+}$: $Mg^{2+}$ mixture containing 1% BSA. To each well 300 µl of 100 mM Tris-HCl, pH 8.0, 0.5% Triton X-100 was added and the the mixture was incubated for 2 min. The $^{125}$I VEGF-binding was quantitated using standard scintillation counting techniques.

$$\text{Percent Inhibition} = \frac{\text{cpm}^{125} \mid VEGF \text{ bound by the ribozyme-treated samples}}{\text{cpm}^{125} \mid VEGF \text{ bound by the Control sample}} \times 100$$

EXAMPLE 3
Effect of Hammerhead Ribozymes Targeted Against flt-1 Receptor on the Binding of VEGF Hammerhead ribozymes targeted to twenty sites within flt-1 RNA were synthesized as described above. Sequence of the ribozymes used are shown in Table II; the length of stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, 3' end of the ribozyme contains a 3'-3' linked inverted abasic ribose.

Referring to FIG. 7, the effect of hammerhead ribozymes targeted against flt-1 receptor on the binding of VEGF to flt-1 on the surface of human microvascular endothelial cells is shown. The majority of the ribozymes tested were able to inhibit the expression of flt-1 and thereby were able to inhibit the binding of VEGF.

In order to determine the specificity of ribozymes targeted against flt-1 RNA, the effect of five anti-flt-1 ribozymes on the binding of VEGF, UPA (urokinase plasminogen activator) and FGF (fibroblast growth factor) to their corresponding receptors were assayed. As shown in FIG. 9, there was significant inhibition of VEGF binding to its receptors on cells treated with anti-flt-1 ribozymes. There was no specific inhibition of the binding of UPA and FGF to their corresponding receptors. These data strongly suggest that anti-flt-1 ribozymes specifically cleave flt-1 RNA and not RNAs encoding the receptors for UPA and FGF, resulting in the inhibition of flt-1 receptor expression on the surface of the cells. Thus the ribozymes are responsible for the inhibition of VEGF binding but not the binding of UPA and FGF.

EXAMPLE 4
Effect of Hammerhead Ribozymes Targeted Against KDR Receptor on the Binding of VEGF Hammerhead ribozymes targeted to twenty one sites within KDR RNA were synthesized as described above. Sequence of the ribozymes used are shown in Table IV; the length of stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose.

Referring to FIG. 8, the effect of hammerhead ribozymes targeted against KDR receptor on the binding of VEGF to KDR on the surface of human microvascular endothelial cells is shown. A majority of the ribozymes tested were able to inhibit the expression of KDR and thereby were able to inhibit the binding of VEGF. As a control, the cells were treated with a ribozyme that is not targeted towards KDR RNA (irrel. RZ); there was no specific inhibition of VEGF binding. The results from this control experiment strongly suggest that the inhibition of VEGF binding observed with anti-KDR ribozymes is a ribozyme-mediated inhibition.

EXAMPLE 5
Effect of Ribozymes Targeted Against VEGF Receptors on Cell Proliferation Cell Preparation 24-well plates are coated with 1.5% gelatin (porcine skin 300 bloom). After 1 hr, excess gelatin is washed off of the plate. Microvascular endothelial cells are plated at 5,000 cells/well (24 well plate) in 200 µl growth media. The cells are allowed to grow for ~18 hr (~1 doubling) to yield ~10,000 cells (25–30% confluent).

Ribozyme Treatment

Media is removed from the cells, and the cells are washed two times with 300 µl 1× PBS: $Ca^{2+}$: $Mg^{2+}$ mixture.

For anti-flt-1 HH ribozyme experiment (FIG. 12) a complex of 500 nM ribozyme; 15 µM LFA (3:1 lipid:phosphate ratio) in 200 µl OptiMEM (5% FCS) media was added to the cells. Incubation of cells is carried out for 6 hr (equivalent to 2–3 VEGF receptor turnovers).

For anti-KDR HH ribozyme experiment (FIG. 13) a complex of 200 nM ribozyme; 5.25 µM LFA (3:1 lipid:phosphate ratio) in 200 µl OptiMEM (5% FCS) media was added to the cells. Incubation of cells is carried out for 3 hr.

Proliferation

After three or six hours, the media is removed from the cells and the cells are washed with 300 μl 1× PBS: $Ca^{2+}$: $Mg^{2+}$mixture. Maintenance media (contains dialyzed 10% FBS) +/−VEGF or basic FGF at 10 ng/ml is added to the cells. The cells are incubated for 48 or 72 h. The cells are trypsinized and counted (Coulter counter). Trypan blue is added on one well of each treatment as control.

Figure 12B:
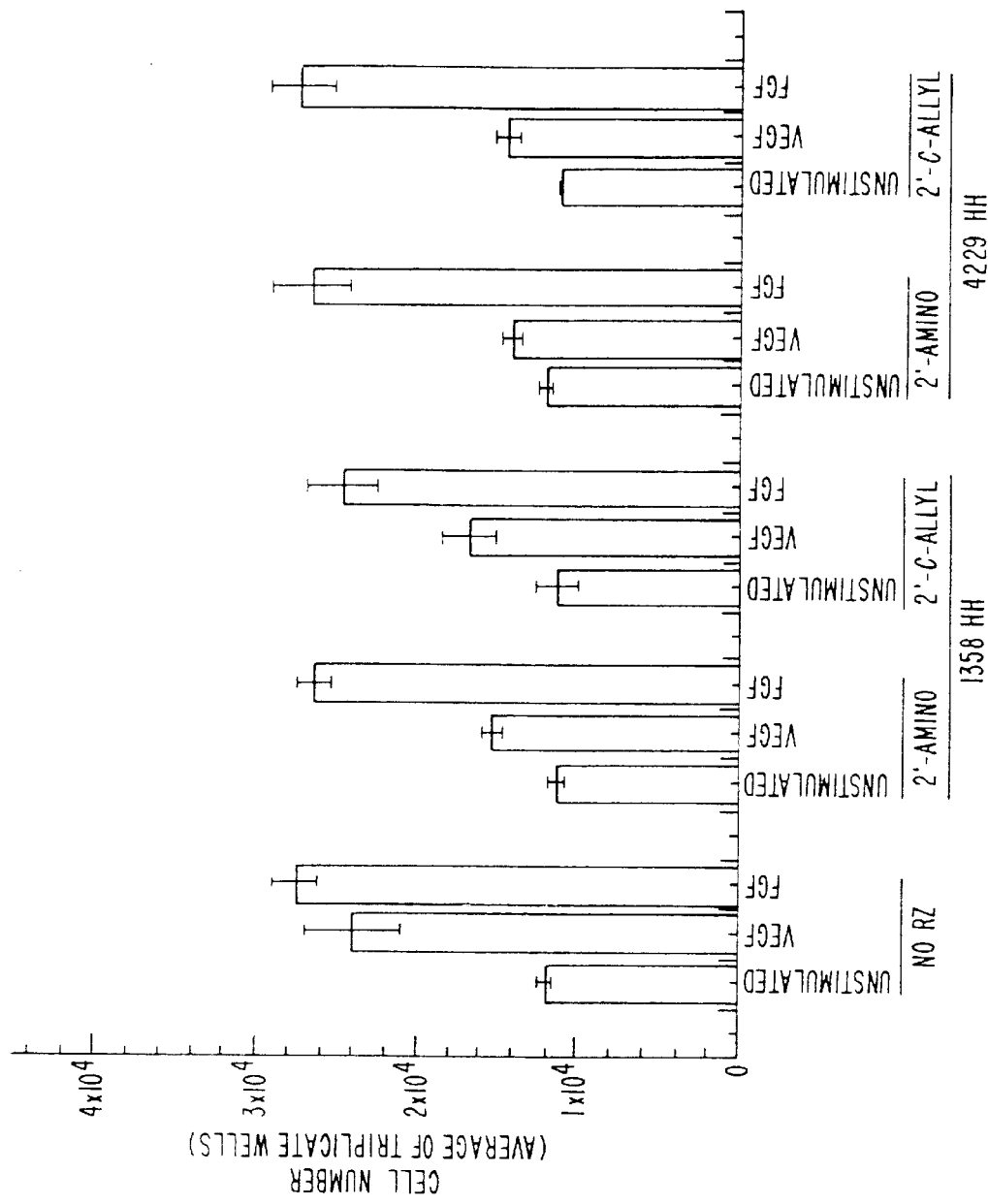

As shown in FIG. 12B, VEGF and basic FGF can stimulate human microvascular endothelial cell proliferation. However, treatment of cells with 1358 HH or 4229 HH ribozymes, targeted against flt-1 mRNA, results in a significant decrease in the ability of VEGF to stimulate endothelial cell proliferation. These ribozymes do not inhibit the FGF-mediated stimulation of endothelial cell proliferation.

Human microvascular endothalial cells were also treated with hammerhead ribozymes targeted against sites 527, 730, 3702 or 3950 within the KDR mRNA. As shown in FIG. 13, all four ribozymes caused significant inhibition of VEGF-mediated induction of cell proliferation. No significant inhibition of cell proliferation was observed when the cells were treated with a hammerhead ribozyme targeted to an irrelevant RNA. Additionally, none of the ribozymes inhibited FGF-mediated stimulation of cell proliferation.

These results strongly suggest that hammerhead ribozymes targeted against either flt-1 or KDR mRNA can specifically inhibit VEGF-mediated induction of endothelial cell proliferation.

EXAMPLE 6

Effect of Antisense Oligonucleotides Targeted Against VEGF Receptors on Cell Proliferation (Colorimetric Assay)

Following are some of the reagents used in the proliferation assay:

Cells: Human aortic endothelial cells (HAEC) from Clonetics®. Cells at early passage are preferably used.

Uptake Medium: EBM (from Clonetics®);1% L-Glutamine;20 mM Hepes;No serum;No antibiotics.

Growth Medium: EGM (from Clonetics®);FBS to 20%;1% L-Glutamine; 20 mM Hepes.

Cell Plating: 96-well tissue culture plates are coated with 0.2% gelatin (50 μl/well). The gelatin is incubated in the wells at room temperature for 15–30 minutes. The gelatin is removed by aspiration and the wells are washed with PBS:$Ca^{2+}$: $Mg^{2+}$mixture. PBS mixture is left in the wells until cells are ready to be added. HAEC cells were detached by trypsin treatment and resuspended at $1.25 \times 10^4$/ml in growth medium. PBS is removed from plates and 200 μl of cells (i.e. $2.5 \times 10^3$ cells/well) are added to each well. The cells are allowed to grow for 48 hours before the proliferation assay.

Assay: Growth medium is removed from the wells. The cells are washed twice with PBS:$Ca^{2+}$: $Mg^{2+}$mixture without antibiotics. A formulation of lipid/antisense oligonucleotide (antisense oligonucleotide is used here as a non-limiting example) complex is added to each well (100 μl/well) in uptake medium. The cells are incubated for 2–3 hours at 37° C. in $C_2$ incubator. After uptake, 100 μl/well of growth medium is added (gives final FBS concentration of 10%). After approximately 72 hours, 40 μl MTS® stock solution (made as described by manufacturer) was added to each well and incubated at 37° C. for 1–3 hours, depending on the color development. (For this assay, 2 hours was sufficient). The intensity of color formation was determined on a plate reader at 490 nM.

Phosphorothioate-substituted antisense oligodeoxynucleotides were custom synthesized by The Midland Certified Reagent Company®, Midland, Tex. Following non-limiting antisense oligodeoxynucleotides targeted against KDR RNA were used in the proliferation assay:

KDR 21 AS: 5'-GCA GCA CCT TGC TCT CCA TCC-3'

SCRAMBLED CONTROL: 5'-CTG CCA ACT TCC CAT GCC TGC-3'

As shown in FIG. 10, proliferation of HAEC cells are specifically inhibited by increasing concentrations of the phosphorothioate anti-KDR-antisense oligodeoxynucleotide. The scrambled antisense oligonucleotide is not expected to bind the KDR RNA and therefore is not expected to inhibit KDR expression. As expected, there is no detectable inhibition of proliferation of HAEC cells treated with a phosphorothioate antisense oligonucleotide with scrambled sequence.

EXAMPLE 7

In Vitro Cleavage of flt-1 RNA by Hammerhead Ribozymes

Referring to FIG. 11A, hammerhead ribozymes (HH) targeted against sites 1358 and 4229 within the flt-1 RNA were synthesized as described above.

RNA Cleavage Assay in vitro

Substrate RNA was 5' end-labeled using [$\gamma$-$^{32}$P] ATP and T4 polynucleotide kinase (US Biochemicals). Cleavage reactions were carried out under ribozyme "excess" conditions. Trace amount ($\leq 1$ nM) of 5' end-labeled substrate and 40 nM unlabeled ribozyme were denatured and renatured separately by heating to 90° C. for 2 min and snap-cooling on ice for 10–15 min. The ribozyme and substrate were incubated, separately, at 37° C. for 10 min in a buffer containing 50 mM Tris-HCl and 10 mM $MgCl_2$. The reaction was initiated by mixing the ribozyme and substrate solutions and incubating at 37° C. Aliquots of 5 μl are taken at regular intervals of time and the reaction is quenched by mixing with equal volume of 2× formamide stop mix. The samples are resolved on 20 % denaturing polyacrylamide gels. The results were quantified and percentage of target RNA cleaved is plotted as a function of time.

Figure 11B:
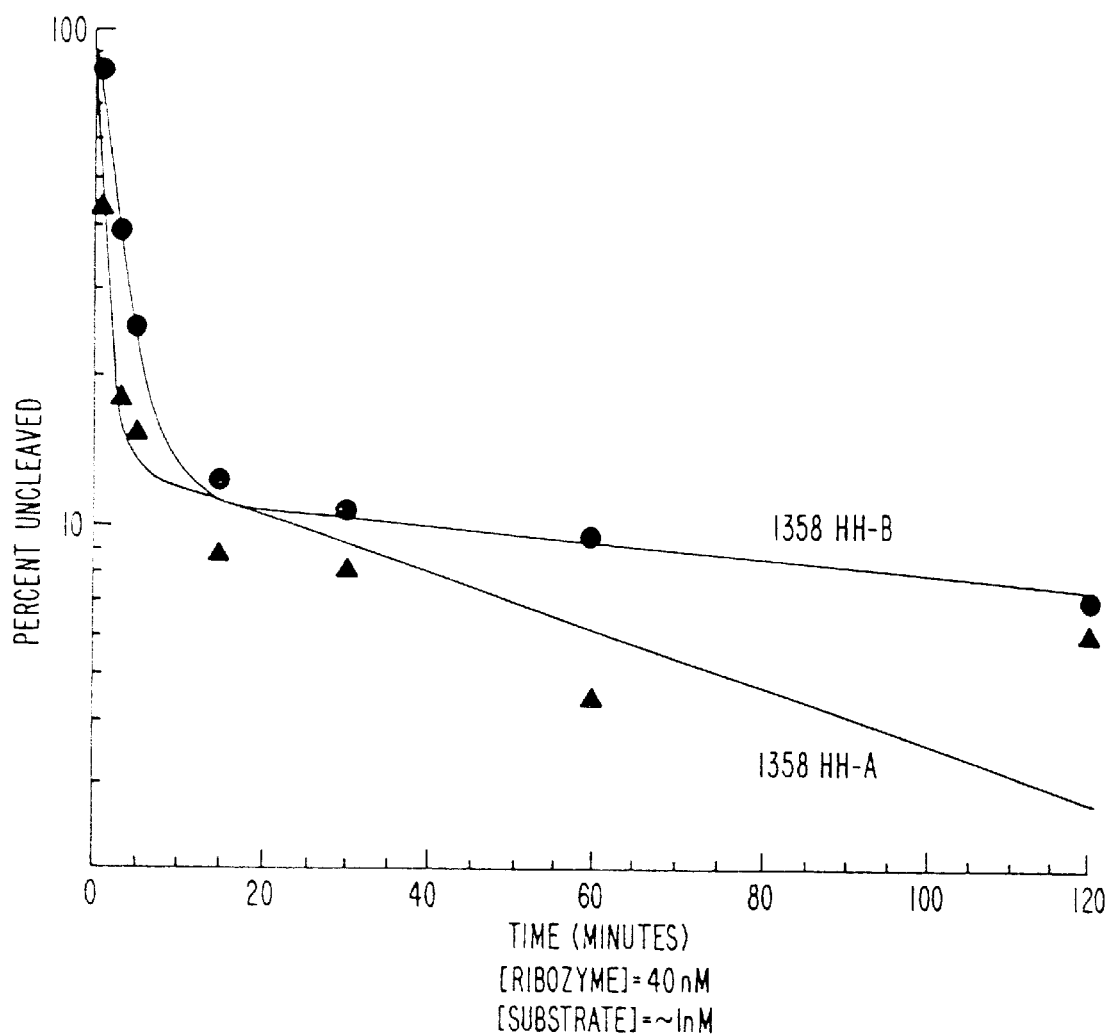

Referring to FIG. 11B and 11C, hammerhead ribozymes targeted against sites 1358 and 4229 within the flt-1 RNA are capable of cleaving target RNA efficiently in vitro.

EXAMPLE 8

In Vitro Cleavage of KDR RNA by Hammerhead Ribozymes

In this non-limiting example, hammerhead ribozymes targeted against sites 726, 527, 3702 and 3950 within KDR RNA were synthesized as described above. RNA cleavage reactions were carried out in vitro essentially as described under Example 7.

Referring to FIGS. 14 and 15, all four ribozymes were able to cleave their cognate target RNA efficiently in a sequence-specific manner.

EXAMPLE 9

In Vitro Cleavage of RNA by Hammerhead Ribozymes Targeted Against Cleavage Sites that are Homologous Between KDR and flt-1 mRNA Because flt-1 and KDR mRNAs are highly homologous in certain regions, some ribozyme target sites are also homologous (see Table X). In this case, a single ribozyme will target both flt-1 and KDR mRNAs. Hammerhead ribozyme (FLT/KDR-I) targeted against one of the homologous sites between flt-1 and KDR (flt-1 site 3388 and KDR site 3151) was synthesized as described above. Ribozymes with either a 3 bp stem II or a 4 bp stem II were synthesized. RNA cleavage reactions were carried out in vitro essentially as described under Example 7.

Referring to FIG. 16, FLT/KDR-I ribozyme with either a 3 or a 4 bp stem II was able to cleave its target RNA efficiently in vitro.

EXAMPLE 10

Effect of Multiple Ribozymes Targeted Against Both flt-1 and KDR RNA on Cell Proliferation Since both flt-1 and KDR receptors of VEGF are involved in angiogenesis, the inhibition of the expression of both of these genes may be an effective approach to inhibit angiogenesis.

Human microvascular endothalial cells were treated with hammerhead ribozymes targeted against sites flt-1 4229 alone, KDR 527 alone, KDR 726 alone, KDR 3950 alone, flt-1 4229+KDR 527, flt-1 4229+KDR 726 or flt-1 4229+ KDR 3950. As shown in FIG. 17, all the combinations of active ribozymes (A) caused significant inhibition of VEGF-mediated induction of cell proliferation. No significant inhibition of cell proliferation was observed when the cells were treated with a catalytically inactive (I) hammerhead ribozymes. Additionally, cells treated with ribozymes targeted against both flt-i and KDR RNAs- flt-1 4229+KDR 527; flt-1 4229+KDR 726; flt-1 4229+KDR 3950, were able to cause a greater inhibition of VEGF-mediated induction of cell proliferation when compared with individual ribozymes targeted against either flt-1 or KDR RNA (see flt-1 4229 alone; KDR 527 alone; KDR 726 alone; KDR 3950 alone). This strongly suggests that treatment of cells with multiple ribozymes may be a more effective means of inhibition of gene expression.

Animal Models

There are several animal models in which the anti-angiogenesis effect of nucleic acids of the present invention, such as ribozymes, directed against VEGF-R mRNAs can be tested. Typically a corneal model has been used to study angiogenesis in rat and rabbit since recruitment of vessels can easily be followed in this normally avascular tissue (Pandey et al., 1995 *Science* 268: 567–569). In these models, a small Teflon or Hydron disk pretreated with an angiogenesis factor (e.g. bFGF or VEGF) is inserted into a pocket surgically created in the cornea. Angiogenesis is monitored 3 to 5 days later. Ribozymes directed against VEGF-R mRNAs would be delivered in the disk as well, or dropwise to the eye over the time course of the experiment. In another eye model, hypoxia has been shown to cause both increased expression of VEGF and neovascularization in the retina (Pierce et al., 1995 *Proc. Natl. Acad. Sci. USA.* 92: 905–909; Shweiki et al., 1992 *J. Clin. Invest,* 91: 2235–2243).

In human glioblastomas, it has been shown that VEGF is at least partially responsible for tumor angiogenesis (Plate et al., 1992 *Nature* 359, 845). Animal models have been developed in which glioblastoma cells are implanted subcutaneously into nude mice and the progress of tumor growth and angiogenesism is studied (Kim et al., 1993 supra; Millauer et al., 1994 supra).

Another animal model that addresses neovascularization involves Matrigel, an extract of basement membrane that becomes a solid gel when injected subcutaneously (Passaniti et al., 1992 *Lab. Invest.* 67: 519–528). When the Matrigel is supplemented with angiogenesis factors such as VEGF, vessels grow into the Matrigel over a period of 3 to 5 days and angiogenesis can be assessed. Again, ribozymes directed against VEGF-R mRNAs would be delivered in the Matrigel.

Several animal models exist for screening of anti-angiogenic agents. These include corneal vessel formation following corneal injury (Burger et al., 1985 Cornea 4: 35–41; Lepri, et al., 1994 *J. Ocular Pharmacol.* 10: 273–280; Ormerod et al., 1990 *Am. J. Pathol.* 137: 1243–1252) or intracorneal growth factor implant (Grant et al., 1993 *Diabetologia* 36: 282–291; Pandey et al. 1995 supra; Zieche et al., 1992 *Lab. Invest* 67: 711–715), vessel growth into Matrigel matrix containing growth factors (Passaniti et al., 1992 supra), female reproductive organ neovascularization following hormonal manipulation (Shweiki et al., 1993 *Clin. Invest.* 91: 2235–2243), several models involving inhibition of tumor growth in highly vascularized solid tumors (O'Reilly et al., 1994 *Cell* 79: 315–328; Senger et al., 1993 *Cancer and Metas. Rev.* 12: 303–324; Takahasi et al., 1994 *Cancer Res.* 54: 4233–4237; Kim et al., 1993 supra), and transient hypoxia-induced neovascularization in the mouse retina (Pierce et al., 1995 *Proc. Natl. Acad. Sci. USA.* 92: 905–909).

The cornea model, described in Pandey et al. supra, is the most common and well characterized anti-angiogenic agent efficacy screening model. This model involves an avascular tissue into which vessels are recruited by a stimulating agent (growth factor, thermal or alkalai burn, endotoxin). The corneal model would utilize the intrastromal corneal implantation of a Teflon pellet soaked in a VEGF-Hydron solution to recruit blood vessels toward the pellet which can be quantitated using standard microscopic and image analysis techniques. To evaluate their anti-angiogenic efficacy, ribozymes are applied topically to the eye or bound within Hydron on the Teflon pellet itself. This avascular cornea as well as the Matrigel (see below) provide for low background assays. While the corneal model has been performed extensively in the rabbit, studies in the rat have also been conducted.

The mouse model (Passaniti et al., supra) is a non-tissue model which utilizes Matrigel, an extract of basement membrane (Kleinman et al., 1986) or Millipore® filter disk, which can be impregnated with growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk would be used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk are avascular; however, it is not tissue. In the Matrigel or Millipore® filter disk model, ribozymes are administered within the matrix of the Matrigel or Millipore® filter disk to test their anti-angiogenic efficacy. Thus, delivery issues in this model, as with delivery of ribozymes by Hydron- coated Teflon pellets in the rat cornea model, may be less problematic due to the homogeneous presence of the ribozyme within the respective matrix.

These models offer a distinct advantage over several other angiogenic models listed previously. The ability to use VEGF as a pro-angiogenic stimulus in both models is highly desirable since ribozymes will target only VEGFr mRNA. In other words, the involvement of other non-specific types of stimuli in the cornea and Matrigel models is not advantageous from the standpoint of understanding the pharmacologic mechanism by which the anti-VEGFr mRNA ribozymes produce their effects. In addition, the models will allow for testing the specificity of the anti-VEGFr mRNA ribozymes by using either a- or bFGF as a pro-angiogenic factor. Vessel recruitment using FGF should not be affected in either model by anti-VEGFr mRNA ribozymes. Other models of angiogenesis including vessel formation in the female reproductive system using hormonal manipulation (Shweiki et al., 1993 supra); a variety of vascular solid tumor models which involve indirect correltations with angiogenesis (O'Reilly et al., 1994 supra; Senger et al., 1993 supra; Takahasi et al., 1994 supra; Kim et al., 1993 supra); and retinal neovascularization following transient hypoxia (Pierce et al., 1995 supra) were not selected for efficacy screening due to their non-specific nature, although there is a correlation between VEGF and angiogenesis in these models.

Other model systems to study tumor angiogenesis is reviewed by Folkman, 1985 Adv. Cancer. Res. 43,175.

flt-1, KDR and/or flk-1 protein levels can be measured clinically or experimentally by FACS analysis. flt-1, KDR and/or flk-1 encoded mRNA levels will be assessed by Northern analysis, RNase-protection, primer extension analysis and/or quantitative RT-PCR. Ribozymes that block flt-1, KDR and/or flk-1 protein encoding mRNAs and therefore result in decreased levels of flt-1, KDR and/or flk-1 activity by more than 20% in vitro will be identified.

Ribozymes and/or genes encoding them are delivered by either free delivery, liposome delivery, cationic lipid delivery, adeno-associated virus vector delivery, adenovirus vector delivery, retrovirus vector delivery or plasmid vector delivery in these animal model experiments (see above).

Patients can be treated by locally administering nucleic acids targeted against VEGF-R by direct injection. Routes of administration may include, but are not limited to, intravascular, intramuscular, subcutaneous, intraarticular, aerosol inhalation, oral (tablet, capsule or pill form), topical, systemic, ocular, intraperitoneal and/or intrathecal delivery.

EXAMPLE 11

Ribozyme-mediated Inhibition of Angiogenesis in vivo

The purpose ot this study was to assess the anti-angiogenic activity of hammerhead ribozymes targeted against flt-1 4229 site in the rat cornea model of VEGF induced angiogenesis (see above). These ribozymes have either active or inactive catalytic core and either bind and cleave or just bind to VEGF-R mRNA of the flt-1 subtype. The active ribozymes, that are able to bind and cleave the target RNA, have been shown to inhibit ($^{125}$I-labeled) VEGF binding in cultured endothelial cells and produce a dose-dependent decrease in VEGF induced endothelial cell proliferation in these cells (see Examples 3–5 above). The catalytically inactive forms of these ribozymes, wherein the ribozymes can only bind to the RNA but cannot catalyze RNA cleavage, fail to show these characteristics. The ribozymes and VEGF were co-delivered using the filter disk method: Nitrocellulose filter disks (Millipore®) of 0.057 diameter were immersed in appropriate solutions and were surgically implanted in rat cornea as described by Pandey et al., supra. This delivery method has been shown to deliver rhodamine-labeled free ribozyme to scleral cells and, in all likelihood cells of the pericorneal vascular plexus. Since the active ribozymes show cell culture efficacy and can be delivered to the target site using the disk method, it is essential that these ribozymes be assessed for in vivo anti-angiogenic activity.

The stimulus for angiogenesis in this study was the treatment of the filter disk with 30 $\mu$M VEGF which is implanted within the cornea's stroma. This dose yields reproducible neovascularization stemming from the pericorneal vascular plexus growing toward the disk in a dose-response study 5 days following implant. Filter disks treated only with the vehicle for VEGF show no angiogenic response. The ribozymes was co-adminstered with VEGF on a disk in two different ribozyme concentrations. One concern with the simultaneous administration is that the ribozymes will not be able to inhibit angiogenesis since VEGF receptors can be stimulated. However, we have observed that in low VEGF doses, the neovascular response reverts to normal suggesting that the VEGF stimulus is essential for maintaining the angiogenic response. Blocking the production of VEGF receptors using simultaneous administration of anti-VEGF-R mRNA ribozymes could attenuate the normal neovascularization induced by the filter disk treated with VEGF.

Materials and Methods:

Stock hammerhead ribozyme solutions
  a. flt-1 4229 (786 $\mu$M)- Active
  b. flt-1 4229 (736 $\mu$M)- Inactive 2. Experimantal Solutions/groups Group 1 Solution 1 Control VEGF solution: 30 $\mu$M in 82 mM Tris base Group 2 Solution 2 flt-1 4229 (1 $\mu$g/$\mu$L) in 30 $\mu$M VEGF/82 mM Tris base Group 3 Solution 3 flt-1 4229 (10 $\mu$g/$\mu$L) in 30 $\mu$M VEGF/82 mM Tris base Group 4 Solution 4 No VEGF, flt-1 4229 (10 $\mu$g/$\mu$L) in 82 mM Tris base Group 5 Solution 5 No VEGF, No ribozyme in 82 mM Tris base 10 eyes per group, 5 animals (Since they have similar molecular weights, the molar concentrations should be essentially similar).

Each solution (VEGF and RIBOZYMES) were prepared as a 2× solution for 1:1 mixing for final concentrations above, with the exception of solution 1 in which VEGF was 2× and diluted with ribozyme diluent (sterile water).

3. VEGF Solutions

The 2× VEGF solution (60 $\mu$M) was prepared from a stock of 0.82 $\mu$g/$\mu$L in 50 mM Tris base. 200 $\mu$L of VEGF stock was concentrated by speed vac to a final volume of 60.8 $\mu$L, for a final concentration of 2.7 $\mu$g/$\mu$L or 60 $\mu$M. Six 10 $\mu$L aliquots was prepared for daily mixing. 2× solutions for VEGF and Ribozyme was stored at 4° C. until the day of the surgery. Solutions were mixed for each day of surgery. Original 2× solutions was prepared on the day before the first day of the surgery.

4. Surgical Solutions

Anesthesia
  stock ketamine hydrochloride 100 mg/mL
  stock xylazine hydrochloride 20 mg/mL
  stock acepromazine 10 mg/mL
  Final anesthesia solution: 50 mg/mL ketamine, 10 mg/mL xylazine, and 0.5 mg/mL acepromazine
  5% povidone iodine for opthalmic surgical wash 2% lidocaine (sterile) for opthalmic administration (2 drops per eye)
  sterile 0.9% NaCl for opthalmic irrigation 5. Surgical Methods Standard surgical procedure as described in Pandey et al., supra. Filter disks were incubated in 1 $\mu$L of each solution for approximately 30 minutes prior to implantation.

5. Experimental Protocol

The animal cornea were treated with the treatment groups as described above. Animals were allowed to recover for 5 days after treatment with daily observation (scoring 0–3). On the fifth day animals were euthanized and digital images of each eye was obtained for quantitaion using Image Pro Plus. Quantitated neovascular surface area were analyzed by ANOVA followed by two post-hoc tests including Dunnets and Tukey-Kramer tests for significance at the 95% confidence level. Dunnets provide information on the significance between the differences within the means of treatments vs. controls while Tukey-Kramer provide information on the significance of differences within the means of each group.

Results are graphically represented in FIG. 18. As shown in the figure, flt-1 4229 active hammerhead ribozyme at both concentrations was effective at inhibiting angiogenesis while the inactive ribozyme did not show any significant reduction in angiogenesis. A statistically signifiant reduction in neovascular surface area was observed only with active ribozymes. This result clearly shows that the ribozymes are capable of significantly inhibiting angiogenesis in vivo. Specifically, the mechanism of inhibition appears to be by the binding and cleavage of target RNA by ribozymes.

Diagnostic Uses

Ribozymes of this invention may be used as diagnostic tools to examine genetic drift and mutations within diseased cells or to detect the presence of flt-1, KDR and/or flk-1 RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with flt-1, KDR and/or flk-1 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., flt-1, KDR and/or flk-1) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

TABLE I

Characteristics of Ribozymes

Group I Introns

Size: ~200 to >1000 nucleotides.
Requires a U in the target sequence immediately 5' of the cleavage site.
Binds 4–16 nucleotides at 5' side of cleavage site.
Over 75 known members of this class. Found in *Tetrahymena thermophila* rRNA, fungal mitochondria, chloroplasts, phage T4, blue-green algae, and others.

RNAseP RN (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Figure 1:
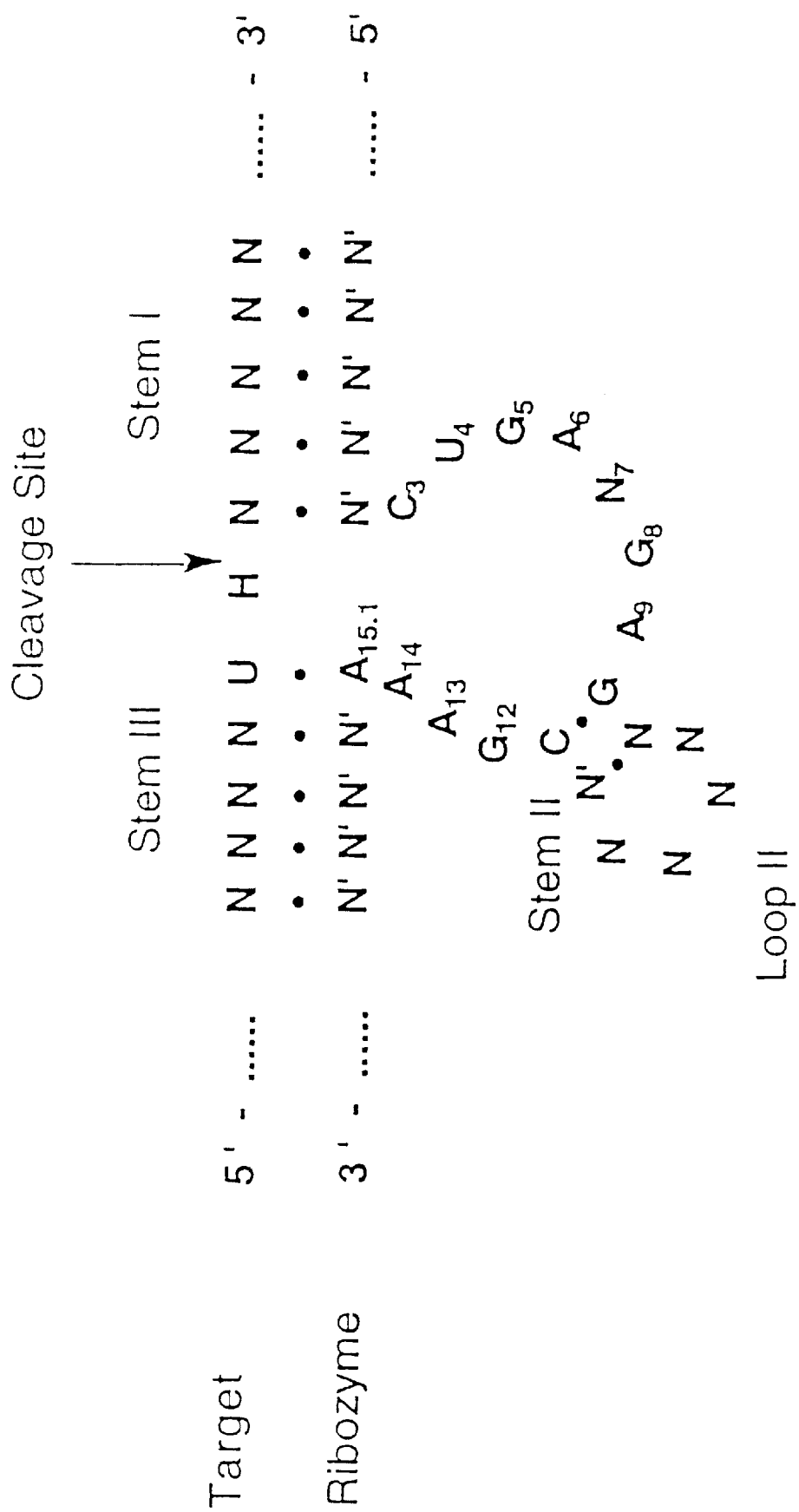

Size: ~13 to 40 nucleotides.
Requires the target sequence UH immediately 5' of the cleavage site.
Binds a variable number of nucleotides on both sides of the cleavage site.
14 known members of this class. Found in a number of plant pathogens (virusoids) that use RNA as the infectious agent (FIG. 1 and 2)

Hairpin Ribozyme

Figure 3:
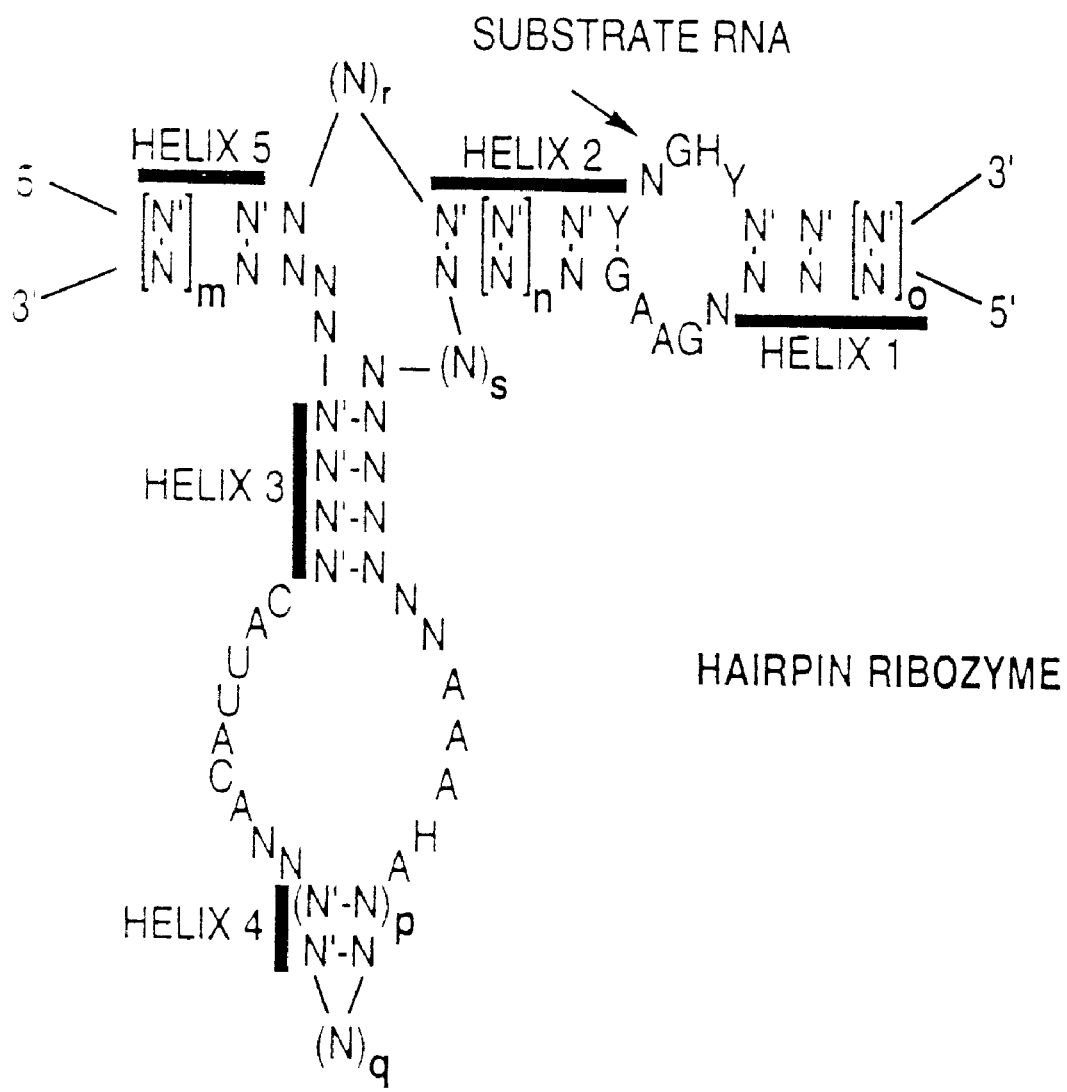

Size: ~50 nucleotides.
Requires the target sequence GUC immediately 3' of the cleavage site.
Binds 4–6 nucleotides at 5' side of the cleavage site and a variable number of the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Figure 4:
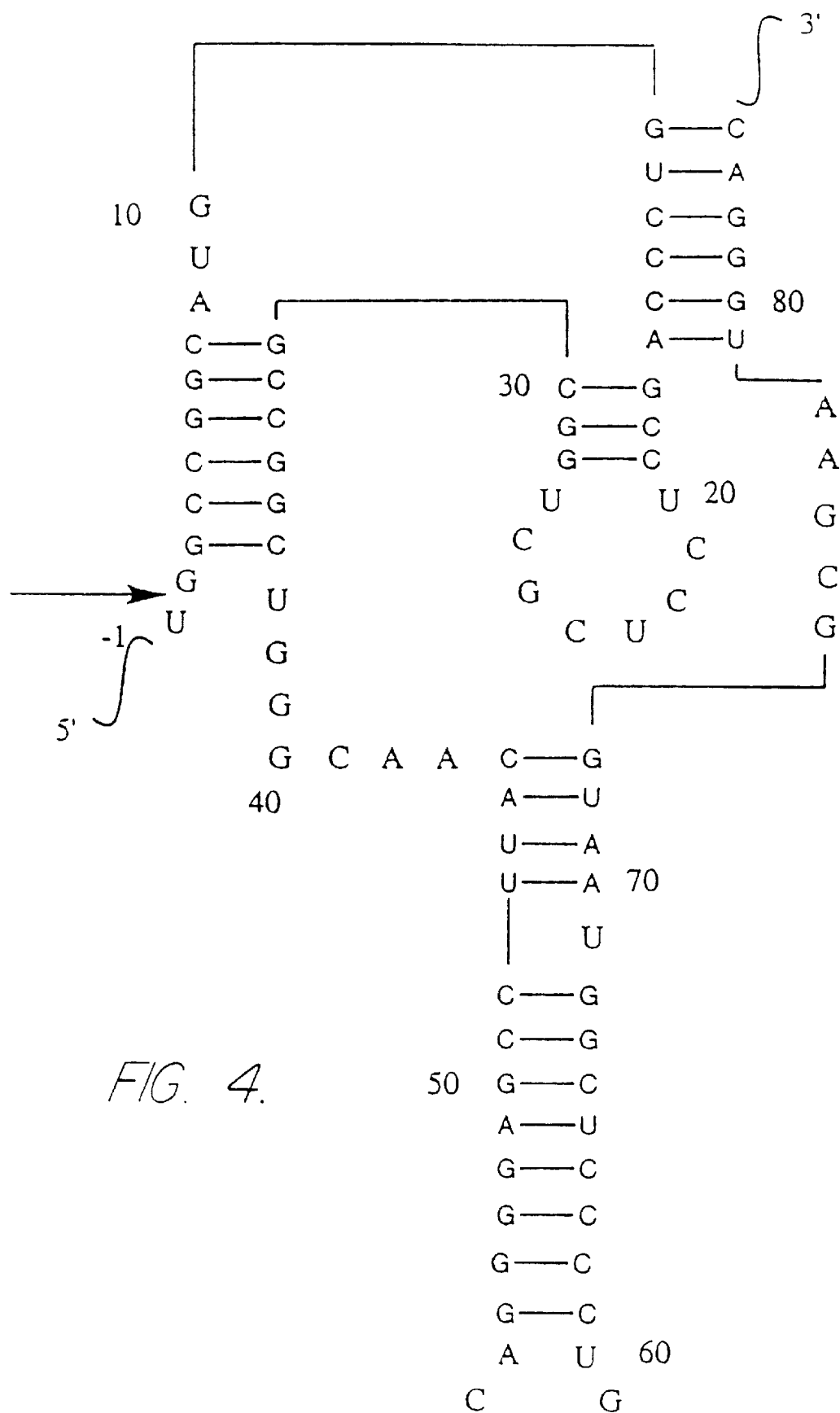
FIG. 4 is a representation of the general structure of the hepatitis delta virus ribozyme domain known in the art.

Size: 50–60 nucleotides (at present).
Sequence requirements not fully determined.
Binding sites and structural requirements not fully determined, although no sequences 5' of cleavage site are required.
Only 1 known member of this class. Found in human HDV (FIG. 4).

Neurospora VS RNA Ribozyme

Figure 5:
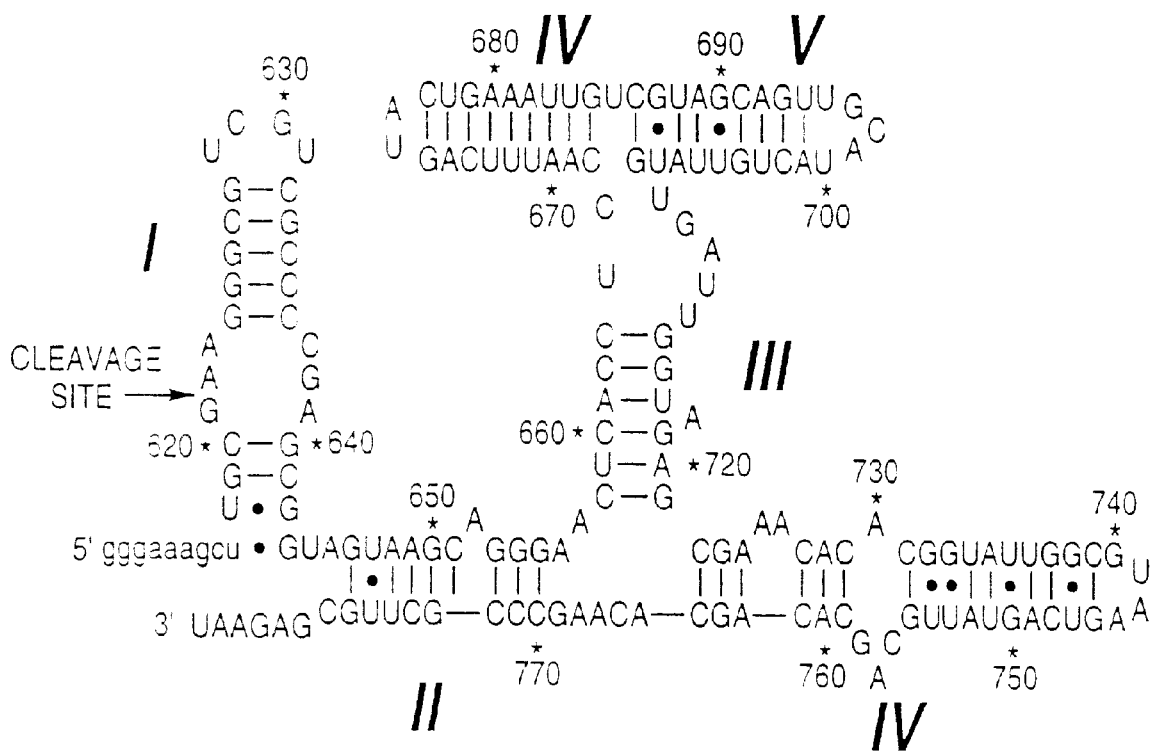
FIG. 5 is a representation of the general structure of the VS RNA ribozyme domain (SEQ ID NO:8).

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human flt1 VEGF Receptor-Hammerhead Ribozyme and Substrate Sequence

| nt. Position | HH Ribozyme | Substrate |
|---|---|---|
| 10 | GCCGAGAG CUGAUGA X GAA AGUGUCCG | CGGACACUC CUCUCGGC |
| 13 | GGAGCCGA CUGAUGA X GAA AGGAGUGU | ACACUCCUC UCGGCUCC |
| 15 | GAGGAGCC CUGAUGA X GAA AGAGGAGU | ACUCCUCUC GGCUCCUC |
| 20 | CCGGGGAG CUGAUGA X GAA AGCCGAGA | UCUCGGCUC CUCCCCGG |
| 23 | CUGCCGGG CUGAUGA X GAA AGGAGCCG | CGCCUCCUC CCCGGCAG |
| 43 | CCCGCCCC CUGAUGA X GAA AGCCGCCG | CGGCGGCUC GGAGCGGG |
| 54 | GAGCCCCG CUGAUGA X GAA AGCCCGCU | AGCGGGCUC CGGGGCUC |
| 62 | CUGCACCC CUGAUGA X GAA AGCCCCGG | CCGGGGCUC GGGUGCGG |
| 97 | CCCCGGGU CUGAUGA X GAA AUCCUCGC | GCGAGGAUU ACCCGGGG |
| 98 | UCCCCGGG CUGAUGA X GAA AAUCCUGG | CGAGGAUUA CCCGGGGA |
| 113 | CAGGAGAC CUGAUGA X GAA ACCACUUC | GAAGUGGUU GUCUCCUG |
| 116 | AGCCAGGA CUGAUGA X GAA ACAACCAC | GUGGUUGUC UCCUGGCU |
| 118 | CCAGCCAG CUGAUGA X GAA AGACAACC | GGUUGUCUC CUGGCUGG |
| 145 | CGCGCCCU CUGAUGA X GAA AGCGCCCG | CGGGCGCUC AGGGCGCG |
| 185 | GGCCGCCA CUGAUGA X GAA AGUCCGUC | GACGGACUC UGGCGGCC |
| 198 | CGGCCAAC CUGAUGA X GAA ACCCGGCC | GGCCGGGUC GUUGGCCG |
| 201 | CCCCGGCC CUGAUGA X GAA ACGACCCG | CGGGUCGUU GGCCGGGG |
| 240 | GUGAGCGC CUGAUGA X GAA ACGCGGCC | GGCCGCGUC GCGCUCAC |
| 246 | ACCAUGGU CUGAUGA X GAA AGCGCGAC | GUCGCGCUC ACCAUGGU |
| 255 | CAGUAGCU CUGAUGA X GAA ACCAUGGU | ACCAUGGUC AGCUACUG |
| 260 | UGUCCCAG CUGAUGA X GAA AGCUCACC | GGUCAGCUA CUGGGACA |
| 276 | CACAGCAG CUGAUGA X GAA ACCCCGGU | ACCGGGGUC CUGCUGUG |
| 294 | ACACAGCU CUGAUGA X GAA AGCAGCGC | GCGCUGCUC AGCUGUCU |
| 301 | GAGAAGCA CUGAUGA X GAA ACAGCUGA | UCAGCUGUC UGCUUCUC |
| 306 | CCUGUGAG CUGAUGA X GAA AGCAGACA | UGUCUGCUU CUCACAGG |
| 307 | UCCUGUGA CUGAUGA X GAA AAGCAGAC | GUCUGCUUC UCACAGGA |
| 309 | GAUCCUGU CUGAUGA X GAA AGAAGCAG | CUGCUUCUC ACAGGAUC |
| 317 | CUGAACUA CUGAUGA X GAA AUCCUGUG | CACAGGAUC UUGUUCAG |
| 319 | ACCUGAAC CUGAUGA X GAA AGAUCCUG | CAGGAUCUA GUUCAGGU |
| 322 | UGAACCUG CUGAUGA X GAA ACUAGAUC | GAUCUAGUU CAGGUUCA |
| 323 | UUGAACCU CUGAUGA X GAA AACUAGAU | AUCUAGUUC AGGUUCAA |
| 328 | UAAUUUUG CUGAUGA X GAA ACCUGAAC | GUUCAGGUU CAAAAUUA |
| 329 | UUAAUUUU CUGAUGA X GAA AACCUGAA | UUCAGGUUC AAAAUUAA |
| 335 | GAUCUUUU CUGAUGA X GAA AUUUUGAA | UUCAAAAUU AAAAGAUC |
| 336 | GGAUCUUU CUGAUGA X GAA AAUUUUGA | UCAAAAUUA AAAGACCC |
| 343 | CAGUUCAG CUGAUGA X GAA AUCUUUUA | UAAAAGAUC CUGAACUG |
| 355 | GCCUUUUA CUGAUGA X GAA ACUCAGUU | AACUGAGUU UAAAAGGC |

TABLE II-continued

Human flt1 VEGF Receptor-Hammerhead Ribozyme and Substrate Sequence

| nt. Position | HH Ribozyme | Substrate |
|---|---|---|
| 356 | UGCCUUUU CUGAUGA X GAA AACAGAGU | ACUGAGUUU AAAAGGCA |
| 357 | GGCCCUUU CUGAUGA X GAA AAACUCAG | CUGAGUUUA AAAGGCAC |
| 375 | GCUUGCAU CUGAUGA X GAA AUGUGCUG | CAGCACAUC AUGCAACC |
| 400 | GCAUUGGA CUGAUGA X GAA AUGCAGUG | CACUCCAUC UCCAAUGC |
| 402 | CUGCAUUG CUGAUGA X GAA AGAUGCAG | CUGCAUCUC CAAUGCAG |
| 427 | AGACCAUU CUGAUGA X GAA AUGGGCUG | CAGCCCAUA AAUGGUCU |
| 434 | CAGGCAAA CUGAUGA X GAA ACCAUUUA | UAAAUGGUC UUUGCCUG |
| 436 | UUCAGGCA CUGAUGA X GAA ACACCAUU | AAUGGUCUU UGCCUGAA |
| 437 | UUUCAGGC CUGAUGA X GAA AAGAUCAU | AUGGUCUUU GCCUGAAA |
| 454 | GCUUUCCU CUGAUGA X GAA ACUCACCA | UGGUGAGUA AGGAAAGC |
| 477 | GAUUUAGU CUGAUGA X GAA AUGCUCAG | CUGAGCAUA ACUAAAUC |
| 481 | GGCAGAUU CUGAUGA X GAA AGUUAUGC | GCAUAACUA AAUCUGCC |
| 485 | CACAGGCA CUGAUGA X GAA AUUUAGUU | AACUAAAUC UGCCUGUG |
| 512 | UACUGCAG CUGAUGA X GAA AUUGUUUG | CAAACAAUU CUGCAGUA |
| 513 | GUACUGCA CUGAUGA X GAA AAUUGUUU | AAACAAUUC UGCAGGAC |
| 520 | GGUUAAAG CUGAUGA X GAA ACUGCAGA | UCUGCAGUA CUUUAACC |
| 523 | CAAGGUUA CUGAUGA X GAA AGUACUGC | GCAGUACUU UAACCUUG |
| 524 | UCAAGGUU CUGAUGA X GAA AAGUACUG | CAGUACUUU AACCUUGA |
| 525 | UUCAAGGU CUGAUGA X GAA AAAGUACU | AGUACUUUA ACCUUGAA |
| 530 | CUGUGUUC CUGAUGA X GAA AGGUUAAA | UUUAACCUU GAACACCG |
| 541 | GUUUGCUU CUGAUGA X GAA AGCUCUGU | ACACAGCUC AAGCAAAC |
| 560 | AGCUGUAG CUGAUGA X GAA AGCCAGUG | CACUGGCUU CUACAGCU |
| 561 | CAGCUGUA CUGAUGA X GAA AAGCCAGU | ACUGGCUUC UACAGCUG |
| 563 | UGCAGCUG CUGAUGA X GAA AGAAGCCA | UGGCUUCUA CAGCUGCA |
| 575 | CAGCUAGA CUGAUGA X GAA AUUUGCAG | CUUCAAAUA UCCAGCUG |
| 577 | UACAGCUA CUGAUGA X GAA AUAUUUGC | GCAAAUAUC UAGCUGUA |
| 579 | GGUACAGC CUGAUGA X GAA AGAUAUUU | AAAUAUCUA GCUGUACC |
| 585 | GAAGUGGG CUGAUGA X GAA ACAGCCAG | CUAGCUGUA CCUACUUC |
| 589 | CUUUGAAG CUGAUGA X GAA AGGUACAG | CUGUACCUA CUUCAAAG |
| 592 | CUUCUUUG CUGAUGA X GAA AGUAGGUA | UACCACUU CAAAGAAG |
| 593 | UCUUCUUU CUGAUGA X GAA AAGGAGGU | ACCACUUC AAAGAAGA |
| 614 | AGAUUGCA CUGAUGA X GAA AUUCUGUU | AACAGAAUC UGCAAUCU |
| 621 | AAUAUAUA CUGAUGA X GAA AUUGCAGA | UCUGCAAUC UAUAUAUU |
| 623 | UAAUAUA CUGAUGA X GAA AGAUUGCA | UGCAAUCUA UUUAUUUA |
| 625 | AAUAAAUA CUGAUGA X GAA AUAGAUUG | CAAUCUAUA UAUUUAUU |
| 627 | CUAAUAAA CUGAUGA X GAA AUAUAGAU | AUCUAUAUA UUUAUUAG |

TABLE II-continued

Human flt1 VEGF Receptor-Hammerhead Ribozyme and
Substrate Sequence

| nt. Position | HH Ribozyme | Substrate |
|---|---|---|
| 629 | CACUAAUA CUGAUGA X GAA AUAUAUAG | CUAUAUAUU UUUUACUG |
| 630 | UCACUAAU CUGAUGA X GAA AAUAUAUA | UAUAUAUUU AUUAGUGA |
| 631 | ACCACUAA CUGAUGA X GAA AAAUAUAU | AUAUAUUUA UUAGUGAU |
| 633 | GUAUCACU CUGAUGA X GAA AUAAAUAU | AUAUUAUUU AGUGAUAC |
| 634 | UGUAUCAC CUGAUGA X GAA AAUAAAUA | UAUUUAUUA GUGAUACA |
| 640 | UCUACCUG CUGAUGA X GAA AUCACUAA | UUAGUGAUA CAGGUAGA |
| 646 | GAAAGGUC CUGAUGA X GAA ACCUGUAU | AUACAGGUA GACCUUUC |
| 652 | CUCUACGA CUGAUGA X GAA AGGUCUAC | GUAGACCUU UCGUAGAG |
| 653 | UCUCUCUG CUGAUGA X GAA AAGGUCUA | UAGACCUUU CGUAGAGA |
| 654 | AUCUCUAC CUGAUGA X GAA AAAGGUCU | AGACCUUUC GUAGAGAU |
| 657 | UACAUCUC CUGAUGA X GAA ACGAAAGG | CCUUUCGUA GAGAUGUA |
| 665 | UUUCACUG CUGAUGA X GAA ACAUCUCU | AGAGAUGUA CAGUGAAA |
| 675 | AUUUCGGG CUGAUGA X GAA AUUUCACU | AGUGAAAUC CCCGAAAU |
| 684 | AGGUGUAU CUGAUGA X GAA AUUUGGGG | CCCGAAAUU AUACACAU |
| 685 | CAUGUGUA CUGAUGA X GAA AAUUUCGG | CCGAAAUUA UACACAUG |
| 687 | GUCAUGUG CUGAUGA X GAA AUAAUUUC | GAAAUUUUA CACAUGAC |
| 711 | GGAAUGAC CUGAUGA X GAA AGCUCCCU | AGGGAGCUC GUCAUUCC |
| 714 | CAGGGAAU CUGAUGA X GAA ACGAGCUC | GAGCUCGUC AUCCCUG |
| 717 | CGGCAGGG CUGAUGA X GAA AUGACGAG | CUCGUCAUU CCCUGCCG |
| 718 | CCGGCAGG CUGAUGA X GAA AAUGACGA | UCGUCAUUC CCUGCCGG |
| 729 | GGUGACCU CUGAUGA X GAA ACCCGGCA | UGCCGGGUU ACGUCACC |
| 730 | AGGUGACG CUGAUGA X GAA AACCCGGC | GCCGGGUUA CGUCACCU |
| 734 | UGUUAGGU CUGAUGA X GAA ACGUAACC | GGUUACGUC ACCUAACA |
| 739 | AGUGAUGU CUGAUGA X GAA AGGUGACG | CGUCACCUA ACAUCACU |
| 744 | GUAACAGU CUGAUGA X GAA AUGUUAGG | CCUAACAUC ACUGUUAC |
| 750 | UUUAAAGU CUGAUGA X GAA ACAGUGAU | AUCACUGUU ACUUUAAA |
| 751 | UUUUAAAG CUGAUGA X GAA AACAGUGA | UCACUGUUA CUUUAAAA |
| 754 | CUUUUUUA CUGAUGA X GAA ACUAACAG | CUGUUACUU UAAAAAG |
| 755 | ACUUUUUU CUGAUGA X GAA AAGUAACA | UGUUACUUU AAAAAGU |
| 756 | AACUUUUU CUGAUGA X GAA AAAGUAAC | GUUACUUUA AAAAGUU |
| 764 | CAAGUGGA CUGAUGA X GAA ACUUUUUU | AAAAAGUU UCCACUUG |
| 765 | UCAAGUGG CUGAUGA X GAA AACUUUUU | AAAAGUUU CCACUGGA |
| 766 | GUCAAGUG CUGAUGA X GAA AAACUUUU | AAAGUUUC CACUUGAC |
| 771 | AAAGUGUC CUGAUGA X GAA AGUGGAAA | UUCCACUU GACACUUU |
| 778 | AGGGAUCA CUGAUGA X GAA AGUGUCAA | UUGACACUU UGAUCCCU |
| 779 | CAGGGCUC CUGAUGA X GAA AAGUGUCA | UGACACUUU GAUCCCUG |
| 783 | CCAUCAGG CUGAUGA X GAA AYCAAAGU | ACUUUGAUC CCUGAUGG |

TABLE II-continued

Human flt1 VEGF Receptor-Hammerhead Ribozyme and Substrate Sequence

| nt. Position | HH Ribozyme | Substrate |
|---|---|---|
| 801 | UCCCAGAU CUGAUGA X GAA AUGCGUUU | AAACGCAUA AUCUGGGA |
| 804 | CUGUCCCA CUGAUGA X GAA AUUAUCUG | CGCAUAAUC UGGGACAG |
| 814 | GCCCUUUC CUGAUGA X GAA ACUGUCCC | GGGACAGUA GAAAGGGC |
| 824 | AUAUGAUG CUGAUGA X GAA AGCCCUUU | AAAGGGCUU CAUCAUAU |
| 825 | GAUAUGAU CUGAUGA X GAA AAGCCCUU | AAGGGCUUC AACAUAUC |
| 828 | UUUGAUAU CUGAUGA X GAA AUGAAGCC | GGCUUCAUC AUAUCAAA |
| 831 | GCAUUUGA CUGAUGA X GAA AUGAUGAA | UUCAUUCUA UCAAAUGC |
| 833 | UUGCAUUU CUGAUGA X GAA AUAUGAUG | CAUCAUAUC AAAUGCAA |
| 845 | UUUCUUUG CUGAUGA X GAA ACGUUGCA | UGCAACGUA CAAAGAAA |
| 855 | AGAACCCC CUGAUGA X GAA AUUUCUUU | AAAGAAAUA GGGCUUCU |
| 861 | CAGGUCAG CUGAUGA X GAA AGCCCUAU | AUAGGGCUU CUGACCUG |
| 862 | ACAGGUCA CUGAUGA X GAA AAGCCCUA | UAGGGCUUC UGACCUGU |
| 882 | UGCCCAUU CUGAUGA X GAA ACUGUUGC | GCAACAGUC AAUGGGCA |
| 892 | CUUAUACA CUGAUGA X GAA AUGCCCAU | AUGGGCAUU UGUAUAAG |
| 893 | UCUUAUAC CUGAUGA X GAA AAUGCCCA | UGGGCAUUU GUAUAAGA |
| 896 | UUGUCUUA CUGAUGA X GAA ACAAAUGC | GCAUUUGUA UAAGACAA |
| 898 | GUUUGUCU CUGAUGA X GAA AUACAAAU | AUUUGUAUA AGACAAAC |
| 908 | GUGUGAGA CUGAUGA X GAA AGUUUGUC | GACAAACUA UCUCACAC |
| 910 | AUGUGUGA CUGAUGA X GAA AUAGUUUG | CAAACUAUC UCACACAU |
| 912 | CGAUGUGU CUGAUGA X GAA AGAUAGUU | AACUAUCUC ACACAUCG |
| 919 | GGUUUGUC CUGAUGA X GAA AUGUGUGA | UCACACAUC GACAAACC |
| 931 | UAUGAUUG CUGAUGA X GAA AUUGGUUU | AAACCAAUA CAAUCAUA |
| 936 | ACAUCUAU CUGAUGA X GAA AUUGUAUU | AAUACAAUC AUAGAUGU |
| 939 | UGGACAUC CUGAUGA X GAA AUGAUUGU | ACAAUCAUA GAUGUCCA |
| 945 | CUUAUUUG CUGAUGA X GAA ACAUCUAU | AUAGAUGUC AAAUAAG |
| 951 | GGUGUGCU CUGAUGA X GAA AUUUGGAC | GUCCAAAUA AGCACACC |
| 969 | AGUAAUUU CUGAUGA X GAA ACUGGGCG | CGCCCAGUC AAAUUACU |
| 974 | CUCUAAGU CUGAUGA X GAA AUUUGACU | AGUCAAAUU ACUUAGAG |
| 975 | CCUCUAAG CUGAUGA X GAA AAUUUGAC | GUCAAAUUA CUUAGAGG |
| 978 | UGGCCUCU CUGAUGA X GAA AGUAAUUU | AAAUUACUU AGAGGCCA |
| 979 | AUGGCCUC CUGAUGA X GAA AAGUAAUU | AAUUACUUA GAGGCCAU |
| 988 | GACAAGAG CUGAUGA X GAA AUGGCCUC | GAGGCCAUA CUCUUGUC |
| 991 | GAGGACAA CUGAUGA X GAA AGUAUGGC | GCCAUACUC UUGUCCUC |
| 993 | UUGAGGAC CUGAUGA X GAA AGAGUAUG | CAUACUCUU GUCCUCAA |
| 996 | CAAUUGAG CUGAUGA X GAA ACAAGAGU | ACUCUUGUC CUCAAUUG |
| 999 | GUACAAUU CUGAUGA X GAA AGGACAAG | CUUGUCCUC AAUUGUAC |

TABLE II-continued

Human flt1 VEGF Receptor-Hammerhead Ribozyme and Substrate Sequence

| nt. Position | HH Ribozyme | Substrate |
|---|---|---|
| 1003 | AGCAGGAC CUGAUGA X GAA AUUGACGA | UCCUCAAUU GUACUGCU |
| 1006 | GGGAGCAG CUGAUGA X GAA ACAAUUGA | UCAAUUGUA CUGCUACC |
| 1012 | GGGAGUGG CUGAUGA X GAA AGCAGUAC | GUACUGCUA CCACUCCC |
| 1018 | GUUCAAGG CUGAUGA X GAA AGUGGUAG | CUACCACUC CCUUGAAC |
| 1022 | UCGUGUUC CUGAUGA X GAA AGGGAGUG | CACUCCCUU GAACACGA |
| 1035 | GUCAUUUG CUGAUGA X GAA ACUCUCGU | ACGAGAGUU CAAAUGAC |
| 1036 | GGUCAUUU CUGAUGA X GAA AACUCUCG | CGAGAGUUC AAAUGACC |
| 1051 | AUCAGGGU CUGAUGA X GAA ACUCCAGG | CCUGGAGUU ACCCUGAU |
| 1052 | CAUCAGGG CUGAUGA X GAA AACUCCAG | CUGGAGUUA CCCUGAUG |
| 1069 | AGCUCUCU CUGAUGA X GAA AUUUUUUU | AAAAAAAUA AGAGAGCU |
| 1078 | CCCUACGG CUGAUGA X GAA AGCUCUCU | AGAGAGCUU CCGUAAGG |
| 1079 | GCCUUACG CUGAUGA X GAA AAGCUCUC | GAGAGCUUC CGUAAGGC |
| 1083 | CGUCGCCU CUGAUGA X GAA ACGGAAGC | GCUUCCGUA AGGCGACG |
| 1095 | CUUUGGUC CUGAUGA X GAA AUUCGUCG | CGACGAAUU GACCAAAG |
| 1108 | GGCAUGGG CUGAUGA X GAA AUUGCUUU | AAAGCAAUU CCCAUGCC |
| 1109 | UGGCAUGG CUGAUGA X GAA AAUUGCUU | AAGCAAUUC CCAUGCCA |
| 1122 | CUGUAGAA CUGAUGA X GAA AUGUUGGC | GCCAACAUA UUCUACAG |
| 1124 | CACUGUAG CUGAUGA X GAA AUUUGUUG | CAACAUAUU CUACAGUG |
| 1125 | ACACUGUA CUGAUGA X GAA AAUAUAUU | AACAUAUUC UACAGUGU |
| 1127 | GAACACUG CUGAUGA X GAA AGAAUAUG | CAUAUUCUA CAGUGUUC |
| 1134 | AUAGUAAG CUGAUGA X GAA ACACUGUA | UACAGUGUU CUUACUAU |
| 1135 | AAUAGUAA CUGAUGA X GAA AACACUGU | ACAGUGUUC UUACUAUU |
| 1137 | UCAAUAGU CUGAUGA X GAA AGAACACU | AGUGUUCUU ACUAUUGA |
| 1138 | GUCAAUAG CUGAUGA X GAA AAGAACAC | GUGUUCUUA CUAUUGAC |
| 1141 | UUUGUCAA CUGAUGA X GAA ACUAAGAA | UUCUUACUA UUGACAAA |
| 1143 | AUUUGUC CUGAUGA X GAA AUAGUAAG | CUUACUAUU GACAAAAU |
| 1173 | CAACUAUA CUGAUGA X GAA AGUCCUUU | AAAGGACUU UUACUUG |
| 1174 | ACAAGCAU CUGAUGA X GAA AAGUCCUU | AAGGACUUU AUACUUGU |
| 1175 | GACAAGGA CUGAUGA X GAA AAAGUCCU | AGGACUUUA UACUUGUC |
| 1177 | ACGACAAG CUGAUGA X GAA AUAAAGUC | GACUUUAUA CUUGUCGU |
| 1180 | UACACGAC CUGAUGA X GAA AGUAUAAA | UUUAUACUU GUCGUGUA |
| 1183 | CCUUACAC CUGAUGA X GAA ACAAGUAU | AUACUUGUC GUGUAAGG |
| 1188 | CCACUCCU CUGAUGA X GAA ACACGACA | UGUCGUGUA AGGAGUGG |
| 1202 | AUUUGAAU CUGAUGA X GAA AUGGUCCA | UGGCUCUUC AUUCAAAU |
| 1205 | CAGAUUUG CUGAUGA X GAA AUGAUGGU | ACCAUCAUU CAAAUCUG |
| 1206 | ACAGAUUU CUGAUGA X GAA AAUGAUGG | CCAUCAUUC AAAUCUGU |
| 1211 | UGUUAACA CUGAUGA X GAA AUUUGAAU | AUUCAAAUC UGUUAACA |

TABLE II-continued

Human flt1 VEGF Receptor-Hammerhead Ribozyme and Substrate Sequence

| nt. Position | HH Ribozyme | Substrate |
|---|---|---|
| 1215 | GAGGUGUU CUGAUGA X GAA ACAGAUUU | AAAUCUGUU AACACCUC |
| 1216 | UGAGGUGU CUGAUGA X GAA AACAGAUU | AAUCUGUUA ACACCUCA |
| 1223 | UAUGCACU CUGAUGA X GAA AGGUGUGA | UAACACCUC AGUGCAUA |
| 1231 | AUCAUAUA CUGAUGA X GAA AUGGACUG | CAGUGCAUA UAUAUGAU |
| 1233 | UUAUCAUA CUGAUGA X GAA AUAUGCAC | GUGCAUAUA UAUGAUAA |
| 1235 | CUUUAUCA CUGAUGA X GAA AUAUAUGC | GCAUAUAUA UGAUAAAG |
| 1240 | GAAUGCUU CUGAUGA X GAA AUCAUAUA | UAUAUGAUA AAGCAUUC |
| 1247 | CAGUGAUG CUGAUGA X GAA AUGCUUUA | UAAAGCAUU CAUCACUG |
| 1248 | ACAGUGAU CUGAUGA X GAA AAUGCUUU | AAAGCAUUC AUAACUGU |
| 1251 | UUCACAGU CUGAUGA X GAA AUGAAUGC | GCAUUCAUC ACUGUGAA |
| 1264 | CUGUUUUC CUGAUGA X GAA AUGUUUCA | UGAAACAUC GAAAACAG |
| 1281 | ACGGUUUC CUGAUGA X GAA AGCACCUG | CAGGUGCUU GAAACCGU |
| 1290 | UUGCCAGC CUGAUGA X GAA ACGGUUUC | GAAACCGUA GCUGGCAA |
| 1304 | GCCGGUAA CUGAUGA X GAA ACCGCUUG | CAAGCGGUC UUACCGGC |
| 1306 | GAGCCGGU CUGAUGA X GAA AGACCGCU | AGCGGUCUU ACCGGCUC |
| 1307 | AGAGCCGG CUGAUGA X GAA AAGACCGC | GCGGUCUUA CCGGCUCU |
| 1314 | UUCAUAGA CUGAUGA X GAA AGCCGGUA | UACCGGCUC UCUAUGAA |
| 1316 | CUUUCAUA CUGAUGA X GAA AGAGCCGG | CCGGCUCUC UAUGAAAG |
| 1318 | CACUUUCA CUGAUGA X GAA AGAGAGCC | GGCUCUCUA UGAAAGUG |
| 1334 | GCGAGGGA CUGAUGA X GAA AUGCCUUC | GAAGGCAUU UCCCUCGC |
| 1335 | GGCGAGGG CUGAUGA X GAA AAUGCCUU | AAGGCAUUU CCCUCGCC |
| 1336 | CGGCGAGG CUGAUGA X GAA AAAUGCCU | AGGCAUUUC CCUCGCCG |
| 1340 | CUUCCGGC CUGAUGA X GAA AGGGAAAU | AUUUCCCUC GCCGGAAG |
| 1350 | AACCAUAC CUGAUGA X GAA ACUUGGGG | CCGGAAGUU GUAUGUUU |
| 1353 | UUUAACCA CUGAUGA X GAA ACAACUUC | GAAGUUUUA UGGUUAAA |
| 1358 | CAUCUUUU CUGAUGA X GAA ACCAUACA | UGUAUGGUU AAAAGAUG |
| 1359 | CCAUCUUU CUGAUGA X GAA AACCAUAC | GUAUGGUUA AAAGAUGG |
| 1370 | UCGCAGGU CUGAUGA X GAA ACCCAUCU | AGAUGGGUU ACCUGCGA |
| 1371 | GUCGCAGG CUGAUGA X GAA AACCCAUC | GAUGGGUUA CCUGCGAC |
| 1388 | AGCGAGCA CUGAUGA X GAA AUUUCUCA | UGAGAAAUC UGCUCGCU |
| 1393 | CAAAUAGC CUGAUGA X GAA AGCAGAUU | AAUCUGCUC GCUAUUUG |
| 1397 | GAGUCGAA CUGAUGA X GAA AGGGAGCA | UGCUCGCUA UUUGACUC |
| 1399 | ACGAGUCA CUGAUGA X GAA AUAGCGAG | CUGGCUAUU UGACUCGU |
| 1400 | CACGAGUC CUGAUGA X GAA AAUAGCGA | UCGCUAUUU GACUCGUG |
| 1405 | GUAGCCAC CUGAUGA X GAA AGUCAAAU | AUUUGACUC GUGGUUAC |
| 1412 | UUAACGAG CUGAUGA X GAA AGCCACGA | UCGUGGCUA CACGUUAA |

TABLE II-continued

Human flt1 VEGF Receptor-Hammerhead Ribozyme and Substrate Sequence

| nt. Position | HH Ribozyme | Substrate |
|---|---|---|
| 1415 | UAAUUAAC CUGAUGA X GAA AGUAGCGA | UGGCUACUC GUUAAUUA |
| 1418 | UGAUAAUU CUGAUGA X GAA ACGAGUAG | CUACUCGUU AAUUAUCA |
| 1419 | UUGAUAAU CUGAUGA X GAA AAGGAAUA | UACUCGUUA AUUAUCAA |
| 1422 | UCCUUGAU CUGAUGA X GAA AUUGACGA | UCGUCAAUU AUCAAGGA |
| 1423 | GUCCUUGA CUGAUGA X GAA AAUUAACG | CGUUAAUUA UCAAGGAC |
| 1425 | ACGUCCUU CUGAUGA X GAA AUAAUUAA | UUAAUUAUC AAGGAGGU |
| 1434 | UCUUCAGU CUGAUGA X GAA ACGUCCUU | AAGGACGUA ACUGAAGA |
| 1456 | GAUUGUAU CUGAUGA X GAA AUUCCCUG | CAGGGAAUU AUACAAUC |
| 1457 | AGAUUCCA CUGAUGA X GAA AAUUCCCU | AGGGAAUUA UACAAUCU |
| 1459 | CAAGAUUG CUGAUGA X GAA AUAAUUCC | GGAAUUAUA CAAUCUUG |
| 1464 | CUCAGCAA CUGAUGA X GAA AUUGUAUA | UAUACAAUC UUGCUGAG |
| 1466 | UGCUCAGC CUGAUGA X GAA AGAUUCUA | UACAAUCUU GCUGAGCA |
| 1476 | GACUGUUU CUGAUGA X GAA AUGCUCAG | CUCAGCAUA AAACAGUC |
| 1484 | ACACAUUU CUGAUGA X GAA ACUGUUUU | AAAACAGUC AAAUGUGU |
| 1493 | GGUUUUUA CUGAUGA X GAA ACACAUUU | AAAUGUGUU UAAAAACC |
| 1494 | AGGUUUUU CUGAUGA X GAA AACACAUU | AAUGUGUUU AAAAACCU |
| 1495 | GAGGUUUU CUGAUGA X GAA AAACACAU | AUGUGUUUA AAAACCUC |
| 1503 | GUGCAAAU CUGAUGA X GAA AGGUUUUU | AAAAACCUC ACUGCCAC |
| 1513 | GACAAUUA CUGAUGA X GAA AGUGGCAG | CUGCCACUC UAAUUGUC |
| 1515 | UUGACAAU CUGAUGA X GAA AGAGUGGC | GCCACUCUA AUUGUCAA |
| 1518 | ACAUUGAC CUGAUGA X GAA AUUAGAGU | ACUCUAAUU GUCAAUGU |
| 1521 | UUCAUUUU CUGAUGA X GAA ACAAUUAG | CUAAUUGUC AAUGUGAA |
| 1539 | UUUUCGUA CUGAUGA X GAA AUCUGGGG | CCCCAGAUU UACGAAAA |
| 1540 | CUUUUCGU CUGAUGA X GAA AAUGUGGG | CCCAGAUUU ACGAAAAG |
| 1541 | CCUUUUCG CUGAUGA X GAA AAAUCUGG | CCAGAUUUA CGAAAAGG |
| 1556 | GAAACGAU CUGAUGA X GAA ACACGGCC | GGCCGUGUC AUCGUUUC |
| 1559 | CUGGAAAC CUGAUGA X GAA AUGACACG | CGUGUCAUC GUUUCCAG |
| 1562 | GGUCUGGA CUGAUGA X GAA ACGAUGAC | GUCAUCGUU CCAGACC |
| 1563 | GGGUCUGG CUGAUGA X GAA AGCGAGGA | UCAUCGUUU CCAGACCC |
| 1564 | CGGGUCCG CUGAUGA X GAA AAACGAUG | CAUCGUUUC CAGACCCG |
| 1576 | UGGGCAGA CUGAUGA X GAA AGCCGGGU | ACCGGCUC UCCACCCA |
| 1578 | AGUGGGUA CUGAUGA X GAA AGAGCCGG | CCCCCUCUC UACCCACU |
| 1580 | CCAGUGGG CUGAUGA X GAA AGAGAGCC | GGCUCUCUA CCCACUGG |
| 1602 | CAAGUCAG CUGAUGA X GAA AUUUGUCU | AGACAAAUC CUGACUUG |
| 1609 | UGCGGUAC CUGAUGA X GAA AGUCAGGA | UCCUGACUU GUACCGCA |
| 1612 | AUAUGCGG CUGAUGA X GAA ACAAGUCA | UGACUUGUA CCGCAUAU |
| 1619 | GGAUACCA CUGAUGA X GAA AUGCGGUA | UACCGCAUA AGGUAUCC |

TABLE II-continued

| Human flt1 VEGF Receptor-Hammerhead Ribozyme and Substrate Sequence | | |
|---|---|---|
| nt. Position | HH Ribozyme | Substrate |
| 1624 | UUGAGGGA CUGAUGA X GAA ACCAUAUG | CAUAUGGUA UCCCUCAA |
| 1626 | GGUUGAGG CUGAUGA X GAA AUACCAUA | UAUGGUAUC CCUCAACC |
| 1630 | UGUAGGUU CUGAUGA X GAA AGGGAGAC | GUAUCCCUC AACCUCCA |
| 1636 | CUUGAUUG CUGAUGA X GAA AGGUUGAG | CUCAACCUA CAAUCAAG |
| 1641 | AACCACUU CUGAUGA X GAA AUUGUAGG | CCCACAAUC AAGUGGUU |
| 1649 | GGUGCCAG CUGAUGA X GAA ACCACUUG | CAAGUGGUU CUGGCACC |
| 1650 | GGGUGCCA CUGAUGA X GAA AACCACUU | AAGUGGUUC UGGCACCC |
| 1663 | AUUAUGGU CUGAUGA X GAA ACAGGGGU | ACCCCUGUA ACCAGAAU |
| 1669 | GGAAUGAU CUGAUGA X GAA AUGGUUAC | GUAACCAUA AUCAUUCC |
| 1672 | UUCGGAAU CUGAUGA X GAA AUUAUGGU | ACCAUAAUC AUUCCGAA |
| 1675 | UGCUUCGG CUGAUGA X GAA AUGAUUAU | AUAAUCAUU CCGAAGCA |
| 1676 | UUGCUUCG CUGAUGA X GAA AAUGAUUA | UAAUCAUUC CGAAGCAA |
| 1694 | UGGAACAA CUGAUGA X GAA AGUCACAC | GUGUGACUU UUGUUCCA |
| 1695 | UUGGAACA CUGAUGA X GAA AAGUCACA | UGUGACUUU UGUUCCAA |
| 1696 | AUUGGAAC CUGAUGA X GAA AAAGUCAC | GUGACUUUU GUUCCAAU |
| 1699 | AUUAUUGG CUGAUGA X GAA ACAAAAGU | ACUUUUGUU CCAAUAAU |
| 1700 | CAUUAUUG CUGAUGA X GAA AACAAAAG | CUUUUGUUC CAAUAAUG |
| 1705 | CUCUUCAU CUGAUGA X GAA AUUGGAAC | GUUCCAAUA AUGAAGAG |
| 1715 | GGAUAAAG CUGAUGA X GAA ACUCUUCA | UGAAGAGUC CUUUAUCC |
| 1718 | CCAGGAUA CUGAUGA X GAA AGGACUCU | AGAGUCCUU UAUCCUGG |
| 1719 | UCCAGGAU CUGAUGA X GAA AAGGACUC | GAGUCCUUU AUCCUGGA |
| 1720 | AUCCAGGA CUGAUGA X GAA AAAGGACU | AGUCCUUUA UCCUGGAU |
| 1722 | GCAUCCAG CUGAUGA X GAA AUAAAGGA | UCCUUUAUC CUGGAUGC |
| 1755 | AUGCUCUC CUGAUGA X GAA AUUCUGUU | AACAGAAUU GAGAGCAU |
| 1764 | CGCUGAGU CUGAUGA X GAA AUGCUCUC | GAGAGCAUC ACUCAGCG |
| 1768 | CAUGCGCU CUGAUGA X GAA AGUGAGGC | CCAUCACUC AGCGCAUG |
| 1782 | CCUUCUAU CUGAUGA X GAA AUUGCCAU | AUGGCAAUA AUAGAAGG |
| 1785 | UUUCCUUC CUGAUGA X GAA AUUAUUGC | GCAAUAAUA GAAGGAAA |
| 1798 | AGCCAUCU CUGAUGA X GAA AUUCUUUC | GAAAGAAUA AGAUGGCU |
| 1807 | CAAGGUGC CUGAUGA X GAA AGCCAUCU | AGAUGGCUA GCACCUUG |
| 1814 | CCACAACC CUGAUGA X GAA AGGUGCUA | UAGCACCUU GGUUGUGG |
| 1818 | UCAGCCAC CUGAUGA X GAA ACCAAGGU | ACCUUGGUU GUGGCUGA |
| 1829 | AAAUUCUA CUGAUGA X GAA AGUCAGCC | GGCUGACUC UAGAAUUU |
| 1831 | AGAAAUUC CUGAUGA X GAA AGAGUCAG | CUGACUCUA GAAUUUCU |
| 1836 | AUUCCAGA CUGAUGA X GAA AUUCUAGA | UCUAGAAUU UCUGGAAU |
| 1837 | GAUUCCAG CUGAUGA X GAA AAUUCUAG | CUAGAAUUU CUGGAAUC |

TABLE II-continued

Human flt1 VEGF Receptor-Hammerhead Ribozyme and Substrate Sequence

| nt. Position | HH Ribozyme | Substrate |
|---|---|---|
| 1838 | AGAUUCCA CUGAUGA X GAA AAAUUCCA | UAGAAUUUC UGGAAUCU |
| 1845 | CAAAUGUA CUGAUGA X GAA AUUCCAGA | UCUGGAAUC UACAUUUG |
| 1847 | UGCAAAUG CUGAUGA X GAA AGAUUCCA | UGGAAUCUA CAUUUGCA |
| 1851 | GCUAUGCA CUGAUGA X GAA AUGUAGAU | AUCUACAUU UGCAUAGC |
| 1852 | AGCUAUGC CUGAUGA X GAA AAUGUAGA | UCUACAUUU GCAUAGCU |
| 1857 | UUGGAAGC CUGAUGA X GAA AUGCAAAU | AUUUGCAUA GCUUCCAA |
| 1861 | UUUAUUGG CUGAUGA X GAA AGCGAUGC | GCAUAGCUU CCAAUAAA |
| 1862 | CUUUAUUG CUGAUGA X GAA AAGCUAUG | CAUAGCUUC CAAUAAAG |
| 1867 | CCCAACUU CUGAUGA X GAA AUUAGAAG | CUUCCAAUA AAGUUGGG |
| 1872 | ACAGUCCC CUGAUGA X GAA ACUUUAUU | AAUAAAGUU GGGACUGU |
| 1893 | UAAAAGCU CUGAUGA X GAA AUGUUUCU | AGAAACAUA AGCUUUUA |
| 1898 | UGAUAUAA CUGAUGA X GAA ACCUCAUG | CAUAAGCUU UUAUAUCA |
| 1899 | GUGAUAUA CUGAUGA X GAA AAGCUUAU | AUAAGCUUU UAUAUCAC |
| 1900 | UGUGAUAU CUGAUGA X GAA AAAGCUUA | UAAGCUUUU AUAUCACA |
| 1901 | CUGUGAUA CUGAUGA X GAA AAAAGCUU | AAGCUUUUA UAUCACAG |
| 1903 | AUCUGUGA CUGAUGA X GAA AUAAAAGC | GCUUUUACA UCACAGAU |
| 1905 | ACAUCUGU CUGAUGA X GAA AUAUAAAA | UUUUUAUC ACAGAUGU |
| 1925 | UAACAUGA CUGAUGA X GAA ACCCAUUU | AAAUGGGUU UCAUGUUA |
| 1926 | UUAACAUG CUGAUGA X GAA AACCCAUU | AAUGGGUUU CAUGUUAA |
| 1927 | GUUAACAU CUGAUGA X GAA AAACCCAU | AUGGGUUUC AUGUUAAC |
| 1932 | UCCAAGUU CUGAUGA X GAA ACAUGAAA | UUUCAUAAU AACUUGGA |
| 1933 | UUCCCAGU CUGAUGA X GAA AACAUGAA | UUCAUGUUA ACUUGGAA |
| 1937 | UUUUUUCC CUGAUGA X GAA AGUUAACA | UGUUAACUU UGUUAACU |
| 1976 | CUGUGCAA CUGAUGA X GAA ACAGUUUC | GAAACUGUC UUGCACAG |
| 1378 | AACUGUGC CUGAUGA X GAA AGACAGUU | AACUGUCUU GCACAGUU |
| 1986 | AACUUGUU CUGAUGA X GAA ACUGUGCA | UGCACAGUU AACAAGUU |
| 1987 | GAACUAAU CUGAUGA X GAA AACUGUGC | GCACAGUUA ACAAGUUC |
| 1994 | UGUAUAAG CUGAUGA X GAA ACUUGUUA | UAACAAGUU CUUAUACA |
| 1995 | CUGUAUAA CUGAUGA X GAA AACUUGUU | AACAAGUUC UUUAUACAG |
| 1997 | CUCUGUAU CUGAUGA X GAA AGAACUUG | CAAGUUCUU AUACAGAG |
| 1998 | UCUCUGUA CUGAUGA X GAA AAGAACUU | AAGUUCUUA UACAGAGA |
| 2000 | CGUCUCUG CUGAUGA X GAA AUAAAGAC | GUUCUUAUA CAGAGACG |
| 2010 | AUCCAAGU CUGAUGA X GAA ACCUCUCU | AGAGACGUU ACUUGGAU |
| 2011 | AAUCCAAG CUGAUGA X GAA AACGUCUC | GAGACGUUA CUUGGAUU |
| 2014 | UAAAAUCC CUGAUGA X GAA AGUAACGU | ACGUUACUU GGAUUUUA |
| 2019 | CGCAGUAA CUGAUGA X GAA AUCCAAGU | ACUUGGAUU UUACUGCG |
| 2020 | CCGCAGUA CUGAUGA X GAA AAUCCAAG | CUUGGAUUU UACUGCGG |

TABLE II-continued

Human flt1 VEGF Receptor-Hammerhead Ribozyme and Substrate Sequence

| nt. Position | HH Ribozyme | Substrate |
|---|---|---|
| 2021 | UCCGCAGU CUGAUGA X GAA AAAUCCCA | UUGGAUUUU ACUGCGGA |
| 2022 | GUCCACAG CUGAUGA X GAA AAAAUCCA | UGGAUUUUA CUGCGGAC |
| 2034 | CUGUUAUU CUGAUGA X GAA ACUGUCCG | CGGACAGUU AAUAACAG |
| 2035 | UCUGUUAU CUGAUGA X GAA AACUGUCC | GGACAGUUA AUAACAGA |
| 2038 | UGUUCUGU CUGAUGA X GAA AUUAACUG | CAGUUAAUA ACAGAACA |
| 2054 | UAAUACUG CUGAUGA X GAA AGUGCAUU | AAUGCACUA CAGUAUUA |
| 2059 | CUUGCUAA CUGAUGA X GAA ACUGUAGU | ACUACAGUA UUAGCAAG |
| 2061 | UGCUUGCU CUGAUGA X GAA AUACUGUA | UACAGUAUU AGCAAGCA |
| 2062 | UUGCUUGC CUGAUGA X GAA AAUACUGU | ACAGUAUUA GCAAGCAA |
| 2082 | UCCUUAGU CUGAUGA X GAA AUGGCCAU | AUGGCCAUC ACUAAGGA |
| 2086 | GUGCUCCU CUGAUGA X GAA AGUGAUGG | CCAUCACUA AGGAGCAC |
| 2096 | GAGUGCUG CUGAUGA X GAA AGUGCUCC | GGAGCACUC CAUCACUC |
| 2100 | UUAAGAGU CUGAUGA X GAA AUGGAGUG | CACUCCAUC ACUCUUAA |
| 2104 | AAGAUUAA CUGAUGA X GAA AGUGAUGG | CCAUCACUC UUAAUCUU |
| 2106 | GUAAGAUU CUGAUGA X GAA AGAGUGAU | AUCACUCUU AAUCUUAC |
| 2107 | GGUAAGAU CUGAUGA X GAA AAGAGUGA | UCACUCUUA AUCUUACC |
| 2110 | GAUGGGAA CUGAUGA X GAA AUUAAGAG | CUCUUAAUC UUACCAUC |
| 2112 | AUGAUGGU CUGAUGA X GAA AGAUUAAG | CUUAAUCUU ACCAUCAU |
| 2113 | CAUGAUGG CUGAUGA X GAA AAGAUUAA | UUAAUCUUA CCAUCAUG |
| 2118 | ACAUUCAU CUGAUGA X GAA AUGGUAAG | CUUACCAUC AUGAAUGU |
| 2127 | UGCAGGGA CUGAUGA X GAA ACAUUCAU | AUGAAUGUU UCCCUGCA |
| 2128 | UUGCAGGG CUGAUGA X GAA AACAUUCA | UGAAUGUUU CCCUGCAA |
| 2129 | CUUGCAGG CUGAUGA X GAA AAACAUUC | GAAUGUUUC CUGCAAG |
| 2140 | GGUGCCUG CUGAUGA X GAA AUCUUGCA | UGCAAGAUU CAGGCACC |
| 2141 | AGGUGUCU CUGAUGA X GAA AAUCUUGC | GCAAGAUUC AGGCACCU |
| 2150 | UGCAGGCA CUGAUGA X GAA AGGUGCCU | AGGCACCUA UGCCUGCA |
| 2172 | CCUGUCCA CUGAUGA X GAA ACAUUCCU | AGGAAUGUA UACACAGG |
| 2174 | CCCCUGUG CUGAUGA X GAA AUACAUUC | GAAUUUAUA CACAGGOG |
| 2190 | UUCUGAGG CUGAUGA X GAA AUUCCUUC | GAAGAAAUC CUCCAGAA |
| 2193 | UUCUUCUG CUGAUGA X GAA AGGAUUUC | GAAAUCCUC CAGAAGAA |
| 2208 | CUGAUUGU CUGAUGA X GAA AUUUCUUU | AAAGAAAUU ACAAUCAG |
| 2209 | UCUGAUUG CUGAUGA X GAA AAUUUCUU | AAGAAAUUA CAAUCAGA |
| 2214 | UGAUCUCU CUGAUGA X GAA AUUGUAAU | AUUACAAUC AGAGAUCA |
| 2221 | UGCUUCCU CUGAUGA X GAA AUCUCUGA | UCAGAGAUC AGGAAGCA |
| 2234 | GCAGGAGG CUGAUGA X GAA AUGGUGCU | AGCACCAUA CCUCCUGC |
| 2238 | UUUCGCAG CUGAUGA X GAA AGGUAUGG | CCAUACCUC CUGCGAAA |

TABLE II-continued

Human flt1 VEGF Receptor-Hammerhead Ribozyme and Substrate Sequence

| nt. Position | HH Ribozyme | Substrate |
|---|---|---|
| 2250 | UGAUCACU CUGAUGA X GAA AGGUUUCG | CGAAACCUC AGUGAUCA |
| 2257 | CACUGUGU CUGAUGA X GAA AUCACUGA | UCAGUGAUC ACACAGUG |
| 2271 | GAACUGCU CUGAUGA X GAA AUGGCCAC | GUGGCCAUC AGCAAUUC |
| 2278 | AGUGGUGG CUGAUGA X GAA ACUGCUGA | UCAGCAGUU CCACCACU |
| 2279 | AAGUGGUG CUGAUGA X GAA AACAGCUG | CAGCAGUUC CACCACUU |
| 2287 | ACAGUCUA CUGAUGA X GAA AGUGGUGG | CCACCACUU UAGACUGU |
| 2288 | GACAGUCU CUGAUGA X GAA AAGUGGUG | CACCACUUU AGACUGUC |
| 2289 | UGACAGUC CUGAUGA X GAA AAAGUGGU | ACCACUUUA GACUGUCA |
| 2296 | AUUAGCAU CUGAUGA X GAA ACAGUCUA | UAGACUGUC AUGCUAAU |
| 2302 | GACACCAU CUGAUGA X GAA AGCAUGAC | GUCAUGCUA AUGGUGUC |
| 2310 | GGCUCGGG CUGAUGA X GAA ACACCAUU | AAUGGUGUC CCCGAGCC |
| 2320 | AGUGAUCU CUGAUGA X GAA AGCCUUGG | CCGAGCCUC AGAUCACU |
| 2325 | AACCAAGU CUGAUGA X GAA AUCUGAGG | CCUCAGAUC ACUUGGUU |
| 2329 | UUUAAAUC CUGAUGA X GAA AGUGAUCU | AGAUCACUU GGUUUAAA |
| 2333 | UGUUUUGA CUGAUGA X GAA ACCAAGUG | CACUUGGUU UAAAAACA |
| 2334 | UUGUUUUU CUGAUGA X GAA AACCAAGU | ACUUGGUUU AAAAACAA |
| 2335 | GUUGUUUU CUGAUGA X GAA AAACCAAG | CUUGGUUUA AAAGAAC |
| 2352 | UCUUGUUG CUGAUGA X GAA AUUUUGUG | CACAAAAUA CAACAAGA |
| 2370 | CCUAAAAU CUGAUGA X GAA AUUCCAGG | CCUGGAAUU AUUUUAGG |
| 2371 | UCCUAAAA CUGAUGA X GAA AAUUCCAG | CUGGAAUUA UUUUAGGA |
| 2373 | GGUCCUAA CUGAUGA X GAA AUAAUUCC | GGAAUUAUU UUAGGACC |
| 2374 | UGGUCCUA CUGAUGA X GAA AAUAAUUC | GAAUUAUUU UAGGACCA |
| 2375 | CUGGUCCU CUGAUGA X GAA AAAUAAUU | AAUUAUUUU AGGACCAG |
| 2376 | CCUGGUCC CUGAUGA X GAA AAAAUAAU | AUUAUUUUA GGACCAGG |
| 2399 | UUUCAAUA CUGAUGA X GAA ACAGCGUG | CACGCUGUU UAUUGAAA |
| 2400 | CUUUCAAU CUGAUGA X GAA AACAGCGU | ACGCUGUUU AUUGAAAG |
| 2401 | UCUUUCAA CUGAUGA X GAA AAACAGCG | CGCUGUUUA UUGAAAGA |
| 2403 | ACUCUUUC CUGAUGA X GAA AUAAACAG | CUGUUUAUU GAAAGAGU |
| 2412 | UCUUCUGU CUGAUGA X GAA ACUCUUUC | GAAAGAGUC ACAGAAGA |
| 2433 | CAGUGAUA CUGAUGA X GAA ACACCUUC | GAAGGUGUC UAUCACUG |
| 2435 | UGCAGUGA CUGAUGA X GAA AGACACCU | AGGUGUCUA UCACUGCA |
| 2437 | UUUGCAGU CUGAUGA X GAA AUAGACAC | GUGUCUAUC ACUGCAAA |
| 2465 | UUUCCACA CUGAUGA X GAA AGCCCUUC | GAAGGGCUC UGUGGAAA |
| 2476 | GUAUGCUG CUGAUGA X GAA ACUUUCCA | UGGAAAGUU CAGCAUAC |
| 2477 | GGUAUGCU CUGAUGA X GAA AACUUUCC | GGAAAGUUC AGCAUACC |
| 2483 | CAGUGAGG CUGAUGA X GAA AUGCUGAA | UUCAGCAUA CCUCACUG |
| 2487 | UGAACAGU CUGAUGA X GAA AGGUAUGC | GCAUACCUC ACUGUUCA |

TABLE II-continued

Human flt1 VEGF Receptor-Hammerhead Ribozyme and Substrate Sequence

| nt. Position | HH Ribozyme | Substrate |
|---|---|---|
| 2493 | GUUCCUUG CUGAUGA X GAA ACAGUGAG | CUCACUGUU CAAGGAAC |
| 2494 | GGUUCCUU CUGAUGA X GAA AACAGUGA | UCACUGUUC AAGGAACC |
| 2504 | ACUUGUCC CUGAUGA X GAA AGGUUCCU | AGGAACCUC GGACAAGU |
| 2513 | CCAGAUUA CUGAUGA X GAA ACUUGUCC | CGACAAGUC UAAUCUOG |
| 2515 | CUCCAGAU CUGAUGA X GAA AGACUUGU | ACAAGUCUA AUCGGAG |
| 2518 | CAGCUCCA CUGAUGA X GAA AUUAGACU | AGUCUAAUC UGGAGCUG |
| 2529 | GUUAGAGU CUGAUGA X GAA AUCAGCUC | GAGCUGAUC ACUCUAAC |
| 2533 | GCAUGUUA CUGAUGA X GAA AGUGAUCA | UGAUCACUC UAACAUGC |
| 2535 | GUGCAUGU CUGAUGA X GAA AGAGUGAU | AUCACUCUA ACAUGCAC |
| 2560 | CCAGAAGA CUGAUGA X GAA AGGUCGAG | CUCCGACUC UCUUCUCG |
| 2562 | AGCCAGAA CUGAUGA X GAA AGAGUUUC | GCGACUCUC UUCUGGCU |
| 2564 | GGAGCCAG CUGAUGA X GAA AGAGAGUC | GACUCUCUU CUGGCUCC |
| 2565 | AGGAGCCA CUGAUGA X GAA AAGAGAGU | ACUCUCUUC UGGCUCCU |
| 2571 | GUUAAUAG CUGAUGA X GAA AGCCAGAA | UUCUGGCUC CUAUUAAC |
| 2574 | AGGGUUAA CUGAUGA X GAA AGGAGCCA | UGGCUCCUA UUAACCCU |
| 2576 | GGAGGGUU CUGAUGA X GAA AUAGGAGC | GCUCCUAUU AACCCUCC |
| 2577 | AGGAGGGU CUGAUGA X GAA AAUAGGAG | CUCCUAUUA ACCUCUCU |
| 2583 | CGGAUAAG CUGAUGA X GAA AGGGUGAA | UUAACCCUC CUUAUCCG |
| 2586 | UUUCGGAU CUGAUGA X GAA AGGAGGGU | ACCCUCCUU AUCCGAAA |
| 2587 | UUUUCGGA CUGAUGA X GAA AAGGAGGG | CCCUCCUUA UCCGAAAA |
| 2589 | AUUUUUCG CUGAUGA X GAA AUAAGGAG | CUCCUUAUC CGAAAAAU |
| 2606 | CAAAAGAA CUGAUGA X GAA ACCUUUUC | GAAAAGGUC UUCUUCUG |
| 2608 | UUCAGAAG CUGAUGA X GAA AGACCUUU | AAAGGUCUU CUUCUGAA |
| 2609 | UUCCAGAA CUGAUGA X GAA AAGACCUU | AAGGUCUUC UUCUGAAA |
| 2611 | UAUUUCAG CUGAUGA X GAA AGAAGACC | GGUCUUCUU CUGAAAUA |
| 2612 | UUAUUUCA CUGAUGA X GAA AAGAAGAC | GUCUUCUUC UGAAAUAA |
| 2619 | UCAGUCUU CUGAUGA X GAA AUUUCAGA | UCUGAAAUA AAGACUGA |
| 2630 | UUGAUAGG CUGAUGA X GAA AGUCAGUC | GACUGAAUA CCUAUCAA |
| 2634 | AUAAUUGA CUGAUGA X GAA AGGUAGUC | GACUACCUA UCAAUUAU |
| 2636 | UUAUAAUU CUGAUGA X GAA AUAGGUAG | CUACCUAUC AAUUAUAA |
| 2640 | UCCAUUAU CUGAUGA X GAA AUUGAUAG | CUAUCAAUU AUAAUCGA |
| 2641 | GUCCAUUA CUGAUGA X GAA AAUUGAUA | UAUCAAUUA UAAUGGAC |
| 2643 | CGGUCCAU CUGAUGA X GAA AUAAUUGA | UCAAUUAUA AUGGACCC |
| 2661 | UCCAAAGG CUGAUGA X GAA ACUUCAUC | GAUGAAGUU CCUUUGGA |
| 2662 | AUCCAAAG CUGAUGA X GAA AACUUCAU | AUGAAGUUC CUUUGGAU |
| 2665 | CUCAUCCA CUGAUGA X GAA AGGAACUU | AAGUUCCUU UGGAUGAG |

TABLE II-continued

Human flt1 VEGF Receptor-Hammerhead Ribozyme and Substrate Sequence

| nt. Position | HH Ribozyme | Substrate |
|---|---|---|
| 2666 | GCUCAUCC CUGAUGA X GAA AAGGAACU | AGUUCCUUU GGAUGAGC |
| 2688 | UCAUAAGG CUGAUGA X GAA AGCCGCUC | GAGCGGCUC CCUUAUGA |
| 2692 | GGCAUCAU CUGAUGA X GAA AGGGAGCC | GGCUCCCUU AUGAUCCC |
| 2693 | UGGCAUCA CUGAUGA X GAA AAGGGAGC | GCUCCCUUA UGAUGCCA |
| 2714 | CCCGGGCA CUGAUGA X GAA ACUCCCAC | GUGGGAGUU UGCCCGGG |
| 2715 | UCCCGGGC CUGAUGA X GAA AACUCCCA | UGGGAGUUU GCCCGGGA |
| 2730 | CCCAGUUU CUGAUGA X GAA AGUCUCUC | GAGAGACUU AAACUGGG |
| 2731 | GCCCAGUU CUGAUGA X GAA AAGUCUCU | AGAGACUUA AACUGGGC |
| 2744 | UUCCAAGU CUGAUGA X GAA AUUUGCCC | GCCCAAAUC ACUUGGAA |
| 2748 | CCUCUUCC CUGAUGA X GAA AGUGAUUU | AAAUCACUU GGAAGAGG |
| 2761 | UUUUCCAA CUGAUGA X GAA AGCCCCUC | GAGGGGGUU UUGGAAAA |
| 2762 | CUUUUCCA CUGAUGA X GAA AAGCCCCU | AGGGGCUUU UGGAAAAG |
| 2763 | ACUUUUCC CUGAUGA X GAA AAAGCCCC | GGGGCUUUU GGAAAAGU |
| 2775 | GAUGCUUG CUGAUGA X GAA ACCACUUU | AAAGUGGUU CAAGCACC |
| 2776 | UGAUGCUU CUGAUGA X GAA AACCACUU | AAGUGGUUC AAGCAUCA |
| 2783 | CAAAUGCU CUGAUGA X GAA AUGCUUGA | UCAAGCAUC AGCAUUUG |
| 2789 | UAAUGCCA CUGAUGA X GAA AUGCUGAU | AUCAGCAUU UGGCAUUA |
| 2790 | UUAAUGCC CUGAUGA X GAA AAUGCUGA | UCAGCAUUU GCCAUUAA |
| 2796 | GAUUUCUU CUGAUGA X GAA AUGCCAAA | UUUGGCAUU AAGAAAUC |
| 2797 | UGAUUUCU CUGAUGA X GAA AAUGCCAA | UUGGCAUUA AGAAAUCA |
| 2804 | ACGUAGGU CUGAUGA X GAA AUUUCUUA | UAAGAAAUC ACCUACGU |
| 2809 | CCGGCACG CUGAUGA X GAA AGGUGAUU | AAUCACCUA CGUGCCGG |
| 2864 | GAGCUUUG CUGAUGA X GAA ACUCCCUG | CAGCGAGUA CAAAGCUC |
| 2872 | AGUCAUCA CUGAUGA X GAA AGCUUUGU | ACAAAGCUC UGAUGACU |
| 2886 | AAGAUUUU CUGAUGA X GAA AGCUCAGU | ACUGAGCCA AAAAUCUU |
| 2892 | UGGGUCAA CUGAUGA X GAA AUUUUUAG | CUAAAAAUC UUGACOCA |
| 2894 | UGUGGGUC CUGAUGA X GAA AGAUUUUU | AAAAAUCUU GACCCACA |
| 2904 | UGGUGGCC CUGAUGA X GAA AUGUGGGU | ACCCACAUU GGCCACCA |
| 2914 | CACGUUCA CUGAUGA X GAA AUGGUGGC | GCCACCAUC UGAACGUG |
| 2925 | AGCAGGUU CUGAUGA X GAA ACCACGUU | AACGUGGUU AACCUGCU |
| 2926 | CAGCAGGU CUGAUGA X GAA AACCACGU | ACGUGGUUA ACCUGCUG |
| 2962 | CACCAUCA CUGAUGA X GAA AGGCCCUC | GAGGGCCUC UGAUGGUG |
| 2973 | UAUUCAAC CUGAUGA X GAA AUCACCAU | AUGGUGAUU GUUGAAUA |
| 2976 | CAGUAUUC CUGAUGA X GAA ACAAUCAC | GUGAUUGUU GAAUACUG |
| 2981 | AUUUGCAG CUGAUGA X GAA AUUCAACA | UGUUGAAUA CUGCAAAU |
| 2990 | GAUUUCCA CUGAUGA X GAA AUUUGCAG | CUGCAAAUA UGGAAAUC |
| 2998 | GUUGGAGA CUGAUGA X GAA AUUUCCAU | AUGGAAAUC UCUCCAAC |

TABLE II-continued

Human flt1 VEGF Receptor-Hammerhead Ribozyme and Substrate Sequence

| nt. Position | HH Ribozyme | Substrate |
|---|---|---|
| 3000 | UAGUUGGA CUGAUGA X GAA AGAUUUCC | GGAAAUCUC UCCAACUA |
| 3002 | GGUAGUUG CUGAUGA X GAA AGAGAUUU | AAAUCUCUC CAACUACC |
| 3008 | UCUUGAGG CUGAUGA X GAA AGUUGGAG | CUCCAACUA CCUCAAGA |
| 3012 | UUGCUCUU CUGAUGA X GAA AGGUAGUU | AACUACCUC AAGAGCAA |
| 3029 | GAAAAAAU CUGAUGA X GAA AGUCACGU | ACGUGACUU AUUUUUUC |
| 3030 | AGAAAAAA CUGAUGA X GAA AAGUCACG | CGUGACUUA UUUUUUCU |
| 3032 | UGAGAAAA CUGAUGA X GAA AUAAGUCA | UGACUUAUU UUUCUCA |
| 3033 | UUGAGAAA CUGAUGA X GAA AAUAAGUC | GACUUAUUU UUUCUCAA |
| 3034 | GUUGAGAA CUGAUGA X GAA AAAUAAGU | ACUUAUUUU UUCUCAAC |
| 3035 | UGUUGAGA CUGAUGA X GAA AAAAUAAG | CUUAUUUUU UCUCAACA |
| 3036 | UUGUUGAG CUGAUGA X GAA AAAAAUAA | UUAUUUUUU CUCAACAA |
| 3037 | CUUGUUGA CUGAUGA X GAA AAAAAAUA | UAUUUUUUC UCAACAAG |
| 3039 | UCCUUGUU CUGAUGA X GAA AGAAAAAA | UUUUUUCUC AACAAGGA |
| 3057 | UCCAUGUG CUGAUGA X GAA AGUGCUGC | GCAGCACUA CACAUGGA |
| 3070 | UUCUUUCU CUGAUGA X GAA AGGCUCCA | UGGAGCCUA AGAAAGAA |
| 3120 | ACGCUAUC CUGAUGA X GAA AGUCUUGG | CCAAGACUA GAUAGCGU |
| 3124 | GGUGACGC CUGAUGA X GAA AGCUAGUC | GACUAGAUA GCGUCACC |
| 3129 | CUGCUGGU CUGAUGA X GAA ACGCUAUC | GAUAGCGUC ACCAGCAG |
| 3146 | AGCUCGCA CUGAUGA X GAA AGCUUUCG | CGAAAGCUU UGCGAGCU |
| 3147 | GAGCUCGC CUGAUGA X GAA AAGCUUUC | GAAAGCUUU GCGAGCUC |
| 3155 | GAAAGCCG CUGAUGA X GAA AGCUCGCA | UGCGAGCUC CGGCUUUC |
| 3161 | CUUCCUGA CUGAUGA X GAA AGCCGGAG | CUCCGGCUU UCAGGAAG |
| 3162 | UCUUCCUG CUGAUGA X GAA AAGCCGGA | UCCGGCUUU CAGGAAGA |
| 3163 | AUCUUCCU CUGAUGA X GAA AAAGCCGG | CCGGCUUUC AGGAAGAU |
| 3172 | CAGACUUU CUGAUGA X GAA AUCUUCCU | AGGAAGAUA AAAGUCUG |
| 3178 | AUCACUCA CUGAUGA X GAA ACUUUUAU | AUAAAAGUC UGAGUGAU |
| 3189 | UCUUCCUC CUGAUGA X GAA ACAUCACU | AGUGAUGUU GAGGAAGA |
| 3205 | ACCGUCAG CUGAUGA X GAA AUCCUCCU | AGGAUGAUU CUUGACGU |
| 3206 | AACCGUCA CUGAUGA X GAA AUCCUCC | GGAGGAUUC UGACGGUU |
| 3214 | CUUGUAGA CUGAUGA X GAA ACCGUCAG | CUGACGGUU UCUACAAG |
| 3215 | CCUUGCAG CUGAUGA X GAA AACCGUCA | UGACGGUUU CUACAAGG |
| 3216 | UCCUUGUA CUGAUGA X GAA AAACCGUC | GACGGUUUC UACAAGGA |
| 3218 | GCUCCUUG CUGAUGA X GAA AGAAACCG | CGGUUUCUA CAAGGAGC |
| 3231 | UCCAAAGU CUGAUGA X GAA AUGGGCUC | GAGCCCAUC ACUAUGGA |
| 3235 | AUCUUCCA CUGAUGA X GAA AGUGAUGG | CCAUCACUA UGGAAGAU |
| 3244 | AGAAAUCA CUGAUGA X GAA AUCUUCCA | UGGAAGAUC UGAUUUCU |

TABLE II-continued

Human flt1 VEGF Receptor-Hammerhead Ribozyme and Substrate Sequence

| nt. Position | HH Ribozyme | Substrate |
|---|---|---|
| 3249 | CUGUAAGA CUGAUGA X GAA AUCAGAUC | GAUCUGAUU UCUUACAG |
| 3250 | ACUGUAAG CUGAUGA X GAA AAUCAGAU | AUCUGAUUU CUUACAGU |
| 3251 | AACUGUAA CUGAUGA X GAA AAAUCAGA | UCUGAUUUC UUACAGUU |
| 3253 | AAAACUGU CUGAUGA X GAA AGAAAUCA | UGAUUUCUU ACAGUUUU |
| 3254 | GAAAACUG CUGAUGA X GAA AAGAAAUC | GAUUUCUUA CAGUUUUC |
| 3259 | CACUUGAA CUGAUGA X GAA ACUGUAAG | CUUACAGUU UUCAAGUG |
| 3260 | CCACUUGA CUGAUGA X GAA AACUGUAA | UUACAGUUU UCAAGUGG |
| 3261 | GCCACUUG CUGAUGA X GAA AAACUGUA | UACAGUUUU CAAGUGGC |
| 3262 | GGCCACUU CUGAUGA X GAA AAAACUGU | ACAGUUUUC AAGUGGCC |
| 3284 | AAGACAGG CUGAUGA X GAA ACUCCAUG | CAUGGAGUU CCUGUCUU |
| 3285 | GAAGACAG CUGAUGA X GAA AACUCCAU | AUGGAGUUC CUGUCUUC |
| 3290 | UUCUGGAA CUGAUGA X GAA ACAGGAAC | GUUCCUGUC UUCCAGAA |
| 3292 | CUUUCUGG CUGAUGA X GAA AGACAGGA | UCCUGUCUU CCAGAAAG |
| 3293 | ACUUUCUG CUGAUGA X GAA AAGACAGG | CCUGUCUUC CAGAAAGU |
| 3306 | UCCCGAUG CUGAUGA X GAA AUGCACUU | AAGUGCAUU CAUCGGGA |
| 3307 | GUCCCGAU CUGAUGA X GAA AAUGCACU | AGUGCAUUC AUCGGGAC |
| 3310 | CAGGUCCC CUGAUGA X GAA AUGAAUGC | GCAUUCAUC GGGACCUG |
| 3333 | GAUAAAAG CUGAUGA X GAA AUGUUUCU | AGAAACAUU CUUUUAUC |
| 3334 | AGAUAAAA CUGAUGA X GAA AAUGUUUC | GAAACAUUC UUUUAUCU |
| 3336 | UCAGAUAA CUGAUGA X GAA AGAAUGUU | AACAUUCUU UUAUCUGA |
| 3337 | CUCAGAUA CUGAUGA X GAA AAGAAUGU | ACAUUCUUU UAUCUGAG |
| 3338 | UCUCAGAU CUGAUGA X GAA AAAGAAUG | CAUUCUUUU AUCUGAGA |
| 3339 | UUCUCAGA CUGAUGA X GAA AAAAGAAU | AUUCUUUUA UCUGAGAA |
| 3341 | UGUUCUCA CUGAUGA X GAA AUAAAAGA | UCUUUUAUC UGAGAACA |
| 3363 | AAAUCACA CUGAUGA X GAA AUCUUCAC | GUGAAGAUU UGUGAUUU |
| 3364 | AAAAUCAC CUGAUGA X GAA AAUCUUCA | UGAAGAUUU GUGAUUUU |
| 3370 | AAGGCCAA CUGAUGA X GAA AUCACAAA | UUUGUGAUU UUGGCCUU |
| 3371 | CAAGGCCA CUGAUGA X GAA AAUCACAA | UUGUGAUUU UGGCCUUG |
| 3372 | GCAAGGCC CUGAUGA X GAA AAAUCACA | UGUGAUUUU GGCCUUGC |
| 3378 | UCUCUGGC CUGAUGA X GAA AGGCCAAA | UUUGGCCUU GCCCGGGA |
| 3388 | CUUAUAAA CUGAUGA X GAA AUCCCGGG | CCCGGGAUA UUUAUAAG |
| 3390 | UUCUUAUA CUGAUGA X GAA AUAUCCCG | CGGGAUAUU UAUAAGAA |
| 3391 | GUUCUUAU CUGAUGA X GAA AAUAUCCC | GGGAUAUUU AUAAGAAC |
| 3392 | GGUUCUGA CUGAUGA X GAA AAAUAUCC | GGAUAUUUA UAAGAACC |
| 3394 | GGGGUUCU CUGAUGA X GAA AUAAAUAU | AUAUUUAUA AGAACCCC |
| 3406 | UCUCACAU CUGAUGA X GAA AUCGGGGU | ACCCCGAUU AUGUGAGA |
| 3407 | UUCUCACA CUGAUGA X GAA AAUCGGGG | CCCCGAUUA UGUGAGAA |

TABLE II-continued

Human flt1 VEGF Receptor-Hammerhead Ribozyme and Substrate Sequence

| nt. Position | HH Ribozyme | Substrate |
|---|---|---|
| 3424 | AAGUCGAG CUGAUGA X GAA AUCUCCUU | AAGGAGAUA CUCGACUU |
| 3427 | AGGAAGUC CUGAUGA X GAA AGUAUCUC | GAGAUACUC GACUUCCU |
| 3432 | UUCAGAGG CUGAUGA X GAA AGUCGAGU | ACUCGACUU CCUCUGAA |
| 3433 | UUUCAGAG CUGAUGA X GAA AAGUCGAG | CUCGACUUC CUCUGAAA |
| 3436 | CCAUUUCA CUGAUGA X GAA AGGAAGUC | GACUUCCUC UGAAAUGG |
| 3451 | AGAUUCGG CUGAUGA X GAA AGCCAUUC | GGAUGGCUC CCGAAUCU |
| 3458 | CAAAGAUA CUGAUGA X GAA AUUCGGGA | UCCCGAAUC UAUCUUUG |
| 3460 | GUCAAAGA CUGAUGA X GAA AGAUUCUG | CCGAAUCUA UCUUUGAC |
| 3462 | UUGUCAAA CUGAUGA X GAA AUAGAUUC | GAAUCUAUC UUUGACAA |
| 3464 | UUUUGUCA CUGAUGA X GAA AGAUAGAU | AUCUAUCUU UGACAAAA |
| 3465 | AUUUUGUC CUGAUGA X GAA AAGAUAGA | UCUAUCUUU GACAAAAU |
| 3474 | GUGCUGUA CUGAUGA X GAA AUUUUGUC | GACAAAAUC UACAGCAC |
| 3476 | UGGUGCUG CUGAUGA X GAA AGAUUUUG | CAAAAUCUA CAGCACCA |
| 3500 | CUCCGUAA CUGAUGA X GAA ACCACACG | CGUGUGGUC UUACGGAG |
| 3502 | UACCCGU CUGAUGA X GAA AGACCACA | UGUGGUCUU ACGGAGUA |
| 3503 | AUACCCG CUGAUGA X GAA AAGACCAC | GUGGUCUUA CGGAGUAU |
| 3510 | CACAGCAA CUGAUGA X GAA ACUCCGUA | UACGGAGUA UUGCUGUG |
| 3512 | CCCACAGC CUGAUGA X GAA AUACUCCG | CGGAGUAUU GCUGUGGG |
| 3525 | AAGGAGAA CUGAUGA X GAA AUUUCCCA | UGGGAAAUC UUCUCCUU |
| 3527 | CUAAGGAG CUGAUGA X GAA AGAUUUCC | GGAAAUCUU CUCCUUAG |
| 3528 | CCUAAGGA CUGAUGA X GAA AAGAUUUC | GAAAUCUUC UCCUUAGG |
| 3530 | CAACUAAG CUGAUGA X GAA AGAAGAUU | AAUCUUCUC CUUAGGUG |
| 3533 | ACCCACCU CUGAUGA X GAA AGGAGAAG | CUUCUCCUU AGGUGGGU |
| 3534 | GACCCACC CUGAUGA X GAA AAGGAGAA | UUCUCCUUA GGUGGGUC |
| 3542 | GGUAUGGA CUGAUGA X GAA ACCCACCU | AGGUGGGUC UCCAUACC |
| 3544 | UGGGUAUG CUGAUGA X GAA AGACCCAC | GUGGGUCUC CAUACCCA |
| 3548 | CUCCUGGG CUGAUGA X GAA AUGGAGAC | GUCUCCAUA CCCAGGAG |
| 3558 | UCCAUUUG CUGAUGA X GAA ACUCCUGG | CCAGGAGUA CAAAUGGA |
| 3575 | GACUGCAA CUGAUGA X GAA AGUCCUCA | UGAGGACUU UUGCAGUC |
| 3576 | CGACUGCA CUGAUGA X GAA AAGUCCUC | GAGGACUUU UGCAGUCG |
| 3577 | GCGACUGC CUGAUGA X GAA AAAGUCCU | AGGACUUUU GCAGUCGC |
| 3583 | CCUCAGGC CUGAUGA X GAA ACUGCAAA | UUUGCAGUC GCCUGAGG |
| 3613 | GUACUCAG CUGAUGA X GAA AGCUCUCA | UGAGAGCUC CUGAGUAC |
| 3620 | GAGUAGAG CUGAUGA X GAA ACUCAGGA | UCCUGAGUA CUCUACUC |
| 3623 | CAGGAGUA CUGAUGA X GAA AGUCUCUC | UGAGUACUC UACUCCUG |
| 3625 | UUCAGGAG CUGAUGA X GAA AGAGUACU | AGUACUCUA CUCCUGAA |

TABLE II-continued

Human flt1 VEGF Receptor-Hammerhead Ribozyme and Substrate Sequence

| nt. Position | HH Ribozyme | Substrate |
|---|---|---|
| 3628 | GAUUUCAG CUGAUGA X GAA AGUAGAGU | ACUCUACUC CUGAAAUC |
| 3636 | AUCUGAUA CUGAUGA X GAA AUUUCAGG | CCUGAAAUC UAUCAGAU |
| 3638 | UGAUCUGA CUGAUGA X GAA AGAUUUCA | UGAAAUCUA UCAGAUCA |
| 3640 | CAUGAUCU CUGAUGA X GAA AUAGAUUU | AAAUCUAUC AGAUCAUG |
| 3645 | UCCAGCAU CUGAUGA X GAA AUCUGAUA | UAUCAGAUC AUGCUGGA |
| 3689 | GUUCUGCA CUGAUGA X GAA AUCUUGGC | GCCAAGAUU UGCAGAAC |
| 3690 | AGUUCUGC CUGAUGA X GAA AAUCUUGG | CCAAGAUUU GCAGAACU |
| 3699 | UUUUCCAC CUGAUGA X GAA AGUUCUGC | GCAGAACUU GUGGAAAA |
| 3711 | AAAUCACC CUGAUGA X GAA AGUUUUUC | GAAAAACUA GGUGAUUU |
| 3718 | UUGAAGCA CUGAUGA X GAA AUCACCUA | UAGGUGAUU UGCUUCAA |
| 3719 | CUUGAAGC CUGAUGA X GAA AAUCAGCU | AGGUGAUUU GCUUCAAG |
| 3723 | UUUGCUUG CUGAUGA X GAA AGCAAAUC | GAUUUGCUU CAAGCAAA |
| 3724 | AUUUGCUU CUGAUGA X GAA AAGCAAAU | AUUUGCUUC AAGCAAAU |
| 3735 | UCCUGUUG CUGAUGA X GAA ACAUUUGC | GCAAAUGUA CAACAGGA |
| 3748 | GUAGUCUU CUGAUGA X GAA ACCAUCCU | AGGAUGGUA AAGACUAC |
| 3755 | UUGGGAUG CUGAUGA X GAA AGUCUUUA | UAAAGACUA CAUCCCAA |
| 3759 | UUGAUUGG CUGAUGA X GAA AUGUAGUC | GACUACAUC CCAAUCAA |
| 3765 | AUGCCAUU CUGAUGA X GAA AUUGGGAU | AUCCCAAUC AAUGCCAU |
| 3774 | CCUGUCAG CUGAUGA X GAA AUGGCAUU | AAUGCCAUA CUGACAGG |
| 3787 | AAACCCAC CUGAUGA X GAA AUUUCCUG | CAGGAAAUA GUGGGUUU |
| 3794 | AGUAUGUA CUGAUGA X GAA ACCCACUA | UAGUGGGUU UACAUACU |
| 3795 | GAGUAUGU CUGAUGA X GAA AACCCACU | AGUGGGUUU ACAUACUC |
| 3796 | UCAGUAUG CUGAUGA X GAA AAACCCAC | GUGGGUUUA CAUACUCA |
| 3800 | GAGUUGAG CUGAUGA X GAA AUGUAAAC | GUUUACAUA CUCAACUC |
| 3803 | CAGGAGUU CUGAUGA X GAA AGUAUGUA | UACAUACUC ACCUCCUG |
| 3808 | GAAGGCAG CUGAUGA X GAA AGUUGAGU | ACUCAACUC CUGCCUUC |
| 3815 | CCUCAGAG CUGAUGA X GAA AGGCAGGA | UCCUGCCUU CUCUGAGG |
| 3816 | UCCUCAGA CUGAUGA X GAA AAGGCAGG | CCUGCCUUC UCUGAGGA |
| 3818 | AGUCCUCA CAGAUGA X GAA AGAAGGCA | UCCCUUCUC UGAGGACU |
| 3827 | CCUUGAAG CUGAUGA X GAA AGUCCUCA | AGAGGACUU CUUCAAGG |
| 3828 | UCCUUGAA CUGAUGA X GAA AAGUCCUC | GAGGACUUC UUCAAGGA |
| 3830 | UUUCCUUG CUGAUGA X GAA AGAAGUCC | GGACUUCUU CAAGGAAA |
| 3831 | CUUUCCUU CUGAUGA X GAA AAGAAGUC | GACUUCUUC AAGGAAAG |
| 3841 | AGCUGAAA CUGAUGA X GAA ACUUUCCU | AGGAAAGUA UUUCAGCU |
| 3843 | GGAGCUGA CUGAUGA X GAA AUACUUUC | GAAAGUAUU UCAGCUCC |
| 3844 | CGGAGCUG CUGAUGA X GAA AAUACUUU | AAAGUAUUU CAGCUCCG |
| 3845 | UCGGAGCU CUGAUGA X GAA AAAUACUU | AAGUAUUUC AGCUCCGA |

TABLE II-continued

Human flt1 VEGF Receptor-Hammerhead Ribozyme and Substrate Sequence

| nt. Position | HH Ribozyme | Substrate |
|---|---|---|
| 3850 | AAACUUCG CUGAUGA X GAA AGCUGAAA | UUUCAGCUC CGAAGUUU |
| 3857 | CUGAAUUA CUGAUGA X GAA ACUUCGGA | UCCGAAGUU UAAUUCAG |
| 3858 | CCUGAAUU CUGAUGA X GAA AACUUCGG | CCGAAGUUU AAUUCAGG |
| 3859 | UCCUGAAU CUGAUGA X GAA AAACUUCG | CGAAGUUUA AUUCAGGA |
| 3862 | GCUUCCUG CUGAUGA X GAA AUUAAACU | AGUUUAAUU CAGGAAGC |
| 3863 | AGCUUCCU CUGAUGA X GAA AAUUAAAC | GUUUAAUUC AGGAAGCU |
| 3872 | CAUCAUCA CUGAUGA X GAA AGCUUCCU | AGGAAGCUC UGAUGAUG |
| 3882 | ACAUAUCU CUGAUGA X GAA ACAUCAUC | GAUGAUGUC AGAUAUGU |
| 3887 | CAUUUACA CUGAUGA X GAA AUCUGACA | UGUCAGAUA UGUAAAUG |
| 3891 | AAAGCAUU CUGAUGA X GAA ACAUAUCU | AGAUAUGUA AAUGCUUU |
| 3898 | GAACUUGA CUGAUGA X GAA AGCAUUUA | UAAAUGCUU UCAAGUUC |
| 3899 | UGAACUUG CUGAUGA X GAA AAGCAUUU | AAAUGCUUU CAAGUUCA |
| 3900 | AUGAACUU CUGAUGA X GAA AAAGCAUU | AAUGCUUUC AAGUUCAU |
| 3905 | GGCUCAUG CUGAUGA X GAA ACUUGAAA | UUUCAAGUU CAUGAGCC |
| 3906 | AGGCUCAU CUGAUGA X GAA AACUUGAA | UUCAAGUUC AUGAGCCU |
| 3924 | AAGGUUUU CUGAUGA X GAA AUUCUUUC | GAAAGAAUC AAAACCUU |
| 3932 | GUUCUUCA CUGAUGA X GAA AGGUUUUG | CAAAACCUU UGAAGAAC |
| 3933 | AGUUCUUC CUGAUGA X GAA AAGGUUUU | AAAACCUUU GAAGAACU |
| 3942 | UUCGGUAA CUGAUGA X GAA AGUUCUUC | GAAGAACUU UUACCGAA |
| 3943 | AUUCGGUA CUGAUGA X GAA AAGUUCUU | AAGAACUUU UACGGAAU |
| 3944 | CAUUCGGU CUGAUGA X GAA AAAGUUCU | AGAACUUUU ACUGAAUG |
| 3945 | GCAUUCGG CUGAUGA X GAA AAAAGUUC | GAACUUUUA CCGAAUGC |
| 3959 | CAAACAUG CUGAUGA X GAA AGGUGGCA | UGCCAGCUC CAUGUUUG |
| 3965 | AGUCAUCA CUGAUGA X GAA ACAUGGAG | CUCCAUGUU UGAUGACU |
| 3966 | UAGUCAUC CUGAUGA X GAA AACAUGGA | UCCAUGUUU GAUGACUA |
| 3974 | CGCCCUGG CUGAUGA X GAA AGUCAUCA | UGAUGACUA CCAGGGCG |
| 3994 | GGCCAACA CUGAUGA X GAA AGUGCUGC | GCAGCACUC UGUUGGCC |
| 3998 | GAGAGGGC CUGAUGA X GAA ACAGAGUG | CACUCUGUU GGCCUCUC |
| 4004 | GCAUGGGA CUGAUGA X GAA AGGCCAAC | GUUGGCCUC UCCCAUGC |
| 4006 | CAGCAUGG CUGAUGA X GAA AGAGGCCA | UGGCCUCUC CCAUGCUG |
| 4022 | UCCAGGUG CUGAUGA X GAA AGCGUUCC | GAAGCGCUU CACCUGGA |
| 4023 | GUCCAGGU CUGAUGA X GAA AAGCGCUU | AAGCGCUUC ACCUGGAC |
| 4052 | UCUUGAGC CUGAUGA X GAA AGGCCUUG | CAAGGCCUC GCUCAAGA |
| 4056 | UCAAUCUU CUGAUGA X GAA AGCGAGGC | GCCUCGCUC AAGAUUGA |
| 4062 | CUCAAGUC CUGAUGA X GAA AUCUUGAG | CUCAAGAUU GACUUGAG |
| 4067 | UUACUCUC CUGAUGA X GAA AGUCAAUC | GAUUGACUU GAGAGUAA |

TABLE II-continued

Human flt1 VEGF Receptor-Hammerhead Ribozyme and Substrate Sequence

| nt. Position | HH Ribozyme | Substrate |
|---|---|---|
| 4074 | UUACUGGU CUGAUGA X GAA ACUCUCAA | UUGAGAGUA ACCAGUAA |
| 4081 | CUUACUUU CUGAUGA X GAA ACUGGUUA | UAACCAGUA AAAGUAAG |
| 4087 | CGACUCCU CUGAUGA X GAA ACUUUUAC | GUAAAAGUA AGGAGUCG |
| 4094 | ACAGCCCC CUGAUGA X GAA ACUCCUUA | UAAGGAGUC GGGGCUGU |
| 4103 | UGACAUCA CUGAUGA X GAA ACAGCCCC | GGGGCUGUC UGAUGUCA |
| 4110 | GGCCUGCU CUGAUGA X GAA ACAGCAGA | UCUGAUGUC AGCAGCUC |
| 4123 | AUGGCAGA CUGAUGA X GAA ACUGGGCC | GGGCCAGUU UCUGCCAU |
| 4124 | AAUGGCAG CUGAUGA X GAA AACUGGGC | GCCCAGUUU CUGCCAUU |
| 4125 | GAAUGGCA CUGAUGA X GAA AAACUGGG | CCCAGUUUC UGCCAUUC |
| 4132 | ACAGCUGG CUGAUGA X GAA AUGGCAGA | UCUGCCAUU CCAGCUGU |
| 4133 | CACAGCUG CUGAUGA X GAA AAUGGCAG | CUGCCAUUC CGGCUGUG |
| 4149 | CCUUCGCU CUGAUGA X GAA ACGUGCCC | GGGCACGUC AGCGAAGG |
| 4169 | CGUAGGUG CUGAUGA X GAA ACCUGGGC | GCGCAGGUU CACCUACG |
| 4170 | UCGUAGGU CUGAUGA X GAA AACCUGGG | CGCAGGUUC ACCUACGA |
| 4175 | CGUGGUCG CUGAUGA X GAA AGGUGAAC | GUUCACCUA CGACCACG |
| 4203 | CAGCACGC CUGAUGA X GAA AUUUUCUU | AGGAAAAUC GCGUGCUG |
| 4214 | GGGGCGGG CUGAUGA X GAA AGCAGCAC | GUGCUGCCC CCCGCCCC |
| 4229 | CCGAGUUG CUGAUGA X GAA AGUCUGGG | CCCAGACUA CAACUCGG |
| 4235 | GGACCACC CUGAUGA X GAA AGUUGUAG | CUACAACUC GGUGGUCC |
| 4242 | GAGUACAG CUGAUGA X GAA ACCACCGA | UCGGUGGUC CUGUACUC |
| 4247 | GGGUGGAG CUGAUGA X GAA ACAGGACC | GGUUCUGUA CUCCACCC |
| 4250 | GUGGGGUG CUGAUGA X GAA AGUACAGG | CCUGUACUC CACCCCAC |
| 4263 | AAACUCUA CUGAUGA X GAA AUGGGUGG | CCACCCAUC UAGAGUUU |
| 4265 | UCAAACUC CUGAUGA X GAA AGAUGGGU | ACCCAUCUA GAGUUUGA |
| 4270 | UCGUGUCA CUGAUGA X GAA ACUCUAGA | UCUAGAGUU UGACACGA |
| 4271 | UUCGUGUC CUGAUGA X GAA AACUCUAG | CUAGAGUUU GACACGAA |
| 4284 | CUAGAAAU CUGAUGA X GAA AGGCUUCG | CGAAGCCUU AUUUCUAG |
| 4285 | UCUAGAAA CUGAUGA X GAA AAGGCUUC | GAAGCCUUA UUUCUAGA |
| 4287 | CUUCUAGA CUGAUGA X GAA AUAAGGCU | AGCCUUAUU UCUAGAAG |
| 4288 | GCUUCUAG CUGAUGA X GAA AAUAAGGC | GCCUUAUUU CUAGAAGC |
| 4289 | UGCUUCUA CUGAUGA X GAA AAAUAAGG | CCUUAUUUC UAGAAGCA |
| 4291 | UGUGCUUC CUGAUGA X GAA AGAAAUAA | UUAUUUCUA GAAGCACA |
| 4305 | GGUAUAAA CUGAUGA X GAA ACACAUGU | ACAUGUGUA UUUAUACC |
| 4307 | GGGGUCUA CUGAUGA X GAA AUACACAU | AUGUGUAUU UAUACCCC |
| 4308 | GGGGGUAU CUGAUGA X GAA AAUACACA | UGUGUAUUU AUACCCCC |
| 4309 | UGGGGGUA CUGAUGA X GAA AAAUACAC | GUGUAUUUA UACCCCCA |
| 4311 | CCUGGGGG CUGAUGA X GAA AUAAAUAC | GUAUUUAUA CCCCCAGG |

TABLE II-continued

Human flt1 VEGF Receptor-Hammerhead Ribozyme and Substrate Sequence

| nt. Position | HH Ribozyme | Substrate |
|---|---|---|
| 4325 | GCAAAAGC CUGAUGA X GAA AGUUUCCU | AGGAAACUA GCUUUUGC |
| 4329 | ACUGGCAA CUGAUGA X GAA AGCUAGUU | AACUAGCUU UUGCCAGU |
| 4330 | UACUGGCA CUGAUGA X GAA AAACUAGU | ACUAGCUUU UGCCAGUA |
| 4331 | AUACUGGC CUGAUGA X GAA AAAGCUAG | CUAGCUUUU GCCAGUAU |
| 4338 | AUGCAUAA CUGAUGA X GAA ACUGGCAA | UUGCCAGUA UUAUGCAU |
| 4340 | AUAUGCAU CUGAUGA X GAA AUACUGGC | GCCAGUAUU AUGCAUAU |
| 4341 | UAUAUGCA CUGAUGA X GAA AAUACUCG | CCAGUAUUA UGCAUAUA |
| 4347 | AACUUAUA CUGAUGA X GAA AUGCAUAA | UUAUGCAUA UAUAAGUU |
| 4349 | UAAACUUA CUGAUGA X GAA AUAUGCAU | AUGCAUAUA UAAGUUUA |
| 4351 | UGUAAACU CUGAUGA X GAA AUAUAUGC | GCAUAUAUA AGUUUACA |
| 4355 | AACGUGUA CUGAUGA X GAA ACUUAUAU | AUAUAAGUU UACACCUU |
| 4356 | AAAGGUGU CUGAUGA X GAA AACUUAUA | UAUAAGUUU ACACCUUU |
| 4357 | UAAGGUG CUGAUGA X GAA AAACUUAU | AUAAGUUUA CACCUUUA |
| 4363 | GAAAGAUA CUGAUGA X GAA AGGUGUAA | UUACACCUU UAUCUUUC |
| 4364 | GGAAAGAU CUGAUGA X GAA AAGGUGUA | UACACCUUU AUCUUUCC |
| 4365 | UAGAAAGA CUGAUGA X GAA AAAGGUGU | ACACCUUUA UCUUUCCA |
| 4367 | CAUGGAAA CUGAUGA X GAA AUAAAGGU | ACCUUUAUC UUUCCAUG |
| 4369 | CCCAUGGA CUGAUGA X GAA AGAUAAAG | CUUUAUCUU UCCAUGGG |
| 4370 | UCCCAUGG CUGAUGA X GAA AAGAUAAA | UUUAUCUUU CCAUGCGA |
| 4371 | CUCCCAUG CUGAUGA X GAA AAAGAUAA | UUAUCUUUC CAUGGGAG |
| 4389 | AUCACAAA CUGAUGA X GAA AGCAGCUG | CAGCUGCUU UUUGUGAU |
| 4390 | AAUCACAA CUGAUGA X GAA AAGCAGCU | AGCUGCUUU UUGUGAUU |
| 4391 | AAAUCACA CUGAUGA X GAA AAAGCAGC | GCUGCUUUU UGUGAUUU |
| 4392 | AAAAUCAC CUGAUGA X GAA AAAAGCAG | CUGCUUUUU GUGAUUUU |
| 4398 | AUUAAAAA CUGAUGA X GAA AUCACAAA | UUUGUGAUU UUAAAAAU |
| 4399 | UAUUAAAA CUGAUGA X GAA AAUCACAA | UUGUGAUUU UUUUAAUA |
| 4400 | CUAUUAAA CUGAUGA X GAA AAAUCACA | UGUGAUUUU UUUAAUAG |
| 4401 | ACUAUUAA CUGAUGA X GAA AAAAUCAC | GUGAUUUUU UUAAUAGU |
| 4402 | CACUAUUA CUGAUGA X GAA AAAAACCA | UGAUUUUUU UAAUAGUG |
| 4403 | GCACUAUU CUGAUGA X GAA AAAAAAUC | GAUUUUUUU AAUAGUGC |
| 4404 | AGCACUAU CUGAUGA X GAA AAAAAAAU | AUUUUUUUA AUAGUGCU |
| 4407 | AAAAGCAC CUGAUGA X GAA AUUAAAAA | UUUUUAAUA GUGCUUUU |
| 4413 | AAAAAAAA CUGAUGA X GAA AGCACUAU | AUAGUGCUU UUUUUUUU |
| 4414 | AAAAAAAA CUGAUGA X GAA AAGCACAA | UAGUGCUUU UUUUUUUU |
| 4415 | CAAAAAAA CUGAUGA X GAA AAAGCACU | AGUGCUUUU UUUUUUUG |
| 4416 | UCAAAAAA CUGAUGA X GAA AAAAGCAC | GUGCUUUUU UUUUUUGA |

TABLE II-continued

Human flt1 VEGF Receptor-Hammerhead Ribozyme and Substrate Sequence

| nt. Position | HH Ribozyme | Substrate |
|---|---|---|
| 4417 | GUCAAAAA CUGAUGA X GAA AAAAAGCA | UGCUUUUUU UUUUUGAC |
| 4418 | AGUCAAAA CUGAUGA X GAA AAAAAAGC | GCUUUUUUU UUUUGACU |
| 4419 | UAGUCAAA CUGAUGA X GAA AAAAAAAG | CUUUUUUUU UUUGACUA |
| 4420 | UUAGUCAA CUGAUGA X GAA AAAAAAAA | UUUUUUUUU UUGACUAA |
| 4421 | GUUAGUCA CUGAUGA X GAA AAAAAAAA | UUUUUUUUU UGACUAAC |
| 4422 | UGUUAGUC CUGAUGA X GAA AAAAAAAA | UUUUUUUUU GACUAACA |
| 4427 | AUUCUUGU CUGAUGA X GAA ACUCAAAA | UUUUGACUA ACAAGAAU |
| 4438 | UCUGGAGU CUGAUGA X GAA ACAUUCUU | AAGAAUGUA ACUCCAGA |
| 4442 | UCUAUCUG CUGAUGA X GAA AGUUACAU | AUGUAACUC CAGAUAGA |
| 4448 | UAUUUCUC CUGAUGA X GAA AUCUGGAG | CUCCAGAUA GAGAAAUA |
| 4456 | CUUGUCAC CUGAUGA X GAA AUUUCUCU | AGAGAAAUA GUGACAAG |
| 4476 | UUUAGCAG CUGAUGA X GAA AGUGUUCU | AGAACACUA CUGCUAAA |
| 4482 | UGAGGAUU CUGAUGA X GAA AGCAGUAG | CUACUGCUA AAUCCUCA |
| 4486 | AACAUGAG CUGAUGA X GAA AUUUAGCA | UGCUAAAUC CUCAUGUU |
| 4489 | AGUAACAU CUGAUGA X GAA AGGAUUUA | UAAAUCCUC AUGUUACU |
| 4494 | CACUGAGU CUGAUGA X GAA ACAUGAGG | CCUCAUGUU ACUCAGUG |
| 4495 | ACACUGAG CUGAUGA X GAA AACAUGAG | CUCAUGUUA CUCAGUGU |
| 4498 | CUAACACU CUGAUGA X GAA AGUAACAU | AUGUUACUC AGUGUUAG |
| 4504 | AUUUCUCU CUGAUGA X GAA ACACUGAG | CUCAGUGUU AGAGAAAU |
| 4505 | GAUUUCUC CUGAUGA X GAA AACACUGA | UCAGUGUUA GAGAAAUC |
| 4513 | UUAGGAAG CUGAUGA X GAA AUUUCUCU | AGAGAAAUC CUUCCUAA |
| 4516 | GGUUUAGG CUGAUGA X GAA AGGAUUUC | GAAAUCCUU CCUAAACC |
| 4517 | GGGUUUGG CUGAUGA X GAA AAGGAUUU | AAAUCCUUC CUAAACCC |
| 4520 | AUUGGGUU CUGAUGA X GAA AGGAAGGA | UCCUUCCUA AACCCAAU |
| 4533 | GAGCAGGG CUGAUGA X GAA AGUCAUUG | CAAUGACUU CCCUGCUC |
| 4534 | GGAGCAGG CUGAUGA X GAA AAGUCAUU | AAUGACUUC CCUGCUCC |
| 4541 | GGGGGUUG CUGAUGA X GAA AGCAGGGA | UCCCUGCUC CAACCCCC |
| 4557 | CGUGCCCU CUGAUGA X GAA AGGUGCCG | CCCCACCUC AGGGCACG |
| 4576 | CUCAAUCA CUGAUGA X GAA ACUGGUCC | GGACCAGUU UGAUUGAG |
| 4577 | CCUCAAUC CUGAUGA X GAA AACUGGUC | GACCAGUUU GAUUGAGG |
| 4581 | AGCUCCUC CUGAUGA X GAA AUCAAACU | AGUUUGAUU GAGGAGCU |
| 4598 | CAUUGGGU CUGAUGA X GAA AUCAGUGC | GCACUGAUC ACCCAAUG |
| 4610 | GGGUACGU CUGAUGA X GAA AUGCAUUG | CAAUGCAUC ACGUACCC |
| 4615 | CAGUGGGG CUGAUGA X GAA ACGUGAUG | CAUCACGUA CCCCACUG |
| 4664 | CUGGGGCU CUGAUGA X GAA ACGGGCUU | AAGCCCGUU AGCCCAG |
| 4665 | CCUGGGGC CUGAUGA X GAA AACGGGCU | AGCCCGUUA GCCCCAGG |
| 4678 | CAGCCAGU CUGAUGA X GAA AUCCCCUG | CAGGGGAUC ACUGGCUG |

TABLE II-continued

Human flt1 VEGF Receptor-Hammerhead Ribozyme and Substrate Sequence

| nt. Position | HH Ribozyme | Substrate |
| --- | --- | --- |
| 4700 | ACUCCCGA CUGAUGA X GAA AUGUUGCU | AGCAACAUC UCGGGAGU |
| 4702 | GGACUCCC CUGAUGA X GAA AGAUGUUG | CAACAUCUC GGGAGUCC |
| 4709 | UGCUAGAG CUGAUGA X GAA ACUCCCGA | UCGGGAGUG CUCUAGCA |
| 4712 | GCCUCCCA CUGAUGA X GAA AGGACUCC | GGAGUCCUC UAGCAGGC |
| 4714 | AGGCCUGC CUGAUGA X GAA AGAGGACU | AGUCCUCUA GCAGGCCU |
| 4723 | ACAUGUCU CUGAUGA X GAA AGGCCUGC | GCAGGCCUA AGACAUGU |
| 4802 | GCGUCUCA CUGAUGA X GAA AUUCUUUC | GAAAGAAUU UGAGACGC |
| 4803 | UGCGUCUC CUGAUGA X GAA AAUUCUUU | AAAGAAUUU GAGACGCA |
| 4840 | GCAUUCCU CUGAUGA X GAA AGCCCCGU | ACGGGGCUC AGCAAUGC |
| 4852 | GCCACUGA CUGAUGA X GAA AUGGCAUU | AAUGCCAUU UCAGUGGC |
| 4853 | AGCCACUG CUGAUGA X GAA AAUGGCAU | AUGCCAUUU CAGUGGCU |
| 4854 | AAGCCACU CUGAUGA X GAA AAAUGGCA | UGCCAUUUC AGUGGCUU |
| 4862 | GAGCUGGG CUGAUGA X GAA AGCCACUG | CAGUGGCUU CCCAGCUC |
| 4863 | AGAGCUGG CUGAUGA X GAA AAGCCACU | AGUGGCUUC CCAGCUCU |
| 4870 | AAGGGUCA CUGAUGA X GAA AGCUGGGA | UCCCAGCUC UGACCCUU |
| 4878 | AAAUGUAG CUGAUGA X GAA AGGGUCAG | CUGACCCUU CUACAUUU |
| 4879 | CAAAUGUA CUGAUGA X GAA AAGGGUCA | UGACCCUUC UACAUUUG |
| 4881 | CUCAAAUG CUGAUGA X GAA AGAAGGGU | ACCCUUCUA CAUUUGAG |
| 4885 | GGCCCUCA CUGAUGA X GAA AUGUAGAA | UUCUACAUU UGAGGGCC |
| 4886 | GGGCCCUC CUGAUGA X GAA AAUGUAGA | UCUACAUUU GAGGGCCC |
| 4929 | AUCCAGAA CUGAUGA X GAA AUGUCCCC | GGGGACAUU UUCUGGAU |
| 4930 | AAUCCAGA CUGAUGA X GAA AAUGUCCC | GGGACAUUU UCUGGAUU |
| 4931 | GAAUCCAG CUGAUGA X GAA AAAUGUCC | GGACAUUUU CUGGAUUC |
| 4932 | AGAAUCCA CUGAUGA X GAA AAAAUGUC | GACAUUUUC UGGAUUCU |
| 4938 | CCUCCCAG CUGAUGA X GAA AUCCAGAA | UUCUGGAUU CUGGGAGG |
| 4939 | GCCUCCCA CUGAUGA X GAA AAUCCAGA | UCUGGAUUC UGGGAGGC |
| 4963 | AAAAAAGA CUGAUGA X GAA AUUUGUCC | GGACAAAUA UCUUUUUU |
| 4965 | CCAAAAAA CUGAUGA X GAA AUAUUUGU | ACAAAUAUC UUUUUUGG |
| 4967 | UUCCAAAA CUGAUGA X GAA AGAUAUUU | AAAUAUCUU UUUUGGAA |
| 4968 | GUUCCAAA CUGAUGA X GAA AAGAUAUU | AAUAUCUUU UUUGGAAC |
| 4969 | AGUUCCAA CUGAUGA X GAA AAAGAUAU | AUUUCUUUU UUGGAACU |
| 4970 | UAGUUCCA CUGAUGA X GAA AAAAGAUA | UAUCUUUUU UGGAACUA |
| 4971 | UUAGUUCC CUGAUGA X GAA AAAAAGAU | AUCUUUUUU GGAACGAA |
| 4978 | AUUUGCUU CUGAUGA X GAA AGUUCCAA | UUGGAACUA AAGCAAAU |
| 4987 | AGGUCUAA CUGAUGA X GAA AUUUGUU | AAGCAAAUU UUAGACCU |
| 4988 | AAGGUCUA CUGAUGA X GAA AAUUUGCU | AGCAAAUUU UAGACCUU |

TABLE II-continued

Human flt1 VEGF Receptor-Hammerhead Ribozyme and Substrate Sequence

| nt. Position | HH Ribozyme | Substrate |
|---|---|---|
| 4989 | AAAGGUCU CUGAUGA X GAA AAAUUUGC | GCAAAUUUU AGACCUUU |
| 4990 | UAAAGGUC CUGAUGA X GAA AAAAUUUG | CAAAUUUUA GACCUUUA |
| 4996 | CAUAGGUA CUGAUGA X GAA AGGUCUAA | UUAGACCUU UACCUAUG |
| 4997 | CCAUAGGU CUGAUGA X GAA AAGGUCUA | UAGACCUUU ACCUAUGG |
| 4998 | UCCAUAGG CUGAUGA X GAA AAAGGUCU | AGACCUUUA CCUAUGGA |
| 5002 | CACUUCCA CUGAUGA X GAA AGGUAAAG | CUUUACCUA UGGAAGUG |
| 5013 | GGACAUAG CUGAUGA X GAA ACCACUUC | GAAGUGGUU CUAUGUCC |
| 5014 | UGGACAUA CUGAUGA X GAA AACCACUU | AAGUGGUUC UAUGUCCA |
| 5016 | AAUGGACA CUGAUGA X GAA AGAACCAC | GUGGUUCUA UGUCCAUU |
| 5020 | UGAGAAUG CUGAUGA X GAA ACAUAGAA | UUCUAUGUC CAUUCUCA |
| 5024 | GGAAUGAG CUGAUGA X GAA AUGGACAU | AUGUCCAUU CUCAUUCG |
| 5025 | ACGAAUGA CUGAUGA X GAA AAUGGACA | UGUCCAUUC UCAUUCGU |
| 5027 | CCACGAAU CUGAUGA X GAA AGAAUCGA | UCCAUUCUC AUUCGUGG |
| 5030 | AUGCCACG CUGAUGA X GAA AUGAGAAU | AUUCUCAUU CGUGGCAU |
| 5031 | CAUGCCAC CUGAUGA X GAA AUGAGAA | UUCUCAUUC GUGGCAUG |
| 5041 | CAAAUCAA CUGAUGA X GAA ACAUGCCA | UGGCAUGUU UUGAUUUG |
| 5042 | ACAAAUCA CUGAUGA X GAA AACAUGCC | GGCAUGUUU UGAUUUCU |
| 5043 | UACAAAUC CUGAUGA X GAA AAACAUGC | GCAUGUUUU GAUUUGUA |
| 5047 | GUUCUACA CUGAUGA X GAA AUCAAAAC | GUUUUGAUU UGUAGCAC |
| 5048 | AGUGCUAC CUGAUGA X GAA AAUCAAAA | UUUUGAUUU GUAGCACU |
| 5051 | CUCAGUGC CUGAUGA X GAA ACAAAUCA | UGAUUUGUA GCACUGAG |
| 5069 | UCAGAGUU CUGAUGA X GAA AGUGCCAC | GUGGCACUC AACUCUGA |
| 5074 | UGGGCUCA CUGAUGA X GAA AGUUGAGU | ACUCAACUC UGAGCCCA |
| 5084 | GCCAAAAG CUGAUGA X GAA AUGGGCUC | GAGCCCAUA CUUUUGGC |
| 5087 | GGAGCCAA CUGAUGA X GAA AGUAUGGG | CCCAUACUU UUGGCUCC |
| 5088 | AGGAGCCA CUGAUGA X GAA AAGUAUGG | CCAUACUUU UGGCUCCU |
| 5089 | GAGGAGCC CUGAUGA X GAA AAAGUAUG | CAUACUUUU GGCUCCUC |
| 5094 | UACUAGAG CUGAUGA X GAA AGCCAAAA | UUUUGGCUC CUCUAGUA |
| 5097 | UCUUACUA CUGAUGA X GAA AGGAGCCA | UGGCUCCUC UAGUAAGA |
| 5099 | CAUCUUAC CUGAUGA X GAA AGAGGAGC | GCUCCUCUA GUAAGAUG |
| 5102 | GUGCAUCU CUGAUGA X GAA ACUAGAGG | CCUCUAGUA AGAUGCAC |
| 5119 | CUCUGGCU CUGAUGA X GAA AGUUUUCA | UGAAAACUU AGCCAGAG |
| 5120 | ACUCUGGC CUGAUGA X GAA AAGUUUUC | GAAAACUUA GCCAGAGU |
| 5129 | GACAACCU CUGAUGA X GAA ACUCUGGC | GCCAGAGUU AGGUUGUC |
| 5130 | AGACAACC CUGAUGA X GAA AACUCUGG | CCAGAGUUA GGUUGUCU |
| 5134 | CUGGAGAC CUGAUGA X GAA ACCUAACU | AGUUAGGUU GUCUCCAG |
| 5137 | GGCCUGGA CUGAUGA X GAA ACAACCUA | UAGGUUGUC UCCAGGCC |

TABLE II-continued

Human flt1 VEGF Receptor-Hammerhead Ribozyme and Substrate Sequence

| nt. Position | HH Ribozyme | Substrate |
|---|---|---|
| 5139 | AUGGCCUG CUGAUGA X GAA AGACAACC | GGUUGUCUC CAGGCCAU |
| 5156 | UUCAGUGU CUGAUGA X GAA AUGCCAUC | GAUGGCCUU ACACUGAA |
| 5157 | UUUCAGUG CUGAUGA X GAA AAGGCCAU | AUGGCUUUA CACUGAAA |
| 5170 | UAGAAUGU CUGAUGA X GAA ACAUUUUC | GAAAAUGUC ACAUUCUA |
| 5175 | CAAAAUAG CUGAUGA X GAA AUGUGACA | UGUCACAUU CUAUUUUG |
| 5176 | CCAAAAUA CUGAUGA X GAA AAUGUGAC | GCCACAUUC UAUUUUGG |
| 5178 | ACCCAAAA CUGAUGA X GAA AGAAUGUG | CACAUUCUA UUUUGGGU |
| 5180 | AUACCCAA CUGAUGA X GAA AUAGAAUG | CAUUCAUUU UUGGGUAU |
| 5181 | AAUACCCA CUGAUGA X GAA AAUAGAAU | AUUCUAUUU UGGGUAUU |
| 5182 | UAAUACCC CUGAUGA X GAA AAAUAGAA | UUCUAUUUU GGGUAUUA |
| 5187 | UAUAUUAA CUGAUGA X GAA ACCCAAAA | UUUUGGGUA UUAAUAUA |
| 5189 | UAUAUAUU CUGAUGA X GAA AUACCCAA | UUGGGUAUU AAUAUAUA |
| 5190 | CUAUAUAU CUGAUGA X GAA AAUACCCA | UGGGUAUUA AUAUAUAG |
| 5193 | GGACUAUA CUGAUGA X GAA AUUAAUAC | GUAUUAAUA UAUAGUCC |
| 5195 | CUGGACUA CUGAUGA X GAA AUAUUAAU | AUUAAUAUA UAGUCCAG |
| 5197 | GUCUGGAC CUGAUGA X GAA AUAUAUUA | UAAUAUAUA GUCCAGAC |
| 5200 | AGUCUCUG CUGAUGA X GAA ACUAUAUA | UAUAUAGUC CAGACACU |
| 5209 | AUUGAGUU CUGAUGA X GAA AGUGUCUG | CAGACACUU AACUCAAU |
| 5210 | AAUUGAGU CUGAUGA X GAA AAGAGUCU | AGACACUUA ACUCAAUU |
| 5214 | AAGAAAUU CUGAUGA X GAA AGUUAAGU | ACUUAACUC AAUUUCUU |
| 5218 | UACCAAGA CUGAUGA X GAA AUUAAGUU | AACUCAAUU UCUUGGUA |
| 5219 | AUACCAAG CUGAUGA X GAA AAUUGAGU | ACUCAAUUU CUUGGUAU |
| 5220 | AAUACCAA CUGAUGA X GAA AAAAUAAG | CUCAAUUUC UUGGUAUU |
| 5222 | AUAAUACC CUGAUGA X GAA AGAAAUUG | CAAUUUCUU GGUAUUAU |
| 5226 | CAGAAUAA CUGAUGA X GAA ACCAAGAA | UUCUUGGUA UUAUUCUG |
| 5228 | AACAGAAU CUGAUGA X GAA AUACCAAG | CUUGGUAUU AUUCUGUU |
| 5229 | AAACAGAA CUGAUGA X GAA AAUACCAA | UUGGUAUUA UUCUGUUU |
| 5231 | CAAACAG CUGAUGA X GAA AUAAUACC | GGUAUUAUU CUGUUUUG |
| 5232 | GCAAAACA CUGAUGA X GAA AAUAAUAC | GUAUUAUUC UGUUUUGC |
| 5236 | CUGUGCAA CUGAUGA X GAA ACAGAAUA | UAUUCUGUU UUGCACAG |
| 5237 | ACUGUGCA CUGAUGA X GAA AACAGAAU | AUUCUGUUU UGCACAGU |
| 5238 | AACUGUGC CUGAUGA X GAA AAACAGAA | UUCUGUUUU UCACAGUU |
| 5246 | UCACAACU CUGAUGA X GAA ACUGUGCA | UGCACAGUU AGUUGUGA |
| 5247 | UUCACAAC CUGAUGA X GAA AACUGUGC | GCACGUUCA GUUGUGAA |
| 5250 | UCUUUCAC CUGAUGA X GAA ACUUACUG | CAGUUAGUU GUGAAAGA |
| 5284 | CUCCUCAG CUGAUGA X GAA ACUGCAUU | AAUGCAGUC CUGAGGAG |

TABLE II-continued

Human flt1 VEGF Receptor-Hammerhead Ribozyme and Substrate Sequence

| nt. Position | HH Ribozyme | Substrate |
|---|---|---|
| 5296 | AUGGAGAA CUGAUGA X GAA ACUCUCCU | AGGAGAGUU UUCUCCAU |
| 5297 | UAUGGAGA CUGAUGA X GAA AACUCUCC | GGAGAGUUU UCUCCUUA |
| 5298 | AUAUGGAG CUGAUGA X GAA AAACUCUC | GAGAGUUUU CUCCAUAU |
| 5299 | GAUAUGGA CUGAUGA X GAA AAAACUCU | AGAGUUUUC UCCAUAUC |
| 5301 | UUGAUAUG CUGAUGA X GAA AGAAAACU | AGUUUCUC CAUAUCAA |
| 5305 | CGUUUUGA CUGAUGA X GAA AUGGAGAA | UUCUCCACA UCAAAACG |
| 5307 | CUCGUUUU CUGAUGA X GAA AUAUUGAG | CUCCAUAUC AAAACGAG |
| 5336 | ACCUUAUU CUGAUGA X GAA ACCUUUUU | AAAAAGGUC AAUAAGGU |
| 5340 | CUUGACCU CUGAUGA X GAA AUUGACCU | AGGUCAAUA AGGUCAAG |
| 5345 | CUUCCCUU CUGAUGA X GAA ACCUUAUU | AAUAAGGUC AAGGGAAG |
| 5361 | GGUAUAGA CUGAUGA X GAA ACGGGUC | GACCCCGUC UCUAUACC |
| 5363 | UUGGUAUA CUGAUGA X GAA AGACGGGG | CCCCGUCUC UAUACCAA |
| 5365 | GGUUGGUA CUGAUGA X GAA AGAGACGG | CCGUCUCCA UACCAACC |
| 5367 | UUGGUUGG CUGAUGA X GAA AUAGAGAC | GUCUCUAUA CCAACCAA |
| 5382 | UGUUGGUG CUGAUGA X GAA AUUGGUUU | AAACCAAUU CACCAACA |
| 5383 | GUGUUGGU CUGAUGA X GAA AAUUGGUU | AACCAAUUC ACCAACAC |
| 5395 | UGGGUCCC CUGAUGA X GAA ACUGUGUU | AACACAGUU GGGACCCA |
| 5417 | ACGUGACU CUGAUGA X GAA ACUUCCUG | CAGGAAGUC AGUCACGU |
| 5421 | GGAAACGU CUGAUGA X GAA ACUGACUU | AAGUCAGUC ACGUUUCC |
| 5426 | GAAAAGGA CUGAUGA X GAA ACGUGACU | AGUCACGUU UCCUUUUC |
| 5427 | UGAAAAGG CUGAUGA X GAA AACGUGAC | GUCACGUUU CCUUUUCA |
| 5428 | AGGAAAAG CUGAUGA X GAA AAACGUGA | UCACGUUUC CUUUUCAU |
| 5431 | UAAUGAA CUGAUGA X GAA AGGAAACG | CGUUUCCUU UUCAUUUA |
| 5432 | UUAAAUGA CUGAUGA X GAA AAGGAAAC | GUUUCCUUU UCAUUUAA |
| 5433 | AUUAAAUG CUGAUGA X GAA AAAGGAAA | UUUCCUUUU CAUUUAAU |
| 5434 | CAUUAAAU CUGAUGA X GAA AAAAGGAA | UUCCUUUUC AUUUAUUG |
| 5437 | CCCCAUUA CUGAUGA X GAA AUGAAAAG | CUUUUCAUU UAAUGGGG |
| 5438 | UCCCCAUU CUGAUGA X GAA AAUGAAAA | UUUUCAUUU AAUGGGGA |
| 5439 | AUCCCCAU CUGAUGA X GAA AAAUGAAA | UUUCAUUUA AUGGGGAU |
| 5448 | GAUAGUGG CUGAUGA X GAA AUCCCCAU | AUGGGGAUU CCACUAUC |
| 5449 | AGAUAGUG CUGAUGA X GAA AAUCCCCA | UGGGGAUUC CACUAUCU |
| 5454 | GUGUGAGA CUGAUGA X GAA AGUGGAAU | AUUCCACUA UCUCACAC |
| 5456 | UAGUGUGA CUGAUGA X GAA AUAGUGGA | UCCACUAUC UCACACUA |
| 5458 | AUUAGUGU CUGAUGA X GAA AGAUAGUG | CACUAUCUC ACACUAAU |
| 5464 | UUUCAGAU CUGAUGA X GAA AGUGUGAG | CUCACACUA AUCUGAAA |
| 5467 | UCCUUUCA CUGAUGA X GAA AUUAGUGU | ACACUAAUC UAAAAGGA |
| 5489 | CGCCAGCU CUGAUGA X GAA AUGCUCUU | AAGAGCAUU AGCUGGCG |

TABLE II-continued

Human flt1 VEGF Receptor-Hammerhead Ribozyme and Substrate Sequence

| nt. Position | HH Ribozyme | Substrate |
|---|---|---|
| 5490 | GCGCCAGC CUGAUGA X GAA AAUGCUCU | AGAGCAUUA GCUGGCGC |
| 5501 | GUCCUGAA CUGAUGA X GAA AUGCGCCA | UGGCGCAUA UUAACCAC |
| 5503 | AAGUGCUU CUGAUGA X GAA AUAUGCGC | GCGCAUAUU AAGCACUU |
| 5504 | AAAGUGCU CUGAUGA X GAA AAUAUGCG | CGCAUAUUA AGCACUUU |
| 5511 | GGAGCUGA CUGAUGA X GAA AGUGCUUA | UAAGCACUU UAAGCUCC |
| 5512 | AGGAGCUU CUGAUGA X GAA AAGUGCUU | AAGGACUUU AAGCUCCU |
| 5513 | AAGGAGCU CUGAUGA X GAA AAAGUGCU | AGCACUUUA AGCUCCUU |
| 5518 | UAGUCAAG CUGAUGA X GAA AGCUUAAA | UUUAAGCUC CUUGAGUA |
| 5521 | UUUUACUC CUGAUGA X GAA AGGAGCUU | AAGCUCCUU GAGUAAAA |
| 5526 | CACCUUUU CUGAUGA X GAA ACUCAAGG | CCUUGAGUA AAAAGGUG |
| 5537 | AAAUUACA CUGAUGA X GAA ACCAGCUU | AAGGUGGUA UGUAAUUU |
| 5541 | GCACAAAU CUGAUGA X GAA AGAAACCA | UGGUAUGUA AUUUAUGC |
| 5544 | CUUGCACA CUGAUGA X GAA AUUACAUA | UAUGUAAUU UAUGCAAG |
| 5545 | CCUUGCAU CUGAUGA X GAA AAUUACAU | AUGUAAUUU AUGCAAGG |
| 5546 | ACCUUGCA CUGAUGA X GAA AAAUUACA | UGUAAUUUA UGCAAGGU |
| 5555 | UGGAGAAA CUGAUGA X GAA ACCUUGCA | UGCAAGGUA UUUCUCCA |
| 5557 | ACUGGAGA CUGAUGA X GAA AUACCUUG | CAAGGUAUU UCUCCAGU |
| 5558 | AACUGGAG CUGAUGA X GAA AAUACCUU | AAGGAAUUU CUCCAGUU |
| 5559 | CAACUGGA CUGAUGA X GAA AAAUACCU | AGGUAUUUC UCCAGUUG |
| 5561 | CCCAACUG CUGAUGA X GAA AGAAAUAC | GUAUUUCUC CAGUUGGG |
| 5566 | UGAGUCCC CUGAUGA X GAA ACUGGAGA | UCUCCAGUU GGGACUCA |
| 5573 | AAUAUCCU CUGAUGA X GAA AGUCCCAA | UUGGGACUC AGGAUAUU |
| 5579 | UUAACUAA CUGAUGA X GAA AUCCUGAG | CUCAGGACA UUAGUUAA |
| 5581 | CAUUAACU CUGAUGA X GAA AUAUCCUG | CAGGAUAUU AGUUAAUG |
| 5582 | UCAUUAAC CUGAUGA X GAA AAUAUCCU | AGGAUAUUA GUUAAUGA |
| 5585 | GGCUCAUU CUGAUGA X GAA ACUAAUAU | AUAUUAGUU AAUGAGCC |
| 5586 | UGGCUCAU CUGAUGA X GAA AACUAAUA | UAUUAGUUA AUGAGCCA |
| 5596 | CUUCUAGU CUGAUGA X GAA AUGGCUCA | UGAGCCAUC ACCAGAAG |
| 5600 | UUUUCUUC CUGAUGA X GAA AGUGAUGG | CCAUCACUA GAAGAAAA |
| 5615 | CAGUUGAA CUGAUGA X GAA AUGGGCUU | AAGCCCAUU UUCAACUG |
| 5616 | GCAGUUGA CUGAUGA X GAA AAUGGGCU | AGCCCAUUU UCAACUGC |
| 5617 | AGCAGUUG CUGAUGA X GAA AAAUGGGC | GCCCAUUUU CAACUCCU |
| 5618 | AAGCAGUU CUGAUGA X GAA AAAAUCGG | CCCAUUUUC AACUGCUU |
| 5626 | AAGUUUCA CUGAUGA X GAA AGCACUUG | CAACUGCUU UGAAACUU |
| 5627 | CAAGUUUC CUGAUGA X GAA AAGCAGUU | AACUGCUUU GAAACUUG |
| 5634 | CCCCAGGC CUGAUGA X GAA AGUUUCAA | UUGAAACUU GCCUGGGG |

TABLE II-continued

Human flt1 VEGF Receptor-Hammerhead Ribozyme and Substrate Sequence

| nt. Position | HH Ribozyme | Substrate |
|---|---|---|
| 5644 | CAUGCUCA CUGAUGA X GAA ACCCCACG | CCUGGGUC UGAGCAUG |
| 5661 | UGUCUCCC CUGAUGA X GAA AUUCCCAU | AUGGGAAUA GGGAGACA |
| 5674 | CCCUUUCC CUGAUGA X GAA ACCCUGUC | GACAGGGUA GGAAACGG |
| 5688 | CUGAAGAG CUGAUGA X GAA AGGCGCCC | GGGCGCCUA CUCUUCAG |
| 5691 | ACCCUGAA CUGAUGA X GAA AGUAGGCG | CCCCUACUC UUCAGGGU |
| 5693 | AGACCCUG CUGAUGA X GAA AGAGUAGG | CCUACUCUU CAGGGUCU |
| 5694 | UAGACCCU CUGAUGA X GAA AAGAGUAG | CUACUCUUC AGGGUCUA |
| 5700 | GAUCUUUA CUGAUGA X GAA ACCCUGAA | UUCAGGGUC UAAAGAUC |
| 5702 | UUGAUCUU CUGAUGA X GAA AGACCCUG | CAGGGUCAA AAGAUCAA |
| 5708 | GCCCACUU CUGAUGA X GAA AUCUUUAG | CUAAAGAUC AAGUGGGC |
| 5719 | AGCGAUCC CUGAUGA X GAA AGGCCCAC | GUGGGCCUU GGAUCGCU |
| 5724 | AGCUUAGC CUGAUGA X GAA AUCCAAGG | CCUUGGAUC GCUAAGCU |
| 5728 | AGCCAGCU CUGAUGA X GAA ACCGAUCC | GGAUCGCUA AGCUGGCU |
| 5737 | AUCAAACA CUGAUGA X GAA AGCCAGCU | AGCUGGCUC UGUUUGAU |
| 5741 | UAGCAUCA CUGAUGA X GAA ACGAAGCC | GGCUCUGUU UGAUGCUA |
| 5742 | AUAGCAUC CUGAUGA X GAA AACAGAGC | CCUCUGUUU GAUGCUAU |
| 5749 | UGCAUAAA CUGAUGA X GAA AGCAUCAA | UUGAUGCUA UUUAUGCA |
| 5751 | CUUGCAUA CUGAUGA X GAA AUAGCAUC | GAUGCUAUU UAUGCAAG |
| 5752 | ACUUGCAU CUGAUGA X GAA AAUAGCAU | AUGCUAUUU AUGCAAGU |
| 5753 | AACUUGCA CUGAUGA X GAA AAAUAGCA | UGCUAUUUA UGCAAGUU |
| 5761 | UAGACCCU CUGAUGA X GAA ACUUGCAU | AUGCAAGUU AGGGUCCA |
| 5762 | AUAGACCC CUGAUGA X GAA AACAAGCA | UGCAAGUUA GGGUCUAU |
| 5767 | AAUACAAA CUGAUGA X GAA ACCCUAAC | GUUAGGGUC UAUGUAUU |
| 5769 | UAAAUACA CUGAUGA X GAA AGACCCUA | UAGGGUCUA UGUAUUUA |
| 5773 | AUCCUAAA CUGAUGA X GAA ACAUAGAC | GUCUAUGUA UUUAGGAU |
| 5775 | GCAUCCUA CUGAUGA X GAA AUACAUAG | CUAUGUAUU UAGGAUGC |
| 5776 | CGCAUCCU CUGAUGA X GAA AAUACAUA | UAUGUAUUU AGGAUGCG |
| 5777 | GCGCAUCC CUGAUGA X GAA AAAUACAU | AUGUAUUUA GGAUGCGC |
| 5788 | CUGAAGAG CUGAUGA X GAA AGGCGCAU | AUGCGCCUA CUCUUCAG |
| 5791 | ACCCUGAA CUGAUGA X GAA AGUACGGG | CGCCUACUC UUCAGGGU |
| 5793 | AGACCCUG CUGAUGA X GAA AGAGUAGG | CCUACUCUU CAGGGUCU |
| 5794 | UAGACCCU CUGAUGA X GAA AACAGUAG | CUACUCUUC AGGCUCCA |
| 5800 | GAUCUUUA CUGAUGA X GAA ACCCUGAA | UUCAGGGUC UAAAGAUC |
| 5802 | UUGAUCUU CUGAUGA X GAA AGACCCUG | CAGGGUCUA AAGAUCAA |
| 5808 | GCCCACUU CUGAUGA X GAA AUCUUUAG | CUAAAGAUC AAGUGGGC |
| 5819 | AGCGAUCC CUGAUGA X GAA AGGCCCAC | GUGGGCCUU GGAUCGCU |
| 5824 | AGCUUAGC CUGAUGA X GAA AUCCAAGG | CCUUGGAUC GCUAAGCU |

TABLE II-continued

Human flt1 VEGF Receptor-Hammerhead Ribozyme and Substrate Sequence

| nt. Position | HH Ribozyme | Substrate |
|---|---|---|
| 5828 | AGCCAGCU CUGAUGA X GAA AGCGAUCC | GGAUCGCUA AGCUGGCU |
| 5837 | AUCAAACA CUGAUGA X GAA AGCCAGCU | AGCUGGCUC UGUUUGAU |
| 5841 | UAGCAUCA CUGAUGA X GAA ACAGAGCC | GGCUCUGUU UGAUGCUA |
| 5842 | AUAGCAUC CUGAUGA X GAA AACAGACC | GCUCUGUUU GAUGCUAU |
| 5849 | UGCAUAAA CUGAUGA X GAA AGCAUCAA | UUGAUGCUA UUUAUGCA |
| 5851 | CUUGCAUA CUGAUGA X GAA AUAGCAUC | GAUGCUAUU UAUGCAAG |
| 5852 | ACUUGCAU CUGAUGA X GAA AAUAGCAU | AUGCUAUUU AUGCAAGU |
| 5853 | AACUUGCA CUGAUGA X GAA AAAUAGCA | UUGCAUUUA UGCAAGUU |
| 5861 | UAGACCCU CUGAUGA X GAA ACUUUCAU | AUGCAAGUU AGGGUCUA |
| 5862 | AUAGACCC CUGAUGA X GAA AACUUGCA | UGCAAGUUA GGGUCUAU |
| 5867 | AAUACAUA CUGAUGA X GAA ACCCUAAC | GUUAGGGUC UAUGUAUU |
| 5869 | UAAAUACA CUGAUGA X GAA AGACCCUA | UAGGGUCUA UGUAUUUA |
| 5873 | AUCCUAAA CUGAUGA X GAA ACAUAGAC | GUCUAUGUA UUUAGGAU |
| 5875 | ACAUCCUA CUGAUGA X GAA AUACAUAG | CUAUGUAUU UAGGAUGU |
| 5876 | GACAUCCU CUGAUGA X GAA AAUACAUA | UAUGUAUUU AGGAUGUC |
| 5877 | AGACAUCC CUGAUGA X GAA AAAUACAU | AUGUAUUUA GGAUGUCU |
| 5884 | AAGGUGCA CUGAUGA X GAA ACAUCCUA | UAGGAUGUC UGCACCUU |
| 5892 | GGCUGCAG CUGAUGA X GAA AGGUGCAG | CUGCACCUU CUGCAGCC |
| 5893 | UGGCUGCA CUGAUGA X GAA AAGGUGCA | UGCACCUUC UGCAGCCA |
| 5904 | CAGCUUCU CUGAUGA X GAA ACUGGCUG | CAGCCAGUC AGAAGCUG |
| 5930 | CAAGCAGC CUGAUGA X GAA AUCCACUG | CAGUGGAUU GCUGCUUC |
| 5937 | UCCCCAAG CUGAUGA X GAA AGCAGCAA | UUGCUGCUU CUUUGGGA |
| 5938 | CUCCCCAA CUGAUGA X GAA AAGCAGCA | UGCUGCUUC UUGGGGAG |
| 5940 | UUCUCCCC CUGAUGA X GAA AGAAGCAG | CUGCUUCUU GGGGAGAA |
| 5953 | AGGAAGCA CUGAUGA X GAA ACUCUUCU | AGAAGAGUA UGCUUCCU |
| 5958 | AUAAAAGG CUGAUGA X GAA AGCAAACU | AGGAUCCUU CCUUUUAU |
| 5959 | GAUAAAAG CUGAUGA X GAA AAGCAUAC | GUAUGCUUC AUUUUAUC |
| 5962 | AUGGAUAA CUGAUGA X GAA AGGAAGCA | UGCUUCCUU UUAUCCAU |
| 5963 | CAUGGAUA CUGAUGA X GAA AAGGAAGC | GCUUCCUUU UAUCCAUG |
| 5964 | ACAUGGAU CUGAUGA X GAA AAAGGAAG | CUUCCUUUU AUCCAUGU |
| 5965 | UACAUGGA CUGAUGA X GAA AAAAGGAA | UUCCUUUUA UCCAUGUA |
| 5967 | AUUACAUG CUGAUGA X GAA AUAAAAGG | CCUUUUAUC CAUGUAAU |
| 5973 | AGUUSSSU CUGAUGA X GAA ACAUGGAU | AUCCAUGUA AUUUAACU |
| 5976 | UACAGUUA CUGAUGA X GAA AUUACAUG | CAUGUAAUU UUACUGUA |
| 5977 | CUACACUU CUGAUGA X GAA AAUUACAU | AUGUAAUUU AACUGUAG |
| 5978 | UCUACAGU CUGAUGA X GAA AAAUUACA | UGUAAUUUA ACUGUAGA |

TABLE II-continued

Human flt1 VEGF Receptor-Hammerhead Ribozyme and Substrate Sequence

| nt. Position | HH Ribozyme | Substrate |
|---|---|---|
| 5984 | UCAGGUUC CUGAUGA X GAA ACACUUAA | UUAACUGUA GAACCUGA |
| 5996 | GUUACUUA CUGAUGA X GAA ACCUCAGG | CCUCAGCUC UAAGUAAC |
| 5998 | CGGUUACU CUGAUGA X GAA AGAGCUCA | UCAGCUCUA AGUAACCG |
| 6002 | UCUUCGGU CUGAUGA X GAA ACUUAGAG | CUCUAAGUA ACCGAAGA |
| 6015 | CAGAGGCA CUGAUGA X GAA ACAUUCUU | AAGAAUGUA UGCCUCUG |
| 6021 | UAAGAACA CUGAUGA X GAA AGGCAUAC | GUAUGCCUC UGUUCUUA |
| 6025 | CACAUAAG CUGAUGA X GAA ACAGAGGC | GCCUCUGUU CUUAUGUG |
| 6026 | GCACAUCA CUGAUGA X GAA AACAGAGG | CCUCUGUUC UUAUUUGC |
| 6028 | UGGCACAU CUGAUGA X GAA AGAACAGA | UCUGUUCUU AUGUGCCA |
| 6029 | GUGCCACA CUGAUGA X GAA AAGAACAG | CUGUUCUUA UGUGCCAC |
| 6040 | UAAACAAG CUGAUGA X GAA AUGUGGCA | UGCCACAUC CUUGUUUA |
| 6043 | CUUUAAAC CUGAUGA X GAA AGGAUGUG | CACAUCCUU GUUUAAAG |
| 6046 | AGCCUUCA CUGAUGA X GAA ACAAGGAU | AUCCUUGUU UAAGGCU |
| 6047 | GAGCCUUU CUGAUGA X GAA AACAAGGA | UCCUUGUUU AAAGGCUC |
| 6048 | AGAGCCUU CUGAUGA X GAA AAACAAGG | CCUUGUUUA AAGGCUCU |
| 6055 | CAUACAGA CUGAUGA X GAA ACCCUUUA | UAAAGGCUC UCUGUAUG |
| 6057 | UUCAUACA CUGAUGA X GAA AGAGCCUU | AAGGCUCUC UGUAUGAA |
| 6061 | UCUCUUCA CUGAUGA X GAA ACAGAGAG | CUCUCUCUA UGAAGAGA |
| 6079 | GUGCUGAU CUGAUGA X GAA ACCCUCCC | GGGACCGUC AUCAGCAC |
| 6082 | AAUGUGCU CUGAUGA X GAA AUGACGGU | ACCGUCAUC AGCACAUU |
| 6090 | CACUAGGG CUGAUGA X GAA AUGUGCUG | CAGCACAUU CCCUAGUG |
| 6091 | UCACUAGG CUGAUGA X GAA AAUGUGCU | AGCACAUUC CCUAGUGA |
| 6095 | AGGCUCAC CUGAUGA X GAA AGGGAAUG | CAUUCCCCA GUGAGCCU |
| 6104 | GGAGCCAG CUGAUGA X GAA AGGCUCAC | GUGAGCCUA CUGGCUCC |
| 6111 | GCUGCCAG CUGAUGA X GAA AGCCAGGA | UACUGGCUC CUGGCAGC |
| 6124 | UUCCACAA CUGAUGA X GAA AGCCGCUG | CAGCGGCUU UGUGGAA |
| 6125 | CUUCCACA CUGAUGA X GAA AAGCCGCU | AGCGGCUUU UGUCGAAG |
| 6126 | UCUUCCAC CUGAUGA X GAA AAAGCCGC | GCGGCUUUU GGGAAGA |
| 6137 | UGGCUAGU CUGAUGA X GAA AGUCUUCC | GGAAGACUC ACUAGCCA |
| 6141 | CUUCUGGC CUGAUGA X GAA AGUGAGUC | GACUCACUA GCCAGAAG |
| 6166 | GUGGAGAG CUGAUGA X GAA ACUGUCCC | GGGACAGUC CUCUCCAC |
| 6169 | UUGGUGGA CUGAUGA X GAA AGGACUGU | ACAGUCCUC UCCACCAA |
| 6171 | UCUUGGUG CUGAUGA X GAA AGAGGACU | AGUCCUCUC CACCAAGA |
| 6181 | UGGAUUUA CUGAUGA X GAA AUCUUGGU | ACCAAGAUC UAAAUCCA |
| 6183 | UUUCGAUU CUGAUGA X GAA AGGUCUUG | CAAGACUCA AAUCCAAA |
| 6187 | UUUGUUUG CUGAUGA X GAA AUUUAGAU | AUCUAAAUC CAAACAAA |
| 6204 | UCUGGCUC CUGAUGA X GAA AGCCUGCU | AGCAGGCUA GAGCCAGA |

TABLE II-continued

Human flt1 VEGF Receptor-Hammerhead Ribozyme and Substrate Sequence

| nt. Position | HH Ribozyme | Substrate |
|---|---|---|
| 6226 | ACAACAAA CUGAUGA X GAA AUUUGUCC | GGACAAAUC UUUGUUGU |
| 6228 | GAACAACA CUGAUGA X GAA AGAUUUGU | ACAAAUCUU UGUUGUUC |
| 6229 | GGAACAAC CUGAUGA X GAA AAGAUUUG | CAAAUCUUU GUUGUUCC |
| 6232 | AGAGGAAC CUGAUGA X GAA ACAAAGAU | AUCUUUGUU GUUCCUCU |
| 6235 | AGAAGAGG CUGAUGA X GAA ACAACAAA | UUUGUUGUU CCUCUUCU |
| 6236 | AAGAAGAG CUGAUGA X GAA AACAACAA | UUGUUGUUC CUCUUCUU |
| 6239 | GUAAAGAA CUGAUGA X GAA AGGAACAA | UUGUUCCUC UUCUUUAC |
| 6241 | GUGUAAAG CUGAUGA X GAA AGAGGAAC | GUUCCUCUU CUUUACAC |
| 6242 | UGUGUAAA CUGAUGA X GAA AAGAGGAA | UUCCUCUUC UUUACACA |
| 6244 | UAUGUAAA CUGAUGA X GAA AGAAGAGG | CCUCUUCUU UACACACA |
| 6245 | GUAUGUGU CUGAUGA X GAA AAGAAGAG | CUCUUCUUU ACACAUAC |
| 6246 | CGUAUGUG CUGAUGA X GAA AAAGAAGA | UCUUCUUUA CACAUACG |
| 6252 | GGUUUGCG CUGAUGA X GAA AUGUGUAA | UUACACAUA CGCAAACC |
| 6280 | AUUUAUAA CUGAUGA X GAA AUUGCCAG | CUGGCAAUU UUAUAAAU |
| 6281 | GAUUUAUA CUGAUGA X GAA AAUUGCCA | UGGCAAUUU UAUAAAUC |
| 6282 | UGAUUUAU CUGAUGA X GAA AAAUUGCC | GGCAAUUUU AUAAACCA |
| 6283 | CUGAUUUA CUGAUGA X GAA AAAAUUGC | GCAAUUUUA UAAAUCAG |
| 6285 | ACCUGAUU CUGAUGA X GAA AUAAAAUU | AAUUUUAUA AAUCAGGU |
| 6289 | AGUUACCU CUGAUGA X GAA AUUUAUAA | UUAUAAAUC AGGUAACU |
| 6294 | CUUCCAGU CUGAUGA X GAA ACCUGAUU | AAUCAGGUA ACUGGAAG |
| 6308 | CUGAGUUU CUGAUGA X GAA ACCUCCUU | AAGGAGGUU AAACUCAG |
| 6309 | UCUGAGUU CUGAUGA X GAA AACCUCCU | AGGAGGUUA AACUCAGA |
| 6314 | UUUUUUCU CUGAUGA X GAA AGUUUAAC | GUUAAACUC AGAAAAAA |
| 6331 | AAUUGACU CUGAUGA X GAA AGGUCUUC | GAAGACCUC AGUCAAUU |
| 6335 | AGAGAAUU CUGAUGA X GAA ACUGACGU | ACCUCAGUC AAUUCUCU |
| 6339 | AAGUAGAG CUGAUGA X GAA AUUGACUG | CAGUCAAUU CUCUACUU |
| 6340 | AAAGUAGA CUGAUGA X GAA AAUUGACU | AGUCAAUUC UCUACUUU |
| 6342 | AAAAGUA CUGAUGA X GAA AGAAUUGA | UCAAUUCUC UACUUUUU |
| 6344 | AAAAAAG CUGAUGA X GAA AGAGAAUU | AAUUCUCUA CUUUUUUU |
| 6347 | AAAAAAAA CUGAUGA X GAA AGUAGAGA | UCUCUACUU UUUUUUUU |
| 6348 | AAAAAAAA CUGAUGA X GAA AAGUAGAG | CUCUACUUU UUUUUUUU |
| 6349 | AAAAAAAA CUGAUGA X GAA AAAGUAGA | UCUACUUUU UUUUUUUU |
| 6350 | AAAAAAAA CUGAUGA X GAA AAAAGUAG | CUACUUUUU UUUUUUUU |
| 6351 | AAAAAAAA CUGAUGA X GAA AAAAAGUA | UACUUUUUU UUUUUUUU |
| 6352 | AAAAAAAA CUGAUGA X GAA AAAAAAGU | ACUUUUUUU UUUUUUUU |
| 6353 | AAAAAAAA CUGAUGA X GAA AAAAAAAG | CUUUUUUUU UUUUUUUU |

TABLE II-continued

Human flt1 VEGF Receptor-Hammerhead Ribozyme and Substrate Sequence

| nt. Position | HH Ribozyme | Substrate |
|---|---|---|
| 6354 | GAAAAAAA CUGAUGA X GAA AAAAAAA | UUUUUUUUU UUUUUUUC |
| 6355 | GGAAAAAA CUGAUGA X GAA AAAAAAA | UUUUUUUUU UUUUUUCC |
| 6356 | UGGAAAAA CUGAUGA X GAA AAAAAAA | UUUUUUUUU UUUUUCCA |
| 6357 | UUGGAAAA CUGAUGA X GAA AAAAAAA | UUUUUUUUU UUUUCCAA |
| 6358 | UUUGGAAA CUGAUGA X GAA AAAAAAA | UUUUUUUUU UUUCCAAA |
| 6359 | AUUUGGAA CUGAUGA X GAA AAAAAAA | UUUUUUUUU UUCCAAAU |
| 6360 | GAUUUGGA CUGAUGA X GAA AAAAAAA | UUUUUUUUU UCCAAAUC |
| 6361 | UGAUUUGG CUGAUGA X GAA AAAAAAA | UUUUUUUUU CCAAAUCA |
| 6362 | CUGAUUUG CUGAUGA X GAA AAAAAAA | UUUUUUUUC CAAAUCAG |
| 6368 | UAUUAUCU CUGAUGA X GAA AUUUGGAA | UUCCAAAUC AGAUAAUA |
| 6373 | UGGGCUAU CUGAUGA X GAA AUCUGAUU | AAUCAGAUA AUAGCCCA |
| 6376 | UGCUGGGC CUGAUGA X GAA AUUAUCUG | CAGAUAAUA GCCCAGCA |
| 6388 | GUUAUCAC CUGAUGA X GAA AUUUGCUG | CAGCAAAUA GUGAUAAC |
| 6394 | UUAUUUGU CUGAUGA X GAA AUCACUUU | AUAGUGAUA ACAAAUAA |
| 6401 | UAAGGUUU CUGAUGA X GAA AUUUGUUA | UAACAAAUA AAACCUUA |
| 6408 | GAACAGCU CUGAUGA X GAA AGGUUUUA | UAAAACCUU AGCUGUUC |
| 6409 | UGAACAGC CUGAUGA X GAA AAGGUUUU | AAAACCUUA GCUGUUCA |
| 6415 | AAGACAUG CUGAUGA X GAA ACAGCUAA | UUAGCUGUU CAUGUCUU |
| 6416 | CAAGACAU CUGAUGA X GAA AACAGCUA | UAGCUGUUC AUGUCUUG |
| 6421 | GAAAUCAA CUGAUGA X GAA ACAUGAAC | GUUCAUGUC UUGAUUUC |
| 6423 | UUGAAAUC CUGAUGA X GAA AGACAUGA | UCAUGUCUU GAUUUCAA |
| 6427 | AUUAUUGA CUGAUGA X GAA AUGAAGAC | GUCUUGAUU UCAAUAAU |
| 6428 | AAUUAUUG CUGAUGA X GAA AAUCAAGA | UCUUGAUUU CAAUAAUU |
| 6429 | UAAUUAUU CUGAUGA X GAA AAAUCAAG | CUUGAUUUC AAUAAUUA |
| 6433 | GAAUUAAU CUGAUGA X GAA AUUGAAAU | AUUUCAAUA AUUAAUUC |
| 6436 | UAAGAAUU CUGAUGA X GAA AUUAUUGA | UCAAUAAUU AAUUCUUA |
| 6437 | UUAAGAAU CUGAUGA X GAA AAUUAUUG | CAAUAAUUA AUUCUUAA |
| 6440 | UGAUUAAG CUGAUGA X GAA AUUAAUUA | UAAUUAAUU CUUAAUCA |
| 6441 | AUGAUUAA CUGAUGA X GAA AAUUAAUU | AAUUAAUUC UUAAUCAU |
| 6443 | UAAUGAUU CUGAUGA X GAA AGAAUUAA | UUAAUUCUU AAUCAUUA |
| 6444 | UUAAUGAU CUGAUGA X GAA AAGAAUUA | UAAUUCUUA AUCAUUAA |
| 6447 | CUCUUAAU CUGAUGA X GAA AUUAAGAA | UUCUUAAUC AUUAAGAG |
| 6450 | GGUCUCUU CUGAUGA X GAA AUGAUUAA | UUAAUCAUU AAGAGACC |
| 6451 | UGGUCUCU CUGAUGA X GAA AAUGAUUA | UAAUCAUUA AGAGACCA |
| 6461 | GUAUUUAU CUGAUGA X GAA AUGGUCUC | GAGACCAUA AUAAAUAC |
| 6464 | GGAGUAUU CUGAUGA X GAA AUUAUGGU | ACCAUAAUA AAUACUCC |
| 6468 | AAAAGGAG CUGAUGA X GAA AUUUAUUA | UAAUAAAUA CUCCUUUU |

TABLE II-continued

Human flt1 VEGF Receptor-Hammerhead Ribozyme and Substrate Sequence

| nt. Position | HH Ribozyme | Substrate |
|---|---|---|
| 6471 | UGGAAAAG CUGAUGA X GAA AGUAUUUA | UAAAUACUC CUUUUCAA |
| 6474 | CUCUUGAA CUGAUGA X GAA AGGAGUAU | AUACCCUU UUCAAGAG |
| 6475 | UCUCUUGA CUGAUGA X GAA AAGGAGUA | UACUCCUUU UAAGAGA |
| 6476 | UUCUCUUG CUGAUGA X GAA AAAGGAGU | ACUCCUUUU CAAGAGAA |
| 6477 | UUUCUCUU CUGAUGA X GAA AAAAGGAG | CUCUUUUUC AAGAGAAA |
| 6497 | ACAAUUCU CUGAUGA X GAA AUGGUUUU | AAAACCAUU AGAAUUGU |
| 6498 | AACAAUUC CUGAUGA X GAA AAUGGUUU | AAACCAUUA GAAUUGUU |
| 6503 | UGAGUAAC CUGAUGA X GAA AUUCUAAU | AUUAGAAUU GUUACUCA |
| 6506 | AGCUGAGU CUGAUGA X GAA ACAAUUCU | AGAAUUGUU ACUCAGCU |
| 6507 | GAGCUGAG CUGAUGA X GAA AACAAUUC | GAAUUGUUA CUCAGCUC |
| 6510 | AAGGAGCU CUGAUGA X GAA AGUAACAA | UUGUUACUC AGCUCCUU |
| 6515 | GUUUGAAG CUGAUGA X GAA AGCUGAGU | ACUCAGCUC CUUCAAAC |
| 6518 | UGAGUUUG CUGAUGA X GAA AGGAGCUG | CAGCUCCUU CAAACUCA |
| 6519 | CUGAGUUU CUGAUGA X GAA AAGGAGCU | AGCUCCUUC AAACUCAG |
| 6525 | ACAAACCU CUGAUGA X GAA AGUUUGAA | UUCAAACUC AGGUUUGU |
| 6530 | AUGCUACA CUGAUGA X GAA ACCUGAGU | ACUCAGGUU UGUAGCAU |
| 6531 | UAUGCUAC CUGAUGA X GAA AACCUGAG | CUCAGGUUU GUAGCAUA |
| 6534 | AUGUAUGC CUGAUGA X GAA ACAAACCU | AGGUUUGUA GCAUACAU |
| 6539 | GACUCAUG CUGAUGA X GAA AUGCUACA | UGUAGCAUA CAUGAGUC |
| 6547 | GAAGGAUG CUGAUGA X GAA ACUCAUGU | ACAUGAGUC CAUCCAUC |
| 6551 | GACUGAUG CUGAUGA X GAA AUGGACUC | GAGUCCAUC CAUCAGUC |
| 6555 | CUUUGACU CUGAUGA X GAA AUGGAUGG | CCAUCCAUC AGUCAAAG |
| 6559 | CAUUCUUU CUGAUGA X GAA ACUGAUGG | CCAUCAGUC AAAGAAUG |
| 6570 | CCAGAUGG CUGAUGA X GAA ACCAUUCU | AGAAUGGUU CCAUCUGG |
| 6571 | UCCAGAUG CUGAUGA X GAA AACCAUUC | GAAUGGUUC CAUCUGGA |
| 6575 | AGACUCCA CUGAUGA X GAA AUGGAACC | GGUUCCAUC UGGAGUCU |
| 6582 | UACAUUAA CUGAUGA X GAA ACUCCAGA | UCUGGAGUC UUAAUGUA |
| 6584 | UCUACAUU CUGAUGA X GAA AGACUCCA | UGGAGUCUU AAUGUAGA |
| 6585 | UUCUACAU CUGAUGA X GAA AAGACUCC | GGAGUCUUA AUGUAGAA |
| 6590 | UUUCUUUC CUGAUGA X GAA ACAUUAAG | CUUAAUGUA GAAAGAAA |
| 6609 | AUUAUUAC CUGAUGA X GAA AGUCUCCA | UGGAGACUU GUAAUAAU |
| 6612 | CUCAUUUU CUGAUGA X GAA ACAAGUCU | AGACUUGUA AUAAUGAG |
| 6615 | UAGCUCAU CUGAUGA X GAA AUUACAAG | CUUGUAAUA AUGAGCUA |
| 6623 | UUUGUAAC CUGAUGA X GAA AGCUCAUU | AAUGAGCUA GUUACAAA |
| 6626 | CACUUUGU CUGAUGA X GAA ACUAGCUC | GAGCUAGUU ACAAAGUG |
| 6627 | GCACUUUG CUGAUGA X GAA AACUAGCU | AGCUAGUUA CAAAGUGC |

TABLE II-continued

Human flt1 VEGF Receptor-Hammerhead Ribozyme and Substrate Sequence

| nt. Position | HH Ribozyme | Substrate |
|---|---|---|
| 6637 | UAAUGAAC CUGAUGA X GAA AGCACUUU | AAAGUGCUU GUUCAUUA |
| 6640 | UUUUAAUG CUGAUGA X GAA ACAAGCAC | GUGCUUGUU CAUUAAAA |
| 6641 | AUUUUAAU CUGAUGA X GAA AACAAGCA | UGCUUGUUC AUUAAAAU |
| 6644 | GCUAUUUU CUGAUGA X GAA AUGAACAA | UUGUUCAUU AAAAUAGC |
| 6645 | UGCUAUUU CUGAUGA X GAA AAUGAACA | UGUUCAUUA AAAUAGCA |
| 6650 | UUCAGUGC CUGAUGA X GAA AUUUUAUU | AUUAAAAUA GCACUGAA |
| 6662 | CAUGUUUC CUGAUGA X GAA AUUUUCAG | CUGAAAAUU GAAACAUG |
| 6674 | UAUCAGUU CUGAUGA X GAA AUUCAUGU | ACAUGAAUU AACUGAUA |
| 6675 | UUAUCAGU CUGAUGA X GAA AAUUCAUG | CAUGAAUUA ACUGAUAA |
| 6682 | UGGAAUAU CUGAUGA X GAA AUCAGUUA | UAACUGAUA AUAUUCCA |
| 6685 | GAUUGGAA CUGAUGA X GAA AUUAUCAG | CUGAUAAUA UUCCAAUC |
| 6687 | AUGAUUGG CUGAUGA X GAA AUAUUAUC | GAUAAUAUU CCAAUCAU |
| 6688 | AAUGAUUG CUGAUGA X GAA AAUAUUAU | AUAAUAUUC CAAUCAUU |
| 6693 | UGGCAAAU CUGAUGA X GAA AUUGGAAU | AUUCCAAUC AUUUGCCA |
| 6696 | AAAUGGCA CUGAUGA X GAA AUGAUUGG | CCAAUCAUU UGCCAUUU |
| 6697 | UAAAUGGC CUGAUGA X GAA AAUGAUUG | CAAUCAUUU GCCAUUUA |
| 6703 | UUGUCAUA CUGAUGA X GAA AUGGCAAA | UUUGCCAUU UAUGACAA |
| 6704 | UUUGUCAU CUGAUGA X GAA AAUGGCAA | UUGCCAUUU AUGACAAA |
| 6705 | UUUUGCCA CUGAUGA X GAA AAAUGGCA | UGCCAUUUA UGACAAAA |
| 6719 | UUAGUGCC CUGAUGA X GAA ACCAUUUU | AAAAUGGUU CCCACUAA |
| 6726 | UUCUUUGU CUGAUGA X GAA AGUGCCAA | UUGGCACUA ACAAAGAA |
| 6743 | CUGAAAGG CUGAUGA X GAA AGUGCUCG | CGAGCACUU CCUUUCAG |
| 6744 | UCUGAAAG CUGAUGA X GAA AAGUGCUC | GAGCACUUC CUUUCAGA |
| 6747 | AACUCUGA CUGAUGA X GAA AGGAAGUG | CACUUCCUU UCAGAGUU |
| 6748 | AAACUCUG CUGAUGA X GAA AAGGAAGU | ACUUCCUUU CAGACUUU |
| 6749 | GAAACCCU CUGAUGA X GAA AAACGAAG | CUCCUUUUC AGAGUUUC |
| 6755 | AUCUCAGA CUGAUGA X GAA ACUCUGAA | UUCAGAGUU UCUGACAU |
| 6756 | UAUCUCAG CUGAUGA X GAA AACUCUGA | UCAGAGUUU CUGAGAUA |
| 6757 | UUAUCUCA CUGAUGA X GAA AAACUCUG | CAGAGUUUC UGAGAUAA |
| 6764 | ACGUACAU CUGAUGA X GAA AUCUCAGA | UCUGAGAAA AUGUACGU |
| 6769 | GUUCCACG CUGAUGA X GAA ACAUUAUC | GAUAAUGUA CGUGCAAC |
| 6781 | UCCACCCA CUGAUGA X GAA ACUGUUCC | GGAACAGUC UGGGUGGA |
| 6814 | AAGACACA CUGAUGA X GAA ACUUGCAC | GUGCAACUC UGUGUCUU |
| 6820 | ACUGACAA CUGAUGA X GAA ACACAGAC | GUCUGUGUC UUGUCAGU |
| 6822 | GGACUGAC CUGAUGA X GAA AGACACAG | CUGUGUCUU GUCAGUCC |
| 6825 | CUUGGACU CUGAUGA X GAA ACAAACCA | UGUCUUGUC AGUCCAAG |
| 6829 | ACUUCUUG CUGAUGA X GAA ACUGACAA | UUGUCAGUC CAAGAAGU |

TABLE II-continued

Human flt1 VEGF Receptor-Hammerhead Ribozyme and Substrate Sequence

| nt. Position | HH Ribozyme | Substrate |
|---|---|---|
| 6851 | CUAAAAUU CUGAUGA X GAA ACAUCUCG | CGAGAUGUU AAUUUUAG |
| 6852 | CCUAAAAU CUGAUGA X GAA AACAUCCC | GAGAUGUUA AUUUUAGG |
| 6855 | GUCCCUAA CUGAUGA X GAA AUUAACAU | AUGUUAAUU UUAGGGAC |
| 6856 | GGUCCCUA CUGAUGA X GAA AAUUAACA | UGUUAAUUU UAGGGACC |
| 6857 | GGGUCCCU CUGAUGA X GAA AAAUUAAC | GUUAAUUUU AGGGACCC |
| 6858 | CGGGUCCC CUGAUGA X GAA AAAAUUAA | UUAAUUUUA GGGACCCG |
| 6872 | UAGGGAAC CUGAUGA X GAA AGGCACGG | CCGUGCCUU GUUUCCUA |
| 6875 | GGCUAGGA CUGAUGA X GAA ACAACGCA | UGCCUUGUU UCCUAGCC |
| 6876 | GGGCUAGG CUGAUGA X GAA AACAAGGC | GCCUUGUUU CCUAGCCC |
| 6877 | UGGGCUAG CUGAUGA X GAA AAACAAGG | CCUUGUUUC CUCGCCCA |
| 6880 | UUGUGGGC CUGAUGA X GAA AGGAAACA | UGUUCCUA GCCCACAA |
| 6901 | AUCUGUUU CUGAUGA X GAA AUGUUUGC | GCAAACAUC AAACAGAU |
| 6910 | CUAGCGAG CUGAUGA X GAA AUCUGUUU | AAACAGAUA CUCGCUAG |
| 6913 | AGGCUAGC CUGAUGA X GAA AGUGUCUC | CAGAUACUC GCUAGCCU |
| 6917 | AAUGAGGC CUGAUGA X GAA AGCGAGUA | UACUCGCUA GCCUCAUU |
| 6922 | AUUUAAAU CUGAUGA X GAA AGGCUAGC | GCUAGCCUC AUUUAAAU |
| 6925 | UCAAUUUA CUGAUGA X GAA AUGAGGCU | AGCCUCAUU UAAAUUGA |
| 6926 | AUCAAUUU CUGAUGA X GAA AAUGAGGC | GCCUCAUUU AAAUUGAU |
| 6927 | AAUCAAUU CUGAUGA X GAA AAAUGAGG | CCUCAUUUA AAUUGAUU |
| 6931 | CUUUAAUC CUGAUGA X GAA AUUUAAAU | AUUUAAAUU GAUUAAAG |
| 6935 | CCUCCUUU CUGAUGA X GAA AUCAAUUU | AAAUUGAUU AAAGGAGG |
| 6936 | UCCUCCUU CUGAUGA X GAA AAUCAAUU | AAUUGAUUA AAGGAGGA |
| 6951 | CGGCCAAA CUGAUGA X GAA AAGCACUC | GAGUGCAUC UUUGGCCG |
| 6953 | GUCGGCCA CUGAUGA X GAA AGAUGCAC | GUGCAUCUU UGGCCGAC |
| 6954 | UGUCGGCC CUGAUGA X GAA AAGAUGCA | UGCAUCUUU GGCCGACA |
| 6970 | CACACAGU CUGAUGA X GAA ACACCACU | AGUGGUGUA ACUGUGUG |
| 7026 | AACACACA CUGAUGA X GAA ACACCCAC | GUGGGUGUA UGUGUGUU |
| 7034 | AUGCACAA CUGAUGA X GAA ACACACAU | AUGUGUGUU UUGUGCAU |
| 7035 | UAUGCACA CUGAUGA X GAA AACACACA | UGUGUGUUU UGUGCAUA |
| 7036 | UAUGCACA CUGAUGA X GAA AAACACAC | GUGUGUUUU GUGCAUAA |
| 7043 | UAAAUAGU CUGAUGA X GAA AUGCACAA | UUGUGCAUA ACUAUUUA |
| 7047 | UCCUUAAA CUGAUGA X GAA AGUUAUGC | GCAUAACUA UUUAAGGA |
| 7049 | UUUCCUUA CUGAUGA X GAA AUAGUGAU | AUAACUAUU UAGGAAA |
| 7050 | GUUUCCUU CUGAUGA X GAA AAUAGUUA | UAACUAUUU AGGGAAAC |
| 7051 | AGUUUCCU CUGAUGA X GAA AAAUAGUU | AACCAUUUA AAGAAACU |
| 7065 | AACUUUAA CUGAUGA X GAA AUUCCAGU | ACUGGAAUU UUAAGUU |

TABLE II-continued

Human flt1 VEGF Receptor-Hammerhead Ribozyme and Substrate Sequence

| nt. Position | HH Ribozyme | Substrate |
|---|---|---|
| 7066 | UAACUUAA CUGAUGA X GAA AAUUCCAG | CUGGAAUUU UAAAGUUA |
| 7067 | GUAACUUU CUGAUGA X GAA AAAUUCCA | UGGAAUUUU AAAGUUAC |
| 7068 | AGGAACUU CUGAUGA X GAA AAAAUUCC | GGAAUUUUA AAGUUACU |
| 7073 | AUAAAAGU CUGAUGA X GAA ACUUUAAA | UUUAAAGUU ACUUUUAU |
| 7074 | UAUAAAAG CUGAUGA X GAA AACUUUAA | UUAAAGUUA CUUUUAUA |
| 7077 | UUGUAUAA CUGAUGA X GAA AGUAACUU | AAGUUACUU UUAUACAA |
| 7078 | UUUGUAUA CUGAUGA X GAA AAGUAACU | AGUUACUUU UAUACAAA |
| 7079 | GUUUGUAU CUGAUGA X GAA AAAGUAAC | GUUACUUUU AUACAAAC |
| 7080 | GGUUUGUA CUGAUGA X GAA AAAAGUAA | UUACUUUUA UACAAACC |
| 7082 | UUGGUUUG CUGAUGA X GAA AUAAAAGU | ACUUUCAUA CAAACCAA |
| 7095 | GUAGCUUA CUGAUGA X GAA AUUCUUGG | CCAAGAAUA UAUGCUAC |
| 7097 | CUGUAGCA CUGAUGA X GAA AUAUUCUU | AAGAAUAUA UGCUACAG |
| 7102 | UAUAUCUG CUGAUGA X GAA AGCAUAUA | UAUAUGCUA CAGAUAUA |
| 7108 | CUGUCUUA CUGAUGA X GAA AUCUGUAG | CUACAGAUA UAAGACAG |
| 7110 | GCCUGUCU CUGAUGA X GAA AUAUCUGU | ACAGAUAUA AGACAGAC |
| 7124 | UAGGACCA CUGAUGA X GAA ACCAUGCC | GACAUGGUU UGGUCCUA |
| 7125 | AUAGGACC CUGAUGA X GAA AACCAUGU | ACAUGGUUU GCUCUUAU |
| 7129 | AAAUAUAG CUGAUGA X GAA ACCAAACC | GGUUUGGUC CUAUAUUU |
| 7132 | UAGAAAUA CUGAUGA X GAA AGGACCAA | UUGGUCCUA UAUUUCUA |
| 7134 | ACUAGAAA CUGAUGA X GAA AUAGGACC | GGUCCUAUA UUUCUAGU |
| 7136 | UGACUAGA CUGAUGA X GAA AUAUAGGA | UCCUAUAUU UCUAGUCA |
| 7137 | AUGACUAG CUGAUGA X GAA AAUAUAGG | CCUAUAUUU CUAGUCAU |
| 7138 | CAUGACUA CUGAUGA X GAA AAAUAUAG | CUAUAUUUC UAGUCAUG |
| 7140 | AUCAUGAC CUGAUGA X GAA AGAAAUAU | AUAUUUCUA GUCAUGAU |
| 7143 | UUCAUCAU CUGAUGA X GAA ACUAGAAA | UUUCUAGUC AUGAUGAA |
| 7155 | AUACAAAA CUGAUGA X GAA ACAUUCAU | AUGAAUGUA UUUUGUAU |
| 7157 | GUAUACAA CUGAUGA X GAA AUACAUUC | GAAUGUAUU UUGUAUAC |
| 7158 | GGUAUACA CUGAUGA X GAA AAUACAUU | AAUGUAUUU UGUAUACC |
| 7159 | UGGUAUAC CUGAUGA X GAA AAAUACAU | AUGUAUUUU GUAUACCA |
| 7162 | AGAUGGUA CUGAUGA X GAA ACAAAAUA | UAUUUUGUA UACCAUCU |
| 7164 | GAAGAUGG CUGAUGA X GAA AUACAAAA | UUUUGUAUA CCAUCUUC |
| 7169 | UAUAUGAA CUGAUGA X GAA AUGGUAUA | UAUACCAUC UUCAUAUA |
| 7171 | AUUAUAUG CUGAUGA X GAA AGAUGGUA | UACCAUCUU CAUAUAAU |
| 7172 | UAUUAUAU CUGAUGA X GAA AAGAUGGU | ACCAUCUUC AUAUAAUA |
| 7175 | GUAUAUUA CUGAUGA X GAA AUGAAGAU | AUCUUCAUA UAAUAUAC |
| 7177 | AAGUAUAU CUGAUGA X GAA AUAUGAAG | CUUCAUAUA AUAUACUU |
| 7180 | UUUAAGUA CUGAUGA X GAA AUUAUAUG | CAUAUAAUA UACUUAAA |

TABLE II-continued

Human flt1 VEGF Receptor-Hammerhead Ribozyme and Substrate Sequence

| nt. Position | HH Ribozyme | Substrate |
|---|---|---|
| 7182 | UUUUUAAG CUGAUGA X GAA AUAUUAUA | UAUAAUAUA CUUAAAAA |
| 7185 | AUAUUUUU CUGAUGA X GAA AGUAUAUU | AAUAUACUU AAAAAUAU |
| 7186 | AAUAUUUU CUGAUGA X GAA AAGUAUAU | AUAUACUUA AAAAUAUU |
| 7192 | UUAAGAAA CUGAUGA X GAA AUUUUUAA | UUAAAAAUA UUUCUUAA |
| 7194 | AAUUAAGA CUGAUGA X GAA AUAUUUUU | AAAAAUAUU UCUUAAUU |
| 7195 | CAAUUAAG CUGAUGA X GAA AAUAUUUU | AAAAUAUUU CUUAAUUG |
| 7196 | CCAAUUAA CUGAUGA X GAA AAAUAUUU | AAAUAUUUC UUAAUUGG |
| 7198 | UCCCAAUU CUGAUGA X GAA AGAAAUAU | AUAUUUCUU AAUUGGGA |
| 7199 | AUCCCAAU CUGAUGA X GAA AAGAAAUA | UAUUUCUUA AUUGGGAU |
| 7202 | CAAAUCCC CUGAUGA X GAA AUUAAGAA | UUCUUAAUU GGGAUUUG |
| 7208 | CGAUUACA CUGAUGA X GAA AUCCCAAU | AUUGGGAUU UGUAAUCG |
| 7209 | ACGAUUAC CUGAUGA X GAA AAUCCCAA | UUGGGAUUU GUAAUCGU |
| 7212 | GGUACGAU CUGAUGA X GAA ACAAAUCC | GGAUUUGUA AUCGUACC |
| 7215 | GUUGGUAC CUGAUGA X GAA AUUACAAA | UUUGUAAUC GUACCAAC |
| 7218 | UAAGUUCG CUGAUGA X GAA ACGAUUAC | GUAAUCGUA CCAACUUA |
| 7225 | UAUCAAUU CUGAUGA X GAA AGUUGGUA | UACCAACUU AAUUGAUA |
| 7226 | UUAUCAAU CUGAUGA X GAA AAGUUGGU | ACCAACUUA AUUGAUAA |
| 7229 | AGUUUAUC CUGAUGA X GAA AUUAAGUU | AACUUAAUU GAUAAACU |
| 7233 | GCCAAGUU CUGAUGA X GAA AUCAAUUA | UAAUUGAUA AACUUGGC |
| 7238 | CAGUUGCC CUGAUGA X GAA AGUUUAUC | GAUAAACUU GGCAACUG |
| 7249 | GAACAUAA CUGAUGA X GAA AGCAGUUG | CAACUGCUU UUAUGUUC |
| 7250 | AGAACAUA CUGAUGA X GAA AAGCAGUU | AACUGCUUU UAUGUUCU |
| 7251 | CAGAACAU CUGAUGA X GAA AAAGCAGU | ACUGCUUUU AUUUCUG |
| 7252 | ACAGAACA CUGAUGA X GAA AAAAGCAG | CUGCUUUUA UGUUCUGU |
| 7256 | GAAGACAG CUGAUGA X GAA ACAUAAAA | UUUUAUGUU CUGUCUCC |
| 7257 | AAGAGACA CUGAUGA X GAA AACAUAAA | UUUAUGUUC UGUCUCCU |
| 7261 | UGGAAGGA CUGAUGA X GAA ACAGAACA | UGUUCUGUC UCCUUCCA |
| 7263 | UAUGGAAG CUGAUGA X GAA AGACAAAA | UUCUGUCUC CUUCCAUA |
| 7266 | AUUUAUGG CUGAUGA X GAA AGGAGACA | UGUCUCCUU CCAUAAAU |
| 7267 | AAUUUAUG CUGAUGA X GAA AAGGAGAC | GUCUCCUUC CAUAAAUU |
| 7271 | GAAAAAUU CUGAUGA X GAA AUGGAAGG | CCUUCCAUA AAUUUUUC |
| 7275 | UUUUGAAA CUGAUGA X GAA AUUUAUGG | CCAUAAAUU UUUCAAAA |
| 7276 | AUUUGAA CUGAUGA X GAA AAUUUAUG | CAUAAAUUU UUCAAAAU |
| 7277 | UAUUUUGA CUGAUGA X GAA AAAUUUAU | AUAAAUUUU UCAAAUA |
| 7278 | GUAUUUUG CUGAUGA X GAA AAAAUUUA | UAAAUUUUU CAAAAUAC |
| 7279 | AGUAUUUU CUGAUGA X GAA AAAAAUUU | AAAUUUUUC AAAAUACU |

TABLE II-continued

Human flt1 VEGF Receptor-Hammerhead Ribozyme and Substrate Sequence

| nt. Position | HH Ribozyme | Substrate |
|---|---|---|
| 7285 | UGAAUUAG CUGAUGA X GAA AUUUUGAA | UUCAAAAUA CUAAUUCA |
| 7288 | UGUUGAAU CUGAUGA X GAA AGUAUUUU | AAAAUACUA AUUCAACA |
| 7291 | CUUUGUUG CUGAUGA X GAA AUUAGUAU | AUACUAAUU CAACAAAG |
| 7292 | UCUUUCUU CUGAUGA X GAA AAUUAGUA | UACUAAUUC AACAAAGA |
| 7308 | AAAAAAAA CUGAUGA X GAA AGCUUUUU | AAAAGCUC UUUUUUUU |
| 7310 | GGAAAAAA CUGAUGA X GAA AGAGCUUU | AAAGCUCUU UUUUUUCC |
| 7311 | AGGAAAAA CUGAUGA X GAA AAGAGCUU | AAGCUCUUU UUUUUCCU |
| 7312 | UAGGAAAA CUGAUGA X GAA AAAGAGCU | AGCUCUUUU UUUUCCUA |
| 7313 | UUAGGAAA CUGAUGA X GAA AAAAGAGC | GCUCUUUUU UUUCCUAA |
| 7314 | UUUAGGAA CUGAUGA X GAA AAAAAGAG | CUCUUUUUU UUCCUAAA |
| 7315 | UUUUAGGA CUGAUGA X GAA AAAAAAGA | UCUUUUUUU UCCCAAAA |
| 7316 | AUUUUAGG CUGAUGA X GAA AAAAAAAG | CUUUUUUUU CCUAAAAU |
| 7317 | UAUUUUAG CUGAUGA X GAA AAAAAAAA | UUUUUUUUC CUAAAAUA |
| 7320 | GUUUAUUU CUGAUGA X GAA AGGAAAAA | UUUUUCCUA AAAUAAAC |
| 7325 | UUUGAGUU CUGAUGA X GAA AUUUUAGG | CCUAAAAUA AACUCAAA |
| 7330 | AUAAAUUU CUGAUGA X GAA AGUUUAUU | AAUAAACUC AAAUUUAU |
| 7335 | CAAUGAUA CUGAUGA X GAA AUUUGAGU | ACUCAAAUU UAUCCUUG |
| 7336 | ACAAGGAU CUGAUGA X GAA AAUUUAAG | CUCAAAUUU AUCCUUGU |
| 7337 | AACAAGGA CUGAUGA X GAA AAAUUUGA | UCAAADUUA UCCUUGUU |
| 7339 | UAAACAAG CUGAUGA X GAA AUAAAUUU | AAAUUUAUC CUUGUUUA |
| 7342 | CCCUAAAC CUGAUGA X GAA AGGAUAAA | UUUAUCCUU GUUUAGAG |
| 7345 | CUGCUCUA CUGAUGA X GAA ACAAGGAU | AUCCUUGUU UAGAGCAG |
| 7346 | UCUGCUCU CUGAUGA X GAA AACAAGGA | UCCUUGUUU AGAGCAGA |
| 7347 | CUCUGCUC CUGAUGA X GAA AAACAAGG | CCUUGUUUA GAGCAGAG |
| 7362 | UUUUUCUU CUGAUGA X GAA AUUUUUCU | AGAAAAAUU AAGAAAAA |
| 7363 | GUUUUUCU CUGAUGA X GAA AAUUUUUC | GAAAAAUUA AGAAAAAC |
| 7373 | CCAUUUCA CUGAUGA X GAA AGUUUUUC | GAAAAACUU UGAAAUGG |
| 7374 | ACCAUUUC CUGAUGA X GAA AAGUUUUU | AAAAACUUU GAAAUGGU |
| 7383 | UUUUUUGA CUGAUGA X GAA ACCAUUUC | GAAAUGGUC UCAAAAAA |
| 7385 | AAUUUUUU CUGAUGA X GAA AGACCAUU | AAUGGUCUC AAAAAAUU |
| 7393 | UAUUUAGC CUGAUGA X GAA AUUUUUUG | CAAAAAAUU GCUAAAUA |
| 7397 | AAAAUAUU CUGAUGA X GAA AGCAAUUU | AAAUUGCUA AAUAUUUU |
| 7401 | AUUGAAAA CUGAUGA X GAA AUUUAGCA | UGCUAAAUA UUUUCAAU |
| 7403 | CCAUUGAA CUGAUGA X GAA AUAUUUAG | CUAAAUAUU UUCAAUGG |
| 7404 | UCCAUUGA CUGAUGA X GAA AAUAUUUA | UAAAUAUUU UCAAUGGA |
| 7405 | UUCCAUUG CUGAUGA X GAA AAAUAUUU | AAAUAUUUU CAAUGGAA |
| 7406 | UUUCCAUU CUGAUGA X GAA AAAAUAUU | AAUAUUUUC AAUGGAAA |

TABLE II-continued

Human flt1 VEGF Receptor-Hammerhead Ribozyme and Substrate Sequence

| nt. Position | HH Ribozyme | Substrate |
|---|---|---|
| 7418 | CUAACAUU CUGAUGA X GAA AGUUUCC | GGAAAACUA AAUGUUAG |
| 7424 | GCUAAACU CUGAUGA X GAA ACAUUUAG | CUAAAUGUU AGUUUAGC |
| 7425 | AGCUAAAC CUGAUGA X GAA AACAUUUA | UAAAUGUUA GUUUAGCU |
| 7428 | AUCAGCUA CUGAUGA X GAA ACUAACAU | AUGUUAGUU UAGCUGAU |
| 7429 | AAUCAGCU CUGAUGA X GAA AACUAACA | UGUUAGUUU AGCUGAUU |
| 7430 | CAAUCAGC CUGAUGA X GAA AAACUAAC | GUUAGUUUA GCUGAUUG |
| 7437 | CCCCAUAC CUGAUGA X GAA AUCACCCA | UAGCUGAUU GUAUGGGG |
| 7440 | AAACCCCA CUGAUGA X GAA ACAAUCAG | CUGAUUGUA UGGGGUUU |
| 7447 | GGUUCGAA CUGAUGA X GAA ACCCCAUA | UAUGGGGUU UUCGAACC |
| 7448 | AGGUUCGA CUGAUGA X GAA AACCCCAU | AUGGGGUUU UCGAACCU |
| 7449 | AAGGUUCG CUGAUGA X GAA AAACCCCA | UGGGGUUUU CGAACCUU |
| 7450 | AAAGGUUC CUGAUGA X GAA AAAACCCC | GGGGUUUUC GAACCUUU |
| 7457 | AAAAGUGA CUGAUGA X GAA AGGUUCGA | UCGAACCUU UCACUUUU |
| 7458 | AAAAAGUG CUGAUGA X GAA AAGGUUCG | CGAACCUUU CACUUUUU |
| 7459 | CAAAAAGU CUGAUGA X GAA AAAGGUUC | GAACCUUUC ACUUUUUG |
| 7463 | CAAACAAA CUGAUGA X GAA AGUGAAAG | CUUUCACUU UUUGUUUG |
| 7464 | ACAAACAA CUGAUGA X GAA AAGUGAAA | UUUCACUUU UUGUUUGU |
| 7465 | AACAAACA CUGAUGA X GAA AAAGUGAA | UUCACUUUU UGUUUGUU |
| 7466 | AAACAAAC CUGAUGA X GAA AAAAGUGA | UCACUUUUU GUUUGUUU |
| 7469 | GUAAAACA CUGAUGA X GAA ACAAAAAG | CUUUUUGUU UGUUUUAC |
| 7470 | GGUAAAAC CUGAUGA X GAA AACAAAAA | UUUUUGUUU GUUUUACC |
| 7473 | AUAGGUAA CUGAUGA X GAA ACAAACAA | UUGUUUGUU UUACCUAU |
| 7474 | AAUAGAAA CUGAUGA X GAA AACAAACA | UGUUUGUUU UACCUAUU |
| 7475 | AAAUAGGU CUGAUGA X GAA AAACAAAC | GUUUGUUUU ACCUAUUU |
| 7476 | GAAAUAGG CUGAUGA X GAA AAAACAAA | UUUGUUUUA CCUAUUUC |
| 7480 | UUGUGAAA CUGAUGA X GAA AGGUAAAA | UUUUACCUA UUUCACAA |
| 7482 | AGUUGUGA CUGAUGA X GAA AUAGGUAA | UUACCUAUU UCACAACU |
| 7483 | CAGUUGUG CUGAUGA X GAA AAUAGGUA | UACCUAUUU CACAACAG |
| 7484 | ACAGUUGU CUGAUGA X GAA AAAUAGGU | ACCUAUUUC ACAACUGU |
| 7495 | UGGCAAUU CUGAUGA X GAA ACACAGUU | AACUGUGUA AAUUGCCA |
| 7499 | UUAUUGGC CUGAUGA X GAA AUUUACAC | GUGUAAAUU GCCACCAA |
| 7506 | ACAGGAAU CUGAUGA X GAA AUUGGCAA | UUGCCAAUA AUUCCUGU |
| 7509 | UGGACAGG CUGAUGA X GAA AUUAUUGG | CCAAUAAUU CCUGUCCA |
| 7510 | AUGGACAG CUGAUGA X GAA AAUUAUUG | CAAUAAUUC CUGUCCAU |
| 7515 | UUUUCAUG CUGAUGA X GAA ACAGGAAU | AUUCCUGUC CAUGAAAA |
| 7531 | CACUGGAU CUGAUGA X GAA AUUUGCAU | AUGCAAAUU AUCCAGUG |

TABLE II-continued

Human flt1 VEGF Receptor-Hammerhead Ribozyme and Substrate Sequence

| nt. Position | HH Ribozyme | Substrate |
|---|---|---|
| 7532 | ACACUGGA CUGAUGA X GAA AAUUUGCA | UGCAAAUUA UCCAGUGU |
| 7534 | CUACACUG CUGAUGA X GAA AUAAUUUG | CAAAUUAUC CAGUGUAG |
| 7541 | AAUAUAUC CUGAUGA X GAA ACACUGGA | UCCAGUGUA GAUAUAUU |
| 7545 | GUCAAAUA CUGAUGA X GAA AUCUACAC | GUGUAGAUA UAUUUGAC |
| 7547 | UGGUCAAA CUGAUGA X GAA AUAUCUAC | GUAGAUAUA UUUCACCA |
| 7549 | GAUGGUCA CUGAUGA X GAA AUAUAUCU | AGAUAUAUU UGACCAUC |
| 7550 | UGAUGGUC CUGAUGA X GAA AAUAUAUC | GAUAUAUUU GACCAUCA |
| 7557 | CAUAGGGU CUGAUGA X GAA AUGGUCAA | UUGACCAUC ACCCUAUG |
| 7563 | AAUACCCA CUGAUGA X GAA AGGGUGAU | AUCACCCUA UGGAUAUU |
| 7569 | CUAGCCAA CUGAUGA X GAA AUCCAUAG | CUAUGGAUA UUGGCUAG |
| 7571 | AACUAGCC CUGAUGA X GAA AUAUCCAU | AUGGAUAUU GGCUAGUU |
| 7576 | GGCAAAAC CUGAUGA X GAA AGCCAAUA | UAUUGGCUA GUUUUGCC |
| 7579 | AAAGGCAA CUGAUGA X GAA ACUAGUCA | UGGCUAGUU UUGCCUUU |
| 7580 | UAAAGCCA CUGAUGA X GAA AACUAGCC | GGCUAGUUU UGCCUUUA |
| 7581 | AUAAAGGC CUGAUGA X GAA AAACUAGC | GCUAGUUUU GCCUUUAU |
| 7586 | GCUUAAUA CUGAUGA X GAA AGGCAAAA | UUUUGCCUU UAUUAAGC |
| 7587 | UGCUUAAU CUGAUGA X GAA AAGGCAAA | UUUGCCUUU AUUAAGCA |
| 7588 | UUGCUUAA CUGAUGA X GAA AAAGGCAA | UUGCCUUUA UUAAGCAA |
| 7590 | AUUUGCUU CUGAUGA X GAA AUAAAGGC | GCCUUUAUU AAGCAAAU |
| 7591 | AAUUUGCU CUGAUGA X GAA AAUAAAGG | CCUUUAUUA AGCAAAUU |
| 7599 | CUGAAAUG CUGAUGA X GAA AUUUGCUU | AAGCAAAUU CAUUUCAG |
| 7600 | GCUGAAAU CUGAUGA X GAA AAUUUGCU | AGCAAAUUC AUUUCAGC |
| 7603 | CAGGCUGA CUGAUGA X GAA AUGAAUUU | AAAUUCAUU UCAGCCUG |
| 7604 | UCACGGUG CUGAUGA X GAA AAUGAAUU | AAUUCAUUU CAGCCUGA |
| 7605 | UUCAGGCU CUGAUGA X GAA AAAUGAAU | AUUCAUUUC AGCCUGAA |
| 7617 | UAUAGGCA CUGAUGA X GAA ACAUUCAG | CUGAAUGUC UGCCUAUA |
| 7623 | AGAAUAUA CUGAUGA X GAA ACGCAGAC | GUCUGCCUA UAUAUUCU |
| 7625 | AGAGAAUA CUGAUGA X GAA AUAGGCAG | CUGCCUAUA UAUUCUCU |
| 7627 | GCAGAGAA CUGAUGA X GAA AUAUAGGC | GCCUAUAUA UCCUCUCC |
| 7629 | GAGCAGAG CUGAUGA X GAA AUAUAUAG | CUAUAUAUU CUCUGCUC |
| 7630 | AGAGCAGA CUGAUGA X GAA AAUAUAUA | UAUAUAUUC UCUGCUCU |
| 7632 | AAAGACCA CUGAUGA X GAA AGAAUAUA | UAUAUUCUC UGCUCUUU |
| 7637 | AAUACAAA CUGAUGA X GAA ACCAGAGA | UCUCUGCUC UUUGUAUU |
| 7639 | AGAAUACA CUGAUGA X GAA AGAGCAGA | UCUGCUCUU UCUAUUCU |
| 7640 | GAGAAUAC CUGAUGA X GAA AAGAGCAG | CUGCUCUUU GUAUUCUC |
| 7643 | AAGGAGAA CUGAUGA X GAA ACAAACAG | CUCUUUGUA UUCUCCUU |
| 7645 | CAAACCAG CUGAUGA X GAA AUACAAAG | CUUUGUAUU CUCCUUUG |

TABLE II-continued

Human flt1 VEGF Receptor-Hammerhead Ribozyme and Substrate Sequence

| nt. Position | HH Ribozyme | Substrate |
|---|---|---|
| 7646 | UCAAAGGA CUGAUGA X GAA AAUACAAA | UUUGUAUUC UCCUUUGA |
| 7648 | CUUCAAAG CUGAUGA X GAA AGAAUACA | UUUUUUCUC CUUUGAAC |
| 7651 | CGGGUUCA CUGAUGA X GAA AGGAGAAU | AUUCUCCUU UGAACCCG |
| 7652 | ACGGGUUC CUGAUGA X GAA AAGGAGAA | UUCUCCUUU GAACCCGU |
| 7661 | GAUGUUUU CUGAUGA X GAA ACGGGUUC | GAACCCGUU AAAACAUC |
| 7662 | GGAUGUUU CUGAUGA X GAA AACGGGUU | AACCCGUUA AAACAUCC |
| 7669 | UGCCACAG CUGAUGA X GAA AUGUUUUA | UAAAACAUC CUGUGGCA |

Where "X" represents stem II region of a HH ribozyme (Hertel et al., 1992 Nucleic Acids Res. 20 3252). The length of stem II may be ≧ 2 base-pairs.

TABLE III

Human fLt1 VEGF Receptor-Hairpin Ribozyme and Substrate sequence

| nt. Position | HP Ribozyme Sequence | Substrate |
|---|---|---|
| 16 | CGGGGAGG AGAA GAGAGG ACCAGAGAAACACACGUUGUGGUACAUUACCUGGUA | CCUCUCG GCU CCUCCCCG |
| 39 | CCGCUCCG AGAA GCCGCC ACCAGAGAAACACACGUUGUGGUACAUUACCUGGUA | GGCGGCG GCU CGGAGCGG |
| 180 | CCGCCAGA AGAA GUCCUC ACCAGAGAAACACACGUUGUGGUACAUUACCUGGUA | GAGGACG GAC UCUGGCGG |
| 190 | AACGACCC AGAA GCCAGA ACCAGAGAAACACACGUUGUGGUACAUUACCUGGUA | UCUGGCG GCC GGGUCGUU |
| 278 | GCGCGCAC AGAA GGACCC ACCAGAGAAACACACGUUGUGGUACAUUACCUGGUA | GGGUCCU GCU GUGCGCGC |
| 290 | GACAGCUG AGAA GCGCGC ACCAGAGAAACACACGUUGUGGUACAUUACCUGGUA | GCGCGCU GCU CAGCUGUC |
| 295 | AAGCGAGAC AGAA GAGCAG ACCAGAGAAACACACGUUGUGGUACAUUACCUGGUA | CUGCUCA GCU GUCUGCUU |
| 298 | GAGAAGCA AGAA GCUGAG ACCAGAGAAACACACGUUGUGGUACAUUACCUGGUA | CUCAGCU GUC UGCUUCUC |
| 302 | CUGUGAGA AGAA GACAGC ACCAGAGAAACACACGUUGUGGUACAUUACCUGGUA | GCUGUCU GCU UCUCACAG |
| 420 | CAUUUAUG AGAA GCUUCC ACCAGAGAAACACACGUUGUGGUACAUUACCUGGUA | GGAAGCA GCC CAUAAAUG |
| 486 | CUUCCACA AGAA GAUUUA ACCAGACAAACACACGUUGUGGUACAUUACCUGGUA | UAAAUCU GCC UGUGGAAG |
| 537 | UUUGCUUG AGAA GUGUUC ACCAGAGAAACACACGUUGUGGUACAUUACCUGGUA | GAACACA GCU CAAGCAAA |
| 565 | AUAUUUGC AGAA GUAGAA ACCAGAGAAACACACGUUGUGGUACAUUACCUGGUA | UUCUACA GCU GCAAAUAU |
| 721 | CGUAACCC AGAA GGGAAU ACCAGAGAAACACACGUUGUGGUACAUUACCUGGUA | AUUCCCU GCC GGGUUACG |
| 786 | CGUUUUCC AGAA GGGAUC ACCAGAGAAACACACGUUGUGGUACAUUACCUGGUA | GAUCCCU GAU GGAAAACG |
| 863 | CUUCACAG AGAA GAAGCC ACCAGAGAAACACACGUUGUGGUACAUUACCUGGUA | GGCUUCU GAC CUGUGAAG |
| 1056 | UUUUUUUC AGAA GGGUAA ACCAGAGAAACACACGUUGUGGUACAUUACCUGGUA | UUACCCU GAU GAAAAAAA |
| 1301 | GCCGGUAA AGAA GCUUGC ACCAGAGAAACACACGUUGUGGUACAUUACCUGGUA | GCAAGCG GUC UUACCGGC |
| 1310 | UCAUAGAG AGAA GGUAAG ACCAGAGAAACACACGUUGUGGUACAUUACCUGGUA | CUUACCG GCU CUCUAUGA |
| 1389 | AAAUAGCG AGAA GAUUUC ACCAGAGAAACACACGUUGUGGUACAUUACCUGGUA | GAAAUCU GCU CGCUAUUU |
| 1535 | UUUCGUAA AGAA GGGGUU ACCAGAGAAACACACGUUGUGGUACAUUACCUGGUA | AACCCCA GAU UUACGAAA |
| 1566 | AGAGCCGG AGAA GGAAAC ACCAGAGAAACACACGUUGUGGUACAUUACCUGGUA | GUUUCCA GAC CCGGCUCU |
| 1572 | GGGUAGAG AGAA GGGUCU ACCAGAGAAACACACGUUGUGGUACAUUACCUGGUA | AGACCCG GCU CUCUACCC |

TABLE III-continued

Human fLt1 VEGF Receptor-Hairpin Ribozyme and Substrate sequence

| nt. Position | HP Ribozyme Sequence | Substrate |
|---|---|---|
| 1604 | CGGUACAA AGAA GGAUUU ACCAGAGAAACACACGUUGUGGUACAUUACCUGGUA | AAAUCCU GAC UUGUACCG |
| 1824 | AUUCUAGA AGAA GCCACA ACCAGAGAAACACACGUUGUGGUACAUUACCUGGUA | UGUGGCU GAC UCUAGAAU |
| 1908 | UUUGGCAC AGAA GUGAUA ACCAGAGAAACACACGUUGUGGUACAUUACCUGGUA | UAUCACA GAU GUGCCAAA |
| 1949 | CUCCUUCC AGAA GCAUUU ACCAGAGAAACACACGUUGUGGUACAUUACCUGGUA | AAAUGCC GAC GGAAGGAG |
| 1973 | CUGUGCAA AGAA GUUUCA ACCAGAGAAACACACGUUGUGGUACAUUACCUGGUA | UGAAACU GUC UUGCACAG |
| 2275 | AGUGGUGG AGAA GCUGAU ACCAGAGAAACACACGUUGUGGUACAUUACCUGGUA | AUCAGCA GUU CCACCACU |
| 2321 | ACCAAGUG AGAA GAGGCU ACCAGAGAAACACACGUUGUGGUACAUUACCUGGUA | AGCCUCA GAU CACUUGGU |
| 2396 | UUUCAAUA AGAA GCGUGC ACCAGAGAAACACACGUUGUGGUACAUUACCUGGUA | GCACGCU GUU UAUUGAAA |
| 2490 | GUUCCUUG AGAA GUGAGG ACCAGAGAAACACACGUUGUGGUACAUUACCUGGUA | CCUCACU GUU CAAGGAAC |
| 2525 | UUAGAGUG AGAA GCUCCA ACCAGAGAAACACACGUUGUGGUACAUUACCUGGUA | UGGAGCU GAU CACUCUAA |
| 2625 | GAUAGGUA AGAA GUCUUU ACCAGAGAAACACACGUUGUGGUACAUUACCUGGUA | AAAGACU GAC UACCUAUC |
| 2652 | GGAACUUC AGAA GGGUCC ACCAGAGAAACACACGUUGUGGUACAUUACCUGGUA | GGACCCA GAU GAAGUUCC |
| 2684 | CAUAAGGG AGAA GCUCAC ACCAGAGAAACACACGUUGUGGUACAUUACCUGGUA | GUGAGCG GCU CCCUUAUG |
| 2816 | CAGCCACA AGAA GGCACG ACCAGAGAAACACACGUUGUGGUACAUUACCUGGUA | CGUGCCG GAC UGUGGCUG |
| 2873 | GCUCAGUC AGAA GAGCUU ACCAGAGAAACACACGUUGUGGUACAUUACCUGGUA | AAGCUCU GAC GACUGAGC |
| 2930 | AGGCUCCC AGAA GGUUAA ACCAGAGAAACACACGUUGUGGUACAUUACCUGGUA | UUAACCU GCU GGGAGCCU |
| 2963 | CAAUCACC AGAA GAGGCC ACCAGAGAAACACACGUUGUGGUACAUUACCUGGUA | GGCCUCU GAU GGUGAUUG |
| 3157 | UUCCUGAA AGAA GGAGCU ACCAGAGAAACACACGUUGUGGUACAUUACCUGGUA | AGCUCCG GCU UUCAGGAA |
| 3207 | UAGAAACC AGAA GAAUCC ACCAGAGAAACACACGUUGUGGUACAUUACCUGGUA | GGAUUCU GAC GGUUUCUA |
| 3211 | CUUGUAGA AGAA GUCAGA ACCAGAGAAACACACGUUGUGGUACAUUACCUGGUA | UCUGACG GUU UCUACAAG |
| 3245 | UGUAAGAA AGAA GAUCUU ACCAGAGAAACACACGUUGUGGUACAUUACCUGGUA | AAGAUCU GAU UUCUUACA |
| 3256 | CACUUGAA AGAA GUAAGA ACCAGAGAAACACACGUUGUGGUACAUUACCUGGUA | UCUUACA GUU UUCAAGUG |
| 3287 | UUCUGGAA AGAA GCAACU ACCAGAGAAACACACGUUGUGGUACAUUACCUGGUA | AGUUCCU GUC UUCCAGAA |
| 3402 | CUCACAUA AGAA GGGUUC ACCAGAGAAACACACGUUGUGGUACAUUACCUGGUA | GAACCCC GAU UAUGUGAG |
| 3580 | CCUCAGGC AGAA GCAAAA ACCAGAGAAACACACGUUGUGGUACAUUACCUGGUA | UUUUGCA GUC GCCUGAGG |
| 3641 | CCAGCAUG AGAA GAUAGA ACCAGAGAAACACACGUUGUGGUACAUUACCUGGUA | UCUAUCA GAU CAUGCUGG |
| 3655 | UCUGUGCC AGAA GUCCAG ACCAGAGAAACACACGUUGUGGUACAUUACCUGGUA | CUGGACU GCU GGCACAGA |
| 3810 | UCAGAGAA AGAA GGAGUU ACCAGAGAAACACACGUUGUGGUACAUUACCUGGUA | AACUCCU GCC UUCUCUGA |
| 3846 | AACUUCGG AGAA GAAAUA ACCAGAGAAACACACGUUGUGGUACAUUACCUGGUA | UAUUUCA GCU CGGAAGUU |
| 3873 | CUGACAUC AGAA GAGCUU ACCAGAGAAACACACGUUGUGGUACAUUACCUGGUA | AAGCUCU GAU GAUGUCAG |
| 3995 | GAGAGGCC AGAA GAGUGC ACCAGAGAAACACACGUUGUGGUACAUUACCUGGUA | GCACUCU GUU GGCCUCUC |
| 4100 | UGACAUCA AGAA GCCCCG ACCAGAGAAACACACGUUGUGGUACAUUACCUGGUA | CGGGGCU GUC UGAUGUCA |
| 4104 | CUGCUGAC AGAA GACAGC ACCAGAGAAACACACGUUGUGGUACAUUACCUGGUA | GCUGUCU GAU GUCAGCAG |
| 4120 | AUGGCAGA AGAA GGGCCU ACCAGAGAAACACACGUUGUGGUACAUUACCUGGUA | AGGCCCA GUU UCUGCCAU |
| 4135 | GUGCCCAC AGAA GGAAUG ACCAGAGAAACACACGUUGUGGUACAUUACCUGGUA | CAUUCCA GCU GUGGGCAC |
| 4210 | GGGCGGGG AGAA GCACGC ACCAGAGAAACACACGUUGUGGUACAUUACCUGGUA | GCGUGCU GCU CCCCGCCC |
| 4217 | AGUCUGGG AGAA GGGAGC ACCAGAGAAACACACGUUGUGGUACAUUACCUGGUA | GCUCCCC GCC CCCAGACU |

TABLE III-continued

Human fLt1 VEGF Receptor-Hairpin Ribozyme and Substrate sequence

| nt. Position | HP Ribozyme Sequence | Substrate |
|---|---|---|
| 4224 | GAGUUGUA AGAA GGGGGC ACCAGAGAAACACACGUUGUGGUACAUUACCUGGUA | GCCCCCA GAC UACAACUC |
| 4382 | CAAAAAGC AGAA GGCUCC ACCAGAGAAACACACGUUGUGGUACAUUACCUGGUA | GGAGCCA GCU GCUUUUUG |
| 4385 | UCACAAAA AGAA GCUGGC ACCAGAGAAACACACGUUGUGGUACAUUACCUGGUA | GCCAGCU GCU UUUUGUGA |
| 4537 | GGGGUUGG AGAA GGGAAG ACCAGAGAAACACACGUUGUGGUACAUUACCUGGUA | CUUCCCU GCU CCAACCCC |
| 4573 | CUCAAUCA AGAA GGUCCU ACCAGAGAAACACACGUUGUGGUACAUUACCUGGUA | AGGACCA GUU UGAUUGAG |
| 4594 | AUUGGGUG AGAA GUGCAG ACCAGAGAAACACACGUUGUGGUACAUUACCUGGUA | CUGCACU GAU CACCCAAU |
| 4628 | GGCUGCAG AGAA GGCCCA ACCAGAGAAACACACGUUGUGGUACAUUACCUGGUA | UGGGCCA GCC CUGCAGCC |
| 4636 | GGGUUUUG AGAA GCAGGG ACCAGAGAAACACACGUUGUGGUACAUUACCUGGUA | CCCUGCA GCC CAAAACCC |
| 4866 | AGGGUCAG AGAA GGGAAG ACCAGAGAAACACACGUUGUGGUACAUUACCUGGUA | CUUCCCA GCU CUGACCCU |
| 4871 | GUAGAAGG AGAA GAGCUG ACCAGAGAAACACACGUUGUGGUACAUUACCUGGUA | CAGCUCU GAC CCUUCUAC |
| 4905 | CGCUGUCC AGAA GCUCCU ACCAGAGAAACACACGUUGUGGUACAUUACCUGGUA | AGGAGCA GAU GGACAGCG |
| 5233 | CUGUGCAA AGAA GAAUAA ACCAGAGAAACACACGUUGUGGUACAUUACCUGGUA | UUAUUCU GUU UUGCACAG |
| 5281 | CUCCUCAG AGAA GCAUUU ACCAGAGAAACACACGUUGUGGUACAUUACCUGGUA | AAAUGCA GUC CUGAGGAG |
| 5319 | UUUCCUCC AGAA GCCCUC ACCAGAGAAACACACGUUGUGGUACAUUACCUGGUA | GAGGGCU GAU GGAGGAAA |
| 5358 | GGUAUAGA AGAA GGGUCU ACCAGAGAAACACACGUUGUGGUACAUUACCUGGUA | AGACCCC GUC UCUAUACC |
| 5392 | UGGGUCCC AGAA GUGUUG ACCAGAGAAACACACGUUGUGGUACAUUACCUGGUA | CAACACA GUU GGGACCCA |
| 5563 | UGAGUCCC AGAA GGAGAA ACCAGAGAAACACACGUUGUGGUACAUUACCUGGUA | UUCUCCA GUU GGGACUCA |
| 5622 | AGUUUCAA AGAA GUUGAA ACCAGAGAAACACACGUUGUGGUACAUUACCUGGUA | UUCAACU GCU UUGAAACU |
| 5738 | UAGCAUCA AGAA GAGCCA ACCAGAGAAACACACGUUGUGGUACAUUACCUGGUA | UGGCUCU GUU UGAUGCUA |
| 5838 | UAGCAUCA AGAA GAGCCA ACCAGAGAAACACACGUUGUGGUACAUUACCUGGUA | UGGGUCU GUU UGAUGCUA |
| 5933 | CCCCAAGA AGAA GCAAUC ACCAGAGAAACACACGUUGUGGUACAUUACCUGGUA | GAUUGCU GCU UCUUGGGG |
| 6022 | CACAUAAG AGAA GAGGCA ACCAGAGAAACACACGUUGUGGUACAUUACCUGGUA | UGCCUCU GUU CUUAUGUG |
| 6120 | UCCACAAA AGAA GCUGCC ACCAGAGAAACACACGUUGUGGUACAUUACCUGGUA | GGCAGCG GCU UUUGUGGA |
| 6163 | GUGGAGAG AGAA GUCCCA ACCAGAGAAACACACGUUGUGGUACAUUACCUGGUA | UGGGACA GUC CUCUCCAC |
| 6270 | AAAUUGCC AGAA GUCACA ACCAGAGAAACACACGUUGUGGUACAUUACCUGGUA | UGUGACA GCU GGCAAUUU |
| 6412 | AAGACAUG AGAA GCUAAG ACCAGAGAAACACACGUUGUGGUACAUUACCUGGUA | CUUAGCU GUU CAUGUCUU |
| 6511 | UUUGAAGG AGAA GAGUAA ACCAGAGAAACACACGUUGUGGUACAUUACCUGGUA | UUACUCA GCU CCUUCAAA |
| 6778 | UCCACCCA AGAA GUUCCA ACCAGAGAAACACACGUUGUGGUACAUUACCUGGUA | UGGAACA GUC UGGGUGGA |
| 6826 | ACUUCUUG AGAA GACAAG ACCAGAGAAACACACGUUGUGGUACAUUACCUGGUA | CUUGUCA GUC CAAGAAGU |
| 7245 | AACAUAAA AGAA GUUGCC ACCAGAGAAACACACGUUGUGGUACAUUACCUGGUA | GGCAACU GCU UUUAUGUU |
| 7258 | UGGAAGGA AGAA GAACAU ACCAGAGAAACACACGUUGUGGUACAUUACCUGGUA | AUGUUCU GUC UCCUUCCA |
| 7433 | CCCAUACA AGAA GCUAAA ACCAGAGAAACACACGUUGUGGUACAUUACCUGGUA | UUUAGCU GAU UGUAUGGG |
| 7512 | UUUUCAUG AGAA GGAAUU ACCAGAGAAACACACGUUGUGGUACAUUACCUGGUA | AAUUCCU GUC CAUGAAAA |
| 7606 | GACAUUCA AGAA GAAAUG ACCAGAGAAACACACGUUGUGGUACAUUACCUGGUA | CAUUUCA GCC UGAAUGUC |
| 7618 | AAUAUAUA AGAA GACAUU ACCAGAGAAACACACGUUGUGGUACAUUACCUGGUA | AAUGUCU GCC UAUAUAUU |
| 7633 | AUACAAAG AGAA GAGAAU ACCAGAGAAACACACGUUGUGGUACAUUACCUGGUA | AUUCUCU GCU CUUUGUAU |

Table IV

Human KDR VEGF Receptor-Hammerhead Ribozyme and Substrate Sequence

| nt. Position | HH Ribozyme Sequence | Substrate |
|---|---|---|
| 21 | CACAGGGC CUGAUGA X GAA ACGGCCAG | CUGGCCGUC GCCCUGUG |
| 33 | UCCACGCA CUGAUGA X GAA AGCCACAG | CUGUGGCUC UGCGUGGA |
| 56 | AACCCACA CUGAUGA X GAA AGGCGGCC | GGCCGCCUC UGUGGGUU |
| 64 | ACUAGGCA CUGAUGA X GAA ACCCACAG | CUGUGGGUU UGCCUAGU |
| 65 | CACUAGGC CUGAUGA X GAA AACCCACA | UGUGGGUUU GCCUAGUG |
| 70 | AGAAACAC CUGAUGA X GAA AGGCAAAC | GUUUGCCUA GUGUUUCU |
| 75 | UCAAGAGA CUGAUGA X GAA ACACUAGG | CCUAGUGUU UCUCUUGA |
| 76 | AUCAAGAG CUGAUGA X GAA AACACUAG | CUAGUGUUU CUCUUGAU |
| 77 | GAUCAAGA CUGAUGA X GAA AAACACUA | UAGUGUUUC UCUUGAUC |
| 79 | CAGAUCAA CUGAUGA X GAA AGAAACAC | GUGUUUCUC UUGAUCUG |
| 81 | GGCAGAUC CUGAUGA X GAA AGAGAAAC | GUUUCUCUU GAUCUGCC |
| 85 | CCUGGGGA CUGAUGA X GAA AUCAAGAG | CUCUUGAUC UGCCCAGG |
| 96 | UGUAUGCU CUGAUGA X GAA AGCCUGGG | CCCAGGCUC AGCAUACA |
| 102 | UCUUUUUG CUGAUGA X GAA AUGCUGAG | CUCAGCAUA CAAAAAGA |
| 114 | AUUGUAAG CUGAUGA X GAA AUGUCUUU | AAAGACAUA CUUACAAU |
| 117 | UUAAUUGU CUGAUGA X GAA AGUAUGUC | GACAUACUU ACAAUUAA |
| 118 | CUUAAUUG CUGAUGA X GAA AAGUAUGU | ACAUACUUA CAAUUAAG |
| 123 | UUAGCCUU CUGAUGA X GAA AUUGUAAG | CUUACAAUU AAGGCUAA |
| 124 | AUUAGCCU CUGAUGA X GAA AAUUGUAA | UUACAAUUA AGGCUAAU |
| 130 | AGUUGUAU CUGAUGA X GAA AGCCUUAA | UUAAGGCUA AUACAACU |
| 133 | AAGAGUUG CUGAUGA X GAA AUUAGCCU | AGGCUAAUA CAACUCUU |
| 139 | AAUUUGAA CUGAUGA X GAA AGUUGUAU | AUACAACUC UUCAAAUU |
| 141 | GUAAUUUG CUGAUGA X GAA AGAGUUGU | ACAACUCUU CAAAUUAC |
| 142 | AGUAAUUU CUGAUGA X GAA AAGAGUUG | CAACUCUUC AAAUUACU |
| 147 | CUGCAAGU CUGAUGA X GAA AUUUGAAG | CUUCAAAUU ACUUGCAG |
| 148 | CCUGCAAG CUGAUGA X GAA AAUUUGAA | UUCAAAUUA CUUGGAGG |
| 151 | UCCCCUGC CUGAUGA X GAA AGUAAUUU | AAAUUACUU GCAGGGGA |
| 170 | GCCAGUCC CUGAUGA X GAA AGUCCCUC | GAGGGACUU GGACUGGC |
| 180 | UUGGGCCA CUGAUGA X GAA AGCCAGUC | GACUGGCUU UGGCCCAA |
| 181 | AUUGGGCC CUGAUGA X GAA AAGCCAGU | ACUGGcUUU GGCCCAAU |
| 190 | ACUCUGAU CUGAUGA X GAA AUUGGGCC | GGCCCAAUA AUCAAAGU |
| 193 | GCCACUCU CUGAUGA X GAA AUUAUUGG | CCAAUAAUC AGAGUGGC |
| 243 | UUACAGAA CUGAUGA X GAA AGGCCAUC | GAUGGCCUC UUCUGUAA |
| 245 | UCUUACAG CUGAUGA X GAA ACAGGCCA | UGGCCUCUU CUGUAAGA |
| 246 | GUCUUACA CUGAUGA X GAA AAGAGGCC | GGCCUCUUC UGUAAGAC |
| 250 | GAGUGUCU CUGAUGA X GAA ACAGAAGA | UCUUCUGUA AGACACUC |
| 258 | GGAAUUGU CUGAUGA X GAA AGUGUCUU | AAGACACUC ACAAUUCC |

Table IV-continued

Human KDR VEGF Receptor-Hammerhead Ribozyme and Substrate Sequence

| nt. Position | HH Ribozyme Sequence | Substrate |
|---|---|---|
| 264 | ACUUUUGG CUGAUGA X GAA AUUGUGAG | CUCACAAUU CCAAAAGU |
| 265 | CACUUUUG CUGAUGA X GAA AAUUGUGA | UCACAAUUC CAAAAGUG |
| 276 | UCAUUUCC CUGAUGA X GAA AUCACUUU | AAAGUGAUC GGAAAUGA |
| 296 | AGCACUUG CUGAUGA X GAA AGGCUCCA | UGGAGCCUA CAAGUGCU |
| 305 | CCCGGUAG CUGAUGA X GAA AGCACUUG | CAAGUGCUU CUACCGGG |
| 306 | UCCCGGUA CUGAUGA X GAA AAGCACUU | AAGUGCUUC UACCGGGA |
| 308 | UUUCCCGG CUGAUGA X GAA AGAAGCAC | GUGCUUCUA CCGGGAAA |
| 323 | CCGAGGCC CUGAUGA X GAA AGUCAGUU | AACUGACUU GGCCUCGG |
| 329 | AAAUGACC CUGAUGA X GAA AGGCCAAG | CUUGGCCUC GGUCAUUU |
| 333 | ACAUAAAU CUGAUGA X GAA ACCGAGGC | GCCUCGGUC AUUUAUGU |
| 336 | UAGACAUA CUGAUGA X GAA AUGACCGA | UCGGUCAUU UAUGUCUA |
| 337 | AUAGACAU CUGAUGA X GAA AAUGACCG | CGGUCAUUU AUGUCUAU |
| 338 | CAUAGACA CUGAUGA X GAA AAAUGACC | GGUCAUUUA UGUCUAUG |
| 342 | UGAACAUA CUGAUGA X GAA ACAUAAAU | AUUUAUGUC UAUGUUCA |
| 344 | CUUGAACA CUGAUGA X CAA AGACAUAA | UUAUGUCUA UGUUCAAG |
| 348 | UAAUCUUG CUGAUGA X GAA ACAUAGAC | GUCUAUGUU CAAGAUUA |
| 349 | GUAAUCUU CUGAUGA X GAA AACAUAGA | UCUAUGUUC AAGAUUAC |
| 355 | AGAUCUGU CUGAUGA X GAA AUCUUGAA | UUCAAGAUU ACAGAUCU |
| 356 | GAGAUCUG CUGAUGA X GAA AAUCUUGA | UCAAGAUUA CAGAUCUC |
| 362 | UAAAUGGA CUGAUGA X GAA AUCUGUAA | UUACAGAUC UCCAUUUA |
| 364 | AAUAAAUG CUGAUGA X GAA AGAUCUGU | ACAGAUCUC CAUUUAUU |
| 368 | AAGCAAUA CUGAUGA X GAA AUGGAGAU | AUCUCCAUU UAUUGCUU |
| 369 | GAAGCAAU CUGAUGA X GAA AAUGGAGA | UCUCCAUUU AUUGCUUC |
| 370 | AGAAGCAA CUGAUGA X GAA AAAUGGAG | CUCCAUUUA UUGCUUCU |
| 372 | ACAGAAGC CUGAUGA X GAA AUAAAUGG | CCAUUUAUU GCUUCUGU |
| 376 | ACUAACAG CUGAUGA X GAA AGCAAUAA | UUAUUGCUU CUGUUAGU |
| 377 | CACUAACA CUGAUGA X GAA AAGCAAUA | UAUUGCUUC UGUUAGUG |
| 381 | UGGUCACU CUGAUGA X GAA ACAGAAGC | GCUUCUGUU AGUGACCA |
| 382 | UUGGUCAC CUGAUGA X GAA AACAGAAG | CUUCUGUUA GUGACCAA |
| 399 | AUGUACAC CUGAUGA X GAA ACUCCAUG | CAUGGAGUC GUGUACAU |
| 404 | CAGUAAUG CUGAUGA X GAA ACACGACU | AGUCGUGUA CAUUACUG |
| 408 | UUCUCAGU CUGAUGA X GAA AUGUACAC | GUGUACAUU ACUGAGAA |
| 409 | GUUCUCAG CUGAUGA X GAA AAUGUACA | UGUACAUUA CUGAGAAC |
| 438 | AGACAUGG CUGAUGA X GAA AUCACCAC | GUGGUGAUU CCAUGUCU |
| 439 | GAGACAUG CUGAUGA X GAA AAUCACCA | UGGUGAUUC CAUGUCUC |
| 445 | GGACCCGA CUGAUGA X GAA ACAUGGAA | UUCCAUGUC UCGGGUCC |

Table IV-continued

Human KDR VEGF Receptor-Hammerhead Ribozyme and Substrate Sequence

| nt. Position | HH Ribozyme Sequence | Substrate |
|---|---|---|
| 447 | AUGGACCC CUGAUGA X GAA AGACAUGG | CCAUGUCUC GGGUCCAU |
| 452 | UUGAAAUG CUGAUGA X GAA ACCCGAGA | UCUCGGGUC CAUUUCAA |
| 456 | AGAUUUGA CUGAUGA X GAA AUGGACCC | GGGUCCAUU UCAAAUCU |
| 457 | GAGAUUUG CUGAUGA X GAA AAUGGACC | GGUCCAUUU CAAAUCUC |
| 458 | UGAGAUUU CUGAUGA X GAA AAAUGGAC | GUCCAUUUC AAAUCUCA |
| 463 | CACGUUGA CUGAUGA X GAA AUUUGAAA | UUUCAAAUC UCAACGUG |
| 465 | GACACGUU CUGAUGA X GAA AGAUUUGA | UCAAAUCUC AACGUGUC |
| 473 | CACAAAGU CUGAUGA X GAA ACACGUUG | CAACGUGUC ACUUUGUG |
| 477 | CUUGCACA CUGAUGA X GAA AGUGACAC | GUGUCACUU UGUGCAAG |
| 478 | UCUUGCAC CUGAUGA X GAA AAGUGACA | UGUCACUUU GUGCAAGA |
| 488 | UUUCUGGG CUGAUGA X GAA AUCUUGCA | UGCAAGAUA CCCAGAAA |
| 503 | CAGGAACA CUGAUGA X GAA AUCUCUUU | AAAGAGAUU UGUUCCUG |
| 504 | UCAGGAAC CUGAUGA X GAA AAUCUCUU | AAGAGAUUU GUUCCUGA |
| 507 | CCAUCAGG CUGAUGA X GAA ACAAAUCU | AGAUUUGUU CCUGAUGG |
| 508 | ACCAUCAG CUGAUGA X GAA AACAAAUC | GAUUUGUUC CUGAUGGU |
| 517 | AAUUCUGU CUGAUGA X GAA ACCAUCAG | CUGAUGGUA ACAGAAUU |
| 525 | UCCCAGGA CUGAUGA X GAA AUUCUGUU | AACAGAAUU UCCUGGGA |
| 526 | GUCCCAGG CUGAUGA X GAA AAUUCUGU | ACAGAAUUU CGGGGAC |
| 527 | UGUCCCAG CUGAUGA X GAA AAAUUCUG | CAGAAUUUC CUGGGACA |
| 548 | GAAAAGUA CUGAUGA X GAA AGCCCUUC | GAAGGGCUU UACUAUUC |
| 549 | GGAAUAGU CUGAUGA X GAA AAGCCCUU | AAGGGCUUU ACUAUUCC |
| 550 | GCGAAUAG CUGAUGA X GAA AAAGCCCU | AGGGCUUUA CUAUUCCC |
| 553 | GCUGGGAA CUGAUGA X GAA AGUAAAGC | GCUUUACUA UUCCCAGC |
| 555 | UAGCUGGG CUGAUGA X GAA AUAGUAAA | UUUACUAUU CCCAGCUA |
| 556 | GUAGCUGG CUGAUGA X GAA AAUAGUAA | UUACUAUUC CCAGCUAC |
| 563 | UGAUCAUG CUGAUGA X GAA AGCUGGGA | UCCCAGCUA CAUGAUCA |
| 570 | GCAUAGCU CUGAUGA X GAA AUCAUGUA | UACAUGAUC AGCUAUGC |
| 575 | UGCCAGCA CUGAUGA X GAA AGCUGAUC | GAUCAGCUA UGCUGGCA |
| 588 | UCACAGAA CUGAUGA X GAA ACCAUGCC | GCCAUGGUC UUCUGUGA |
| 590 | CUUCACAG CUGAUGA X GAA AGACCAUG | CAUGGUCUU CUGUGAAG |
| 591 | GCUUCACA CUGAUGA X GAA AAGACCAU | AUGGUCUUC UGUGAAGC |
| 606 | UCAUCAUU CUGAUGA X GAA AUUUUUGC | GCAAAAAUU AAUGAUGA |
| 607 | UUCAUCAU CUGAUGA X GAA AAUUUUUG | CAAAAAUUA AUGAUGAA |
| 619 | AGACUGGU CUGAUGA X GAA ACUUUCAU | AUGAAAGUU ACCAGUCU |
| 620 | UAGACUGG CUGAUGA X GAA AACUUUCA | UGAAAGUUA CCAGUCUA |
| 626 | ACAUAAUA CUGAUGA X GAA ACUGGUAA | UUACCAGUC UAUUAUGU |
| 628 | GUACAUAA CUGAUGA X GAA AGACUGGU | ACCAGUCUA UUAUGUAC |

Table IV-continued

Human KDR VEGF Receptor-Hammerhead Ribozyme and Substrate Sequence

| nt. Position | HH Ribozyme Sequence | Substrate |
|---|---|---|
| 630 | AUGUACAU CUGAUGA X GAA AUAGACUG | CAGUCUAUU AUGUACAU |
| 631 | UAUGUACA CUGAUGA X GAA AAUAGACU | AGUCUAUUA UGUACAUA |
| 635 | CAACUAUG CUGAUGA X GAA ACAUAAUA | UAUUAUGUA CAUAGUUG |
| 639 | ACGACAAC CUGAUGA X GAA AUGUACAU | AUGUACAUA GUUGUCGU |
| 642 | ACAACGAC CUGAUGA X GAA ACUAUGUA | UACAUAGUU GUCGUUGU |
| 645 | CCUACAAC CUGAUGA X GAA ACAACUAU | AUAGUUGUC GUUGUAGG |
| 648 | UACCCUAC CUGAUGA X GAA ACGACAAC | GUUGUCGUU GUAGGGUA |
| 651 | CUAUACCC CUGAUGA X GAA ACAACGAC | GUCGUUGUA GGGUAUAG |
| 656 | AAAUCCUA CUGAUGA X GAA ACCCUACA | UGUAGGGUA UAGGAUUU |
| 658 | AUAAAUCC CUGAUGA X GAA AUACCCUA | UAGGGUAUA GGAUUUAU |
| 663 | ACAUCAUA CUGAUGA X GAA AUCCUAUA | UAUAGGAUU UAUGAUGU |
| 664 | CACAUCAU CUGAUGA X GAA AAUCCUAU | AUAGGAUUU AUGAUGUG |
| 665 | CCACAUCA CUGAUGA X GAA AAAUCCUA | UAGGAUUUA UGAUGUGG |
| 675 | GGACUCAG CUGAUGA X GAA ACCACAUC | GAUGUGGUU CUGAGUCC |
| 676 | CGGACUCA CUGAUGA X GAA AACCACAU | AUGUGGUUC UGAGUCCG |
| 682 | AUGAGACG CUGAUGA X GAA ACUCAGAA | UUCUGAGUC CGUCUCAU |
| 686 | UUCCAUGA CUGAUGA X GAA ACGGACUC | GAGUCCGUC UCAUGGAA |
| 688 | AAUUCCAU CUGAUGA X GAA AGACGGAC | GUCCGUCUC AUGGAAUU |
| 696 | GAUAGUUC CUGAUGA X GAA AUUCCAUG | CAUGGAAUU GAACUAUC |
| 702 | CCAACAGA CUGAUGA X GAA AGUUCAAU | AUUGAACUA UCUGUUGG |
| 704 | CUCCAACA CUGAUGA X GAA AUAGUUCA | UGAACUAUC UGUUGGAG |
| 708 | UUUUCUCC CUGAUGA X GAA ACAGAUAG | CUAUCUGUU GGAGAAAA |
| 720 | UUUAAGAC CUGAUGA X GAA AGCUUUUC | GAAAAGCUU GUCUUAAA |
| 723 | CAAUUUAA CUGAUGA X GAA ACAAGCUU | AAGCUUGUC UUAAAUUG |
| 725 | UACAAUUU CUGAUGA X GAA AGACAAGC | GCUUGUCUU AAAUUGUA |
| 726 | GUACAAUU CUGAUGA X GAA AAGACAAG | CUUGUCUUA AAUUGUAC |
| 730 | UGCUGUAC CUGAUGA X GAA AUUUAAGA | UCUUAAAUU GUACAGCA |
| 733 | UCUUGCUG CUGAUGA X GAA ACAAUUUA | UAAAUUGUA CAGCAAGA |
| 750 | CCCACAUU CUGAUGA X GAA AGUUCAGU | ACUGAACUA AAUGUGGG |
| 762 | UUGAAGUC CUGAUGA X GAA AUCCCCAC | GUGGGGAUU GACUUCAA |
| 767 | CCCAGUUG CUGAUGA X GAA AGUGAAUC | GAUUGACUU CAACUGGG |
| 768 | UCCCAGUU CUGAUGA X GAA AAGUCAAU | AUUGACUUC AACUGGGA |
| 779 | AAGAAGGG CUGAUGA X GAA AUUCCCAG | CUGGGAAUA CCCUUCUU |
| 784 | CUUCGGAG CUGAUGA X GAA AGGGUAUU | AAUACCCUU CUUCGGAG |
| 785 | GCUUCGAA CUGAUGA X GAA AAGGGUAU | AUACCCUUC UUCGAAGC |
| 787 | AUGCUUCG CUGAUGA X GAA AGAAGGGU | ACCCUUCUU CGAAGCAU |

Table IV-continued

Human KDR VEGF Receptor-Hammerhead Ribozyme and Substrate Sequence

| nt. Position | HH Ribozyme Sequence | Substrate |
|---|---|---|
| 788 | GAUGCUUC CUGAUGA X GAA AAGAAGGG | CCCUUCUUC GAAGCAUC |
| 796 | CUUAUGCU CUGAUGA X GAA AUGCUUCG | CGAAGCAUC AGCAUAAG |
| 802 | AAGUUUCU CUGAUGA X GAA AUGCUGAU | AUCAGCAUA AGAAACUU |
| 810 | CGGUUUAC CUGAUGA X GAA AGUUUCUU | AAGAAACUU GUAAACCG |
| 813 | UCUCGGUU CUGAUGA X GAA ACAAGUUU | AAACUUGUA AACCGAGA |
| 825 | UGGGUUUU CUGAUGA X GAA AGGUCUCG | GGAGACCUA AAAACCCA |
| 836 | CACUCCCA CUGAUGA X GAA ACUGGGUU | AACCCAGUC UGGGAGUG |
| 857 | UGCUCAAA CUGAUGA X GAA AUUUCUUC | GAAGAAAUU UUUGAGCA |
| 858 | GUGCUCAA CUGAUGA X GAA AAUUUCUU | AAGAAAUUU UUGAGCAC |
| 859 | GGUGCUCA CUGAUGA X GAA AAAUUUCU | AGAAAUUUU UGAGCACC |
| 860 | AGGUGCUC CUGAUGA X GAA AAAAUUUC | GAAAUUUUU GAGCACCU |
| 869 | CUAUAGUU CUGAUGA X GAA AGGUGCUC | GAGCACCUU AACUAUAG |
| 870 | UCUAUAGU CUGAUGA X GAA AAGGUGCU | AGCACCUUA ACUAUAGA |
| 874 | ACCAUCUA CUGAUGA X GAA AGUUAAGG | CCUUAACUA UAGAUGGU |
| 876 | ACACCAUC CUGAUGA X GAA AUAGUUAA | UUAACUAUA GAUGGUGU |
| 885 | CUCCGGGU CUGAUGA X GAA ACACCAUC | GAUGGUGUA ACCCGGAG |
| 905 | AGGUGUAC CUGAUGA X GAA AUCCUUGG | CCAAGGAUU GUACACCU |
| 908 | CACAGGUG CUGAUGA X GAA ACAAUCCU | AGGAUUGUA CACCUGUG |
| 923 | GCCCACUG CUGAUGA X GAA AUGCUGCA | UGCAGCAUC CAGUGGGC |
| 956 | CCCUGACA CUGAUGA X GAA AUGUGCUG | CAGCACAUU UGUCAGGG |
| 957 | ACCCUGAC CUGAUGA X GAA AAUGUGCU | AGCACAUUU GUCAGGGU |
| 960 | UGGACCCU CUGAUGA X GAA ACAAAUGU | ACAUUUGUC AGGGUCCA |
| 966 | UUUUCAUG CUGAUGA X GAA ACCCUGAC | GUCAGGGUC CAUGAAAA |
| 979 | AGCAACAA CUGAUGA X GAA AGGUUUUU | AAAAACCUU UUGUUGCU |
| 980 | AAGCAACA CUGAUGA X GAA AAGGUUUU | AAAACGUUU UGUUGCCU |
| 981 | AAAGCAAC CUGAUGA X GAA AAAGGUUU | AAACCUUUU GUUGCUUU |
| 984 | CCAAAAGC CUGAUGA X GAA ACAAAAGG | CCUUUUGUU GCUUUUGG |
| 988 | ACUUCCAA CUGAUGA X GAA AGCAACAA | UUGUUGCUU UUGGAAGU |
| 989 | CACUUCCA CUGAUGA X GAA AAGCAACA | UGUUGCUUU UGGAAGUG |
| 990 | CCACUUCC CUGAUGA X GAA AAAGCAAC | GUUGCUUUU GGAAGUGG |
| 1007 | CCACCAGA CUGAUGA X GAA AUUCCAUG | CAUGGAAUC UGUGGUGG |
| 1009 | UUCCACCA CUGAUGA X GAA AGAUUCCA | UGGAAUCUC UGGUGGAA |
| 1038 | GGGAUUCU CUGAUGA X GAA ACACGCUC | GAGCGUGUC AGAAUCCC |
| 1044 | UUCGCAGG CUGAUGA X GAA AUUCUGAC | GUCAGAAUC CUGCGAA |
| 1055 | AACCAAGG CUGAUGA X GAA ACUUCGCA | UGCAAGUA CCUUGGUU |
| 1059 | GGGUAACC CUGAUGA X GAA AGGUACUU | AAGUACCUU GGUUACCC |
| 1063 | GGGUGGGU CUGAUGA X GAA ACCAAGGU | ACCUUGGUU ACCCACCC |

Table IV-continued

Human KDR VEGF Receptor-Hammerhead Ribozyme and Substrate Sequence

| nt. Position | HH Ribozyme Sequence | Substrate |
|---|---|---|
| 1064 | GGGGUGGG CUGAUGA X GAA AACCAAGG | CCUUGGUUA CCCACCCC |
| 1080 | UACCAUUU CUGAUGA X GAA AUUUCUGG | CCAGAAAUA AAAUGGUA |
| 1088 | CAUUUUUA CUGAUGA X GAA ACCAUUUU | AAAAUGGUA UAAAAAUG |
| 1090 | UCCAUUUU CUGAUGA X GAA AUACCAUU | AAUGGUAUA AAAAUGGA |
| 1101 | UCAAGGGG CUGAUGA X GAA AUUCCAUU | AAUGGAAUA CCCCUUGA |
| 1107 | UUGGACUC CUGAUGA X GAA AGGGGUAU | AUACCCCUU GAGUCCAA |
| 1112 | UGUGAUUG CUGAUGA X GAA ACUCAAGG | CCUUGAGUC CAAUCACA |
| 1117 | AAUUGUGU CUGAUGA X GAA AUUGGACU | AGUCCAAUC ACACAAUU |
| 1125 | CCCGCUUU CUGAUGA X GAA AUUGUGUG | CACACAAUU AAAGCGGG |
| 1126 | CCCGGCUU CUGAUGA X GAA AAUUGUGU | ACACAAUUA AAGCGGGG |
| 1140 | AUCGUCAG CUGAUGA X GAA ACAUGCCC | GGGCAUGUA CUGACGAU |
| 1149 | ACUUCCAU CUGAUGA X GAA AUCGUCAG | CUGACGAUU AUGGAAGU |
| 1150 | CACUUCCA CUGAUGA X GAA AAUCGUCA | UGACGAUUA UGGAAGUG |
| 1180 | GACAGUGU CUGAUGA X GAA AUUUCCUG | CAGGAAAUU ACACUGUC |
| 1181 | UGACAGUG CUGAUGA X GAA AAUUUCCU | AGGAAAUUA CACUGUCA |
| 1188 | GUAAGGAU CUGAUGA X GAA ACAGUGUA | UACACUGUC AUCCUUAC |
| 1191 | UUGGUAAG CUGAUGA X GAA AUGACAGU | ACUGUCAUC CUUACCAA |
| 1194 | GGAUUGGU CUGAUGA X GAA AGGAUGAC | GUCAUCCUU ACCAAUCC |
| 1195 | GGGAUUGG CUGAUGA X GAA AAGGAUGA | UCAUCCUUA CCAAUCCC |
| 1201 | UGAAAUGG CUGAUGA X GAA AUUGGUAA | UUACCAAUC CAUUUCA |
| 1206 | UCCUUUGA CUGAUGA X GAA AUGGGAUU | AAUCCCAUU UCAAGGA |
| 1207 | CUCGUUUG CUGAUGA X GAA AAUGGGAU | AUCCCAUUU CAAAGGAG |
| 1208 | UCUCCUUU CUGAUGA X GAA AAAUGGGA | UCCCAUUUC AAAGGAGA |
| 1233 | ACCAGAGA CUGAUGA X GAA ACCACAUG | CAUGUGGUC UCUCUGGU |
| 1235 | CAACCAGA CUGAUGA X GAA AGACCACA | UGUGGUCUC UCUGGUUG |
| 1237 | CACAACCA CUGAUGA X GAA AGAGACCA | UGGUCUCUC UGGUUGUG |
| 1242 | ACAUACAC CUGAUGA X GAA ACCAGAGA | UCUCUGGUU GUGUAUGU |
| 1247 | GUGGGACA CUGAUGA X GAA ACACAACC | GGUUGUGUA UGUCCCAC |
| 1251 | UGGGGUGG CUGAUGA X GAA ACAUACAC | GUGUAUGUC CACCCCA |
| 1263 | UUCUCACC CUGAUGA X GAA AUCUGGGG | CCCCAGAUU GGUGACAA |
| 1274 | AGAUUAGA CUGAUGA X GAA AUUUCUCA | UGAGAAAUC UCUAAUCU |
| 1276 | AGAGAUUA CUGAUGA X GAA AGAUUUCU | AGAAAUCUC UAAUCUCU |
| 1278 | GGAGAGAU CUGAUGA X GAA AGAGAUUU | AAAUCUCUA AUCUCUCC |
| 1281 | ACAGGAGA CUGAUGA X GAA AUUAGAGA | UCUCUAAUC UCCUGU |
| 1283 | CCACAGGA CUGAUGA X GAA AGAUUAGA | UCUAAUCUC UCCUGUGG |
| 1285 | AUCCACAG CUGAUGA X GAA AGAGAUUA | UAAUCUCUC CUGUGGAU |

Table IV-continued

Human KDR VEGF Receptor-Hammerhead Ribozyme and Substrate Sequence

| nt. Position | HH Ribozyme Sequence | Substrate |
|---|---|---|
| 1294 | CUGGUAGG CUGAUGA X GAA AUCCACAG | CUGUGGAUU CCUACCAG |
| 1295 | ACUGGUAG CUGAUGA X GAA AAUCCACA | UGUGGAUUC CUACCAGU |
| 1298 | CGUACUGG CUGAUGA X GAA AGGAAUCC | GGAUUCCUA CCAGUACG |
| 1304 | UGGUGCCG CUGAUGA X GAA ACUGGUAG | CUACCAGUA CGCCACCA |
| 1315 | CAGCGUUU CUGAUGA X GAA AGUGGUGC | GCACCACUC AAACGCUG |
| 1330 | AUAGACCG CUGAUGA X GAA ACAUGUCA | UGACAUGUA CGGUCUAU |
| 1335 | AUGGCAUA CUGAUGA X GAA ACCGUACA | UGUACGGUC UAUGCCAU |
| 1337 | GAAUGGCA CUGAUGA X GAA AGACCGUA | UACGGUCUA UGCCAUUC |
| 1344 | GGGGGAGG CUGAUGA X GAA AUGGCAUA | UAUGCCAUU CCUCCCCC |
| 1345 | CGGGGGAG CUGAUGA X GAA AAUGGCAU | AUGCCAUUC CUCCCCCG |
| 1348 | AUGCGGGG CUGAUGA X GAA AGGAAUGG | CCAUUCCUC CCCCGCAU |
| 1357 | GUGGAUGU CUGAUGA X GAA AUGCGGGG | CCCCGCAUC ACAUCCAC |
| 1362 | UACCAGUG CUGAUGA X GAA AUGUGAUG | CAUCACAUC CACUGGUA |
| 1370 | ACUGCCAA CUGAUGA X GAA ACCAGUGG | CCACUGGUA UUGGCAGU |
| 1372 | CAACUGCC CUGAUGA X GAA AUACCAGU | ACUGGUAUU GCCAGUUG |
| 1379 | CUUCCUCC CUGAUGA X GAA ACUGCCAA | UUGGCAGUU GGAGGAAG |
| 1416 | GUCACUGA CUGAUGA X GAA ACAGCUUG | CAAGCUGUC UCAGUGAC |
| 1418 | UUGUCACU CUGAUGA X GAA AGACAGCU | AGCUGUCUC AGUGACAA |
| 1433 | CACAAGGG CUGAUGA X GAA AUGGGUUU | AAACCCAUA CCCUUGUG |
| 1438 | UUCUUCAC CUGAUGA X GAA AGGGUAUG | CAUACCCUU GUGAACAA |
| 1466 | CUCCCUGG CUGAUGA X GAA AGUCCUCC | GGAGGACUU CCAGGGAG |
| 1467 | CCUCCCUG CUGAUGA X GAA AAGUCCUC | GAGGACUUC CAGGGAGG |
| 1480 | UUCAAUUU CUGAUGA X GAA AUUUCCUC | GAGGAAAUA AAAUUGAA |
| 1485 | UUAACUUC CUGAUGA X GAA AUUUUAUU | AAUAAAAUU GAAGUUAA |
| 1491 | UUUUUAUU CUGAUGA X GAA ACUUCAAU | AUUGAAGUU AAUAAAAA |
| 1492 | AUUUUUAU CUGAUGA X GAA AAGUUCAA | UUGAAGUUA AUAAAAAU |
| 1495 | UGGAUUUU CUGAUGA X GAA AUUAACUU | AAGUUAAUA AAAAUCAA |
| 1501 | AGCAAAUU CUGAUGA X GAA AUUUUUAU | AUAAAAAUC AAUUUGCU |
| 1505 | UUAGAGCA CUGAUGA X GAA AUUGAUUU | AAAUCAAUU UGCUCUAA |
| 1506 | AUUAGAGC CUGAUGA X GAA AAUUGAUU | AAUCAAUUU GCUCUAAU |
| 1510 | UUCAAUUA CUGAUGA X GAA AGCAAAUU | AAUUUGCUC UAAUAGAA |
| 1512 | CCUUCAAU CUGAUGA X GAA AGAGCAAA | UUUGCUCUA AUUGAAGG |
| 1515 | UUUCCUUC CUGAUGA X GAA AUUAGAGC | GCUCUAAUU GAAGCAAA |
| 1536 | AGGGUACU CUGAUGA X GAA ACAGUUUU | AAAACUGUA AGUACCCU |
| 1540 | AACAAGGG CUGAUGA X GAA ACUUACAG | CUGUAAGUA CCCUUGUU |
| 1545 | UGGAUAAC CUGAUGA X GAA AGGGUACU | AGUACCCUU CUUAUCCA |
| 1548 | GCUUGGAU CUGAUGA X GAA ACAAGGGU | ACCCUUGUU AUCCAAGC |

Table IV-continued

Human KDR VEGF Receptor-Hammerhead Ribozyme and Substrate Sequence

| nt. Position | HH Ribozyme Sequence | Substrate |
|---|---|---|
| 1549 | CGCUUGGA CUGAUGA X GAA AACAAGGG | CCCUUGUUA UCCAAGCG |
| 1551 | GCCGCUUG CUGAUGA X GAA AUAACAAG | CUUGUUAUC CAAGCGGC |
| 1568 | ACAAAGCU CUGAUGA X GAA ACACAUUU | AAAUGUGUC AGCUUUGU |
| 1573 | UUUGUACA CUGAUGA X GAA AGCUGACA | UGUCAGUUU UGUACAAA |
| 1574 | AUUUGUAC CUGAUGA X GAA AAGCUGAC | GUCAGCUUU GUACAAAU |
| 1577 | CACAUUUG CUGAUGA X GAA ACAAAGCU | AGCUUUGUA CAAAUGUG |
| 1593 | ACUUUGUU CUGAUGA X GAA ACCGCUUC | GAAGCGGUC AACAAAGU |
| 1602 | CCUCUCCC CUGAUGA X GAA ACUUUGUU | AACAAAGUC GGGAGAGG |
| 1623 | UGGAAGGA CUGAUGA X GAA AUCACCCU | AGGGUGAUC UCCUUCCA |
| 1625 | CGUGGAAG CUGAUGA X GAA AGAUCACC | GGUGAUCUC CUUCCACG |
| 1628 | UCACGUGG CUGAUGA X GAA AGGAGAUC | GAUCUCCUU CCACGUGA |
| 1629 | GUCACGUG CUGAUGA X GAA AAGGAGAU | AUCUCCUUC CACGUGAC |
| 1645 | AAUUCAG CUGAUGA X GAA ACCCCUGG | CCAGGGUC CUGAAAUU |
| 1653 | UGCAAAGU CUGAUGA X GAA AUUUCAGG | CCUGAAAUU ACUUUGCA |
| 1654 | UUGCAAAG CUGAUGA X GAA AAUUUCAG | CUGAAAUUA CUUUGCAA |
| 1657 | AGGUUGCA CUGAUGA X GAA AGUAAUUU | AAAUUACUU UGCAACCU |
| 1658 | CAGGUUGC CUGAUGA X GAA AAGUAAUU | AAUUACUUU GCAACCUG |
| 1697 | ACCACAAA CUGAUGA X GAA ACACGCUC | GAGCGUGUC UUUGUGGU |
| 1699 | GCACCACA CUGAUGA X GAA AGACACGC | GCGUGUCUU UGUGGUGC |
| 1700 | UGCACCAC CUGAUGA X GAA AAGACACG | CGUGUCUUU GUGGUGCA |
| 1721 | CAAACGUA CUGAUGA X GAA AUCUGUCU | AGACAGAUC UACGUUUG |
| 1723 | CUCAAACG CUGAUGA X GAA AGAUCUGU | ACAGAUCUA CGUUUGAG |
| 1727 | GGUUCUCA CUGAUGA X GAA ACGUAGAU | AUCUACGUU UGAGAACC |
| 1728 | AGGUUCUC CUGAUGA X GAA AACGUAGA | UCUACGUUU GAGAACCU |
| 1737 | UACCAUGU CUGAUGA X GAA AGGUUCUC | GAAACCUC ACAUGGUA |
| 1745 | CAAGCUUG CUGAUGA X GAA ACCAUGUG | CACAUGGUA CAAGCUUG |
| 1752 | UGUGGGCC CUGAUGA X GAA AGCUUGUA | UACAAGCUU GGCCCACA |
| 1765 | GAUUGGCA CUGAUGA X GAA AGGCUGUG | CACAGCCUC UGCCAAUC |
| 1773 | CCCACAUG CUGAUGA X GAA AUUGGCAG | CUGCCAAUC CAUGUGGG |
| 1787 | GUGUGGGC CUGAUGA X GAA ACUCUCCC | GGGAGAGUU GCCCACAC |
| 1800 | UUCUUGCA CUGAUGA X GAA ACAGGUGU | ACACCUGUU UGCAAGAA |
| 1801 | GUUCUUGC CUGAUGA X GAA AACAGGUG | CACCUGUUU GCAAGAAC |
| 1811 | GAGUAUCC CUGAUGA X GAA AGUUCUUG | CAAGAACUU GGAUACUC |
| 1816 | CCAAAGAG CUGAUGA X GAA AUCCAAGU | ACUUGGAUA CUCUUUGG |
| 1819 | UUUCCAAA CUGAUGA X GAA AGUAUCCA | UGGAUACUC UUUGGAAA |
| 1821 | AAUUCCA CUGAUGA X GAA AGAGUAUC | GAUACUCUU UGGAAAUU |

Table IV-continued

Human KDR VEGF Receptor-Hammerhead Ribozyme and Substrate Sequence

| nt. Position | HH Ribozyme Sequence | Substrate |
|---|---|---|
| 1822 | CAAUUUCC CUGAUGA X GAA AAGAGUAU | AUACUCUUU GGAAAUUG |
| 1829 | UGGCAUUC CUGAUGA X GAA AUUUCCAA | UUGGAAAUU GAAUGCCA |
| 1844 | UAUUAGAG CUGAUGA X GAA ACAUGGUG | CACCAUGUU CUCUAAUA |
| 1845 | CUAUUAGA CUGAUGA X GAA AACAUGGU | ACCAUGUUC UCUAAUAG |
| 1847 | UGCUAUUA CUGAUGA X GAA AGAACAUG | CAUUUCUC UAAUAGCA |
| 1849 | UGUGCCAU CUGAUGA X GAA AGAGAACA | UGUUCUCUA AUAGCACA |
| 1852 | AUUUGUGC CUGAUGA X GAA AUUAGAGA | UCUCUAAUA GCACAAAU |
| 1866 | AUGAUCAA CUGAUGA X GAA AUGUCAUU | AAUGAGAUU UUGAUCAU |
| 1867 | CAUGAUCA CUGAUGA X GAA AAUGUCAU | AUGAGAUUU UGAUCAUG |
| 1868 | CCAUGAUC CUGAUGA X GAA AAAUGUCA | UGACAUUUU GAUCAUGG |
| 1872 | AGCUCCAU CUGAUGA X GAA AUCAAAAU | AUUGAUCUU AUGGAGCU |
| 1881 | GCAUUCUU CUGAUGA X GAA AGCUCCAU | AUGGAGCUU AAGAAUGC |
| 1882 | UGCAUUCU CUGAUGA X GAA AAGCUCCA | UGGAGCUUA AGAAUGCA |
| 1892 | CCUGCAAG CUGAUGA X GAA AUGCAUUC | GAAUGCAUC CUUGCAGG |
| 1895 | GGUCCUGC CUGAUGA X GAA AGGAUGCA | UGCAUCCUU GCAGGACC |
| 1913 | GGCAGACA CUGAUGA X GAA AGUCUCCU | AGGAGACUA UGUCUGCC |
| 1917 | GCAAGGCA CGGAUGA X GAA ACAUAGUC | GACUAUGUC UGCCUUGC |
| 1923 | UCUUGAGC CUGAUGA X GAA AGGCAGAC | GUCUGCCUU GCUCAAGA |
| 1927 | CCUGUCUU CUGAUGA X GAA AGCAAGGC | GCCUUGCUC AAGACAGG |
| 1954 | GACCACGC CUGAUGA X GAA AUGUCUUU | AAAGACAUU GCGUGGUC |
| 1962 | AGCUGCCU CUGAUGA X GAA ACCACGCA | UGCGUGGUC AGGCAGCU |
| 1971 | AGGACUGU CUGAUGA X GAA AGCUGCCU | AGGCAGCUC ACAGUCUU |
| 1977 | CGCUCUAG CUGAUGA X GAA ACUGUGAG | CUCACAGUC CUAGAGCG |
| 1980 | ACACGCUC CUGAUGA X GAA AGGACUGU | ACAGUCCUA GAGCGUGU |
| 2001 | UUUCCUGU CUGAUGA X GAA AUCGUGGG | CCCACGAUC ACAGGAAA |
| 2020 | UGUCGUCU CUGAUGA X GAA AUUCUCCA | UGGAGAAUC AGACGACA |
| 2032 | UUCCCCAA CUGAUGA X GAA ACUUGUCG | CGACAAGUA UUGGGGAA |
| 2034 | CUUUCCCC CUGAUGA X GAA AUACUUGU | ACAAGUAUU GGGGAAAG |
| 2046 | GAGACUUC CUGAUGA X GAA AUGCUUUC | GAAAGCAUC GAAGUCUC |
| 2052 | GUGCAUGA CUGAUGA X GAA ACUUCGAU | AUCGAAGUC UCAUGCAC |
| 2054 | CCGUGCAU CUGAUGA X GAA AGACUUCG | CGAAGUCUC AUGCACGG |
| 2066 | GAUUCCCA CUGAUGA X GAA AUGCCGUG | CACGCCAUC UGGGAAUC |
| 2074 | UGGAGGGG CUGAUGA X GAA AUUCCCAG | CUGGGAAUC CCCCUCCA |
| 2080 | GAUCUGUG CUGAUGA X GAA AGGGGGAU | AUCCCCCUC CACAGAUC |
| 2088 | AACCACAU CUGAUGA X GAA AUCUGUGG | CCACAGAUC AUGUGGUU |
| 2096 | UAUCUUUA CUGAUGA X GAA ACCACAUG | CAUGUGGUU UAAAGAUA |
| 2097 | UUAUCUUU CUGAUGA X GAA AACCACAU | AUGUGGUUU AAAGAUAA |

Table IV-continued

Human KDR VEGF Receptor-Hammerhead Ribozyme and Substrate Sequence

| nt. Position | HH Ribozyme Sequence | Substrate |
|---|---|---|
| 2098 | AUUAUCUU CUGAUGA X GAA AAACCACA | UGUGGUUUA AAGAUAAU |
| 2104 | GGUCUCAU CUGAUGA X GAA AUCUUUAA | UUAAAGAUA AUGAGACC |
| 2115 | UCUUCUAC CUGAUGA X GAA AGGGUCUC | GAGACCCUU GUAGAAGA |
| 2118 | GAGUCUUC CUGAUGA X GAA ACAAGGGU | ACCCUUGUA GAAGACUC |
| 2126 | CAAUGCCU CUGAUGA X GAA AGUCUUCU | AGAAGACUC AGGCAUUG |
| 2133 | UUCAAUAC CUGAUGA X GAA AUGCCUGA | UCAGGCAUU GUAUUGAA |
| 2136 | UCCUUCAA CUGAUGA X GAA ACAAUGCC | GCCAUUGUA UUGAAGGA |
| 2138 | CAUCCUUC CUGAUGA X GAA AUACAAUG | CAUUGUAUU GAAGGAUG |
| 2160 | CGGAUAGU CUGAUGA X GAA AGGUUCCG | CGGAACCUC ACUAUCCG |
| 2164 | UCUGCGGA CUGAUGA X GAA AGUGAGGU | ACCUCACUA UCCGCAGA |
| 2166 | ACUCUGCG CUGAUGA X GAA AUAGUGAG | CUCACUAUC CGCAGAGU |
| 2196 | CAGGUGUA CUGAUGA X GAA AGGCCUUC | GAAGGCCUC UACACCUG |
| 2198 | GGCAGGUG CUGAUGA X GAA AGAGGCCU | AGGCCUCUA CACCUGCC |
| 2220 | CAGCCAAG CUGAUGA X GAA ACACUGGA | UGCAGUGUU CUUGGCUG |
| 2221 | ACAGCCAA CUGAUGA X GAA AACACUGC | GCAGUGUUC UUGGCUGU |
| 2223 | GCACAGCC CUGAUGA X GAA AGAACACU | AGUGUUCUU GGCUGUGC |
| 2246 | UUAUGAAA CUGAUGA X GAA AUGCCUCC | GGAGGCAUU UUUCAUAA |
| 2247 | AUUAUGAA CUGAUGA X GAA AAUGCCUC | GAGGCAUUU UUCAUAAU |
| 2248 | UAUUAUGA CUGAUGA X GAA AAAUGCCU | AGGCAUUUU UCAUAAUA |
| 2249 | CUAUUAUG CUGAUGA X GAA AAAAUGCC | GGCAUUUUU CAUAAUAG |
| 2250 | UCUAUUAU CUGAUGA X GAA AAAAAUGC | GGAUUUUUC AUAAUAGA |
| 2253 | CCUUCUAU CUGAUGA X GAA AUGAAAAA | UUUUUCAUA AUAGAAGG |
| 2256 | GCACCUUC CUGAUGA X GAA AUUAUGAA | UUCAUAAUA GAAGGUGC |
| 2282 | UGAUUUCC CUGAUGA X GAA AGUUCGUC | GACGAACUU GGAAAUCA |
| 2289 | AGAAUAAU CUGAUGA X GAA AUUUCCAA | UUGGAAAUC AUUAUUCU |
| 2292 | ACUAGAAU CUGAUGA X GAA AUGAUUUC | GAAAUCAUU AUUCUAGU |
| 2293 | UACUAGAA CUGAUGA X GAA AAUGAUUU | AAAUCAUUA UUCUAGUA |
| 2295 | CCUACUAG CUGAUGA X GAA AUAAUGAU | AUCAUUAUU CUAGUAGG |
| 2296 | GCCUACUA CUGAUGA X GAA AAUAAUGA | UCAUUAUUC UAGUAGGC |
| 2298 | GUGCCUAC GUGAUGA X GAA AGAAUAAU | AUUAUUCUA GUAGGGAC |
| 2301 | GUCGUGCC CUGAUGA X GAA ACUAGAAU | AUUCUAGUA GGCACGAC |
| 2316 | AACAUGGC CUGAUGA X GAA AUCACCGU | ACGGUGAUU GCCAUGUU |
| 2324 | GCCAGAAG CUGAUGA X GAA ACAUGGCA | UGCCAUGUU CUUCUGGC |
| 2325 | AGCCAGAA CUGAUGA X GAA AACAUGGC | GCCAUGUUC UUCUGGCU |
| 2327 | GUAGCCAG CUGAUGA X GAA AGAACAUG | CAUGUUCUU CUGGCUAC |
| 2328 | AGUAGCCA GUGAUGA X GAA AAGAACAU | AUGUUCUUC UGGCUACU |

Table IV-continued

Human KDR VEGF Receptor-Hammerhead Ribozyme and Substrate Sequence

| nt. Position | HH Ribozyme Sequence | Substrate |
|---|---|---|
| 2334 | ACAAGAAG CUGAUGA X GAA AGCCAGAA | UUCUGGCUA CUUCUGGU |
| 2337 | AUGACAAG CUGAUGA X GAA AGUAGCCA | UGGCUACUU CUUGUCAU |
| 2338 | GAUGACAA CUGAUGA X GAA AGUAGCC | GGCUACUUC UUGUCAUC |
| 2340 | AUGAUGAC CUGAUGA X GAA AGAAGUAG | CUACUUCUU GUCAUCAU |
| 2343 | AGGAUGAU CUGAUGA X GAA ACAAGAAG | CUUCUUGUC AUCAUCCU |
| 2346 | CCUAGGAU CUGAUGA X GAA AUGACAAG | CUUGUCAUC AUCCUAGG |
| 2349 | GUCCUAG CUGAUGA X GAA AUGAUGAC | GUCAUCAUC CUAGGGAC |
| 2352 | ACGGUCCC CUGAUGA X GAA AGGAUGAU | AUCAUCCUA GGACCGU |
| 2361 | GCCCGCUU CUGAUGA X GAA ACGGUCCC | GGGACCGUU AAGCGGGC |
| 2362 | GGCCCGCU CUGAUGA X GAA AACGGUCC | GGACCGUUA AGCGGGCC |
| 2396 | UGGACAAG CUGAUGA X GAA AGCCUGUC | GACAGGCUA CUUGUCCA |
| 2399 | CGAUGGAC CUGAUGA X GAA AGUAGCCU | AGGCUACUU GUCCAUCG |
| 2402 | UGACGAUG CUGAUGA X GAA ACAAGUAG | CUACUUGUC CAUCGUCA |
| 2406 | UCCAUGAC CUGAUGA X GAA AUGGACAA | UUGUCCAUC GUCAUGGA |
| 2409 | GGAUCCAU CUGAUGA X GAA ACGAUGGA | UCCAUCGUC AUGGAUCC |
| 2416 | UUCAUCUG CUGAUGA X GAA AUCCAUGA | UCAUGGAUC CAGAUGAA |
| 2427 | UCCAAUGG CUGAUGA X GAA AGUUCAUC | GAUGAACUC CAUUGGA |
| 2432 | GUUCAUCC CUGAUGA X GAA AUGGGAGU | ACUCCCAUU GGAUGAAC |
| 2443 | UCGUUCAC CUGAUGA X GAA AUGUUCAU | AUGAACAUU GUGAACGA |
| 2458 | GGCAUCAU CUGAUGA X GAA AGGCAGUC | GACUGCCUU AUGAUGCC |
| 2459 | UGGCAUCA CUGAUGA X GAA AAGGCAGU | ACUGCCUUA UGAUGCCA |
| 2480 | CUCUGGGG CUGAUGA X GAA AUUCCCAU | AUGGGAAUU CCCCAGAG |
| 2481 | UCUCUGGG CUGAUGA X GAA AAUUCCCA | UGGGAAUUC CCCAGAGA |
| 2502 | GGCUUACC CUGAUGA X GAA AGGUUCAG | CUGAACCUA GGUAAGCC |
| 2506 | AAGAGGCU CUGAUGA X GAA ACCUAGGU | ACCUAGGUA AGCCUCUU |
| 2512 | ACGGCCAA CUGAUGA X GAA AGGCUUAC | GUAAGCCUC UUGGCCGU |
| 2514 | CCACGGCC CUGAUGA X GAA AGAGGCUU | AAGCCUCUU GGCCGUGG |
| 2528 | CUUGGCCA CUGAUGA X GAA AGGCACCA | UGGUGCCUU UGGCCAAG |
| 2529 | UCUUGGCC CUGAUGA X GAA AAGGCACC | GGUGCCUUU GGCCAAGA |
| 2541 | UCUGCUUC CUGAUGA X GAA AUCUCUUG | CAAGAGAUU GAAGCAGA |
| 2555 | CAAUUCCA CUGAUGA X GAA AGGCAUCU | AGAUGCCUU UGGAAUUG |
| 2556 | UCAAUUCC CUGAUGA X GAA AAGGCAUC | GAUGCCUUU GGAAUUGA |
| 2562 | GUCUUGUC CUGAUGA X GAA AUUCGAAA | UUUGGAAUU GACAAGAC |
| 2578 | UGUCCUGC CUGAUGA X GAA AGUUGCUG | CAGCAACUU GCAGGACA |
| 2589 | UUGACUGC CUGAUGA X GAA ACUGUCCU | AGGACAGUA GCAGUCAA |
| 2595 | AACAUUUU CUGAUGA X GAA ACUGCUAC | GUAGCAGUC AAAAUGUU |
| 2603 | CUUCUUUC CUGAUGA X GAA ACAUUUUG | CAAAAUGUU GAAAGAAG |

Table IV-continued

Human KDR VEGF Receptor-Hammerhead Ribozyme and Substrate Sequence

| nt. Position | HH Ribozyme Sequence | Substrate |
|---|---|---|
| 2632 | GAGAGCUC CUGAUGA X GAA AUGCUCAC | GUGAGCAUC GAGCUCUC |
| 2638 | AGACAUGA CUGAUGA X GAA AGCUCGAU | AUCGAGCUC UCAUGUCU |
| 2640 | UCAGACAU CUGAUGA X GAA AGAGCUCG | CGAGCUCUC AUGUCUGA |
| 2645 | UGAGUUCA CUGAUGA X GAA ACAUGAGA | UCUCAUGUC UGAACUCA |
| 2652 | AGGAUCUU CUGAUGA X GAA AGUUCAGA | UCUGAACUC AAGAUCCU |
| 2658 | UGAAUGAG CUGAUGA X GAA AUCUUGAG | CUCAAGAUC UCAUUCA |
| 2661 | AUAUGAAU CUGAUGA X GAA AGGAUCUU | AAGAUCCUC AUUCAUAU |
| 2664 | CCAAGAUG CUGAUGA X GAA AUGAGGAU | AUCCUCAUU CAUAUUGG |
| 2665 | ACCAAUAU CUGAUGA X GAA AAUGAGGA | UCCUCAUUC AUAUUGGU |
| 2668 | GUGACCAA CUGAUGA X GAA AUGAAUGA | UCAUUCAUA UUGGUCAC |
| 2670 | UGGGGACC CUGAUGA X GAA AUAUGAAU | AUUCAUAUU GGUCACCA |
| 2674 | GAGAUGGU CUGAUGA X GAA ACCAAUAU | AUAUUGGUC ACCAUCUC |
| 2680 | CACAUUGA CUGAUGA X GAA AUGGUGAC | GUCACCAUC UCAAUGUG |
| 2682 | ACCACAUU CUGAUGA X GAA AGAUGGUG | CACCAUCUC AAUGUGGU |
| 2691 | AGAAGGUU CUGAUGA X GAA ACCACAUU | AAUGUGGUC AACCUUCU |
| 2697 | GCACCUAG CUGAUGA X GAA AGGUUGAC | GUCAACCUU CUAGGUGC |
| 2698 | GGCACCUA CUGAUGA X GAA AAGGUUGA | UCAACCUUC UAGGUGCC |
| 2700 | CAGGCACC CUGAUGA X GAA AGAAGGUU | AACCUUCUA GGUGCCUG |
| 2710 | UGGCUUGG CUGAUGA X GAA ACAGGCAC | GUGCCUGUA CCAAGCCA |
| 2730 | AUCACCAU CUGAUGA X GAA AGUGGCCC | GGGCCACUC AUGUUGAU |
| 2739 | AAUCCAC CUGAUGA X GAA AUCACCAU | AUGGUGAUU GUGGAAUU |
| 2747 | AUUUGCAG CUGAUGA X GAA AUUCCACA | UGUGGAAUU CUGCAAAU |
| 2748 | AAUUUGCA CUGAUGA X GAA AAUUCCAC | GUGGAAUUC UGCAAAUU |
| 2756 | GGUUUCCA CUGAUGA X GAA AUUUGCAG | CUGCAAAUU UGGAAACC |
| 2757 | AGGUUUCC CUGAUGA X GAA AAUUUGCA | UGCAAAUUU GGAAACCU |
| 2768 | GGUAAGUG CUGAUGA X GAA ACAGGUUU | AAACCUGUC CACUUACC |
| 2773 | CCUCAGGU CUGAUGA X GAA AGUGGACA | UGUCCACUU ACCUGAGG |
| 2774 | UCCUCAGG CUGAUGA X GAA AAGUGGAC | GUCCACUUA CCUGAGGA |
| 2798 | AGGGGACA CUGAUGA X GAA AUUCAUUU | AAAUGAAUU UGUCCCCU |
| 2799 | UAGGGGAC CUGAUGA X GAA AAUUCAUU | AAUGAAUUU GUCCCCUA |
| 2802 | UUGUAGGG CUGAUGA X GAA ACAAAUUC | GAAUUUGUC CCUACAA |
| 2807 | UGGUCUUG CUGAUGA X GAA AGGGGACA | UGUCCCCUA CAAGACCA |
| 2828 | CUUGACGG CUGAUGA X GAA AUCGUGCC | GGCACGAUU CCGUCAAG |
| 2829 | CCUUGACG CUGAUGA X GAA AAUCGUGC | GCACGAUUC CGUCAAGG |
| 2833 | UUUCCCUU CUGAUGA X GAA ACGGAAUC | GAUUCCGUC AAGGGAAA |
| 2846 | CUCCAACG CUGAUGA X GAA AGUCUUUC | GAAAGACUA CGUUGGAG |

Table IV-continued

Human KDR VEGF Receptor-Hammerhead Ribozyme and Substrate Sequence

| nt. Position | HH Ribozyme Sequence | Substrate |
|---|---|---|
| 2850 | AUUGCUCC CUGAUGA X GAA ACGUAGUC | GACUACGUU GGAGCAAU |
| 2859 | UCCACAGG CUGAUGA X GAA AUUGCUCC | GGAGCAAUC CCUGUGGA |
| 2869 | CCGUUUCA CUGAUGA X GAA AUCCACAG | CUGUGGAUC UGAAACGG |
| 2882 | UGCUGUCC CUGAUGA X GAA AGCGCCGU | ACGGCGCUU GGACAGCA |
| 2892 | CUACUGGU CUGAUGA X GAA AUGCUGUC | GACAGCAUC ACCAGUAG |
| 2899 | GCUCUGGC CUGAUGA X GAA ACUGGUGA | UCACCAGUA GCCAGAGC |
| 2909 | AGCUGGCU CUGAUGA X GAA AGCUCUGG | CCAGAGCUC AGCCAGCU |
| 2918 | CAAAUCCA CUGAUGA X GAA AGCUGGCU | AGCCAGCUC UGGAUUUG |
| 2924 | CCUCCACA CUGAUGA X GAA AUCCAGAG | CUCUGGAUU UGUGGAGG |
| 2925 | UCCUCCAC CUGAUGA X GAA AAUCCAGA | UCUGGAUUU GUGGAGGA |
| 2939 | CACUGAGG CUGAUGA X GAA ACUUCUCC | GGAGAAGUC CCUCAGUG |
| 2943 | ACAUCACU CUGAUGA X GAA AGGGACUU | AAGUCCCUC AGUGAUGU |
| 2952 | UCUUCUUC CUGAUGA X GAA ACAUCACU | AGUGAUGUA GAAGAAGA |
| 2968 | AUCUUCAG CUGAUGA X GAA AGCUUCCU | AGGAAGCUC CUGAAGAU |
| 2977 | CUUAUACA CUGAUGA X GAA AUCUUGAG | CUGAAGAUC UGUAUAAG |
| 2981 | AGUCCUUA CUGAUGA X GAA ACAGAUCU | AGAUCUGUA UAAGGACU |
| 2983 | GAAGUCCU CUGAUGA X GAA AUACAGAU | AUCUGUAUA AGGACUUC |
| 2990 | AGGUCAGG CUGAUGA X GAA AGUCCUUA | UAAGGACUU CCUGACCU |
| 2991 | AAGGUCAG CUGAUGA X GAA AAGUCCUU | AAGGACUUC CUGACCUU |
| 2999 | GAUGCUCC CUGAUGA X GAA AGGUCAGG | CCUGACCUU GGAGCAUC |
| 3007 | ACAGAUGA CUGAUGA X GAA AUGCUCCA | UGGAGCAUC UCAUCUGU |
| 3009 | UAACAGAU CUGAUGA X GAA AGAUGCUC | GAGCAUCUC AUCUGUUA |
| 3012 | CUGUAACA CUGAUGA X GAA AUGAGAUG | CAUCUCAUC UGUUACAG |
| 3016 | GAAGCUGU CUGAUGA X GAA ACAGAUGA | UCAUCUGUU ACAGCUUC |
| 3017 | GGAAGCUG CUGAUGA X GAA AACAGAUG | CAUCUGUUA CAGCUUCC |
| 3023 | CCAGUGGG CUGAUGA X GAA AGCUGUAA | UUACAGCUU CCAAGGGG |
| 3024 | GCCACUUG CUGAUGA X GAA AAGCUGUA | UACAGCUUC CAAGUGGC |
| 3034 | CAUGCCCU CUGAUGA X GAA AGCCACUU | AAGUGGCUA AGGGCAUG |
| 3047 | AUGCCAAG CUGAUGA X GAA ACUCCAUG | CAUGGAGUU CUUGGCAU |
| 3048 | GAUGCCAA CUGAUGA X GAA AACUCCAU | AUGGAGUUC UUGGCAUC |
| 3050 | GCGAUGCC CUGAUGA X GAA AGAACUCC | GGAGUUCUU GGCAUCGC |
| 3056 | ACUUUCGC CUGAUGA X GAA AUGCCAAG | CUGGGCAUC GCGAAAGU |
| 3067 | CCUGUGGA CUGAUGA X GAA ACACUUUC | GAAAGUGUA UCCACAGG |
| 3069 | UCCCUGUG CUGAUGA X GAA AUACACUU | AAGGGUAUC CACAGGGA |
| 3094 | UAAGAGGA CUGAUGA X GAA AUUUCGUG | CAGAAAAUA UCCUCUUA |
| 3096 | GAUAAGAG CUGAUGA X GAA AUAUUUCG | CGAAAUAUC CUCUUAUC |
| 3099 | UCCGAUAA CUGAUGA X GAA AGGAUAUU | AAUAUCCUC UUAUCGGA |

Table IV-continued

Human KDR VEGF Receptor-Hammerhead Ribozyme and Substrate Sequence

| nt. Position | HH Ribozyme Sequence | Substrate |
|---|---|---|
| 3101 | UCUCCGAU CUGAUGA X GAA AGAGCAUA | UAUCCUCUU AUCGGAGA |
| 3102 | UUCUCCGA CUGAUGA X GAA AAGAGGAU | AUCCUCUUA UCGGAGAA |
| 3104 | UCUUCUCC CUGAUGA X GAA AUAAGAGG | CCUCUUAUC GGAGAAGA |
| 3120 | CAGAUUUU CUGAUGA X GAA ACCACGUU | AACGUGGUU AAAAUCUG |
| 3121 | ACAGAUUU CUGAUGA X GAA AACCACGU | ACGUGGUUA AAAUCUGU |
| 3126 | AAGUCACA CUGAUGA X GAA AUUUUAAC | GUUAAAAUC UGUGACUU |
| 3134 | CCAAGCCA CUGAUGA X GAA AGUCACAG | CUGUGACUU UGGCUUGG |
| 3135 | GCCAAGCC CUGAUGA X GAA AAGUCAGA | UGUGACUUU GGCUUGGC |
| 3140 | CCCGGGCC CUGAUGA X GAA AGCCAAAG | CUUUGGCUU GGCCCGGG |
| 3151 | UUUAUAAA CUGAUGA X GAA AUCCCGGG | CCCGGGAUA UUUAUAAA |
| 3153 | UCUUUAUA CUGAUGA X GAA AUAUCCCG | CGGGAUAUU UAUAAAGA |
| 3154 | AUCUUUAU CUGAUGA X GAA AAUAUCCC | GGGAUAUUU AUAAAGAU |
| 3155 | GAUCUUUA CUGAUGA X GAA AAAUAUCC | GGAUAUUUA UAAAGAUC |
| 3157 | UGGAUCUU CUGAUGA X GAA AUAAAUAU | AUAUUUAUA AAGAUCCA |
| 3163 | AUAAUCUG CUGAUGA X GAA AUCUUUAU | AUAAAGAUC CAGAUUAU |
| 3169 | UCUGACAU CUGAUGA X GAA AUCUGGAU | AUCCAGAUU AUGUCAGA |
| 3170 | UUCUGACA CUGAUGA X GAA AAUCUGGA | UCCAGAUUA UGUCAGAA |
| 3174 | CCUUUUCU CUGAUGA X GAA ACAUAAUC | GAUUAUGUC AGAAAAGG |
| 3190 | AGGGAGGC CUGAUGA X GAA AGCAUCUC | GAGAUGCUC GCCUCCCU |
| 3195 | UUCAAAGG CUGAUGA X GAA AGGCGAGC | GCUCGCCUC CCUUUGAA |
| 3199 | CCAUUUCA CUGAUGA X GAA AGGGAGGC | GCCUCCCUU UGAAAUGG |
| 3200 | UCCAUUUC CUGAUGA X GAA AAGGGAGG | CCUCCCUUU GAAAUGGA |
| 3225 | CUGUCAAA CUGAUGA X GAA AUUGUUUC | GAAACAAUU UUUGACAG |
| 3226 | UCUGUCAA CUGAUGA X GAA AAUUGUUU | AAACAAUUU UUGACAGA |
| 3227 | CUCUGUCA CUGAUGA X GAA AAAUUGUU | AACAAUUUU UGACAGAG |
| 3228 | ACUCUGUC CUGAUGA X GAA AAAAUUGU | ACAAUUUUU GACAGAGU |
| 3239 | GGAUUGUG CUGAUGA X GAA ACACUCUG | CAGAGUGUA CACAAUCC |
| 3246 | UCACUCUG CUGAUGA X GAA AUUGUGUA | UACACAAUC CAGAGUGA |
| 3258 | AAAGACCA CUGAUGA X GAA ACGUCACU | AGUGACGUC UGGUCUUU |
| 3263 | CACCAAAA CUGAUGA X GAA ACCAGACG | CGUCUGGUC UUUUGGUG |
| 3265 | AACACCAA CUGAUGA X GAA AGACCAGA | UCUGGUCUU UUGGUGUU |
| 3266 | AAACACCA CUGAUGA X GAA AAGACCAG | CUGGUCUUU UGGUGUUU |
| 3267 | AAAACACC CUGAUGA X GAA AAAGACCA | UGGUCUUUU GGUGUUUU |
| 3273 | CACAGCAA CUGAUGA X GAA ACACCAAA | UUUGGUGUU UUGCUGUG |
| 3274 | CCACAGCA CUGAUGA X GAA AACACCAA | UUGGUGUUU UGCUGUGG |
| 3275 | CCCACGGC CUGAUGA X GAA AAACACCA | UGGUGUUUU GCUGUGGG |

Table IV-continued

Human KDR VEGF Receptor-Hammerhead Ribozyme and Substrate Sequence

| nt. Position | HH Ribozyme Sequence | Substrate |
|---|---|---|
| 3288 | AAGGAAAA CUGAUGA X GAA AUUUCCCA | UGGGAAAUA UUUUCCUU |
| 3290 | CUAAGGAA CUGAUGA X GAA AUAUUUCC | GCAAAUAUU UUCCUUAG |
| 3291 | CCUAAGGA CUGAUGA X GAA AAUAUUUC | GAAAUAUUU UCCUUAGG |
| 3292 | ACCUAAGG CUGAUGA X GAA AAAUAUUU | AAAUAUUUU CCUUAGGU |
| 3293 | CACCUAAG CUGAUGA X GAA AAAAUAUU | AAUAUUUUC CUUAGGUG |
| 3296 | AAGCACCU CUGAUGA X GAA AGGAAAAU | AUUUUCCUU AGGUGCUU |
| 3297 | GAAGCACC CUGAUGA X GAA AAGGAAAA | UUUUCCUUA GGUGCUUC |
| 3304 | AUAUGGAG CUGAUGA X GAA AGCACCUA | UAGGUGCUU CUCCAUAU |
| 3305 | GAUAUGGA CUGAUGA X GAA AAGCACCU | AGGUGCUUC UCCAUAUC |
| 3307 | AGGAUAUG CUGAUGA X GAA AGAAGCAC | GUGCUUCUC CAUAUCCU |
| 3311 | CCCCAGGA CUGAUGA X GAA AUGGAGAA | UUCUCCAUA UCCUGGGG |
| 3313 | UACCCCAG CUGAUGA X GAA AUAUGGAG | CUCCAUAUC CUGGGGUA |
| 3321 | UCAAUCUU CUGAUGA X GAA ACCCCAGG | CCUGGGGUA AAGAUUGA |
| 3327 | UCUUCAUC CUGAUGA X GAA AUCUUUAC | GUAAAGAUU GAUGAAGA |
| 3338 | GCCUACAA CUGAUGA X GAA AUUCUUCA | UGAAGAAUU UUGUAGGC |
| 3339 | CGCCUACA CUGAUGA X GAA AAUUCUUC | GAAGAAUUU UGUAGGCG |
| 3340 | UCGCCUAC CUGAUGA X GAA AAAUUCUU | AAGAAUUUU GUAGGCGA |
| 3343 | CAAUCGCC CUGAUGA X GAA ACAAAAUU | AAUUUUGUA GGCGAUUG |
| 3350 | CUUCUUUC CUGAUGA X GAA AUCGCCUA | UAGGCGAUU GAAAGAAG |
| 3364 | CCUCAUUC CUGAUGA X GAA AGUUCCUU | AAGGAACUA GAAUGAGG |
| 3382 | UGUAGUAU CUGAUGA X GAA AUCAGGGG | CCCCUGAUU AUACUACA |
| 3383 | GUGUAGUA CUGAUGA X GAA AAUCAGGG | CCCUGAUUA UACUACAC |
| 3385 | UGGUGUAG CUGAUGA X GAA AUAAUCAG | CUGAUUAUA CUACACCA |
| 3388 | UUCUGGUG CUGAUGA X GAA AGUAUAAU | AUUAUACUA CACCAGAA |
| 3401 | UGGUCUGG CUGAUGA X GAA ACAUUUCU | AGAAAUGUA CCAGACCA |
| 3439 | GGGUCUCU CUGAUGA X GAA ACUGGGCU | AGCCCAGUC AGAGACCC |
| 3452 | ACUCUGAA CUGAUGA X GAA ACGUGGGU | ACCCACGUU UUCAGAGU |
| 3453 | AACUCUGA CUGAUGA X GAA AACGUGGG | CCCACGUUU UCAGAGUU |
| 3454 | CAACUCUG CUGAUGA X GAA AAACGUGG | CCACGUUUU CAGAGUUG |
| 3455 | CCAACUCU CUGAUGA X GAA AAAACGUG | CACGUUUUC AGAGUUGG |
| 3461 | GUUCCACC CUGAUGA X GAA ACUCUGAA | UUCAGAGUU GGUGGAAC |
| 3472 | AUUUCCCA CUGAUGA X GAA AUGUUCCA | UGGAACAUU UGGGAAAU |
| 3473 | GAUUUCCC CUGAUGA X GAA AAUGUUCC | GGAACAUUU GGGAAAUC |
| 3481 | UUGCAAGA CUGAUGA X GAA AUUUCCCA | UGGGAAAUC UCUUGCAA |
| 3483 | GCUUGCAA CUGAUGA X GAA AGAUUUCC | GAAAUCUCU UGCAAGC |
| 3485 | UAGCUUGC CUGAUGA X GAA AGAGAUUU | AAAUCUCUU GCAAGCUA |
| 3493 | CUGAGCAU CUGAUGA X GAA AGCUUGCA | UGCAAGCUA AUGCUCAG |

Table IV-continued

Human KDR VEGF Receptor-Hammerhead Ribozyme and Substrate Sequence

| nt. Position | HH Ribozyme Sequence | Substrate |
|---|---|---|
| 3499 | AUCCUGCU CUGAUGA X GAA AGCAUUAG | CUAAUGCUC AGCAGGAU |
| 3518 | GAACAAUG CUGAUGA X GAA AGUCUUUG | CAAAGACUA CAUUGUUC |
| 3522 | GGAAGAAC CUGAUGA X GAA AUGUAGUC | GACUACAUU GUUCUUCC |
| 3525 | AUCGGAAG CUGAUGA X GAA ACAAUGUA | UACAUUGUU CUUCCGAU |
| 3526 | UAUCGGAA CUGAUGA X GAA AACAAUGU | ACAUUGUUC UUCCGAUA |
| 3528 | GAUAUCGG CUGAUGA X GAA AGAACAAU | AUUGUUCUU CCGAUAUC |
| 3529 | UGAUAUCG CUGAUGA X GAA AAGAACAA | UUGUUCUUC CGAUAUCA |
| 3534 | GUCUCUGA CUGAUGA X GAA AUCGGAAG | CUUCCGAUA UCAGAGAC |
| 3536 | AAGUCUCU CUGAUGA X GAA AUAUCGGA | UCCGAUAUC AGAGACUU |
| 3544 | CAUGCUCA CUGAUGA X GAA AGUCUCUG | CAGAGACUU UGAGCAUG |
| 3545 | CCAUGCUC CUGAUGA X GAA AAGUCUCU | AGAGACUUU GAGCAUGG |
| 3562 | GAGUCCAG CUGAUGA X GAA AUCCUCUU | AAGAGGAUU CUGGACUC |
| 3563 | AGAGUCCA CUGAUGA X GAA AAUCCUCU | AGAGGAUUC UGGACUCU |
| 3570 | GGCAGAGA CUGAUGA X GAA AGUCCAGA | UCUGGACUC UCUCUGCC |
| 3572 | UAGGCAGA CUGAUGA X GAA AGAGUCCA | UGGACUCUC UCUGCCUA |
| 3574 | GGUAGGCA CUGAUGA X GAA AGAGAGUC | GACUCUCUC UGCCUACC |
| 3580 | AGGUGAGG CUGAUGA X GAA AGGCAGAG | CUCUGCCUA CCUCACCU |
| 3584 | AAACAGGU CUGAUGA X GAA AGGUAGGC | GCCUACCUC ACCUGUUU |
| 3591 | AUACAGGA CUGAUGA X GAA ACAGGUGA | UCACCUGUU UCCUGUAU |
| 3592 | CAUACAGG CUGAUGA X GAA AACAGGUG | CACCUGUUU CCUGUAUG |
| 3593 | CCAUACAG CUGAUGA X GAA AAACAGGU | ACCUGUUUC CUGUAUGG |
| 3598 | CUCCUCCA CUGAUGA X GAA ACAGGAAA | UUUCCUGUA UGGAGGAG |
| 3615 | GGGUCACA CUGAUGA X GAA ACUUCCUC | GAGGAAGUA UGUGACCC |
| 3629 | CAUAAUGG CUGAUGA X GAA AUUUGGGG | CCCCAAAUU CCAUUAUG |
| 3630 | UCAUAAUG CUGAUGA X GAA AAUUUGGG | CCCAAAUUC CAUUAUGA |
| 3634 | GUUGUCAU CUGAUGA X GAA AUGGAAUU | AAUUCCAUU AUGACAAC |
| 3635 | UGUUGUCA CUGAUGA X GAA AAUGGAAU | AUUCCAUUA UGACAACA |
| 3654 | UACUGACU CUGAUGA X GAA AUUCCUGC | GCAGGAAUC AGUCAGUA |
| 3658 | CAGAUACU CUGAUGA X GAA ACUGAUUC | GAAUCAGUC AGUAUCUG |
| 3662 | UCUGCAGA CUGAUGA X GAA ACUGACUG | CAGUGAGUA UCUGCAGA |
| 3664 | GUUCUGCA CUGAUGA X GAA AUACUGAC | GUCAGUAUC UGCAGAAC |
| 3676 | CUUUCGCU CUGAUGA X GAA ACUGUUCU | AGAACAGUA AGCGAAAG |
| 3702 | AAUGUUUU CUGAUGA X GAA ACACUCAC | GUGAGUGUA AAAACAUU |
| 3710 | UAUCUUCA CUGAUGA X GAA AUGUUUUU | AAAAACAUU UGAAGAUA |
| 3711 | AUAUCUUC CUGAUGA X GAA AAUGUUUU | AAAACAUUU GAAGAUAU |
| 3718 | UAACGGGA CUGAUGA X GAA AUCUUCAA | UUGAAGAUA UCCCGUUA |

Table IV-continued

Human KDR VEGF Receptor-Hammerhead Ribozyme and Substrate Sequence

| nt. Position | HH Ribozyme Sequence | Substrate |
|---|---|---|
| 3720 | UCUAACGG CUGAUGA X GAA AUAUCUUC | GAAGAUAUC CCGUUAGA |
| 3725 | GUUCUUCU CUGAUGA X GAA ACGGGAUA | UAUCCCGUU AGAAGAAC |
| 3726 | GGUUCUUC CUGAUGA X GAA AACGGGAU | AUCCCGUUA GAAGAACC |
| 3741 | AUUACUUU CUGAUGA X GAA ACUUCUGG | CCAGAAGUA AAAGUAAU |
| 3747 | UCUGGGAU CUGAUGA X GAA ACUUUUAC | GUAAAAGUA AUCCCAGA |
| 3750 | UCAUCUGG CUGAUGA X GAA AUUACUUU | AAAGUAAUC CCAGAUGA |
| 3778 | AAGAACCA CUGAUGA X GAA ACCACUGU | ACAGUGGUA UGGUUCUU |
| 3783 | GAGGCAAG CUGAUGA X GAA ACCAUACC | GGUAUGGUU CUUGCCUC |
| 3784 | UGAGGCAA CUGAUGA X GAA AACCAUAC | GUAUGGUUC UUGCCUCA |
| 3786 | UCUGAGGC CUGAUGA X GAA AGAACCAU | AUGGUUCUU GCCUCAGA |
| 3791 | GCUCUUCU CUGAUGA X GAA AGGCAAGA | UCUUGCCUC AGAAGAGC |
| 3808 | GUCUUCCA CUGAUGA X GAA ACUUUUCA | UGAAAACUU UGGAAGAC |
| 3809 | UGUCUUCC CUGAUGA X GAA AAGUUUUC | GAAAACUUU GGAAGACA |
| 3827 | AUGGAGAU CUGAUGA X GAA AUUUGGUU | AACCAAAUU AUCUCCAU |
| 3828 | GAUGGAGA CUGAUGA X GAA AAUUUGGU | ACCAAAUUA UCUCCAUC |
| 3830 | AAGAUGGA CUGAUGA X GAA AUAAUUUG | CAAAUUAUC UCCAUCUU |
| 3832 | AAAAGAUG CUGAUGA X GAA AGAUAAUU | AAUUAUCUC CAUCUUUU |
| 3836 | CACCAAAA CUGAUGA X GAA AUGGAGAU | AUCUCCAUC UUUUGGUG |
| 3838 | UCCACCAA CUGAUGA X GAA AGAUGGAG | CUCCAUCUU UUGGUGGA |
| 3839 | UUCCACCA CUGAUGA X GAA AAGAUGCA | UCCAUCUUU UGGUGGAA |
| 3840 | AUUCCACC CUGAUGA X GAA AAAGAUGG | CCAUCUUUU GGUGGAAU |
| 3872 | AUGCCACA CUGAUGA X GAA ACUCCCUG | CAGGGAGUC UGUGGCAU |
| 3881 | AGCCUUCA CUGAUGA X GAA AUGCCACA | UGUGGCAUC UGAAGGCU |
| 3890 | UCUGGUUU CUGAUGA X GAA AGCCUUCA | UGAAGGCUC AAACCAGA |
| 3908 | CGGACUGG CUGAUGA X GAA AGCCGCUU | AAGCGGCUA CCAGUCCG |
| 3914 | GAUAUCCG CUGAUGA X GAA ACUGGUAG | CUACCAGUC CGGAUAUC |
| 3920 | CGGAGUGA CUGAUGA X GAA AUCCGCAC | GUCCGGAUA UCACUCCG |
| 3922 | AUCGGAGU CUGAUGA X GAA AUAUCCGG | CCGGAUAUC ACUCCGAU |
| 3926 | UGUCAUCG CUGAUGA X GAA AGUGAUAU | AUAUCACUC CGAUGACA |
| 3950 | CACUGGAG CUGAUGA X GAA ACACGGUG | CACCGUGUA CUCCAGUG |
| 3953 | CCUCACUG CUGAUGA X GAA AGUACACG | CGUGUACUC CAGUGAGG |
| 3972 | AGCUUUAA CUGAUGA X GAA AGUUCUGC | GCAGAACUU UUAAAGCU |
| 3973 | CAGCUUUA CUGAUGA X GAA AAGUUCUG | CAGAACUUU UAAAGCUG |
| 3974 | UCAGCUUU CUGAUGA X GAA AAAGUUCU | AGAACUUUU AAAGCUGA |
| 3975 | AUCAGCUU CUGAUGA X GAA AAAAGUUC | GAACUUUUA AAGCUGAU |
| 3984 | CCAAUCUC CUGAUGA X GAA AUCAGCUU | AAGCUGAUA GAGAUGGG |
| 3990 | UGGACUCC CUGAUGA X GAA AUCUCUAU | AUAGAGAUU GGAGUGCA |

Table IV-continued

Human KDR VEGF Receptor-Hammerhead Ribozyme and Substrate Sequence

| nt. Position | HH Ribozyme Sequence | Substrate |
|---|---|---|
| 4006 | GGCUGUGC CUGAUGA X GAA ACCGGUUU | AAACCGGUA GCACAGCC |
| 4020 | GGCUGGAG CUGAUGA X GAA AUCUGGGC | GCCCAGAUU CUCCAGCC |
| 4021 | AGGCUGGA CUGAUGA X GAA AAUCUGGG | CCCAGAUUC UCCAGCCU |
| 4023 | UCAGGCUG CUGAUGA X GAA AGAAUCUG | CAGAUUCUC CAGCCUGA |
| 4052 | CAGGAGGA CUGAUGA X GAA AGCUCAGU | ACUGAGCUC UCCUCCUG |
| 4054 | AACAGGAG CUGAUGA X GAA AGAGGUCA | UGAGCUCUC CUCCUGUU |
| 4057 | UUAAACAG CUGAUGA X GAA AGGAGAGC | GCUCUCCUC CUGUUUAA |
| 4062 | UCCUUUUA CUGAUGA X GAA ACGGGAGG | CCUCCUGUU UAAAAGGA |
| 4063 | UUCCUUUU CUGAUGA X GAA AACAGGAG | CUCCUGUUU AAAAGGAA |
| 4064 | CUUCCUUU CUGAUGA X GAA AAACAGGA | UCCUGUUUA AAAGGAAG |
| 4076 | GGGGUGUG CUGAUGA X GAA AUGCUUCC | GGAAGCAUC CACACCCC |
| 4089 | AUGUCCGG CUGAUGA X GAA AGUUGGGG | CCCCAACUC CCGGACAU |
| 4098 | UCUCAUGU CUGAUGA X GAA AUGUCCGG | CCGGACAUC ACAUGAGA |
| 4110 | UCUGAGCA CUGAUGA X GAA ACCUCUCA | UGAGAGGUC UGCUCAGA |
| 4115 | CAAAAUCU CUGAU&A X GAA AGCAGACC | GGUCUGCUC AGAUUUUG |
| 4120 | CACUUCAA CUGAUGA X GAA AUCUGAGC | GCUCAGAUU UUGAAGUG |
| 4121 | ACAUCUUA CUGAUGA X GAA AAUCUGAG | CUGAGAUUU UGAAGUGU |
| 4122 | AACACUUC CUGAUGA X GAA AAAUCUGA | UCAGAUUUU GAAGUGUU |
| 4130 | GAAAGAAC CUGAUGA X GAA ACACUUCA | UGAAGUGUU GUUCUUUC |
| 4133 | GUGGAAAG CUGAUGA X GAA ACAACACU | AGUGUUGUU CUUUCCAC |
| 4134 | GGUGGAAA CUGAUGA X GAA AACAACAC | GUGUUGUUC UUUCCACC |
| 4136 | CUGGUGGA CUGAUGA X GAA AGAACAAC | GUUGUUCUU UCCACCAG |
| 4137 | GCUGGUGG CUGAUGA X GAA AAGAACAA | UUGUUCUUU CCACCAGC |
| 4138 | UGCUGGUG CUGAUGA X GAA AAAGAACA | UGUUCUUUC CACCAGCA |
| 4153 | AAUGCGGC CUGAUGA X GAA ACUUCCUG | CAGGAAGUA GCCGCAUU |
| 4161 | GAAAAUCA CUGAUGA X GAA AUGCGGCU | AGCCGCAUU UGAUUUUC |
| 4162 | UGAAAAUC CUGAUGA X GAA AAUGCGGC | GCCGCAUUU GAUUUUCA |
| 4166 | GAAAUGAA CUGAUGA X GAA AUCAAAUG | CAUUUGAUU UUCAUUUC |
| 4167 | CGAAAUGA CUGAUGA X GAA AAUCAAAU | AUUUGAUUU UCAUUUCG |
| 4168 | UCGAAAUG CUGAUGA X GAA AAAUCAAA | UUUGAUUUU CAUUUCGA |
| 4169 | GUCGAAAU CUGAUGA X GAA AAAAUCAA | UUGAUUUUC AUUUCGAC |
| 4172 | GUUGUCGA CUGAUGA X GAA AUGAAAAU | AUUUUCAUU UCGACAAC |
| 4173 | UGUUGUCG CUGAUGA X GAA AAUGAAAA | UUUUCAUUU CGACAACA |
| 4174 | CUGUUGUC CUGAUGA X GAA AAAUGAAA | UUUCAUUUC GACAACAG |
| 4194 | UGGAGUCC CUGAUGA X GAA AGGUCCUU | AAGGACCUC GGACUGCA |
| 4214 | GCCUAGAA CUGAUGA X GAA AGCUGGCU | AGCCAGCUC UUCUAGGC |

Table IV-continued

Human KDR VEGF Receptor-Hammerhead Ribozyme and Substrate Sequence

| nt. Position | HH Ribozyme Sequence | Substrate |
|---|---|---|
| 4216 | AAGCCUAG CUGAUGA X GAA AGAGCUGG | CCAGCUCUU CUAGGCUU |
| 4217 | CAAGCCUA CUGAUGA X GAA AAGAGCUG | CAGCUCUUC UAGGCUUG |
| 4219 | CACAAGCC CUGAUGA X GAA AGAAGAGC | GCUCUUCUA GGCUUGUG |

Where "X" represents stem II region of a HH ribozyme (Hertel et al., 1992 Nucleic Acids Res. 20 3252). The length of stem II may be ≧2 base-pairs.

TABLE V

Human KDR VEGF Receptor-Hairpin Ribozyme and Substrate Sequences

| nt. Position | Hairpin Ribozyme Sequence | Substrate |
|---|---|---|
| 11 | CGACGGCC AGAA GCACCU ACCAGAGAAACACACGUUGUGGUACAUUACCUGGUA | AGGUGCU GCU GGCCGUCG |
| 18 | CACAGGGC AGAA GCCAGC ACCAGAGAAACACACGUUGUGGUACAUUACCUGGUA | GCUGGCC GUC GCCCUGUG |
| 51 | CCCACAGA AGAA GCCCGG ACCAGAGAAACACACGUUGUGGUACAUUACCUGGUA | CCGGGCC GCC UCUGUGGG |
| 86 | UGAGCCUG AGAA GAUCAA ACCAGAGAAACACACGUUGUGGUACAUUACCUGGUA | UUGAUCU GCC CAGGCUCA |
| 318 | GAGGCCAA AGAA GUUUCC ACCAGAGAAACACACGUUGUGGUACAUUACCUGGUA | GGAAACU GAC UUGGCCUC |
| 358 | AAAUGGAG AGAA GUAAUC ACCAGAGAAACACACGUUGUGGUACAUUACCUGGUA | GAUUACA GAU CUCCAUUU |
| 510 | CUGUUACC AGAA GGAACA ACCAGAGAAACACACGUUGUGGUACAUUACCUGGUA | UGUUCCU GAU GGUAACAG |
| 623 | ACAUAAUA AGAA GGUAAC ACCAGAGAAACACACGUUGUGGUACAUUACCUGGUA | GUUACCA GUC UAUUAUGU |
| 683 | UUCCAUGA AGAA GACUCA ACCAGAGAAACACACGUUGUGGUACAUUACCUGGUA | UGAGUCC GUC UCAUGGAA |
| 705 | UUUUCUCC AGAA GAUAGU ACCAGAGAAACACACGUUGUGGUACAUUACCUGGUA | ACUAUCU GUU GGAGAAAA |
| 833 | CACUCCCA AGAA GGGUUU ACCAGAGAAACACACGUUGUGGUACAUUACCUGGUA | AAACCCA GUC UGGGAGUG |
| 932 | UCUUGGUC AGAA GCCCAC ACCAGAGAAACACACGUUGUGGUACAUUACCUGGUA | GUGGGCU GAU GACCAAGA |
| 1142 | CCAUAAUC AGAA GUACAU ACCAGAGAAACACACGUUGUGGUACAUUACCUGGUA | AUGUACU GAC GAUUAUGG |
| 1259 | UCUCACCA AGAA GGGGUG ACCAGAGAAACACACGUUGUGGUACAUUACCUGGUA | CACCCCA GAU UGGUGAGA |
| 1332 | AUGGCAUA AGAA GUACAU ACCAGAGAAACACACGUUGUGGUACAUUACCUGGUA | AUGUACG GUC UAUGCCAU |
| 1376 | CUUCCUCC AGAA GCCAAU ACCAGAGAAACACACGUUGUGGUACAUUACCUGGUA | AUUGGCA GUU GGAGGAAG |
| 1413 | GUCACUGA AGAA GGUUGG ACCAGAGAAACACACGUUGUGGUACAUUACCUGGUA | CCAAGCU GUC UCAGUGAC |
| 1569 | UUGUACAA AGAA GACACA ACCAGAGAAACACACGUUGUGGUACAUUACCUGGUA | UGUGUCA GCU UUGUACAA |
| 1673 | GCUCAGUG AGAA GCAUGU ACCAGAGAAACACACGUUGUGGUACAUUACCUGGUA | ACAUGCA GCC CACUGAGC |
| 1717 | AAACGUAG AGAA GUCUGC ACCAGAGAAACACACGUUGUGGUACAUUACCUGGUA | GCAGACA GAU CUACGUUU |
| 1760 | UUGGCAGA AGAA GUGGGC ACCAGAGAAACACACGUUGUGGUACAUUACCUGGUA | GCCCACA GCC UCUGCCAA |
| 1797 | UUCUUGCA AGAA GGUGUG ACCAGAGAAACACACGUUGUGGUACAUUACCUGGUA | CACACCU GUU UGCAAGAA |
| 1918 | UUGAGCAA AGAA GACAUA ACCAGAGAAACACACGUUGUGGUACAUUACCUGGUA | UAUGUCU GCC UUGCUCAA |
| 1967 | GGACUGUG AGAA GCCUGA ACCAGAGAAACACACGUUGUGGUACAUUACCUGGUA | UCAGGCA GCU CACAGUCC |
| 1974 | CGCUCUAG AGAA GUGAGC ACCAGAGAAACACACGUUGUGGUACAUUACCUGGUA | GCUCACA GUC CUAGAGCG |
| 2021 | UACUUGUC AGAA GAUUCU ACCAGAGAAACACACGUUGUGGUACAUUACCUGGUA | AGAAUCA GAC GACAAGUA |
| 2084 | ACCACAUG AGAA GUGGAG ACCAGAGAAACACACGUUGUGGUACAUUACCUGGUA | CUCCACA GAU CAUGUGGU |

TABLE V-continued

Human KDR VEGF Receptor-Hairpin Ribozyme and Substrate Sequences

| nt. Position | Hairpin Ribozyme Sequence | Substrate |
|---|---|---|
| 2418 | GGGAGUUC AGAA GGAUCC ACCAGAGAAACACACGUUGUGGUACAUUACCUGGUA | GCAUCCA GAU GAACUCCC |
| 2453 | CAUCAUAA AGAA GUCGUU ACCAGAGAAACACACGUUGUGGUACAUUACCUGGUA | AACGACU GCC UUAUGAUG |
| 2492 | CUAGGUUC AGAA GGUCUC ACCAGAGAAACACACGUUGUGGUACAUUACCUGGUA | GAGACCG GCU GAACCUAG |
| 2547 | CCAAAGGC AGAA GCUUCA ACCAGAGAAACACACGUUGUGGUACAUUACCUGGUA | UGAAGCA GAU GCCUUUGG |
| 2765 | GGUAAGUG AGAA GGUUUC ACCAGAGAAACACACGUUGUGGUACAUUACCUGGUA | GAAACCU GUC CACUUACC |
| 2914 | AAAUCCAG AGAA GGCUGA ACCAGAGAAACACACGUUGUGGUACAUUACCUGGUA | UCAGCCA GCU CUGGAUUU |
| 2993 | GCUCCAAG AGAA GGAAGU ACCAGAGAAACACACGUUGUGGUACAUUACCUGGUA | ACUUCCU GAC CUUGGAGC |
| 3019 | CACUUGGA AGAA GUAACA ACCAGAGAAACACACGUUGUGGUACAUUACCUGGUA | UGUUACA GCU UCCAAGUG |
| 3165 | CUGACAUA AGAA GGAUCU ACCAGAGAAACACACGUUGUGGUACAUUACCUGGUA | AGAUCCA GAU UAUGUCAG |
| 3378 | GUAGUAUA AGAA GGGGCC ACCAGAGAAACACACGUUGUGGUACAUUACCUGGUA | GGCCCCU GAU UAUACUAC |
| 3404 | CCAGCAUG AGAA GGUACA ACCAGAGAAACACACGUUGUGGUACAUUACCUGGUA | UGUACCA GAC CAUGCUGG |
| 3418 | CCCGUGCC AGAA GUCCAG ACCAGAGAAACACACGUUGUGGUACAUUACCUGGUA | CUGGACU GCU GGCACGGG |
| 3575 | GUGAGGUA AGAA GAGAGA ACCAGAGAAACACACGUUGUGGUACAUUACCUGGUA | UCUCUCU GCC UACCUCAC |
| 3588 | AUACAGGA AGAA GGUGAG ACCAGAGAAACACACGUUGUGGUACAUUACCUGGUA | CUCACCU GUU UCCUGUAU |
| 3689 | CACUCACA AGAA GGCUCU ACCAGAGAAACACACGUUGUGGUACAUUACCUGGUA | AGAGCCG GCC UGUGAGUG |
| 3753 | UGGUUGUC AGAA GGGAUU ACCAGAGAAACACACGUUGUGGUACAUUACCUGGUA | AAUCCCA GAU GACAACCA |
| 3764 | CACUGUCC AGAA GGUUGU ACCAGAGAAACACACGUUGUGGUACAUUACCUGGUA | ACAACCA GAC GGACAGUG |
| 3911 | GAUAUCCG AGAA GGUAGC ACCAGAGAAACACACGUUGUGGUACAUUACCUGGUA | GCUACCA GUC CGGAUAUC |
| 3927 | UCUGUGUC AGAA GAGUGA ACCAGAGAAACACACGUUGUGGUACAUUACCUGGUA | UCACUCC GAU GACACAGA |
| 4011 | AGAAUCUG AGAA GUGCUA ACCAGAGAAACACACGUUGUGGUACAUUACCUGGUA | UAGCACA GCC CAGAUUCU |
| 4016 | GCUGGAGA AGAA GGGCUG ACCAGAGAAACACACGUUGUGGUACAUUACCUGGUA | CAGCCCA GAU UCUCCAGC |
| 4025 | CCGUGUCA AGAA GGAGAA ACCAGAGAAACACACGUUGUGGUACAUUACCUGGUA | UUCUCCA GCC UGACACGG |
| 4059 | UCCUUUUA AGAA GGAGGA ACCAGAGAAACACACGUUGUGGUACAUUACCUGGUA | UCCUCCU GUU UAAAAGGA |
| 4111 | AAAAUCUG AGAA GACCUC ACCAGAGAAACACACGUUGUGGUACAUUACCUGGUA | GAGGUCU GCU CAGAUUUU |
| 4116 | ACUUCAAA AGAA GAGGAG ACCAGAGAAACACACGUUGUGGUACAUUACCUGGUA | CUGCUCA GAU UUUGAAGU |
| 4195 | UCCCUGCA AGAA GAGGUC ACCAGAGAAACACACGUUGUGGUACAUUACCUGGUA | GACCUCG GAC UGCAGGGA |
| 4210 | CCUAGAAG AGAA GGCUCC ACCAGAGAAACACACGUUGUGGUACAUUACCUGGUA | GGAGCCA GCU CUUCUAGG |

TABLE VI

Mouse flk-1 VEGF Receptor-Hammerhead Ribozyme and Substrate sequence

| nt. Position | HH Ribozyme Sequence | Substrate |
|---|---|---|
| 13 | CCGUACCC CUGAUGA X GAA AUUCGCCC | GGGCGAAUU GGGUACGG |
| 18 | GGGUCCCG CUGAUGA X GAA ACCCAAUU | AAUUGGGUA CGGGACCC |
| 31 | UCGACCUC CUGAUGA X GAA AGGGGGGU | ACCCCCUC GAGGUCGA |
| 37 | AUACCGUC CUGAUGA X GAA ACCUqGAG | CUCGAGGUC GACGGUAU |
| 44 | CUUAUCGA CUGAUGA X GAA ACCGUCGA | UCGACGGUA UCCAUAAG |

TABLE VI-continued

Mouse flk-1 VEGF Receptor-Hammerhead Ribozyme and Substrate sequence

| nt. Position | HH Ribozyme Sequence | Substrate |
|---|---|---|
| 46 | AGCUUAUC CUGAUGA X GAA AUACCGUC | GACGGUAUC GAUAAGCU |
| 50 | AUCAAGCU CUGAUGA X GAA AUCGAUAC | GUAUCGAUA AGCUUGAU |
| 55 | UCGAUAUC CUGAUGA X GAA AGCUUAUC | GAUAAGCUU GAUAUCGA |
| 59 | GAAUUCGA CUGAUGA X GAA AUCAAGCU | AGCUUGAUA UCGAAUUC |
| 61 | CCGAAUUC CUGAUGA X GAA AUAUCAAG | CUUGAUAUC GAAUUCGG |
| 66 | UGGGCCCG CUGAUGA X GAA AUUCGAUA | UAUCGAAUU CGGGCCCA |
| 67 | CUGGGCCC CUGAUGA X GAA AAUUCGAU | AUCGAAUUC GGGCCCAG |
| 83 | GGCUGCGG CUGAUGA X GAA ACACAGUC | GACUGUGUC CCGCAGCC |
| 97 | AGCCAGGU CUGAUGA X GAA AUCCCGGC | GCCGGGAUA ACCUGGCU |
| 114 | GUCCGCGG CUGAUGA X GAA AUCGGGUC | GACCCGAUU CCGCGGAC |
| 115 | UGUCCGCG CUGAUGA X GAA AAUCGGGU | ACCCGAUUC CGCGGACA |
| 169 | ACCGGGGA CUGAUGA X GAA AGCGCGGG | CCCGCGCUC UCCCCGGU |
| 171 | AGACCGGG CUGAUGA X GAA AGAGCGCG | CGCGCUCUC CCCGGUCU |
| 178 | CAGCGCAA CUGAUGA X GAA ACCGGGGA | UCCCCGGUC UUGCGCUG |
| 180 | CGCAGCGC CUGAUGA X GAA AGACCGGG | CCCGGUCUU GCGCUGCG |
| 197 | AGAGGCGG CUGAUGA X GAA AUGGCCCC | GGGGCCAUA CCGCCUCU |
| 204 | AAGUCACA CUGAUGA X GAA AGGCGGUA | UACCGCCUC UGUGACUU |
| 212 | CCGCAAAG CUGAUGA X GAA AGUCACAG | CUGUGACUU CUUUGCGG |
| 213 | CCCGCAAA CUGAUGA X GAA AAGUCACA | UGUGACUUC UUUGCGGG |
| 215 | GGCCCGCA CUGAUGA X GAA AGAAGUCA | UGACUUCUU UGCGGGCC |
| 216 | UGGCCCGC CUGAUGA X GAA AAGAAGUC | GACUUCUUU GCGGGCCA |
| 241 | CAGGCACA CUGAUGA X GAA ACUCCUUC | GAAGGAGUC UGUGCCUG |
| 262 | UGGGCACA CUGAUGA X GAA AGCCCAGU | ACUGGGCUC UGUGCCCA |
| 306 | GCGACAGC CUGAUGA X GAA AGCAGCGC | GCGCUGCUA GCUGUCGC |
| 312 | CACAGAGC CUGAUGA X GAA ACAGCUAG | CUAGCUGUC GCUCUGUG |
| 316 | GAACCACA CUGAUGA X GAA AGCGACAG | CUGUCGCUC UGUGGUUC |
| 323 | CCACGCGG CUGAUGA X GAA ACCACAGA | UCUGUGGUU CUGCGUGG |
| 324 | UCCACGCA CUGAUGA X GAA AACCACAG | CUGUGGUUC UGGGUGGA |
| 347 | AACCCACA CUGAUGA X GAA AGGCGGCU | AGCCGCCUC UGUGGGUU |
| 355 | GCCAGUCA CUGAUGA X GAA ACCCACAG | CUGUGGGUU UGACUGGC |
| 356 | CGCCAGUC CUGAUGA X GAA AACCCACA | UGUGGGUUU GACUGGCG |
| 367 | AUGGAGAA CUGAUGA X GAA AUCGCCAG | CUGGCGAUU UUCUCCAU |
| 368 | GAUGGAGA CUGAUGA X GAA AAUCGCCA | UGGCGAUUU UCUCCAUC |
| 369 | GGAUGGAG CUGAUGA X GAA AAAUCGCC | GGCGAUUUU CUCCAUCC |
| 370 | GGGAUGGA CUGAUGA X GAA AAAAUCGC | GCGAUUUUC UCCAUCCC |
| 372 | GGGGGAUG CUGAUGA X GAA AGAAAAUC | GAUUUUCUC CAUCCCCC |
| 376 | CUGGGGGG CUGAUGA X GAA AUGGAGAA | UUCUCCAUC CCCCAAG |

TABLE VI-continued

Mouse flk-1 VEGF Receptor-Hammerhead Ribozyme and Substrate sequence

| nt. Position | HH Ribozyme Sequence | Substrate |
|---|---|---|
| 387 | UGUGUGCU CUGAUGA X GAA AGCUUGGG | CCCAAGCUC AGCACACA |
| 405 | AUUGUCAG CUGAUGA X GAA AUGUCUUU | AAAGACAUA CUGACAAU |
| 414 | UUUGCCAA CUGAUGA X GAA AUGGUCAG | CUGACAAUU UUGGCAAA |
| 415 | AUUUGCCA CUGAUGA X GAA AAUUGUCA | UGACAAUUU UGGCAAAU |
| 416 | UAUUUGCC CUGAUGA X GAA AAAUUGUC | GACAAUUUU GGCAAAUA |
| 424 | AAGGGUUG CUGAUGA X GAA AUUUGCCA | UGGCAAAUA CAACCCUU |
| 432 | GUAAUCUG CUGAUGA X GAA ACGGUUGU | ACAACCCUU CAGAUUAC |
| 433 | AGUAAUCU CUGAUGA X GAA AAGGGUUG | CAACCCUUC AGAUUACU |
| 438 | CUGCAAGU CUGAUGA X GAA AUCUGAAG | CUUCAGAUU ACUUGCAG |
| 439 | CCUGCAAG CUGAUGA X GAA AAUCUGAA | UUCAGAUUA CUUGCAGG |
| 442 | UCCCCUGC CUGAUGA X GAA AGUAAUCU | AGAUUACUU GCAGGGGA |
| 471 | UUGGGCCA CUGAUGA X GAA AGCCAGUC | GACUGGCUU UGGCCCAA |
| 472 | AUGGGCC CUGAUGA X GAA AAGCCAGU | ACUGGCUUU GGCCCAAU |
| 484 | AUCACGCU CUGAUGA X GAA AGCAUUGG | CCAAUGCUC AGCGUGAU |
| 493 | UUCCUCAG CUGAUGA X GAA AUCACGCU | AGCGUGAUU CUGACGAA |
| 494 | UUUCCUCA CUGAUGA X GAA AAUCACGC | GCGUGAUUC UGAGGAAA |
| 507 | GUCACCAA CUGAUGA X GAA ACCCUUUC | GAAAGGGUA UUGGUGAC |
| 509 | CAGUCACC CUGAUGA X GAA AUACCCUU | AAGGGUAUU GGUGACUG |
| 538 | GCAGAAGA CUGAUGA X GAA ACUGUCAC | GUGACAGUA UCUUCUGC |
| 540 | UUGCAGAA CUGAUGA X GAA AUACUGUC | GACAGUAUC UUCUGCAA |
| 542 | UUUUGCAG CUGAUGA X GAA AGAUACUG | CAGUAUCUU CUGCAAAA |
| 543 | GUUUUGCA CUGAUGA X GAA AAGAUACU | AGUAUCUUC UGGAAAAC |
| 555 | GGAAUGGU CUGAUGA X GAA AGUGUUUU | AAAACACUC ACCAUUCC |
| 561 | ACCCUGGG CUGAUGA X GAA AUGGUGAG | CUCACCAUU CCCAGGGU |
| 562 | CACCCUGG CUGAUGA X GAA AAUGGUGA | UCACCAUUC CCAGGGUG |
| 573 | UCAUUUCC CUGAUGA X GAA ACCACCCU | AGGGUGGUU GGAAAUGA |
| 583 | GGCUCCAG CUGAUGA X GAA AUCAUUUC | GAAAUGAUA CUGGAGCC |
| 593 | AGCACUUG CUGAUGA X GAA AGGCUCCA | UGGAGCCUA CAAGUGCU |
| 602 | CCCGGUAC CUGAUGA X GAA AGCACUUG | CAAGUGCUC GUACCGGG |
| 605 | CGUCCGG CUGAUGA X GAA ACGAGCAC | GUGCUCGUA CCGGGACG |
| 615 | GCUAUGUC CUGAUGA X GAA ACGUCCCG | CGGGACGUC GACAUAGC |
| 621 | GUGGAGGC CUGAUGA X GAA AUGUCGAC | GUCGACAUA GCCUCCAC |
| 626 | AAACAGUG CUGAUGA X CAA AGGCUAUG | CAUAGCCUC CACUGUUU |
| 633 | UAGACAUA CUGAUGA X GAA ACAGUGGA | UCCACUGUU UAUGUCUA |
| 634 | AUAGACAU CUGAUGA X GAA AACAGUGG | CCACUGUUU AUGUCUAU |
| 635 | CAUAGACA CUGAUGA X GAA AAACAGUG | CACUGUUUA UGUCUAUG |
| 639 | CGAACAUA CUGAUGA X GAA ACAUAAAC | GUUUAUGUC UAUGUUCG |

TABLE VI-continued

Mouse flk-1 VEGF Receptor-Hammerhead Ribozyme and Substrate sequence

| nt. Position | HH Ribozyme Sequence | Substrate |
|---|---|---|
| 641 | CUCGAACA CUGAUGA X GAA AGACAUAA | UUAUGUCUA UGUUCGAG |
| 645 | UAAUCUCG CUGAUGA X GAA ACAUAGAC | GUCUAUGUU CGAGAUUA |
| 646 | GUAAUCUC CUGAUGA X GAA AACAUAGA | UCUAUGUUC GAGAUUAC |
| 652 | UGAUCUGU CUGAUGA X GAA AUCUCGAA | UUCGAGAUU ACAGAUCA |
| 653 | GUGAUCUG CUGAUGA X GAA AAUCUCGA | UCGAGAUUA CAGAUCAC |
| 659 | UGAAUGGU CUGAUGA X GAA AUCUGUAA | UUACAGAUC ACCAUUCA |
| 665 | AGGCGAUG CUGAUGA X GAA AUGGUGAU | AUCACCAUU CAUCGCCU |
| 666 | GAGGCGAU CUGAUGA X GAA AAUGGUGA | UCACCAUUC AUCGCCUC |
| 669 | ACAGAGGC CUGAUGA X GAA AUGAAUGG | CCAUUCAUC GCCUCUGU |
| 674 | CACUGACA CUGAUGA X GAA AGGCGAUG | CAUCGCCUC UGUCAGUG |
| 678 | UGGUCACU CUGAUGA X GAA ACAGAGGC | GCCUCGGUC AGUGACCA |
| 696 | AUGUACAC CUGAUGA X GAA AUGCCAUG | CAUGGCAUC GUGUACAU |
| 701 | CGGUGAUG CUGAUGA X GAA ACACGAUG | CAUCGUGUA CAUCACCG |
| 705 | UUCUCGGU CUGAUGA X GAA AUGUACAC | GUGUACAUC ACCGAGAA |
| 735 | CGGCAGGG CUGAUGA X GAA AUCACCAC | GUGGUGAUC CCCUGCCG |
| 749 | UUGAAAUC CUGAUGA X GAA ACCCUCGG | CCGAGGGUC GAUUUCAA |
| 753 | AGGUUUGA CUGAUGA X GAA AUCGACCC | GGGUCGAUU UCAAACCU |
| 754 | GAGGUUUG CUGAUGA X GAA AAUCGACC | GGUCGAUUU CAAACCUC |
| 755 | UGAGGUUU CUGAUGA X GAA AAAUCGAC | GUCGAUUUC AAACCUCA |
| 762 | GACACAUU CUGAUGA X GAA AGGUUUGA | UCAAACCUC AAUGUGUC |
| 770 | CGCAAAGA CUGAUGA X GAA ACACAUUG | CAAUGUGUC UCUUUGCG |
| 772 | AGCGCAAA CUGAUGA X GAA AGACACAU | AUGUGUCUC UUUGCGCU |
| 774 | CUAGCGCA CUGAUGA X GAA AGAGACAC | GUGUCUCUU UGCGCUAG |
| 775 | CCUAGCGC CUGAUGA X GAA AAGAGACA | UGUCUCUUU GCGCUAGG |
| 781 | UGGAUACC CUGAUGA X GAA AGCGCAAA | UUUGCGCUA GGUAUCCA |
| 785 | UUUCUGGA CUGAUGA X GAA ACCUAGCG | CGCUAGGUA UCCAGAAA |
| 787 | CUUUUCUG CUGAUGA X GAA AUACCUAG | CUAGGUAUC CAGAAAAG |
| 800 | CCGGAACA CUGAUGA X GAA AUCUCUUU | AAAGAGAUU UGUUCCGG |
| 801 | UCCGGAAC CUGAUGA X GAA AAUCUCUU | AAGAGAUUU GUUCCGGA |
| 804 | CCAUCCGG CUGAUGA X GAA ACAAAUCU | AGAUUUGUU CCGGAUGG |
| 805 | UCCAUCCG CUGAUGA X GAA AACAAAUC | GAUUUGUUC CGGAUGGA |
| 822 | UCCCAGGA CUGAUGA X GAA AUUCUGUU | AAGAGAAUU UCCUGGGA |
| 823 | GUCCCAGG CUGAUGA X GAA AAUUCUGU | ACAGAAUUU CCUGGGAC |
| 824 | UGUCCCAG CUGAUGA X GAA AAAUUCUG | CAGAAUUUC CUGGGACA |
| 840 | GUAAAGCC CUGAUGA X GAA AUCUCGCU | AGCGAGAUA GGCUUUAC |
| 845 | GGAGAGUA CUGAUGA X GAA AGCCUAUC | GAUAGGCUU UACUCUCC |
| 846 | GGGAGAGU CUGAUGA X GAA AAGCCUAU | AUAGGCUUU ACUCUCCC |

TABLE VI-continued

Mouse flk-1 VEGF Receptor-Hammerhead Ribozyme and Substrate sequence

| nt. Position | HH Ribozyme Sequence | Substrate |
|---|---|---|
| 847 | GGGGAGAG CUGAUGA X GAA AAAGCCUA | UACGCUUUA CUCUCCCC |
| 850 | ACUGGGGA CUGAUGA X GAA AGUAAAGC | GCUUUACUC UCCCCAGU |
| 852 | UAACUGGG CUGAUGA X GAA AGAGUAAA | UUUACUCUC CCCAGUUA |
| 859 | GAUCAUGU CUGAUGA X GAA ACUGGGGA | UCCCCAGUU ACAUGAUC |
| 860 | UGAUCAUG CUGAUGA X GAA AACUGGGG | CCCCAGUUA CAUGAUCA |
| 867 | GCAUAGCU CUGAUGA X GAA AUCAUGUA | UACAUGAUC AGCUAUGC |
| 872 | UGCCGGCA CUGAUGA X GAA AGCUGAUC | GAUCAGCUA UGCCGGCA |
| 885 | UCACAGAA CUGAUGA X GAA ACCAUGCC | GGCAUGGUC UUCUGUGA |
| 887 | CCUCACAG CUGAUGA X GAA AGACCAUG | CAUGGUCUU CUGUGAGG |
| 888 | GCCUCACA CUGAUGA X GAA AAGACCAU | AUGGUCUUC UGUGAGGC |
| 903 | UCAUCAUU CUGAUGA X GAA AUCUUUGC | GCAAAGAUC AAUGAUGA |
| 917 | UAGACUGA CUGAUGA X GAA AGGUUUCA | UGAAACCUA UCAGUCUA |
| 919 | GAUAGACU CUGAUGA X GAA AUAGGUUU | AAACCUAUC AGUCUAUC |
| 923 | ACAUGAUA CUGAUGA X GAA ACUGAUAG | CUAUCAGUC UAUCAUGU |
| 925 | GUACAUGA CUGAUGA X GAA AGACUGAU | AUCAGUCUA UCAUGUAC |
| 927 | AUGUACAU CUGAUGA X GAA AUAGACUG | CAGUCUAUC AUGUACAU |
| 932 | CAACUAUG CUGAUGA X GAA ACAUGAUA | UAUCAUGUA CAUAGUUG |
| 936 | ACCACAAC CUGAUGA X GAA AUGUACAU | AUGUACAUA GUUGUGGU |
| 939 | ACAACCAC CUGAUGA X GAA ACUAUGUA | UACAUAGUU GUGGUUGU |
| 945 | UAUCCUAC CUGAUGA X GAA ACCACAAC | GUUGUGGUU GUAGGAUA |
| 948 | CUAUAUCC CUGAUGA X GAA ACAACCAC | GUGGUUGUA GGAUAUAG |
| 953 | AAAUCCUA CUGAUGA X GAA AUCCUACA | UGUAGGAUA UAGGAUUU |
| 955 | AUAAAUCC CUGAUGA X GAA AUAUCCUA | UAGGAUAUA GGAUUUAU |
| 960 | ACAUCAUA CUGAUGA X GAA AUCCUAUA | UAUAGGAUU UAUGAUGU |
| 961 | CACAUCAU CUGAUGA X GAA AAUCCUAU | AUAGGAUUU AUGAUGUG |
| 962 | UCACAUCA CUGAUGA X GAA AAAUCCUA | UAGGAUUUA UGAUGUGA |
| 972 | GGGCUCAG CUGAUGA X GAA AUCACAUC | GAUGUGAUU CUGAGCCC |
| 973 | GGGGCUCA CUGAUGA X GAA AAUCACAU | AUGUGAUUC UGAGCCCC |
| 993 | GAUAGCUC CUGAUGA X GAA AUUUCAUG | CAUGAAAUU GAGCUAUC |
| 999 | CCGGCAGA CUGAUGA X GAA AGCUCAAU | AUUGAGCUA UCUGCCGG |
| 1001 | CUCCGGCA CUGAUGA X GAA AUAGCUCA | UGAGCUAUC UGCCGGAG |
| 1017 | UUUAAGAC CUGAUGA X GAA AGUUUUUC | GAAAACUU GUCUUAAA |
| 1020 | CAAUUUAA CUGAUGA X GAA ACAAGUUU | AAACUUGUC UUAAAUUG |
| 1022 | UACAAUUU CUGAUGA X GAA AGACAAGU | ACUUGUCUU AAAUUUGA |
| 1023 | GUACAAUU CUGAUGA X GAA AAGACAAG | CUUGUCUUA AAUUGUAC |
| 1027 | CGCUGUAC CUGAUGA X GAA AUUUAAGA | UCUUAAAUU GUACCGCG |
| 1030 | UCUCGCUG CUGAUGA X GAA ACAAUUUA | UAAAUUGUA CAGCGAGA |

TABLE VI-continued

Mouse flk-1 VEGF Receptor-Hammerhead Ribozyme and Substrate sequence

| nt. Position | HH Ribozyme Sequence | Substrate |
|---|---|---|
| 1047 | CCCACAUU CUGAUGA X GAA AGCUCUGU | ACAGAGCUC AAUGUGGG |
| 1059 | GUGAAAUC CUGAUGA X GAA AGCCCCAC | GUGGGGGUU GAUUUCAC |
| 1063 | CCAGGUGA CUGAUGA X GAA AUCAAGCC | GGCUUGAUU UCACCUGG |
| 1064 | GCCAGGUG CUGAUGA X GAA AAUCAAGC | GCUUGAUUU CACCUGGC |
| 1065 | UGCCAGGU CUGAUGA X GAA AAAUCAAG | CUUGAUUUC ACCUGGCA |
| 1076 | AAGGUGGA CUGAUGA X GAA AGUGCCAG | CUGGCACUC UCCACCUU |
| 1078 | UGAAGGUG CUGAUGA X GAA AGAGUGCC | GGCACUCUC CACCUUCA |
| 1084 | AGACUUUG CUGAUGA X GAA AGGUGGAG | CUCCACCUU CAAAGUCU |
| 1085 | GAGACUUU CUGAUGA X GAA AAGGUGGA | UCCACCUUC AAAGUCUC |
| 1091 | UAUGAUGA CUGAUGA X GAA ACUUUGAA | UUCAAAGUC UCAUCAUA |
| 1093 | CUUAUGAU CUGAUGA X GAA AGACUUUG | CAAAGUCUC AUCAUAAG |
| 1096 | CUUCUUAU CUGAUGA X GAA AUGAGACU | AGUCUCAUC AUAAGAAG |
| 1099 | AAUCUUCU CUGAUGA X GAA AUGAUGAG | CUCAUCAUA AGAAGAUU |
| 1107 | CGGUUUAC CUGAUGA X GAA AUCUUCUU | AAGAAGAUU GUAAACCG |
| 1110 | UCCCGGUU CUGAUGA X GAA ACAAUCUU | AAGAUUGUA AACCGGGA |
| 1130 | UCCCAGGA CUGAUGA X GAA AGGGUUUC | GAAACCCUU UCCUGGGA |
| 1131 | GUCCAGG CUGAUGA X GAA AAGGGUUU | AAACCCUUU CCUGGGAC |
| 1132 | AGUCCCAG CUGAUGA X GAA AAAGGGUU | AACCCUUUC CUGGGACU |
| 1154 | UGCUCAAA CUGAUGA X GAA ACAUCUUC | GAAGAUGUU UUUGAGCA |
| 1155 | GUGCUCAA CUGAUGA X GAA AACAUCUU | AAGAUGUUU UUGAGCAC |
| 1156 | GGUGCUCA CUGAUGA X GAA AAACAUCU | AGAUGUUUU UGAGCACC |
| 1157 | AGGUGCUC CUGAUGA X GAA AAAACAUC | GAUGUUUUU GAGCACCU |
| 1166 | CUAUUGUC CUGAUGA X GAA AGGUGCUC | GAGCACCUU ACAAUAG |
| 1173 | ACACUUUC CUGAUGA X GAA AUUGUCAA | UUGAGAAUA GAAAGUGU |
| 1205 | CACAGGUG CUGAUGA X GAA AUUCCCCU | AGGGGAAUA CACCUGUG |
| 1215 | CUGGACGC CUGAUGA X GAA ACACAGGU | ACCUGUGUA GCGUCCAG |
| 1220 | GUCCACUG CUGAUGA X GAA ACGCUACA | UGUAGCGUC CAGUGGAC |
| 1236 | UUUCUCUU CUGAUGA X GAA AUCAUCCG | CGGAUGAUC AAGAGAAA |
| 1246 | AAAUGUUC CUGAUGA X GAA AUUUCUCU | AGAGAAAUA GAACAUUU |
| 1253 | CUCGGACA CUGAUGA X GAA AUGUUCUA | UAGAACAUU UGUCCGAG |
| 1254 | ACUCGGAC CUGAUGA X GAA AAUGUUCU | AGAACAUUU GUCCGAGU |
| 1257 | UGAACUCG CUGAUGA X GAA ACAAAUGU | ACAUUUGUC CGAGUUCA |
| 1263 | UUUGUGUG CUGAUGA X GAA ACUCGGAC | GUCCGAGUU CACACAAA |
| 1264 | CUUUGUGU CUGAUGA X GAA AACUCGGA | UCCGAGUUC ACACAAAG |
| 1276 | AGCAAUAA CUGAUGA X GAA AGGCUUUG | CAAAGCCUU UUAUUGCU |
| 1277 | AAGCAAUA CUGAUGA X GAA AAGGCUUU | AAAGCCUUU UAUUGCUU |
| 1278 | AAAGAAAU CUGAUGA X GAA AAAGGCUU | AAGCCUUUU AUUGCUUU |

TABLE VI-continued

Mouse flk-1 VEGF Receptor-Hammerhead Ribozyme and Substrate sequence

| nt. Position | HH Ribozyme Sequence | Substrate |
|---|---|---|
| 1279 | GAAAGCAA CUGAUGA X GAA AAAAGGCU | AGCCUUUUA UUGCUUUC |
| 1281 | CCGAAAGC CUGAUGA X GAA AUAAAAGG | CCUUUUAUU GCUUUCGG |
| 1285 | ACUACCGA CUGAUGA X GAA AGCAAUAA | UUAUUGCUU UCGGUAGU |
| 1286 | CACUACCG CUGAUGA X GAA AAGCAAUA | UAUUGCUUU CGGUAGUG |
| 1287 | CCACUACC CUGAUGA X GAA AAAGCAAU | AUUGCUUUC GGGAGUGG |
| 1291 | CAUCCCAC CUGAUGA X GAA ACCGAAAG | CUUUCGGUA GUGGGAUG |
| 1304 | CCACCAAA CUGAUGA X GAA AUUUCAUC | GAUGAAAUC UUUGGUGG |
| 1306 | UUCCACCA CUGAUGA X GAA AGAUUUCA | UGAAAUCUU UGGUGGAA |
| 1307 | CUUCCACC CUGAUGA X GAA AAGAUUUC | GAAAUCUUU GGUGGAAG |
| 1330 | UCGGACUU CUGAUGA X GAA ACUGCCCA | UGGGCAGUC AAGUCCGA |
| 1335 | GGGAUUCG CUGAUGA X GAA ACUUGACU | AGUCAAGUC CGAAUCCC |
| 1341 | UUCACAGG CUGAUGA X GAA AUUCGGAC | GUCCGAAUC CUGUGAA |
| 1352 | AACUGAGA CUGAUGA X GAA ACUUCACA | UGUGAAGUA UCUCAGUU |
| 1354 | GUAACUGA CUGAUGA X GAA AUACUUCA | UGAAGUAUC UCAGUUAC |
| 1356 | GGGUAACU CUGAUGA X GAA AGAUACUU | AAGUAUCUC AGUUACCC |
| 1360 | AGCUGGGU CUGAUGA X GAA ACUGAGAU | AUCUCAGUU ACCCAGCU |
| 1361 | GAGCUGGG CUGAUGA X GAA AACUGAGA | UCUCAGUUA CCCAGCUC |
| 1369 | GAUAUGAG CUGAUGA X GAA AGCUGGGU | ACCCAGCUC CUGAUAUC |
| 1375 | CCAUUUGA CUGAUGA X GAA AUCAGGAG | CUCCUGAUA UCAAAUGG |
| 1377 | UACCAUUU CUGAUGA X GAA AUAUCAGG | CCUGAUAUC AAAUGGUA |
| 1385 | CAUUUCUG CUGAUGA X GAA ACCAUUUG | CAAAUGGUA CAGAAAUG |
| 1404 | UUGGACUC CUGAUGA X GAA AUCGGCCU | AGGCCAUU GAGUCCAA |
| 1409 | UGUAGUUG CUGAUGA X GAA ACUCAAUG | CAUUGAGUC CAACUACA |
| 1415 | UCAUUGUG CUGAUGA X GAA AGUUGGAC | GUCCAACUA CACAAUGA |
| 1425 | UCGCCAAC CUGAUGA X GAA AUCAUUGU | ACAAUGAUU GUUGGCGA |
| 1428 | UCAUCGCC CUGAUGA X GAA ACAAUCAU | AUGAUUCUU GGCGAUGA |
| 1440 | AUGAUGGU CUGAUGA X GAA AGUUCAUC | GAUGAACUC ACCAUCAU |
| 1446 | ACUUCCAU CUGAUGA X GAA AUGGUGAG | CUCACCAUC AUGGAAGU |
| 1478 | UGACCGUG CUGAUGA X GAA AGUUUCCU | AGGAAACUA CACGGUCA |
| 1485 | GUGAGGAU CUGAUGA X GAA ACCGUGUA | UACACGGUC AUCCUCAC |
| 1488 | UUGGUGAG CUGAUGA X GAA AUGACCGU | ACGGUCAUC CUCACCAA |
| 1491 | GGGUUGGU CUGAUGA X GAA AGGAUGAC | GUCAUCCUC ACCAACCC |
| 1503 | UCCAUUGA CUGAUGA X GAA AUGGGGUU | AACCCCAUU CAAUGGA |
| 1504 | CUCCAUUG CUGAUGA X GAA AAUGGGGU | ACCCCAUUU CAAUGGAG |
| 1505 | UCUCCAUU CUGAUGA X GAA AAAUGGGG | CCCCAUUUC AAUGCAGA |
| 1530 | ACCAGAGA CUGAUGA X GAA ACCAUGUG | CACAUGGUC UCUCUGGU |
| 1532 | CAACCAGA CUGAUGA X GAA AGACCAUG | CAUGGUCUC UCUGGUUG |

TABLE VI-continued

Mouse flk-1 VEGF Receptor-Hammerhead Ribozyme and Substrate sequence

| nt. Position | HH Ribozyme Sequence | Substrate |
|---|---|---|
| 1534 | CACAACCA CUGAUGA X GAA AGAGACCA | UGGUCUCUC UGGUUGUG |
| 1539 | ACAUUCAC CUGAUGA X GAA ACCAGAGA | UCUCUGGUU GUGAAUGU |
| 1548 | UGGGGUGG CUGAUGA X GAA ACAUUCAC | GUGAAUGUC CCACCCCA |
| 1560 | UUCUCACC CUGAUGA X GAA AUCUGGGG | CCCCAGAUC GGUGAGAA |
| 1574 | GCGAGAUC CUGAUGA X GAA AGGCUUUC | GAAAGCCUU GAUCUCGC |
| 1578 | AUAGGCGA CUGAUGA X GAA AUCAAGGC | GCCUUGAUC UCGCCUAU |
| 1580 | CCAUAGGC CUGAUGA X GAA AGAUCAAG | CUUGAUCUC GCCUAUGG |
| 1585 | GGAAUCCA CUGAUGA X GAA AGGCGAGA | UCUCGCCUA UGGAUUCC |
| 1591 | CUGGUAGG CUGAUGA X GAA AUCCAUAG | CUAUGGAUU CCUACCAG |
| 1592 | ACUGGUAG CUGAUGA X GAA AAUCCAUA | UAUGGAUUC CUACCACU |
| 1595 | CAUACUGG CUGAUGA X GAA AGGAAUCC | GGAUUCCUA CCAGUAUG |
| 1601 | UGGUCCCA CUGAUGA X GAA ACUGGUAG | CUACCAGUA UGGGACCA |
| 1619 | UGCAUGUC CUGAUGA X GAA AUGUCUGC | GCAGACAUU GACAUGCA |
| 1632 | UUGGCGUA CUGAUGA X GAA ACUGUGCA | UGCACAGUC UACGCCAA |
| 1634 | GGUUGGCG CUGAUGA X GAA AGACUGUG | CACAGUCUA CGCCAACC |
| 1645 | GUGCAGGG CUGAUGA X GAA AGGGUUGG | CCAACCCUC CCCUGCAC |
| 1659 | UACCACUG CUGAUGA X GAA AUGUGGUG | CACCACAUC CAGUGGGA |
| 1667 | GCUGCCAG CUGAUGA X GAA ACCACUGG | CCAGUGGUA CUGGCAGC |
| 1677 | GCUUCUUC CUGAUGA X GAA AGCUGCCA | UGGCAGCUA GAAGAAGC |
| 1691 | GUCUGUAG CUGAUGA X GAA AGCAGGCU | AGCCUGCUC CUACAGAC |
| 1694 | CGGGUCUG CUGAUGA X GAA AGGAGCAG | CUGCUCCUA CAGACCCG |
| 1718 | UACAAGCA CUGAUGA X GAA ACGGGCUU | AAGCCCGUA UGCUUGUA |
| 1723 | UUCUUUAC CUGAUGA X rAA AGCAUACG | CGUAUGCUU GUAAAGAA |
| 1726 | CCAUUCUU CUGAUGA X GAA ACAAGCAU | AUGCUUGUA AAGAAUGG |
| 1750 | CCCCUGGA CUGAUGA X GAA AUCCUCCA | UGGAGGAUU UCCAGGGG |
| 1751 | CCCCCUGG CUGAUGA X GAA AAUCCUCC | GGAGGAUUU CCAGGGGG |
| 1752 | CCCCCCUG CUGAUGA X GAA AAAUCCUC | GAGGAUUUC CAGGGGGG |
| 1770 | GUGACUUC CUGAUGA X GAA AUCUUGUU | AACAAGAUC GAAGUCAC |
| 1776 | UUUUUGGU CUGAUGA X GAA ACUUCGAU | AUCGAAGUC ACCAAAAA |
| 1790 | UCAGGGCA CUGAUGA X GAA AUUGGUUU | AAACCAAUA UGCCCUGA |
| 1800 | UUUCCUUC CUGAUGA X GAA AUCAGGGC | GCCCUGAUU GAAGGAAA |
| 1821 | AGCGUACU CUGAUGA X GAA ACAGUUUU | AAAACUGUA AGUACGCU |
| 1825 | GACCAGCG CUGAUGA X GAA ACUUACAG | CUGUAAGUA CGCUGGUC |
| 1833 | GCUUGGAU CUGAUGA X GAA ACCAGCGU | ACGCUGGUC AUCCAAGC |
| 1836 | GCAGCUUG CUGAUGA X GAA AUGACCAG | CUGGUCAUC CAAGCUGC |
| 1853 | ACAACGCU CUGAUGA X GAA ACACGUUG | CAACGUGUC AGCGUUGU |
| 1859 | AUUUGUAC CUGAUGA X GAA ACGCUGAC | GUCAGCGUU GUACAAAU |

TABLE VI-continued

Mouse flk-1 VEGF Receptor-Hammerhead Ribozyme and Substrate sequence

| nt. Position | HH Ribozyme Sequence | Substrate |
|---|---|---|
| 1862 | CACAUUUG CUGAUGA X GAA ACAACGCU | AGCGUUGUA CAAAUGUG |
| 1878 | GCUUUGUU CUGAUGA X GAA AUGGCUUC | GAAGCCAUC AACAAAGC |
| 1905 | AAGGAGAU CUGAUGA X GAA ACCCUCUC | GAGAGGGUC AUCUCCUU |
| 1908 | UGGAAGGA CUGAUGA X GAA AUGACCCU | AGGGUCAUC UCCUUCCA |
| 1910 | CAUGGAAG CUGAUGA X GAA AGAUGACC | GGUCAUCUC CUUCCAUG |
| 1913 | UCACAUGG CUGAUGA X GAA AGGAGAUG | CAUCUCCUU CCAUGUGA |
| 1914 | AUCACAUG CUGAUGA X GAA AAGGAGAU | AUCUCCUUC CAUGUGAU |
| 1923 | GGACCCCU CUGAUGA X GAA AUCACAUG | CAUGUGAUC AGGGGUCC |
| 1930 | AAUUUCAG CUGAUGA X GAA ACCCCUGA | UCAGGGGUC CUGAAAUU |
| 1938 | UGCACAGU CUGAUGA X GAA AUUUCAGG | CCUGAAAUU ACUGUGCA |
| 1939 | UUGCACAG CUGAUGA X GAA AAUUUCAG | CUGAAAUUA CUGUGCAA |
| 1982 | ACAACAGG CUGAUGA X GAA ACACACUC | GAGUGUGUC CCUGUUGU |
| 1988 | CAGUGCAC CUGAUGA X GAA ACAGGGAC | GUCCCUGUU GUGCACUG |
| 2008 | CUCAAACG CUGAUGA X GAA AUUUCUGU | ACAGAAAUA CGUUUGAG |
| 2012 | GGUUCUCA CUGAUGA X GAA ACGUAUUU | AAAUACGUU UGAGAACC |
| 2013 | AGGUUCUC CUGAUGA X GAA AACGUAUU | AAUACGUUU GAGAACCU |
| 2022 | UACCACGU CUGAUGA X GAA AGGUUCUC | GAGAACCUC ACGUGGUA |
| 2030 | CAAGCUUG CUGAUGA X GAA ACCACGUG | CACGUGGUA CAAGCUUG |
| 2037 | UGUGAGCC CUGAUGA X GAA AGCUUGUA | UACAAGCUU GGCUCACA |
| 2042 | UUGCCUGU CUGAUGA X GAA AGCCAAGC | GCUUGGCUC ACAGGCAA |
| 2054 | UGUGGACC CUGAUGA X GAA AUGUUGCC | GGCAACAUC GGUCCACA |
| 2058 | CCCAUGUG CUGAUGA X GAA ACCGAUGU | ACAUCGGUC CACAUGGG |
| 2072 | GUGUCAGU CUGAUGA X GAA AUUCGCCC | GGGCGAAUC ACUCACAC |
| 2076 | ACUGGUGU CUGAUGA X GAA AGUGAUUC | GAAUCACUC ACACCAGU |
| 2085 | UUCUUGCA CUGAUGA X GAA ACUGGUGU | ACACCAGUU UGCAAGAA |
| 2086 | GUUCUUGC CUGAUGA X GAA AACUGGUG | CACCAGUUU GCAAGAAC |
| 2096 | GAGCAUCC CUGAUGA X GAA AGUUCUUG | CAAGAACUU GGAUGCUC |
| 2104 | UUUCCAAA CUGAUGA X GAA AGCAUCCA | UGGAUGCUC UUUGGAAA |
| 2106 | AGUUUCCA CUGAUGA X GAA AGAGCAUC | GAUGCUCUU UGGAAACU |
| 2107 | CAGUUUCC CUGAUGA X GAA AAGAGCAU | AUGCUCUUU GGAAACUG |
| 2129 | UGUUAGAA CUGAUGA X GAA ACAUGGUG | CACCAUGUU UUCUAACA |
| 2130 | CUGUUAGA CUGAUGA X GAA AACAUGGU | ACCAUGUUU UCUAACAG |
| 2131 | GCUGUUAG CUGAUGA X GAA AAACAUGG | CCAUGUUUU CUAACAGC |
| 2132 | UGCUGUUA CUGAUGA X GAA AAAACAUG | CAUGUUUUC UAACAGCA |
| 2134 | UGUGCUGU CUGAUGA X GAA AGAAAACA | UGUUUUCUA ACAGCACA |
| 2151 | ACAAUCAA CUGAUGA X GAA AUGUCAUU | AAUGACAUC UUGAUUGU |
| 2153 | CCACAAUC CUGAUGA X GAA AGAUGUCA | UGACAUCUU GAUUGUGG |

TABLE VI-continued

Mouse flk-1 VEGF Receptor-Hammerhead Ribozyme and Substrate sequence

| nt. Position | HH Ribozyme Sequence | Substrate |
|---|---|---|
| 2157 | AAUGCCAC CUGAUGA X GAA AUCAAGAU | AUCUUGAUU GUGGCAUU |
| 2165 | CAUUCUGA CUGAUGA X GAA AUGCCACA | UGUGGCAUU UCAGAAUG |
| 2166 | GCAUUCUG CUGAUGA X GAA AAUGCCAC | GUGGCAUUU CAGAAUGC |
| 2167 | GGCAUUCU CUGAUGA X GAA AAAUGCCA | UGGCAUUUC AGAAUGCC |
| 2177 | CCUGCAGA CUGAUGA X GAA AGGCAUUC | GAAUGCCUC UCUGCAGG |
| 2179 | GUCCUGCA CUGAUGA X GAA AGAGGCAU | AUGCCUCUC UGCAGGAC |
| 2198 | AGCAAACA CUGAUGA X GAA AGUCGCCU | AGGGACUA UGUUUGCU |
| 2202 | GCAGAGCA CUGAUGA X GAA ACAUAGUC | GACUAUGUU UGCUCUGC |
| 2203 | AGCAGAGC CUGAUGA X GAA AACAUAGU | ACUAUGUUU GCUCUGCU |
| 2207 | CUUGAGCA CUGAUGA X GAA AGCAAACA | UGUUUGCUC UGCUCAAG |
| 2212 | CUUAUCUU CUGAUGA X GAA AGCAGAGC | GCUCUGCUC AAGAUAAG |
| 2218 | GGUCUUCU CUGAUGA X GAA AUCUUGAG | CUCAAGAUA AGAAGACC |
| 2239 | GACCAGGC CUGAUGA X GAA AUGUCUUU | AAAGACAUU GCCUGGUC |
| 2247 | AGCUGUUU CUGAUGA X GAA ACCAGGCA | UGCCUGGUC AAACAGCU |
| 2256 | AGGAUGAU CUGAUGA X GAA AGCUGUUU | AAACAGCUC AUCAUCCU |
| 2259 | UCUAGGAU CUGAUGA X GAA AUGAGCUG | CAGCUCAUC AUCCUAGA |
| 2262 | CGCUCUAG CUGAUGA X GAA AUGAUGAG | CUCAUCAUC CUAGAGCG |
| 2265 | AUGCGCUC CUGAUGA X GAA AGGAUGAU | AUCAUCCUA GAGCGCAU |
| 2286 | UUUCCGGU CUGAUGA X GAA AUCAUGGG | CCCAUGAUC ACCGGAAA |
| 2296 | AUUCUCCA CUGAUGA X GAA AUUUCCGG | CCGGAAAUC UGGAGAAU |
| 2305 | UGUUGUCU CUGAUGA X GAA AUUCUCCA | UGGAGAAUC AGACAACA |
| 2319 | GUCUCGCC CUGAUGA X GAA AUGGUUGU | ACAACCAUU GGCGAGAC |
| 2331 | GUCACUUC CUGAUGA X GAA AUGGUCUC | GAGACCAUU GAAGUGAC |
| 2341 | UGCUGGGC CUGAUGA X GAA AGUCACUU | AAGUGACUU GCCCAGCA |
| 2351 | GAUUUCCA CUGAUGA X GAA AUGCUGGG | CCCAGCAUC UGCAAAUC |
| 2359 | UGGGGUAG CUGAUGA X GAA AUUUCCAG | CUGCAAAUC CUACCCCA |
| 2362 | GUGUGGGG CUGAUGA X GAA AGGAUUUC | GAAAUCCUA CCCCACAC |
| 2373 | AACCAUGU CUGAUGA X GAA AUGUGUGG | CCACACAUU ACAUGGUU |
| 2374 | GAACCAUG CUGAUGA X GAA AAUGUGUG | CACACAUUA CAUGGUUC |
| 2381 | UGUCUUUG CUGAUGA X GAA ACCAUGUA | UACAUGGUU CAAAGACA |
| 2382 | UUGUCUUU CUGAUGA X GAA AACCAUGU | ACAUGGUUC AAAGACAA |
| 2403 | GAAUCUUC CUGAUGA X GAA ACCAGGGU | ACCCUGGUA GAAGAUUC |
| 2410 | AAUGCCUG CUGAUGA X GAA AUCUUCUA | UAGAAGAUU CAGGCAUU |
| 2411 | CAAUGCCU CUGAUGA X GAA AAUCUUCU | AGAAGAUUC AGGCAUUG |
| 2418 | CUCAGUAC CUGAUGA X GAA AUGCCUGA | UCAGGCAUU GUACUGAG |
| 2421 | UCUCUCAG CUGAUGA X GAA ACAAUGCC | GGCAUUGUA CUGAGAGA |
| 2449 | CCUGCGGA CUGAUGA X GAA AGUCAGAU | ACCUGACUA UCCGCAGG |

TABLE VI-continued

Mouse flk-1 VEGF Receptor-Hammerhead Ribozyme and Substrate sequence

| nt. Position | HH Ribozyme Sequence | Substrate |
|---|---|---|
| 2451 | ACCCUGCG CUGAUGA X GAA AUAGUCAG | CUGACUAUC CGCAGGGU |
| 2481 | CAGGUGUA CUGAUGA X GAA AGGCCUCC | GGAGGCCUC UACACCUG |
| 2483 | GGCAGGUG CUGAUGA X GAA AGAGGCCU | AGGCCUCUA CACCUGCC |
| 2505 | CAGCCAAG CUGAUGA X GAA ACAUUGCA | UGCAAUGUC CUUGGCUG |
| 2508 | GCACAGCC CUGAUGA X GAA AGGACAUU | AAUGUCCUU GGCUGUGC |
| 2532 | AUUAUGAA CUGAUGA X GAA AGCGUCUC | GAGACGCUC UUCAUAAU |
| 2534 | CUAUUAUG CUGAUGA X GAA AGAGCGUC | GACGCUCUU CAUAAUAG |
| 2535 | UCUAUUAU CUGAUGA X GAA AAGAGCGU | ACGCUCUUC AUAAUAGA |
| 2538 | CCUUCUAU CUGAUGA X GAA AUGAAGAG | CUCUUCAUA AUAGAAGG |
| 2541 | GCACCUUC CUGAUGA X GAA AUUAUGAA | UUCAUAAUA GAAGGUGC |
| 2567 | UGACUUCC CUGAUGA X GAA AGUUGGUC | GACCAACUU GGAAGUCA |
| 2574 | AGGAUAAU CUGAUGA X GAA ACUUCCAA | UUGGAAGUC AUUAUCCU |
| 2577 | ACGAGGAU CUGAUGA X GAA AUGACUUC | GAAGUCAUU AUCCUCGU |
| 2578 | GACGAGGA CUGAUGA X GAA AAUGACUU | AAGUCAUUA UCCUCGUC |
| 2580 | CCGACGAG CUGAUGA X GAA AUAAUGAC | GUCAUUAUC CUCGUCGG |
| 2583 | GUGCCGAC CUGAUGA X GAA AGGAUAAU | AUUAUCCUC GUCGGCAC |
| 2586 | GCAGUGCC CUGAUGA X GAA ACGAGGAU | AUCCUCGUC GGCACUGC |
| 2601 | AACAUGGC CUGAUGA X GAA AUCACUGC | GCAGUGAUU GCCAUGUU |
| 2609 | GCCAGAAG CUGAUGA X GAA ACAUGGCA | UGCCAUGUU CUUCUGGC |
| 2610 | AGCCAGAA CUGAUGA X GAA AACAUGGC | GCCAUGUUC UUCUGGCU |
| 2612 | GGAGCCAG CUGAUGA X GAA AGAACAUG | CAUGUUCUU CUGGCUCC |
| 2613 | AGGAGCCA CUGAUGA X GAA AAGAACAU | AUGUUCUUC UGGCUCCU |
| 2619 | ACAAGAAG CUGAUGA X GAA AGCCAGAA | UUCUGGCUC CUUCUUGU |
| 2622 | AUGAGAAG CUGAUGA X GAA AGGAGCCA | UGGCUCCUU CUUGUCAU |
| 2623 | AAUGACAA CUGAUGA X GAA AAGGAGCC | GGCUCCUUC UUGUCAUU |
| 2625 | ACAAUGAC CUGAUGA X GAA AGAAGGAG | CUCCUUCUU GUCAUUGU |
| 2628 | AGGACAAU CUGAUGA X GAA ACAAGAAG | CUUCUUGUC AUUGCCU |
| 2631 | CGUAGGAG CUGAUGA X GAA AUGACAAG | CUUGUCAUU GUCCUACG |
| 2634 | GUCCGUAG CUGAUGA X GAA ACAAUGAC | GUCAUUGUC CUACGGAC |
| 2637 | ACGGUCCG CUGAUGA X GAA AGGACAAU | AUUGUCCUA CGGACCGU |
| 2646 | GCCCGCUU CUGAUGA X GAA ACGGUCCG | CGGACCGUU AAGCGGGC |
| 2647 | GGCCCGCU CUGAUGA X GAA AACGGUCC | GGACCGUUA AGCGGGCC |
| 2681 | UAGACAAG CUGAUGA X GAA AGCCUGUC | GACAGGCUA CUUGUCUA |
| 2684 | CAAUAGAC CUGAUGA X GAA AGUAGCCU | AGGCUACUU GUCUAUUG |
| 2687 | UGACAAUA CUGAUGA X GAA ACAAGUAG | CUACUUGUC UAUUGUCA |
| 2689 | CAUGACAA CUGAUGA X CAA AGACAAGU | ACUUGUCUA UUGUCAUG |
| 2691 | UCCAUGAC CUGAUGA X GAA AUAGACAA | UUGUCUAUU GUCAUGGA |

TABLE VI-continued

Mouse flk-1 VEGF Receptor-Hammerhead Ribozyme and Substrate sequence

| nt. Position | HH Ribozyme Sequence | Substrate |
|---|---|---|
| 2694 | GGAUCCAU CUGAUGA X GAA ACAAUAGA | UCUAUUGUC AUGGAUCC |
| 2701 | UUCAUCUG CUGAUGA X GAA AUCCAUGA | UCAUGGAUC CAGAUGAA |
| 2711 | CCAAGGGC CUGAUGA X GAA AUUCAUCU | AGAUGAAUU GCCCUUGG |
| 2717 | GCUCAUCC CUGAUGA X GAA AGGGCAAU | AUUGCCCUU GGAUGAGC |
| 2738 | CAUAAGGC CUGAUGA X GAA AGCGUUCA | UGAACGCUU GCCUUAUG |
| 2743 | GGCAUCAU CUGAUGA X GAA AGGCAAGC | GCUUGCCUU AUGAUGCC |
| 2744 | UGGCAUCA CUGAUGA X GAA AAGGCAAG | CUUGCCUUA UGAUGCCA |
| 2765 | CCCUGGGG CUGAUGA X GAA AUUCCCAC | GUGGGAAUU CCCCAGGG |
| 2766 | UCCCUCGG CUGAUGA X GAA AAUUCCCA | UCGGAAUUC CCCAGGGA |
| 2787 | GGUUUUCC CUGAUGA X GAA AGUUUCAG | CUGAAACUA GGAAAACC |
| 2797 | GCGGCCAA CUGAUGA X GAA AGGUUUUC | GAAAACCUC UUGGCCGC |
| 2799 | CCGCGGCC CUGAUGA X GAA AGAGGGUU | AAACCUCUU GGCCGCGG |
| 2813 | CUUGGCCG CUGAUGA X GAA AGGCACCG | CGGUGCCUU CGGCCAAG |
| 2814 | ACUUGGCC CUGAUGA X GAA AAGGCACC | GGUGCCUUC GGCCAAGU |
| 2826 | UCUGCCUC CUGAUGA X GAA AUCACUUG | CAAGUGAUU GAGGCAGA |
| 2839 | AAUUCCAA CUGAUGA X GAA AGCGUCUG | CAGACGCUU UUGGAAUU |
| 2840 | CAAUUCCA CUGAUGA X GAA AAGCGUCU | AGACGCUUU UGGAAUUG |
| 2841 | UCAAUUCC CUGAUGA X GAA AAAGCGUC | GACGCUUUU GGAAUUGA |
| 2847 | GUCUUGUC CUGAUGA X GAA AUUCCAAA | UUUGGAAUU GACAAGAC |
| 2863 | UGUUUUGC CUGAUGA X GAA AGUCGCUG | CAGCGACUU GCAAAACA |
| 2874 | UUGACGGC CUGAUGA X GAA ACUGUUUU | AAAACAGUA GCCGUCAA |
| 2880 | AACAUCUU CUGAUGA X GAA ACGGCUAC | GUAGCCGUC AAGAUGUU |
| 2888 | CUUCUUUC CUGAUGA X GAA ACAUCUUG | CAACAUGUU GAAAGAAG |
| 2917 | GAGGGCUC CUGAUGA X GAA AUGCUCGC | GCGAGCAUC GAGCCCUC |
| 2925 | UCAGACAU CUGAUGA X GAA AGGGCUCG | CGAGCCCUC AUGUCUGA |
| 2930 | UGAGUUCA CUGAUGA X GAA ACAUGAGG | CCUCAUGUC UGAACUCA |
| 2937 | AGGAUCUU CUGAUGA X GAA AGUUCAGA | UCUGAACUC AAGAUCCU |
| 2943 | UGGAUGAG CUGAUGA X GAA AUCUUGAG | CUCAAGAUC CUCAUCCA |
| 2946 | AUGUGGAU CUGAUGA X GAA AGGAUCUU | AAGAUCCUC AUCCACAU |
| 2949 | CCAAUGUG CUGAUGA X GAA AUGAGGAU | AUCCUCAUC CACAUUGG |
| 2955 | UGGUGACC CUGAUGA X GAA AUGUGGAU | AUCCACAUU GGUCACCA |
| 2959 | GAGAUGGU CUGAUGA X GAA ACCAAUGU | ACAUUGGUC ACCAUCUC |
| 2965 | CACAUUGA CUGAUGA X GAA AUGGUGAC | GUCACCAUC UCAAUGUG |
| 2967 | ACCACAUU CUGAUGA X GAA AGAUGGUG | CACCAUCUC AAUGUGUU |
| 2982 | GCGCCUAG CUGAUGA X GAA AGGUUCAC | GUGAACCUC CUAGGCGC |
| 2985 | CAGGCGCC CUGAUGA X GAA AGGAGGUU | AACCUCCUA GGCGCCUG |
| 3013 | CACCAUGA CUGAUGA X GAA AGGCCCUC | GAGGGCCUC UCAUGGUG |

TABLE VI-continued

Mouse flk-1 VEGF Receptor-Hammerhead Ribozyme and Substrate sequence

| nt. Position | HH Ribozyme Sequence | Substrate |
|---|---|---|
| 3015 | AUCACCAU CUGAUGA X GAA AGAGGCCC | GGGCCUCUC AUGGUGAU |
| 3024 | AAUUCCAC CUGAUGA X GAA AUCACCAU | AUGGUGAUU GUGGAAUU |
| 3032 | ACUUGCAG CUGAUGA X GAA AUUCCACA | UGUGGAAUU CUGCAAGU |
| 3033 | AACUUGCA CUGAUGA X GAA AAUUCCAC | GUGGAAUUC UGCAAGUU |
| 3041 | CGUUUCCA CUGAUGA X GAA ACUUGCAG | CUGGAAGUU UGGAAACC |
| 3042 | ACGUUUCC CUGAUGA X GAA AACUUGCA | UGCAAGUUU GGAAACCU |
| 3051 | UAAGUUGA CUGAUGA X GAA AGGUUUCC | GGAAACCUA UCAACUUA |
| 3053 | AGUAAGUU CUGAUGA X GAA AUAGGUUU | AAACCUAUC AACUUACU |
| 3058 | CCGUAAGU CUGAUGA X GAA AGUUGAUA | UAUCAACUU ACUUACGG |
| 3059 | CCCGUAAG CUGAUGA X GAA AAGUUGAU | AUCAACUUA CUUACGGG |
| 3062 | UGCCCCGU CUGAUGA X GAA AAUAAGUU | AACUUACUU ACGGGGCA |
| 3063 | UUGCCCCG CUGAUGA X GAA AAGUAAGU | ACUUACUUA CGGGGCAA |
| 3083 | AGGGAACA CUGAUGA X GAA AUUCAUUU | AAAUGAAUU UGUUCCCU |
| 3084 | UAGGGAAC CUGAUGA X GAA AAUUCAUU | AAUGAAUUU GUUCCCUA |
| 3087 | UUAUAGGG CUGAUGA X GAA ACAAAUUC | GAAUUUGUU CCCUAUAA |
| 3088 | CUUAUAGG CUGAUGA X GAA AACAAAUU | AAUUUGUUC CCUAUAAG |
| 3092 | UGCUCUUA CUGAUGA X GAA AGGGAACA | UGUUCCCUA UAAGAGCA |
| 3094 | UUUGCUCU CUGAUGA X GAA AUAGGGAA | UUCCCUAUA AGAGCAAA |
| 3113 | CCUGGCGG CUGAUGA X GAA AGCGUGCC | GGCACGCUU CCGCCAGG |
| 3114 | CCCUGGCG CUGAUGA X GAA AAGCGUGC | GCACGCUUC CGCCAGGG |
| 3131 | CCCCAACG CUGAUGA X GAA AGUCCUUG | CAAGGACUA CGUUGGGG |
| 3135 | AGCUCCCC CUGAUGA X GAA ACGUAGUC | GACUACGUU GGGGAGCU |
| 3144 | UCCACGGA CUGAUGA X GAA AGCUCCCC | GGGGAGCUC UCCGUGGA |
| 3146 | GAUCCACG CUGAUGA X GAA AGAGCUCC | GGAGCUCUC CGUGGAUC |
| 3154 | UCUUUUCA CUGAUGA X GAA AUCCACGG | CCGUGGAUC UGAAAAGA |
| 3167 | UGCUGUCC CUGAUGA X GAA AGCGUCUU | AAGACGCUU GGACAGCA |
| 3177 | CUGCUGGU CUGAUGA X GAA AUGCUGUC | GACAGCAUC ACCACCAG |
| 3194 | AGCUGGCA CUGAUGA X GAA AGCUCUGG | CCAGAGCUC UGCCAGCU |
| 3203 | CAAAGCCU CUGAUGA X GAA AGCUGGCA | UGCCAGCUC AGGCUUUG |
| 3209 | CCUCAACA CUGAUGA X GAA AGCCUGAG | CUCAGGCUU UGUUGAGG |
| 3210 | UCCUCAAC CUGAUGA X GAA AAGCCUGA | UCAGGCUUU GUUGAGGA |
| 3213 | UUCUCCUC CUGAUGA X GAA ACAAAGCC | GGCUUUGUU GAGGAGAA |
| 3224 | CACUGAGC CUGAUGA X GAA AUUUCUCC | GGAGAAAUC GCUCAGUG |
| 3228 | ACAUCACU CUGAUGA X GAA AGCGAUUU | AAAUCGCUC AGUGAUGU |
| 3237 | UCUUCCUC CUGAUGA X GAA ACAUCACU | AGUGAUGUA GAGGAAGA |
| 3253 | UUCUUCAG CUGAUGA X GAA AGCUUCUU | AAGAAGCUU CUGAAGAA |
| 3254 | GUUCUUCA CUGAUGA X GAA AAGCUUCU | AGAAGCUUC UGAAGAAC |

TABLE VI-continued

Mouse flk-1 VEGF Receptor-Hammerhead Ribozyme and Substrate sequence

| nt. Position | HH Ribozyme Sequence | Substrate |
|---|---|---|
| 3266 | AGUCCUUG CUGAUGA X GAA ACAGUUCU | AGAACUGUA CAAGGACU |
| 3275 | AGGUCAGG CUGAUGA X GAA AGUCCUUG | CAAGGACUU CCUGACCU |
| 3276 | AAGGUCAG CUGAUGA X GAA AAGUCCUU | AAGGACUUC CUGACCUU |
| 3284 | GAUGCUCC CUGAUGA X GAA AGGUCAGG | CCUGACCUU GGAGCAUC |
| 3292 | ACAGAUGA CUGAUGA X GAA AUGCUCCA | UGGAGCAUC UCAUCUGU |
| 3294 | UAACAGAU CUGAUGA X GAA AGAUGCUC | GAGCAUCUC AUCUGUUA |
| 3297 | CUGUAACA CUGAUGA X GAA AUGAGAUG | CAUCUCAUC UGUUACAG |
| 3301 | GAAGCUGU CUGAUGA X GAA ACAGAUGA | UCAUCUGUU ACAGCUUC |
| 3302 | GGAAGCUG CUGAUGA X GAA AACAGAUG | CAUCUGUUA CAGCUUCC |
| 3308 | CCACUUGG CUGAUGA X GAA AGCUGUAA | UUACAGCUU CCAAGUGG |
| 3309 | GCCACUUG CUGAUGA X GAA AAGCUGUA | UACAGCUUC CAAGUGGC |
| 3319 | CAUGCCCU CUGAUGA X GAA AGCCACUU | AAGUGGCUA AGGGCAUG |
| 3332 | AUGCCAAG CUGAUGA X GAA ACUCCAUG | CAUGGAGUU CUUGGCAU |
| 3333 | GAUGCCAA CUGAUGA X GAA AACUCCAU | AUGGAGUUC UUGGCAUC |
| 3335 | UUGAUGCC CUGAUGA X GAA AGAACUCC | GGAGUUCUU GGCAUCAA |
| 3341 | ACUUCCUU CUGAUGA X GAA AUGCCAAG | CUUGGCAUC AAGGAAGU |
| 3352 | CCUGUGGA CUGAUGA X GAA ACACUUCC | GGAAGUGGA UCCACAGG |
| 3354 | UCCCUGUG CUGAUGA X GAA AUACACUU | AAGUGUAUC CACAGGGA |
| 3381 | GAUAGGAG CUGAUGA X GAA AUGUUUCG | CGAAACAUU CUCCUAUC |
| 3382 | CGAUAGGA CUGAUGA X GAA AAUGUUUC | GAAACAUUC UCCUAUCG |
| 3384 | UCCGAUAG CUGAUGA X GAA AGAAUGUU | AACAUUCUC CUAUCGGA |
| 3387 | UUCUCCGA CUGAUGA X GAA AGGAGAAU | AUUCUCCUA UCGGAGAA |
| 3389 | UCUUCUCC CUGAUGA X GAA AUAGGAGA | UCUCCUAUC GGAGAAGA |
| 3405 | CAGAUCUU CUGAUGA X GAA ACCACAUU | AAUGUGGUU AAGAUCUG |
| 3406 | ACAGAUCU CUGAUGA X GAA AACCACAU | AUGUGGJUA AGAUCUGU |
| 3411 | AAGUCACA CUGAUGA X GAA AUCUUAAC | GUUAAGAUC UGUGACUU |
| 3419 | CCAAGCCG CUGAUGA X GAA AGUCACAG | GUGUGACUU CGGCUUGG |
| 3420 | GCCAAGCC CUGAUGA X GAA AAGUCACA | UGUGACUUC GGCUUGGC |
| 3425 | CCCGGGCC CUGAUGA X GAA AGCCGAAG | CUUCGGCUU GGCCCGGG |
| 3438 | UCUUUAUA CUGAUGA X GAA AUGUCCCG | CGGGACAUU UAUAAAGA |
| 3439 | GUCUUUAU CUGAUGA X GAA AAUGUCCC | GGGACAUUU AUAAAGAC |
| 3440 | GGUCUUUA CUGAUGA X GAA AAAUGUCC | GGACAUUUA UAAAGACC |
| 3442 | CGGGUCUU CUGAUGA X GAA AUAAAUGU | ACAUUUAUA AAGACCCG |
| 3454 | UCUGACAU CUGAUGA X GAA AUCCGGGU | ACCCGGAUU AUGUCAGA |
| 3455 | UUCUGACA CUGAUGA X GAA AAUCCGGG | CCCGGAUUA UGUCAGAA |
| 3459 | CCUUUUCU CUGAUGA X GAA ACAUAAUC | GAUUAUGUC AGAAAGG |
| 3480 | UUCAAAGG CUGAUGA X GAA AGUCGGGC | GCCCGACUC CCUUUGAA |

TABLE VI-continued

Mouse flk-1 VEGF Receptor-Hammerhead Ribozyme and Substrate sequence

| nt. Position | HH Ribozyme Sequence | Substrate |
|---|---|---|
| 3484 | CCACUUCA CUGAUGA X GAA AGGGAGUC | GACUCCCUU UGAAGUGG |
| 3485 | UCCACUUC CUGAUGA X GAA AAGGGAGU | ACUCCCUUU GAAGUGGA |
| 3510 | CUGUCAAA CUGAUGA X GAA AUGGUUUC | CAAACCAUU UUUGACAG |
| 3511 | UCUGUCAA CUGAUGA X GAA AAUGGUUU | AAACCAUUU UUGACAGA |
| 3512 | CUCUGUCA CUGAUGA X GAA AAAUGGUU | AACCAUUUU UGACAGAG |
| 3513 | ACUCUGUC CUGAUGA X GAA AAAAUGGU | ACCAUUUUU GACAGAGU |
| 3522 | AUUGUGUA CUGAUGA X GAA ACUCUGUC | GACAGAGUA UACACAAU |
| 3524 | GAAUUGUG CUGAUGA X GAA AUACUCUG | CAGAGUAUA CACAAUUC |
| 3531 | UCGCUCUG CUGAUGA X GAA AUUGUGUA | UACACAAUU CAGAGCGA |
| 3532 | AUCGCUCU CUGAUGA X GAA AAUUGUGU | ACACAAUUC AGAGCGAU |
| 3548 | CACCGAAA CUGAUGA X GAA ACCACACA | UGUGUGGUC UUUCGGUG |
| 3550 | CACACCGA CUGAUGA X GAA AGACCACA | UGUGGUCUU UCGGUGUG |
| 3551 | ACACACCG CUGAUGA X GAA AAGACCAC | GUGGUCUUU CGGUGUGU |
| 3552 | AACACACC CUGAUGA X GAA AAAGACCA | UGGUCUUUC GGUGUGUU |
| 3560 | CCCAGAGC CUGAUGA X GAA ACACACCG | CGGUGUGUU GCUCUGGG |
| 3564 | AUUUCCCA CUGAUGA X GAA AGCCACAC | GUGUUGCUC UGGGAAAU |
| 3573 | AAGGAAAA CUGAUGA X GAA AUUUCCCA | UGGGAAAUA UUUUCCUU |
| 3575 | CUAAGGAA CUGAUGA X GAA AUAUUUCC | GGAAAUAUU UUCCUUAG |
| 3576 | CCUAAGGA CUGAUGA X GAA AAUAUUUC | GAAAUAUUU UCCUUAGG |
| 3577 | ACCUAAGG CUGAUGA X GAA AAAUAUUU | AAAUAUUUU CCUUAGGU |
| 3578 | CACCUAAG CUGAUGA X GAA AAAAUAUU | AAUAUUUUC CUUAGGUG |
| 3581 | AGGCACCU CUGAUGA X GAA AGGAAAAU | AUUUUCCUU AGGUGCCU |
| 3582 | GAGGCACC CUGAUGA X GAA AAGGAAAA | UUUUCCUUA GGUGCCUC |
| 3590 | GGUAUGGG CUGAUGA X GAA AGGCACCU | AGGUGCCUC CCCAUACC |
| 3596 | CCCCAGGG CUGAUGA X GAA AUGGGGAG | CUCCCCAUA CCCUGGGG |
| 3606 | UGAAUCUU CUGAUGA X GAA ACCCCAGG | CCUGGGGUC AAGAUUGA |
| 3612 | UCUUCAUC CUGAUGA X GAA AUCUUGAC | GUCAAGAUU GAUGAAGA |
| 3623 | UCCUACAA CUGAUGA X GAA AUUCUUCA | UGAAGAAUU UUGUAGGA |
| 3624 | CUCCUACA CUGAUGA X GAA AAUUCUUC | GAAGAAUUU UGUAGGAG |
| 3625 | UCUCCUAC CUGAUGA X GAA AAAUUCUU | AAGAAUUUU GUAGGAGA |
| 3628 | CAAUCUCC CUGAUGA X GAA ACAAAAUU | AAUUUUGUA GGAGAUUG |
| 3635 | CUUCUUUC CUGAUGA X GAA AUCUCCUA | UAGGAGAUU GAAAGAAG |
| 3649 | CCGCAUUC CUGAUGA X GAA AGUUCCUU | AAGGAACUA GAAUGCGG |
| 3661 | GUAGUCAG CUGAUGA X GAA AGCCCGCA | UGCGGGCUC CUGACUAC |
| 3668 | GGGUAGUG CUGAUGA X GAA AGUCAGGA | UCCUGACUA CACUACCC |
| 3673 | UUCUGGGG CUGAUGA X GAA AGUGUAGU | ACUACACUA CCCCACAA |
| 3686 | UGGUCUGG CUGAUGA X GAA ACAUUUCU | AGAAAUGUA CCAGACCA |

TABLE VI-continued

Mouse flk-1 VEGF Receptor-Hammerhead Ribozyme and Substrate sequence

| nt. Position | HH Ribozyme Sequence | Substrate |
|---|---|---|
| 3734 | CUGAAAAC CUGAUGA X GAA AGGGUCUC | GAGACCCUC GUUUCAG |
| 3737 | ACUCUGAA CUGAUGA X GAA ACGAGGGU | ACCCUCGUU UUCAGAGU |
| 3738 | AACUCUGA CUGAUGA X GAA AACGAGGG | CCCUCGUUU UCAGAGUU |
| 3739 | CAACUCUG CUGAUGA X GAA AAACGAGG | CCUCGUUUU CAGAGUUG |
| 3740 | CCAACUCU CUGAUGA X GAA AAAACGAG | CUCGUUUUC AGAGUUGG |
| 3746 | GCUCCACC CUGAUGA X GAA ACUCUGAA | UUCAGAGUU GGUGGAGC |
| 3757 | GUUUCCCA CUGAUGA X GAA AUGCUCCA | UGGAGCAUU UGGGAAAC |
| 3758 | GGUUUCCC CUGAUGA X GAA AAUGCUCC | GGAGCAUUU GGGAAACC |
| 3768 | GCUUGCAG CUGAUGA X GAA AGCUUUUC | GGAAACCUC CUGCAAGC |
| 3803 | GAACAAUA CUGAUGA X GAA AGUCUUUG | CAAAGACUA UAUUGUUC |
| 3805 | AAGAACAA CUGAUGA X GAA AUAGUCUU | AAGACUAUA UUGUUCUU |
| 3807 | GGAAGAAC CUGAUGA X GAA AUAUAGUC | GACUAUAUU GUUCUUCC |
| 3810 | AUGGAAG CUGAUGA X GAA ACAAUAUA | UAUAUUGUU CUUCCAAU |
| 3811 | CAUUGGAA CUGAUGA X GAA AACAAUAU | AUAUUGUUC UUCCAAUG |
| 3813 | GACAUUGG CUGAUGA X GAA AGAACAAU | AUUGUUCUU CCAAUGUC |
| 3814 | UGACAUUG CUGAUGA X GAA AAGAACAA | UUGUUCUUC CAAUGUCA |
| 3821 | GUGUCUCU CUGAUGA X GAA ACAUUGGA | UCCAAUGUC AGAGACAC |
| 3847 | GAGUCCAG CUGAUGA X GAA AUCCUCUU | AAGAGGAUU CUGGACUC |
| 3848 | AGAGUCCA CUGAUGA X GAA AAUCCUCU | AGAGGAUUC UGGACUCU |
| 3855 | GGCAGGGA CUGAUGA X GAA AGUCCAGA | UCUGGACUC UCCCUGCC |
| 3857 | UAGGCAGG CUGAUGA X GAA AGAGUCCA | UGGACUCUC CUGCCUA |
| 3865 | AGGUGAGG CUGAUGA X GAA AGGCAGGG | CCCUGCCUA CCUCACCU |
| 3869 | AAACAGGU CUGAUGA X GAA AGGUAGGC | GCCUACCUC ACCUGUUU |
| 3876 | AUACAGGA CUGAUGA X GAA ACAGGUGA | UCACCUGUU UCCUGUAU |
| 3877 | CAUACAGG CUGAUGA X GAA AACAGGUG | CACCUGUUU CCUGUAUG |
| 3878 | CCAUACAG CUGAUGA X GAA AAACAGGU | ACCUGUUUC CUGUAUGG |
| 3883 | UUCCUCCA CUGAUGA X GAA ACAGGAAA | UUUCCUGUA UGGAGGAA |
| 3914 | CAUAAUGG CUGAUGA X GAA AUUUGGGG | CCCCAAAUU CCAUUAUG |
| 3915 | UCAUAAUG CUGAUGA X GAA AAUUUGGG | CCCAAAUUC CAUUAUGA |
| 3919 | GUUGUCAU CUGAUGA X GAA AUGGAAUU | AAUUCCAUU AUGACAAC |
| 3920 | UGUUGUCA CUGAUGA X GAA AAUGGAAU | AUUCCAUUA UGACAACA |
| 3939 | UAAUGACU CUGAUGA X GAA AUUCCUGC | GCAGGAAUC AGUCAUUA |
| 3943 | GAGAUAAU CUGAUGA X GAA ACUGAUUC | GAAUCAGUC AUUAUCUC |
| 3946 | CUGGAGAU CUGAUGA X GAA AUGACUGA | UCAGUCAUU AUCUCCAG |
| 3947 | UCUGGAGA CUGAUGA X GAA AAUGACUG | CAGUCAUUA UCUCCAGA |
| 3949 | GUUCUGGA CUGAUGA X GAA AUAAUGAC | GUCAUUAUC UCCAGAAC |
| 3951 | CUGUUCUG CUGAUGA X GAA AGAUAAUG | CAUUAUCUC CAGAACAG |

TABLE VI-continued

Mouse flk-1 VEGF Receptor-Hammerhead Ribozyme and Substrate sequence

| nt. Position | HH Ribozyme Sequence | Substrate |
|---|---|---|
| 3961 | CUUUCGCU CUGAUGA X GAA ACUGUUCU | AGAACAGUA AGCGAAAG |
| 3987 | AAUGUUUU CUGAUGA X GAA ACACUCAC | GUGAGUGUA AAAACAUU |
| 3995 | UAUCUUCA CUGAUGA X GAA AUGUUUUU | AAAAACAUU UGAAGAUA |
| 3996 | AUAUCUUC CUGAUGA X GAA AAUGUUUU | AAACAUUU GAAGAUAU |
| 4003 | CAAUGGGA CUGAUGA X GAA AUCUUCAA | UUGAAGAUA UCCCAUUG |
| 4005 | UCCAAUGG CUGAUGA X GAA AUAUCUUC | GAAGAUAUC CCAUUGGA |
| 4010 | GUUCCUCC CUGAUGA X GAA AUGGGAUA | UAUCCCAUU GGAGGAAC |
| 4026 | AUCACUUU CUGAUGA X GAA ACUUCUGG | CCAGAAGUA AAAGUGAU |
| 4035 | UCAUCUGG CUGAUGA X GAA AUCACUUU | AAAGUGAUC CCAGAUGA |
| 4068 | GAUGCAAG CUGAUGA X GAA ACCAUCCC | GGGAUGGUC CUUGCAUC |
| 4071 | UCUGAUGC CUGAUGA X GAA AGGACCAU | AUGGUCCUU GCAUCAGA |
| 4076 | GCUCUUCU CUGAUGA X GAA AUGCAAGG | CCUUGCAUC AGAAGAGC |
| 4093 | GUCUUCCA CUGAUGA X GAA AGUUUUCA | UGAAAACUC UGGAAGAC |
| 4112 | AUGGAGAU CUGAUGA X GAA AUUUGUUC | GAACAAAUU AUCUCCAU |
| 4113 | GAUGGAGA CUGAUGA X GAA AAUUUGUU | AACAAAUUA UCUCCAUC |
| 4115 | AAGAUGGA CUGAUGA X GAA AUAAUUUG | CAAAUUAUC UCCAUCUU |
| 4117 | AAAAGAUG CUGAUGA X GAA AGAUAAUU | AAUUAUCUC CAUCUUUU |
| 4121 | CACGAAAA CUGAUGA X GAA AUGGAGAU | AUCUCCAUC UUUUGGUG |
| 4123 | UCCACCAA CUGAUGA X GAA AGAUGGAG | CUCCAUCUU UUGGUGGA |
| 4124 | UUCCACCA CUGAUGA X GAA AAGAUGGA | UCCAUCUUU UGGUGGAA |
| 4125 | AUUCCACC CUGAUGA X GAA AAAGAUGG | CCAUCUUUU GGUGGAAU |
| 4144 | CCUGCUUU CUGAUGA X GAA ACUGGGCA | UGCCCAGUA AAAGCAGG |
| 4157 | AGGCCACA CUGAUGA X GAA ACUCCCUG | CAGGGAGUC UGUGGCCU |
| 4166 | AGCCUUCC CUGAUGA X GAA AGGCCACA | UGUCGCCUC GGAAGGCU |
| 4175 | UCUGCUUG CUGAUGA X GAA AGCCUUCC | GGAAGGCUC CAACCAGA |
| 4193 | CAGACUGG CUGAUGA X GAA AGCCACUG | CAGUGGCUA CCAGUCUG |
| 4199 | GAUACCCA CUGAUGA X GAA ACUGGUAG | CUACCAGUC UGGGUAUC |
| 4205 | CUGAGUGA CUGAUGA X GAA ACCCAGAC | GUCUGGGUA UCACUCAG |
| 4207 | AUCUGAGU CUGAUGA X GAA AUACCCAG | CUGGGUAUC ACUCAGAU |
| 4211 | UGUCAUCU CUGAUGA X GAA AGUGAUAC | GUAUCACUC AGAUGACA |
| 4235 | CGCUGGAG CUGAUGA X GAA ACACGGUG | CACCGUGUA CUCCAGCG |
| 4238 | CGUCGCUG CUGAUGA X GAA AGUACACG | CGUGUACUC CAGCGACG |
| 4257 | AUCUUUAA CUGAUGA X GAA AGUCCUGC | GCAGGACUU UUAAAGAU |
| 4258 | CAUCUUUA CUGAUGA X GAA AAGUCCUG | CAGGACUUU UAAGAUG |
| 4259 | CCAUCUUU CUGAUGA X GAA AAAGUCCU | AGGACUUUU AAAGAUGG |
| 4260 | ACCAUCUU CUGAUGA X GAA AAAAGUCC | GGACUUUUA AAGAUGGU |
| 4281 | UCAGCGUG CUGAUGA X GAA ACUGGAGC | GCUCAGUU CACGCUGA |

TABLE VI-continued

Mouse flk-1 VEGF Receptor-Hammerhead Ribozyme and Substrate sequence

| nt. Position | HH Ribozyme Sequence | Substrate |
|---|---|---|
| 4282 | GUCAGCGU CUGAUGA X GAA AACUGCAG | CUGCAGUUC ACGCUGAC |
| 4292 | UGGUCCCU CUGAUGA X GAA AGUCAGCG | CGCUGACUC AGGGACCA |
| 4311 | CAGGAGGU CUGAUGA X GAA AGCUGCAG | CUGCAGCUC ACCUCCUG |
| 4316 | UUAAACAG CUGAUGA X CAA AGGUGAGC | GCUCACCUC CUCUUUAA |
| 4321 | UCCAUUUA CUGAUGA X GAA ACAGGAGG | CCUCCUGUU UAAAUGGA |
| 4322 | UUCCAUUU CUGAUGA X GAA AACAGGAG | CUCCUCUUU AAAUGGAA |
| 4323 | CUUCCAUU CUGAUGA X GAA AAACAGGA | UCCUGUUUA AAUGGAAG |
| 4336 | CGGGACAG CUGAUGA X GAA ACCACUUC | GAAGUGGUC CUGUCCCG |
| 4341 | GGAGCCGG CUGAUGA X GAA ACAGGACC | GGUCCUGUC CCGGCUCC |
| 4348 | UGGGGGCG CUGAUGA X GAA AGCCGGGA | UCCCGGCUC CGCCCCCA |
| 4360 | AUUUCCAG CUGAUGA X GAA AGUUGGGG | CCCCAACUC CUGGAAAU |
| 4369 | UCUCUCGU CUGAUGA X GAA AUUUCCAG | CUGGAAAUC ACGAGAGA |
| 4387 | GAAAAUCU CUGAUGA X GAA AGCAGCAC | GUGCUGCUU AGAUUUUC |
| 4388 | UGAAAAUC CUGAUGA X GAA AACCAGCA | UGCUGCUUA GAUUUUCA |
| 4392 | CACUUGAA CUGAUGA X GAA AUCUAAGC | GCUUAGAUU UUCAAGUG |
| 4393 | ACACUUGA CUGAUGA X GAA AAUCUAAG | CUUAGAUUU UCAAGUGU |
| 4394 | AACACUUG CUGAUGA X GAA AAAUCUAA | UUAGAUUUU CAAGUGUU |
| 4395 | CAACACUU CUGAUGA X GAA AAAAUCUA | UAGAUUUUC AAGUGUUG |
| 4402 | GAAAGAAC CUGAUGA X GAA ACACUUGA | UCAAGUGUU GUUCUUUC |
| 4405 | GUGGAAAG CUGAUGA X GAA ACAACACU | AGUGUUGUU CUUUCCAC |
| 4406 | GGUGGAAA CUGAUGA X GAA AACAACAC | GUGUUGUUC UUUCCACC |
| 4408 | GUGGUGGA CUGAUGA X GAA AGAACAAC | GUUGUUCUU UCCACCAC |
| 4409 | GGUGGUGG CUGAUGA X GAA AAGAACAA | UUGUUCUUU CCACCACC |
| 4410 | GGGUGGUG CUGAUGA X GAA AAAGAACA | UGUUCUUUC CACCACCC |
| 4425 | AAUGUGGC CUGAUGA X GAA ACUUCCGG | CCGGAAGUA GCCACAUU |
| 4433 | GAAAAUCA CUGAUGA X GAA AUGUGGCU | AGCCACAUU UGAUUUUC |
| 4434 | UGAAAAUC CUGAUGA X GAA AAUGUGGC | GCCACAUUU GAUUUUCA |
| 4438 | AAAAUGAA CUGAUGA X GAA AUCAAAUG | CAUUUGAUU UUCAUUUU |
| 4439 | AAAAAUGA CUGAUGA X GAA AAUCAAAU | AUUUGAUUU UCAUUUUU |
| 4440 | CAAAAAUG CUGAUGA X GAA AAAUCAAA | UUUGAUUUU CAUUUUUG |
| 4441 | CCAAAAAU CUGAUGA X GAA AAAAUCAA | UUGAUUUUC AUUUUUGG |
| 4444 | CCUCCAAA CUGAUGA X GAA AUGAAAAU | AUUUUCAUU UUUGGAGG |
| 4445 | UCCUCCAA CUGAUGA X GAA AAUGAAAA | UUUUCAUUU UUGGAGGA |
| 4446 | CUCCUCCA CUGAUGA X GAA AAAUGAAA | UUUCAUUUU UGGAGGAG |
| 4447 | CCUCCUCC CUGAUGA X GAA AAAAUGAA | UUCAUUUUU GGAGGAGG |
| 4461 | UGGAGUCU CUGAUGA X GAA AGGUCCCU | AGGGACCUC AGACUGCA |
| 4477 | CUGAGGAC CUGAUGA X GAA AGCUCCUU | AAGGAGCUU GUCCUCAG |

TABLE VI-continued

Mouse flk-1 VEGF Receptor-Hammerhead Ribozyme and Substrate sequence

| nt. Position | HH Ribozyme Sequence | Substrate |
|---|---|---|
| 4480 | GCCCUGAG CUGAUGA X GAA ACAAGCUC | GAGCUUGUC UCAGGGC |
| 4483 | AAUGCCCU CUGAUGA X GAA AGGACAAG | CLUUJCCUC AGGGCAUU |
| 4491 | UCUCUGGA CUGAUGA X GAA AUGCCCUG | CAGGGCAUU UCCAGAGA |
| 4492 | UUCUCUGG CUGAUGA X GAA AAUGCCCU | AGGGCAUUU CCAGAGAA |
| 4493 | CUUCUCUG CUGAUGA X GAA AAAUGCCC | GGGCAUUUC CAGAGAAG |
| 4525 | GUAGAGUC CUGAUGA X GAA ACACAUUC | GAAUGUGUU GACUCUAC |
| 4530 | AGAGAGUA CUGAUGA X GAA AGUCAACA | UGUUGACUC UACUCUCU |
| 4532 | AAAGAGAG CUGAUGA X GAA AGAGUCAA | UUGACUCUA CUCUCUUU |
| 4535 | GGAAAAGA CUGAUGA X GAA AGUAGAGU | ACUCUACUC UCUUUUCC |
| 4537 | AUGGAAAA CUGAUGA X GAA AGAGUAGA | UCUACUCUC UUUUCCAU |
| 4539 | GAAUGGAA CUGAUGA X GAA AGAGAGUA | UACUCUCUU UUCCAUUC |
| 4540 | UGAAUGGA CUGAUGA X GAA AAGAGAGU | ACUCUCUUU UCCAUUCA |
| 4541 | AUGAAUGG CUGAUGA X GAA AAAGAGAG | CUCUCUUUU CCAUUCAU |
| 4542 | AAUGAAUG CUGAUGA X GAA AAAAGAGA | UCUCUUUUC CAUUCAUU |
| 4546 | UUUAAAUG CUGAUGA X GAA AUGGAAAA | UUUUCCAUU CAUUUAAA |
| 4547 | UUUUAAAU CUGAUGA X GAA AAUGGAAA | UUUCCAUUC AUUUAAAA |
| 4550 | GACUUUUA CUGAUGA X GAA AUGAAUGG | CCAUUCAUU UAAAAGUC |
| 4551 | GGACUUUU CUGAUGA X GAA AAUGAAUG | CAUUCAUUU AAAAGUCC |
| 4552 | AGGACUUU CUGAUGA X GAA AAAUGAAU | AUUCAUUUA AAAGUCCU |
| 4558 | UUAUAUAG CUGAUGA X GAA ACUUUUAA | UUAAAAGUC CUAUAUAA |
| 4561 | ACAUUAUA CUGAUGA X GAA AGGACUUU | AAAGUCCUA UAUAAUGU |
| 4563 | GCACAUUA CUGAUGA X GAA AUAGGACU | AGUCCUAUA UAAUGUGC |
| 4565 | GGGCACAU CUGAUGA X GAA AUAUAGGA | UCCUAUAUA AUGUGCCC |
| 4583 | GGUAGUGA CUGAUGA X GAA ACCACAGC | GCUGUGGUC UCACUACC |
| 4585 | CUGGUAGU CUGAUGA X GAA AGACCACA | UGUGGUCUC ACUACCAG |
| 4589 | UUAACUGG CUGAUGA X GAA AGUGAGAC | GUCUCACUA CCAGUUAA |
| 4595 | UUUGCUUU CUGAUGA X GAA ACUGGUAG | CUACCAGUU AAAGAAAA |
| 4596 | UUUUGCUU CUGAUGA X GAA AACUGGUA | UACCAGUUA AAGCAAAA |
| 4609 | GUGUUUGA CUGAUGA X GAA AGUCUUUU | AAAAGACUU UCAAACAC |
| 4610 | CGUGUUUG CUGAUGA X GAA AAGUCUUU | AAAGACUUU CAAACACG |
| 4611 | ACGUGUUU CUGAUGA X GAA AAAGUCUU | AAGACUUUC AAACACGU |
| 4625 | GGAGGACA CUGAUGA X GAA AGUCCACG | CGUGGACUC UGUCCUCC |
| 4629 | UCUUGGAG CUGAUGA X GAA ACAGAGUC | GACUCUGUC CUCCAAGA |
| 4632 | ACUUCUUG CUGAUGA X GAA AGGACAGA | UCUGUCCUC CAAGAAGU |
| 4654 | GUUUCACA CUGAUGA X GAA AGGUGCCG | CGGCACCUC UGUGAAAC |
| 4668 | GCCCAUUC CUGAUGA X GAA AUCCAGUU | AACUGGAUC GAAUGGGC |
| 4683 | AACACACA CUGAUGA X GAA AGCAUUGC | GCAAUGCUU UGUGUGUU |

TABLE VI-continued

Mouse flk-1 VEGF Receptor-Hammerhead Ribozyme and Substrate sequence

| nt. Position | HH Ribozyme Sequence | Substrate |
|---|---|---|
| 4684 | CAACACAC CUGAUGA X GAA AAGCAUUG | CAAUGCUUU GUGUGUUG |
| 4691 | CCAUCCUC CUGAUGA X GAA ACACACAA | UUGUGUGUU GAGGAUGG |
| 4709 | GGCCCUGG CUGAUGA X GAA ACAUCUCA | UGAGAUGUC CCAGGGCC |
| 4722 | GGUAGACA CUGAUGA X GAA ACUCGGCC | GGCCGAGUC UGUCUACC |
| 4726 | CCAAGGUA CUGAUGA X GAA ACAGACUC | GAGUCUGUC UACCUUGG |
| 4728 | CUCCAAGG CUGAUGA X GAA AGACAGAC | GUCUGUCUA CCUUGGAG |
| 4732 | AAGCCUCC CUGAUGA X GAA AGGUAGAC | GUCUACCUU GGAGGCUU |
| 4740 | CCUCCACA CUGAUGA X GAA AGCCUCCA | UGGAGGCUU UGUGGAGG |
| 4741 | UCCUCCAC CUGAUGA X GAA AAGCCUCC | GGAGGGUUU GUGGAGGA |
| 4758 | UUGGCUCA CUGAUGA X GAA AGCCCGCA | UGCGGGCUA UGAGCGAA |
| 4771 | CCACACUU CUGAUGA X GAA ACACUUGG | CCAAGUGUU AAGUGUGG |
| 4772 | CCCACACU CUGAUGA X GAA AACACUUG | CAAGUGUUA AGUGUGGG |
| 4811 | CUCGGAGC CUGAUGA X GAA ACUUGCGC | GCGCAAGUC GCUCGGAG |
| 4815 | GGGUUUCC CUGAUGA X GAA AGCGACUU | AAGUCGCUC GGAGCG |
| 4826 | CAGGCUCC CUGAUGA X GAA ACGGCUCU | AGAGCGGUU GGAGCCUG |
| 4844 | GCCAGCAC CUGAUGA X GAA AUGCAUCU | AGAUGCAUU GUGCUGGC |
| 4854 | CUCCACCA CUGAUGA X GAA AGCCAGCA | UGCUGGCUC UGGUGGAG |
| 4870 | CAGGCCAC CUGAUGA X GAA AGCCCACC | GGUGGGCUU GUGGCCUG |
| 4880 | CGUUUCCU CUGAUGA X GAA ACAGGCCA | UGGCCUGUC AGGAAACG |
| 4908 | CAAAACCA CUGAUGA X GAA ACCCUGCC | GGCAGGGUU UGGUUUUG |
| 4909 | CCAAAACC CUGAUGA X GAA AACCCUGC | GCAGGCUUU GGUUUUGG |
| 4913 | CCUUCCAA CUGAUGA X GAA ACCAAACC | GGUUUGGUU UUGGAAGG |
| 4914 | ACCUUCCA CUGAUGA X GAA AACCAAAC | GUUUGGUUU UGGAAGGU |
| 4915 | AACCUUCC CUGAUGA X GAA AAACCAAA | UUUGGGUUU GGAAGGUU |
| 4923 | AGCACGCA CUGAUGA X GAA ACCUUCCA | UGGAAGGUU UGCGUGCU |
| 4924 | GAGCACGC CUGAUGA X GAA AACCUUCC | GGAAGGUUU GCGUGCUC |
| 4932 | ACUGUGAA CUGAUGA X GAA AGCACGCA | UGCGUGCUC UUCACAGU |
| 4934 | CGACUGUG CUGAUGA X GAA AGAGCACG | CGUGCUCUU CACAGUCG |
| 4935 | CCGACUGU CUGAUGA X GAA AAGAGCAC | GUGCUCUUC ACAGUCGG |
| 4941 | UGUAACCC CUGAUGA X GAA ACUGUGAA | UUCACAGUC GGGUUACA |
| 4946 | UCGCCUGU CUGAUGA X GAA ACCCGACU | AGUCGGGUU ACAGGCGA |
| 4947 | CUCGCCUG CUGAUGA X GAA AACCCGAC | GUCGGGUUA CAGGCGAG |
| 4957 | CCACAGGG CUGAUGA X GAA ACUCGCCU | AGGCGAGUU CCCUGUGG |
| 4958 | GCCACAGG CUGAUGA X GAA AACUCGCC | GGCGAGUUC CCUGUGGC |
| 4969 | GAGUAGGA CUGAUGA X GAA ACGCCACA | UGUGGCGUU UCCUACUC |
| 4970 | GGAGUAGG CUGAUGA X GAA AACGCCAC | GUGGCGUUU CCUACUCC |
| 4971 | AGGAGUAG CUGAUGA X GAA AAACGCCA | UGGCGUUUC CUACUCCU |

TABLE VI-continued

Mouse flk-1 VEGF Receptor-Hammerhead Ribozyme and Substrate sequence

| nt. Position | HH Ribozyme Sequence | Substrate |
|---|---|---|
| 4974 | AUUAGGAG CUGAUGA X GAA AGGAAACG | CGUUUCCUA CUCCUAAU |
| 4977 | CUCAUUAG CUGAUGA X GAA AGUAGGAA | UUCCUACUC CUAAUGAG |
| 4980 | ACUCUCAU CUGAUGA X GAA AGGAGUAG | CUACUCCUA AUGAGAGU |
| 4989 | CCGGAAGG CUGAUGA X GAA ACUCUCAU | AUGAGAGUU CCUUCCGG |
| 4990 | UCCGGAAG CUGAUGA X GAA AACUCUCA | UGAGAGUUC CUUCCGGA |
| 4993 | GAGUCCGG CUGAUGA X GAA AGGAACUC | GAGUUCCUU CCGGACUC |
| 4994 | AGAGUCCG CUGAUGA X GAA AAGGAACU | AGUUCCUUC CGGACUCU |
| 5001 | ACACGUAA CUGAUGA X GAA AGUCCGGA | UCCGGACUC UUACGUGU |
| 5003 | AGACACGU CUGAUGA X GAA AGAGUCCG | CGGACUCUU ACGUGUCU |
| 5004 | GAGACACG CUGAUGA X GAA AAGAGUCC | GGACUCUUA CGUGUCUC |
| 5010 | GGCCAGGA CUGAUGA X GAA ACACGUAA | UUACGUGUC UCCUGGCC |
| 5012 | CAGGCCAG CUGAUGA X GAA AGACACGU | ACGUGUCUC CUGGCCUG |
| 5046 | GAAGGAGC CUGAUGA X GAA AGCUGCAU | AUGCAGCUU GCUCCUUC |
| 5050 | UGAGGAAG CUGAUGA X GAA AGCAAGCU | AGCUUGCUC CUUCCUCA |
| 5053 | AGAUGAGG CUGAUGA X GAA AGGAGCAA | UUGCUCCUU CCUCAUCU |
| 5054 | GAGAUGAG CUGAUGA X GAA AAGGAGCA | UGCUCCUUC CUCAUCUC |
| 5057 | UGAGAGAU CUGAUGA X GAA AGGAAGGA | UCCUUCCUC AUCUCUCA |
| 5060 | GCCUGAGA CUGAUGA X GAA AUGAGGAA | UUCCUCAUC UCUCGGGC |
| 5062 | CAGCCUGA CUGAUGA X GAA AGAUGAGG | CCUCAUCUC UCAGGCUG |
| 5064 | CACAGCCU CUGAUGA X GAA AGAGAUGA | UCAUCUCUC AGGCUGUG |
| 5076 | UCUGAAUU CUGAUGA X GAA AGGCACAG | CUGUGCCUU AAUUCAGA |
| 5077 | UUCUGAAU CUGAUGA X GAA AAGGCACA | UGUGCCUUA AUUCAAAA |
| 5080 | GUGUUCUG CUGAUGA X GAA AUUAAGGC | GCCUUAAUU CAGAACAC |
| 5081 | GGUGUUCU CUGAUGA X GAA AAUUAAGG | CCUUAAUUC AGAACACC |
| 5105 | CCUCUGCC CUGAUGA X GAA ACGUUCCU | AGGAACGUC GGCAGAGG |
| 5116 | CCCGUCAG CUGAUGA X GAA AGCCUCUG | CAGAGGCUC CUGACGGG |
| 5135 | GUUCUCAC CUGAUGA X GAA AUUCUUCG | CGAAGAAUU GUGAGAAC |
| 5156 | GAAACCCU CUGAUGA X GAA AGUUUCUG | CAGAAACUC AGGGUUUC |
| 5162 | CCAGCAGA CUGAUGA X GAA ACCCUGAG | CUCAGGGUU UCUGCUGG |
| 5163 | CCCAGCAG CUGAUGA X GAA AACCCUGA | UCAGGGUUU CUGCUGGG |
| 5164 | ACCCAGCA CUGAUGA X GAA AAACCCUG | CAGGGUUUC UGCUGGGU |
| 5203 | AACCCUCA CUGAUGA X GAA ACCUGCCA | UGGCAGGUC UGAGGGUU |
| 5211 | UGACAGAG CUGAUGA X GAA ACCCUCAG | CUGAGGGUU CUCUGUCA |
| 5212 | UGGACAGA CUGAUGA X GAA AACCCUCA | UGAGGGUUC UCUGUCAA |
| 5214 | ACUGGACA CUGAUGA X GAA AGAACCCU | AGGGUUCUC UGUCAAGU |
| 5218 | CGCCACUU CUGAUGA X GAA ACAGAGAA | UUCUCUGUC AAGUGGCG |
| 5229 | UGAGCCUU CUGAUGA X GAA ACCGCCAC | GUGGCGGUA AAGGCUCA |

TABLE VI-continued

Mouse flk-1 VEGF Receptor-Hammerhead Ribozyme and Substrate sequence

| nt. Position | HH Ribozyme Sequence | Substrate |
|---|---|---|
| 5236 | ACCAGCCU CUGAUGA X GAA AGCCUUUA | UAAAGGCUC AGGCUGGU |
| 5247 | AGAGGAAG CUGAUGA X GAA ACACCAGC | GCUGGUGUU CUUCCUCU |
| 5248 | UAGAGGAA CUGAUGA X GAA AACACCAG | CUGGUGUUC UUCCUCUA |
| 5250 | GAUAGAGG CUGAUGA X GAA AGAACACC | GGUGUUCUU CCUCUAUC |
| 5251 | AGAUAGAG CUGAUGA X GAA AAGAACAC | GUGUUCUUC CUCUAUCU |
| 5254 | UGGAGAUA CUGAUGA X GAA AGGAAGAA | UUCUUCCUC UAUCUCCA |
| 5256 | AGUGGAGA CUGAUGA X GAA AGAGGAAG | CUUCCUCUA UCUCCACU |
| 5258 | GGAGUGGA CUGAUGA X GAA AUAGAGGA | UCCUCUAUC UCCACUCC |
| 5260 | CAGGAGUG CUGAUGA X GAA AGAUAGAG | CUCUAUCUC CACUCCUG |
| 5265 | CCUGACAG CUGAUGA X GAA AGUGGAGA | UCUCCACUC CUGUCAGG |
| 5270 | GGGGGCCU CUGAUGA X GAA ACAGGAGU | ACUCCUGUC AGGCCCCC |
| 5283 | AUACUGAG CUGAUGA X GAA ACUUGGGG | CCCCAAGUC UCACAUAU |
| 5286 | AAAAUACU CUGAUGA X GAA AGGACUUG | CAAGUCCUC AGUAUUUU |
| 5290 | AGCUAAAA CUGAUGA X GAA ACUGAGGA | UCCUCAGUA UUUUAGCU |
| 5292 | AAAGCUAA CUGAUGA X GAA AUACUGAG | CUCAGUAUU UUAGCUUU |
| 5293 | CAAAGCUA CUGAUGA X GAA AAUACUGA | UCAGUAUUU UAGCUUUG |
| 5294 | ACAAAGCU CUGAUGA X GAA AAAUACUG | CAGUAUUUU AGCUUUGU |
| 5295 | CAGAAAGC CUGAUGA X GAA AAAAUACU | AGUAUUUUA GCUUUGUG |
| 5299 | AAGCCACA CUGAUGA X GAA AGCUAAAA | UUUUAGCUU UGUGGCUU |
| 5300 | GAAGCCAC CUGAUGA X GAA AAGCUAAA | UUUAGCUUU GUGGUUUC |
| 5307 | CCAUCAGG CUGAUGA X GAA AGCCACAA | UUGUGGCUU CCUGAUGG |
| 5308 | GCCAUCAG CUGAUGA X GAA AAGCCACA | UGUGGCUUC CUGAUGGC |
| 5325 | CCAAUUAA CUGAUGA X GAA AUUUUUCU | AGAAAAAUC UUAAUUGG |
| 5327 | AACCAAUU CUGAUGA X GAA AGAUUUUU | AAAAAUCUU AAUUGGUU |
| 5328 | CAACCAAU CUGAUGA X GAA AAGAUUUU | AAAAUCUUA AUUGGUUG |
| 5331 | AACCAACC CUGAUGA X GAA AUUAAGAU | AUCUUAAUU GGUUGGUU |
| 5335 | AGCAAACC CUGAUGA X GAA ACCAAUUA | UAAUUGGUU GCUUUGCU |
| 5339 | GGAGAGCA CUGAUGA X GAA ACCAACCA | UGGUUGGUU UGCUCUCC |
| 5340 | UGGAGAGC CUGAUGA X GAA AACCAACC | GGUUGGUUU GCUCUCCA |
| 5344 | UAUCUGGA CUGAUGA X GAA AGCAAACC | GGUUUGCUC UCCAGAUA |
| 5346 | AUUAUCUG CUGAUGA X GAA AGAGCAAA | UUUGCUCUC CAGAUAAU |
| 5352 | CUAGUGAU CUGAUGA X GAA AUCUGGAG | CUCCAGAUA AUCACUAG |
| 5355 | UGGCUAGU CUGAUGA X GAA AUUAUCUG | CAGAUAAUC ACUAGCCA |
| 5359 | AAUCUGGC CUGAUGA X GAA AGUGAUUA | UAAUCACUA GCCAGAUU |
| 5367 | AAUUUCGA CUGAUGA X GAA AUCUGGCU | AGCCAGAUU UCGAAAUU |
| 5368 | UAAUUUCG CUGAUGA X GAA AAUCUGGC | GCCAGAUUU CGAAAUUA |
| 5369 | GUAAUUUC CUGAUGA X GAA AAAUCUGG | CCAGAUUUC GAAAUUAC |

TABLE VI-continued

Mouse flk-1 VEGF Receptor-Hammerhead Ribozyme and Substrate sequence

| nt. Position | HH Ribozyme Sequence | Substrate |
|---|---|---|
| 5375 | UAAAAAGU CUGAUGA X GAA AUUUCGAA | UUCGAAAUU ACUUUUUA |
| 5376 | CUAAAAAG CUGAUGA X GAA AAUUUCGA | UCGAAAUUA CUUUUUAG |
| 5379 | CGGCUAAA CUGAUGA X GAA AGUAAUUU | AAAUUACUU UUUAGCCG |
| 5380 | UCGGCUAA CUGAUGA X GAA AAGUAAUU | AAUUACUUU UUAGCCGA |
| 5381 | CUCGGCUA CUGAUGA X GAA AAAGUAAU | AUUACUUUU UAGCCGAG |
| 5382 | CCUCGGCU CUGAUGA X GAA AAAAGUAA | UUACUUUUU AGCCGAGG |
| 5383 | ACCUCGGC CUGAUGA X GAA AAAAAGUA | UACUUUUUA GCCGAGGU |
| 5392 | GUUAUCAU CUGAUGA X GAA ACCUCGGC | GCCGAGGUU AUGAUAAC |
| 5393 | UGUUAUCA CUGAUGA X GAA AACCUCGG | CCGAGGUUA UGAUAACA |
| 5398 | GUAGAUGU CUGAUGA X GAA AUCAUAAC | GUUAUGAUA ACAUCUAC |
| 5403 | AUACAGUA CUGAUGA X GAA AUGUUAUC | GAUAACAUC UACUGUAU |
| 5405 | GGAUACAG CUGAUGA X GAA AGAUGUUA | UAACAUCUA CUGUAUCC |
| 5410 | CUAAAGGA CUGAUGA X GAA ACAGUAGA | UCUACUGUA UCCUUUAG |
| 5412 | UUCUAAAG CUGAUGA X GAA AUACAGUA | UACUGUAUC CUUUAGAA |
| 5415 | AAAUUCUA CUGAUGA X GAA AGGAUACA | UGUAUCCUU UAGAAUUU |
| 5416 | AAAAUUCU CUGAUGA X GAA AAGGAUAC | GUAUCCUUU AGAAUUUU |
| 5417 | UAAAAUUC CUGAUGA X GAA AAAGGAUA | UAUCCUUUA GAAUUUUA |
| 5422 | UAGGUUAA CUGAUGA X GAA AUUCUAAA | UUUAAAAUU UUAACCUA |
| 5423 | AUAGGUUA CUGAUGA X GAA AAUUCUAA | UUAGAAUUU UAACCWU |
| 5424 | UAUAGGUU CUGAUGA X GAA AAAUUCUA | UAGAAUUUU AACCUAUA |
| 5425 | UUAUAGGU CUGAUGA X GAA AAAAUUCU | AGAAUUUUA ACCUAUAA |
| 5430 | UAGUUUGA CUGAUGA X GAA AGGUUAAA | UUUAACCUA UAAAACUA |
| 5432 | CAUAGUUU CUGAUGA X GAA AUAGGUGA | UAACCUAUA AAACUAUG |
| 5438 | AGUAGACA CUGAUGA X GAA AGUUUUAU | AUAAAACUA UGUCUACU |
| 5442 | AACCAGUA CUGAUGA X GAA ACAUAGUU | AACUAUGUC UACUGGUU |
| 5444 | GAAACCAG CUGAUGA X GAA AGACAUAG | CUAUGUCUA CUGGUUUC |
| 5450 | CAGGCAGA CUGAUGA X GAA ACCAGUAG | CUACUGGUU UCUGCCUG |
| 5451 | ACAGGCAG CUGAUGA X GAA AACCAGUA | UACUGGUUU CUGCCUGU |
| 5452 | CACAGGCA CUGAUGA X GAA AAACCAGU | ACUGGUUUC UGCCUGUG |

Where "X" represents stem II region of a HH ribozyme (Hertel et al., 1992 Nucleic Acids Res. 20 3252). The length of stem II may be ≧2 base-pairs.

TABLE VII

Mouse flk-1 VEGF receptor-Hairpin Ribozyme and Substrate Sequences

| nt. Position | HP Ribozyme Sequences | Substrate |
|---|---|---|
| 74 | GGGACACA AGAA GGGCCC ACCAGAGAAACACACGUUGUGGUACAUUACCUGGUA | GGGCCCA GAC UGUGUCCC |
| 88 | GUUAUCCC AGAA GCGGGA ACCAGAGAAACACACGUUGUGGUACAUUACCUGGUA | UCCCGCA GCC GGGAUAAC |

TABLE VII-continued

Mouse flk-1 VEGF receptor-Hairpin Ribozyme and Substrate Sequences

| nt. Position | HP Ribozyme Sequences | Substrate |
|---|---|---|
| 105 | GGAAUCGG AGAA GCCAGG ACCAGAGAAACACACGUUGUGGUACAUUACCUGGUA | CCUGGCU GAC CCGAUUCC |
| 110 | UCCGCGGA AGAA GGUCAG ACCAGAGAAACACACGUUGUGGUACAUUACCUGGUA | CUGACCC GAU UCCGCGGA |
| 125 | CGGCUGUC AGAA GUGUCC ACCAGAGAAACACACGUUGUGGUACAUUACCUGGUA | GGACACC GCU GACAGCCG |
| 132 | CCAGCCGC AGAA GUCAGC ACCAGAGAAACACACGUUGUGGUACAUUACCUGGUA | GCUGACA GCC GCGGCUGG |
| 138 | CUGGCUCC AGAA GCGGCU ACCAGAGAAACACACGUUGUGGUACAUUACCUGGUA | AGCCGCG GCU GGAGCCAG |
| 175 | CAGCGCAA AGAA GGGGAG ACCAGAGAAACACACGUUGUGGUACAUUACCUGGUA | CUCCCCG GUC UUGCGCUG |
| 199 | GUCACAGA AGAA GUAUGG ACCAGAGAAACACACGUUGUGGUACAUUACCUGGUA | CCAUACC GCC UCUGUGAC |
| 309 | CACAGAGC AGAA GCUAGC ACCAGAGAAACACACGUUGUGGUACAUUACCUGGUA | GCUAGCU GUC GCUCUGUG |
| 342 | CCCACAGA AGAA GCUCGG ACCAGAGAAACACACGUUGUGGUACAUUACCUGGUA | CCGAGCC GCC UCUGUGGG |
| 434 | UGCAAGUA AGAA GAAGGG ACCAGAGAAACACACGUUGUGGUACAUUACCUGGUA | CCCUUCA GAU UACUUGCA |
| 630 | UAGACAUA AGAA GUGGAG ACCAGAGAAACACACGUUGUGGUACAUUACCUGGUA | CUCCACU GUU UAUGUCUA |
| 655 | GAAUGGUG AGAA GUAAUC ACCAGAGAAACACACGUUGUGGUACAUUACCUGGUA | GAUUACA GAU CACCAUUC |
| 739 | CGACCCUC AGAA GGGGAU ACCAGAGAAACACACGUUGUGGUACAUUACCUGGUA | AUCCCCU GCC GAGGGUCG |
| 807 | CUGUUUCC AGAA GGAACA ACCAGAGAAACACACGUUGUGGUACAUUACCUGGUA | UGUUCCG GAU GGAAACAG |
| 920 | ACAUGAUA AGAA GAUAGG ACCAGAGAAACACACGUUGUGGUACAUUACCUGGUA | CCUAUCA GUC UAUCAUGU |
| 1002 | UUUUCUCC AGAA GAUAGC ACCAGAGAAACACACGUUGUGGUACAUUACCUGGUA | GCUAUCU GCC GGAGAAAA |
| 1229 | UCUUGAUC AGAA GUCCAC ACCAGAGAAACACACGUUGUGGUACAUUACCUGGUA | GUGGACG GAU GAUCAAGA |
| 1365 | AUAUCAGG AGAA GGGUAA ACCAGAGAAACACACGUUGUGGUACAUUACCUGGUA | UUACCCA GCU CCUGAUAU |
| 1556 | UCUCACCG AGAA GGGGUG ACCAGAGAAACACACGUUGUGGUACAUUACCUGGUA | CACCCCA GAU CGGUGAGA |
| 1629 | UUGGCGUA AGAA GUGCAU ACCAGAGAAACACACGUUGUGGUACAUUACCUGGUA | AUGCACA GUC UACGCCAA |
| 1687 | UCUGUAGG AGAA GGCUUC ACCAGAGAAACACACGUUGUGGUACAUUACCUGGUA | GAAGCCU GCU CCUACAGA |
| 1696 | UUGGCCGG AGAA GUAGGA ACCAGAGAAACACACGUUGUGGUACAUUACCUGGUA | UCCUACA GAC CCGGCCAA |
| 1796 | UUCCUUCA AGAA GGGCAU ACCAGAGAAACACACGUUGUGGUACAUUACCUGGUA | AUGCCCU GAU UGAAGGAA |
| 1950 | GGCUGGGC AGAA GGUUGC ACCAGAGAAACACACGUUGUGGUACAUUACCUGGUA | GCAACCU GCU GCCCAGCC |
| 1953 | GUUGGCUG AGAA GCAGGU ACCAGAGAAACACACGUUGUGGUACAUUACCUGGUA | ACCUGCU GCC CAGCCAAC |
| 1985 | CAGUGCAC AGAA GGGACA ACCAGAGAAACACACGUUGUGGUACAUUACCUGGUA | UGUCCCU GUU GUGCACUG |
| 2055 | CCCAUGUG AGAA GAUGUU ACCAGAGAAACACACGUUGUGGUACAUUACCUGGUA | AACAUCG GUC CACAUGGG |
| 2082 | UUCUUGCA AGAA GGUGUG ACCAGAGAAACACACGUUGUGGUACAUUACCUGGUA | CACACCA GUU UGCAAGAA |
| 2208 | UUAUCUUG AGAA GAGCAA ACCAGAGAAACACACGUUGUGGUACAUUACCUGGUA | UUGCUCU GCU CAAGAUAA |
| 2252 | GGAUGAUG AGAA GUUUGA ACCAGAGAAACACACGUUGUGGUACAUUACCUGGUA | UCAAACA GCU CAUCAUCC |
| 2444 | UGCGGAUA AGAA GGUUCC ACCAGAGAAACACACGUUGUGGUACAUUACCUGGUA | GGAACCU GAC UAUCCGCA |
| 2639 | GCUUAACG AGAA GUAGGA ACCAGAGAAACACACGUUGUGGUACAUUACCUGGUA | UCCUACG GAC CGUUAAGC |
| 2703 | GGCAAUUC AGAA GGAUCC ACCAGAGAAACACACGUUGUGGUACAUUACCUGGUA | GGAUCCA GAU GAAUUGCC |
| 2777 | CUAGUUUC AGAA GGUCCC ACCAGAGAAACACACGUUGUGGUACAUUACCUGGUA | GGGACCG GCU GAAACUAG |
| 2832 | CCAAAAGC AGAA GCCUCA ACCAGAGAAACACACGUUGUGGUACAUUACCUGGUA | UGAGGCA GAC GCUUUUGG |
| 3199 | AAAGCCUG AGAA GGCAGA ACCAGAGAAACACACGUUGUGGUACAUUACCUGGUA | UCUGCCA GCU CAGCCUUU |
| 3278 | GCUCCAAG AGAA GGAAGU ACCAGAGAAACACACGUUGUGGUACAUUACCUGGUA | ACUUCCU GAC CUUGGAGC |

TABLE VII-continued

Mouse flk-1 VEGF receptor-Hairpin Ribozyme and Substrate Sequences

| nt. Position | HP Ribozyme Sequences | Substrate |
|---|---|---|
| 3304 | CACUUGGA AGAA GUAACA ACCAGAGAAACACACGUUGUGGUACAUUACCUGGUA | UGUUACA GCU UCCAAGUG |
| 3421 | CCGGGCCA AGAA GAAGUC ACCAGAGAAACACACGUUGUGGUACAUUACCUGGUA | GACUUCG GCU UGGCCCGG |
| 3450 | CUGACAUA AGAA GGGUCU ACCAGAGAAACACACGUUGUGGUACAUUACCUGGUA | AGACCCG GAU UAUGUCAG |
| 3475 | CAAAGGGA AGAA GGCAUC ACCAGAGAAACACACGUUGUGGUACAUUACCUGGUA | GAUGCCC GAC UCCCUUUG |
| 3663 | GUAGUGUA AGAA GGAGCC ACCAGAGAAACACACGUUGUGGUACAUUACCUGGUA | GGCUCCU GAC UACACUAC |
| 3689 | CCAGCAUG AGAA GGUACA ACCAGAGAAACACACGUUGUGGUACAUUACCUGGUA | UGUACCA GAC CAUGCUGG |
| 3703 | CUCAUGCC AGAA GUCCAG ACCAGAGAAACACACGUUGUGGUACAUUACCUGGUA | CUGGACU GCU GGCAUGAG |
| 3860 | GUGAGGUA AGAA GGGAGA ACCAGAGAAACACACGUUGUGGUACAUUACCUGGUA | UCUCCCU GCC UACCUCAC |
| 3873 | AUACAGGA AGAA GGUGAG ACCAGAGAAACACACGUUGUGGUACAUUACCUGGUA | CUCACCU GUU UCCUGUAU |
| 4038 | UGGCUGUC AGAA GGGAUC ACCAGAGAAACACACGUUGUGGUACAUUACCUGGUA | GAUCCCA GAU GACAGCCA |
| 4181 | AGCCACUG AGAA GGUUGG ACCAGAGAAACACACGUUGUGGUACAUUACCUGGUA | CCAACCA GAC CAGUGGCU |
| 4196 | GAUACCCA AGAA GGUAGC ACCAGAGAAACACACGUUGUGGUACAUUACCUGGUA | GCUACCA GUC UGGGUAUC |
| 4212 | UCUGUGUC AGAA GAGUGA ACCAGAGAAACACACGUUGUGGUACAUUACCUGGUA | UCACUCA GAU GACACAGA |
| 4278 | UCAGCGUG AGAA GCAGCA ACCAGAGAAACACACGUUGUGGUACAUUACCUGGUA | UGCUGCA GUU CACGCUGA |
| 4287 | GUCCCUGA AGAA GCGUGA ACCAGAGAAACACACGUUGUGGUACAUUACCUGGUA | UCACGCU GAC UCAGGGAC |
| 4307 | AGGAGGUG AGAA GCAGUG ACCAGAGAAACACACGUUGUGGUACAUUACCUGGUA | CACUGCA GCU CACCUCCU |
| 4318 | UCCAUUUA AGAA GGAGGU ACCAGAGAAACACACGUUGUGGUACAUUACCUGGUA | ACCUCCU GUU UAAAUGGA |
| 4338 | GGAGCCGG AGAA GGACCA ACCAGAGAAACACACGUUGUGGUACAUUACCUGGUA | UGGUCCU GUC CCGGCUCC |
| 4344 | GGGGGCGG AGAA GGGACA ACCAGAGAAACACACGUUGUGGUACAUUACCUGGUA | UGUCCCG GCU CCGCCCCC |
| 4349 | GAGUUGGG AGAA GAGCCG ACCAGAGAAACACACGUUGUGGUACAUUACCUGGUA | CGGGUCC GCC CCCAACUC |
| 4383 | AAAAUCUA AGAA GCACCU ACCAGAGAAACACACGUUGUGGUACAUUACCUGGUA | AGGUGCU GCU UAGAUUUU |
| 4462 | UCCUUGCA AGAA GAGGUC ACCAGAGAAACACACGUUGUGGUACAUUACCUGGUA | GACCUCA GAC UGCAAGGA |
| 4574 | GAGACCAC AGAA GGGCAC ACCAGAGAAACACACGUUGUGGUACAUUACCUGGUA | GUGCCCU GCU GUGGUCUC |
| 4626 | UCUUGGAG AGAA GAGUCC ACCAGAGAAACACACGUUGUGGUACAUUACCUGGUA | GGACUCU GUC CUCCAAGA |
| 4723 | CCAAGGUA AGAA GACUCG ACCAGAGAAACACACGUUGUGGUACAUUACCUGGUA | CGAGUCU GUC UACCUUGG |
| 4823 | CAGGCUCC AGAA GCUCUC ACCAGAGAAACACACGUUGUGGUACAUUACCUGGUA | GAGAGCG GUU GGAGCCUG |
| 4836 | CACAAUGC AGAA GCAGGC ACCAGAGAAACACACGUUGUGGUACAUUACCUGGUA | GCCUGCA GAU GCAUUGUG |
| 4896 | ACCCUGCC AGAA GCCUUU ACCAGAGAAACACACGUUGUGGUACAUUACCUGGUA | AAAGGCG GCC GGCAGGGU |
| 4938 | UGUAACCC AGAA GUGAAG ACCAGAGAAACACACGUUGUGGUACAUUACCUGGUA | CUUCACA GUC GGGUUACA |
| 4996 | ACGUAAGA AGAA GGAAGG ACCAGAGAAACACACGUUGUGGUACAUUACCUGGUA | CCUUCCG GAC UCUUACGU |
| 5042 | AAGGAGCA AGAA GCAUCA ACCAGAGAAACACACGUUGUGGUACAUUACCUGGUA | UGAUGCA GCU UGCUCCUU |
| 5118 | UCGGCCCC AGAA GGAGCC ACCAGAGAAACACACGUUGUGGUACAUUACCUGGUA | GGCUCCU GAC GGGGCCGA |
| 5165 | CUCCACCC AGAA GAAACC ACCAGAGAAACACACGUUGUGGUACAUUACCUGGUA | G(GGJCU GCU CGGUGGAG |
| 5310 | UUUCUGCC AGAA GGAAGC ACCAGAGAAACACACGUUGUGGUACAUUACCUGGUA | GCUUCCU GAU GGCAGAAA |
| 5363 | AUUUCGAA AGAA GGCUAG ACCAGAGAAACACACGUUGUGGUACAUUACCUGGUA | CUAGCCA GAU UUCGAAAU |
| 5453 | AGCACACA AGAA GAAACC ACCAGAGAAACACACGUUGUGGUACAUUACCUGGUA | GGUUUCU GCC UGUGUGGU |

Table VIII

Mouse flt-1 VEGF Receptor-Hammerhead Ribozyme and Substrate Sequence

| nt. Position | HH Ribozyme | Substrate |
|---|---|---|
| 17 | GUGAGCAA CUGAUGU X GAA ACGCGGCC | GGCCGCGUC UUGCUCAC |
| 19 | UGGUGAGC CUGAUGU X GAA AGACGCGG | CCGCGUCUU GCUCACCA |
| 23 | ACCAUGGU CUGAUGU X GAA AGCAAGAC | GUCUUGCUC ACCAUGGU |
| 32 | CAGCAGCU CUGAUGU X GAA ACCAUGGU | ACCAUGGUC AGCUGCUG |
| 53 | UAAGGCAA CUGAUGU X GAA ACCGCGGU | ACCGCGGUC UUGCCUUA |
| 55 | CGUAAGGC CUGAUGU X GAA AGACCGCG | CGCGGUCUU GCCUUACG |
| 60 | CAGCGCGU CUGAUGU X GAA AGGCAAGA | UCUUGCCUU ACGCGCUG |
| 61 | GCAGCGCG CUGAUGU X GAA AAGGCAAG | CUUGCCUUA CGCGCUGC |
| 71 | AGACACCC CUGAUGU X GAA AGCAGCGC | GCGCUGCUC GGGUGUCU |
| 78 | GAGAAGCA CUGAUGU X GAA ACACCCGA | UCGGGUGUC UGCUUCUC |
| 83 | CCUGUGAG CUGAUGU X GAA AGCAGACA | UGUCUGCUU CUCACAGG |
| 84 | UCCUGUGA CUGAUGU X GAA AAGCAGAC | GUCUGCUUC UCACAGGA |
| 86 | UAUCCUGU CUGAUGU X GAA AGAAGCAG | CUGCUUCUC ACAGGAUA |
| 94 | CUGAGCCA CUGAUGU X GAA AUCCUGUG | CACAGGAUA UGGCUCAG |
| 100 | UCGACCCU CUGAUGU X GAA AGCCAUAU | AUAUGGCUC AGGGUCGA |
| 106 | UUAACUUC CUGAUGU X GAA ACCCUGAG | CUCAGGGUC GAAGUUAA |
| 112 | GCACUUUU CUGAUGU X GAA ACUUCGAC | GUCGAAGUU AAAAGUGC |
| 113 | GGCACUUU CUGAUGU X GAA AACUUCGA | UCGAAGUUA AAAGUGCC |
| 132 | GCCUUUUA CUGAUGU X GAA ACUCAGUU | AACUGAGUU UAAAAGGC |
| 133 | UGCCUUUU CUGAUGU X GAA AACUCAGU | ACUGAGUUU AAAAGGCA |
| 134 | GUGCCUUU CUGAUGU X GAA AAACUCAG | CUGAGUUUA AAAGGCAC |
| 152 | GCUUGCAU CUGAUGU X GAA ACAUGCUG | CAGCAUGUC AUGCAAGC |
| 171 | GAGAAAGA CUGAUGU X GAA AGUCUGGC | GCCAGACUC UCUUUCUC |
| 173 | UUGAGAAA CUGAUGU X GAA AGAGUCUG | CAGACUCUC UUUCUCAA |
| 175 | ACUUGAGA CUGAUGU X GAA AGAGAGUC | GACUCUCUU UCUCAAGU |
| 176 | CACUUGAG CUGAUGU X GAA AAGAGAGU | ACUCUCUUU CUCAAGUG |
| 177 | GCACUUGA CUGAUGU X GAA AAAGAGAG | CUCUCUUUC UCAAGUGC |
| 179 | CUGCACUU CUGAUGU X GAA AGAAAGAG | CUCUUUCUC AAGUGCAG |
| 205 | GAGACCAU CUGAUGU X GAA AGUGGGCU | AGCCCACUC AUGGUCUC |
| 211 | UGGGCAGA CUGAUGU X GAA ACCAUGAG | CUCAUGGUC UCUGCCCA |
| 213 | CGUGGGCA CUGAUGU X GAA AGACCAUG | CAUGGUCUC UGCCCACG |
| 254 | GGGGGAGU CUGAUGU X GAA AUGCUCAG | CUGAGCAUC ACUCCCCC |
| 258 | CGAUGGGG CUGAUGU X GAA AGUGAUGC | GCAUCACUC CCCAUCG |
| 265 | CACAGGCC CUGAUGU X GAA AUGGGGGA | UCCCCCAUC GGCCUGUG |
| 282 | UUGCCUGU CUGAUGU X GAA AUCCCUCC | GGAGGGAUA ACAGGCAA |
| 292 | UGCUGCAG CUGAUGU X GAA AUUGCCUG | CAGGCAAUU CUGCAGCA |
| 293 | GUGCUGCA CUGAUGU X GAA AAUUGCCU | ACCCAAUUC UGCAGCAC |

Table VIII-continued

Mouse flt-1 VEGF Receptor-Hammerhead Ribozyme and Substrate Sequence

| nt. Position | HH Ribozyme | Substrate |
|---|---|---|
| 304 | CCAAGGUC CUGAUGU X GAA AGGUGCUG | CAGCACCUU GACCUUGG |
| 310 | CCGUGUCC CUGAUGU X GAA AGGUCAAG | CUUGACCUU GGACACGG |
| 341 | CAGGUGUA CUGAUGU X GAA AGGCCCGU | ACGGGCCUC UACACCUG |
| 343 | UACAGGUG CUGAUGU X GAA AGAGGCCC | GGGCCUCUA CACCUGUA |
| 351 | GAGGUAUC CUGAUGU X GAA ACAGGUGU | ACACCUGUA GAUACCUC |
| 355 | UAGGGAGG CUGAUGU X GAA AUCUACAG | CUGUAGAUC CCUCCCUA |
| 359 | GAUGUAGG CUGAUGU X GAA AGGUAUCU | AGAUACCUC CUACAUC |
| 363 | AGUAGAUG CUGAUGU X GAA AGGGAGGU | ACCUCCCUA CAUCUACU |
| 367 | UCGAAGUA CUGAUGU X GAA AUGUAGGG | CCCUACAUC UACUUCGA |
| 369 | CUUCGAAG CUGAUGU X GAA AGAUGUAG | CUACAUCUA CUUCGAAG |
| 372 | UUUCUUCG CUGAUGU X GAA AGUAGAUG | CAUCUACUU CGAAGAAA |
| 373 | UUUUCUUC CUGAUGU X GAA AAGUAGAU | AUCUACUUC GAAGAAAA |
| 394 | AGAUUGAA CUGAUGU X GAA AUUCCGCU | AGCGGAAUC UUCAAUCU |
| 396 | GUAGAUUG CUGAUGU X GAA AGAUUCCG | CGGAAUCUU CAAUCUAC |
| 397 | UGUAGAUU CUGAUGU X GAA AAGAUUCC | GGAAUCUUC AAUCUACA |
| 401 | AAUAUGUA CUGAUGU X GAA AUUGAAGA | UCUUCAAUC UACAUAUU |
| 403 | CAAAUAUG CUGAUGU X GAA AGAUUGAA | UUCAAUCUA CAUAUUUG |
| 407 | CUAACAAA CUGAUGU X GAA AUGUAGAU | AUCUACAUA UUUGUUAG |
| 409 | CACUAACA CUGAUGU X GAA AUAUGUAG | CUACAUAUU UGUUAGUG |
| 410 | UCACUAAC CUGAUGU X GAA AAUAUGUA | UACAUAUUU GUUAGUGA |
| 413 | GCAUCACU CUGAUGU X GAA ACAAAUAU | AUAUUUGUU AGUGAUGC |
| 414 | UGCAUCAC CUGAUGU X GAA AACAAAUA | UAUUUGUUA GUGAUGCA |
| 429 | UAUGAAAG CUGAUGU X GAA ACUCCCUG | CAGGGAGUC CUUUCAUA |
| 432 | CUCUAUGA CUGAUGU X GAA AGGACUCC | GGAGUCCUU UCAUAGAG |
| 433 | UCUCUAUG CUGAUGU X GAA AAGGACUC | GAGUCCUUU CAUAGAGA |
| 434 | AUCUCUAU CUGAUGU X GAA AAAGGACU | AGUCCUUUC AUAGAGAU |
| 437 | UGCAUCUC CUGAUGU X GAA AUGAAAGG | CCUUUCAUA GAGAUGCA |
| 455 | AGUUUGGG CUGAUGU X GAA AUGUCAGU | ACUGACAUA CCCAAACU |
| 464 | AUGUGCAC CUGAUGU X GAA AGUUUGGG | CCCAAACUU GUGCACAU |
| 491 | GGGAUGAU CUGAUGU X GAA AGCUGUCU | AGACAGCUC AUCAUCCC |
| 494 | CAGGGAU CUGAUGU X GAA AUGAGCUC | CAGCUCAUC AUCCCUG |
| 497 | CGGCAGGG CUGAUGU X GAA AUGAUGUG | CUCAUCAUC CCUGCCG |
| 514 | CGUGGGU CUGAUGU X GAA ACGUCACC | GGUGACGUC ACCCAACG |
| 524 | GUGACUGU CUGAUGU X GAA ACGUUGGG | CCCAACGUC ACAGUCAC |
| 530 | UUUAGGGU CUGAUGU X GAA ACUGUGAC | GUCACAGUC ACCCUAAA |
| 536 | AACUUUUU CUGAUGU X GAA AGGGUGAC | GUCACCCUA AAAAGUU |

Table VIII-continued

Mouse flt-1 VEGF Receptor-Hammerhead Ribozyme and Substrate Sequence

| nt. Position | HH Ribozyme | Substrate |
|---|---|---|
| 544 | CAAAUGGA CUGAUGU X GAA ACUUUUU | AAAAAGUU UCCAUUUG |
| 545 | UCAAAUGG CUGAUGU X GAA AACUUUU | AAAAGUUU CCAUUUGA |
| 546 | AUCAAAUG CUGAUGU X GAA AAACUUU | AAAGUUUC CAUUUGAU |
| 550 | GAGUAUCA CUGAUGU X GAA AUGGAAAC | GUUUCCAUU UGAUACUC |
| 551 | AGAGUAUC CUGAUGU X GAA AAUGGAAA | UUUCCAUUU GAUACUCU |
| 555 | GGUAAGAG CUGAUGU X GAA AUCAAAUG | CAUUUGAUA CUCUUACC |
| 558 | AGGGGUAA CUGAUGU X GAA AGUAUCAA | UUGAUACUC UUACCCCU |
| 560 | UCAGGGGU CUGAUGU X GAA AGAGUAUC | GAUACUCUU ACCCCUGA |
| 561 | AUCAGGGG CUGAUGU X GAA AAGAGUAU | AUACUCUUA CCCCUGAU |
| 581 | UCCCAUGU CUGAUGU X GAA AUUCUUUG | CAAAGAAUA ACAUGGGA |
| 594 | GCCUCUCC CUGAUGU X GAA ACUGUCCC | GGGAGAGUA GGAGAGGC |
| 604 | CUAUUAUA CUGAUGU X GAA AGCCUCUC | GAGAGGCUU UAUAAUAG |
| 605 | GCUAUUAU CUGAUGU X GAA AAGCCUCU | AGAGGCUUU AUAAUAGC |
| 606 | UGCUAUUA CUGAUGU X GAA AAAGCCUC | GAGGCUUUA UAAUAGCA |
| 608 | UUUGCUAU CUGAUGU X GAA AUAAAGCC | GGCUUUAUA AUAGCAAA |
| 611 | GCAUUUGC CUGAUGU X GAA AUUAUAAA | UUUAUAAUA GCAAAUGC |
| 625 | UCUCUUUG CUGAUGU X GAA ACGUUGCA | UGCAACGUA CAAAGAGA |
| 635 | AGCAGUCC CUGAUGU X GAA AUCUCUUU | AAAGAGAUA GGACUGCU |
| 662 | UGCCCGUU CUGAUGU X GAA ACGGUGGC | GCCACCGUC AACGGGCA |
| 676 | UUGUCUGG CUGAUGU X GAA ACAGGUGC | GCACCUGUA CCAGACAA |
| 688 | GGGUCAGA CUGAUGU X GAA AGUUUGUC | CAGAAACUA UCUGACCC |
| 690 | AUGGGUCA CUGAUGU X GAA AUAGUUUG | CAAACUAUC UGACCCAU |
| 699 | GGUCUGCC CUGAUGU X GAA AUGGGUCA | UGACCCAUC GGCAGACC |
| 711 | UAGGAUUG CUGAUGU X GAA AUUGGUCU | AGACCAAUA CAAUCCUA |
| 716 | ACAUCUAG CUGAUGU X GAA AUUGUAUU | AAUACAAUC CUAGAUGU |
| 719 | UGGACAUC CUGAUGU X GAA AGGAUUGU | ACAAUCCUA GAUGUCCA |
| 725 | CGUAUUUG CUGAUGU X GAA ACAUCUAG | CUAGAUGUC CAAAUAGC |
| 731 | GGCGGGCG CUGAUGU X GAA AUUUGGAC | GUCCAAAUA CGCCCGCC |
| 758 | UGCCCGUG CUGAUGU X GAA AGCAGUCU | AGACUGCUC CACGGGCA |
| 771 | GAGGACAA CUGAUGU X GAA AGUCUGCC | GGCAGACUC UUGUCCUC |
| 773 | UUGAGGAC CUGAUGU X GAA AGAGUCUG | CAGACUCUU GUCCUCAA |
| 776 | CAGUUGAG CUGAUGU X GAA ACAAGAGU | ACUCUUGUC CUCAACUG |
| 779 | GUGCAGUU CUGAUGU X GAA AGGACAAG | CUUGUCCUC AACUGCAC |
| 803 | CUCGUAUU CUGAUGU X GAA AGCUCCGU | ACGGAGCUC AAUACGAG |
| 807 | CACCCUCG CUGAUGU X GAA AUUGAGCU | AGCUCAAUA CGAGGGUG |
| 831 | ACCAGGGU CUGAUGU X GAA AUUCCAGC | GCUGGAAUU ACCCUGGU |
| 832 | UACCAGGG CUGAUGU X GAA AAUUCCAG | CUGGAAUUA CCCUGGUA |

Table VIII-continued

Mouse flt-1 VEGF Receptor-Hammerhead Ribozyme and Substrate Sequence

| nt. Position | HH Ribozyme | Substrate |
|---|---|---|
| 840 | AGUUGCUU CUGAUGU X GAA ACCAGGGU | ACCCUGGUA AAGCAACU |
| 849 | UGCUCUCU CUGAUGU X GAA AGUUGCUU | AAGCAACUA AGAGAGCA |
| 859 | GCCUUAUA CUGAUGU X GAA AUGCUCUC | GAGAGCAUC UAUAAGGC |
| 861 | CUGCCUUA CUGAUGU X GAA AGAUGCUC | GAGCAUCUA UAAGGCAG |
| 863 | CGCUGCCU CUGAUGU X GAA AUAGAUGC | GCAUCUAUA AGGCAGCG |
| 875 | CUCCGGUC CUGAUGU X GAA AUCCGCUG | CAGCGGAUU GACCGGAG |
| 888 | GUUGUGGG CUGAUGU X GAA AUGGCUCC | GGAGCCAUU CCCACAAC |
| 889 | UGUUGUGG CUGAUGU X GAA AAUGGCUC | GAGCCAUUC CCACAACA |
| 904 | CACUGUGG CUGAUGU X GAA ACACAUUG | CAAUGUGUU CCACAGUG |
| 905 | ACACUGUG CUGAUGU X GAA AACACAUU | AAUGUGUUC CACAGUGU |
| 914 | AUCUUAAG CUGAUGU X GAA ACACUGUG | CACAGUGUU CUUAAGAU |
| 915 | GAUCUUAA CUGAUGU X GAA AACACUGU | ACAGUGUUC UUAAGAUC |
| 917 | UUGAUCUU CUGAUGU X GAA AGAACACU | AGUGUUCUU AAGAUCAA |
| 918 | GUUGAUCU CUGAUGU X GAA AAGAACAC | GUGUUCUUA AGAUCAAC |
| 923 | ACAUUGUU CUGAUGU X GAA AUCUUAAG | CUUAAGAUC AACAAUGU |
| 953 | CAGGUGUA CUGAUGU X GAA AGCCCCUU | AAGGGGCUC UACACCUG |
| 955 | GACAGGUG CUGAUGU X GAA AGAGCCCC | GGGGCUCUA CACCUGUC |
| 963 | CUUCACGC CUGAUGU X GAA ACAGGUGU | ACACCUGUC GCGUGAAG |
| 979 | GGAACGAG CUGAUGU X GAA ACCCACUC | GAGUGGGUC CUCGUUCC |
| 982 | ACUGGAAC CUGAUGU X GAA AGGACCCA | UGGGUCCUC GUUCCAGU |
| 985 | AAGACUGG CUGAUGU X GAA ACGAGGAC | GUCCUCGUU CCAGUCUU |
| 986 | AAAGACUG CUGAUGU X GAA AACGAGGA | UCCUCGUUC CAGUCUUU |
| 991 | UGUUGAAA CUGAUGU X GAA ACUGGAAC | GUUCCAGUC UUUCAACA |
| 993 | GGUGUUGA CUGAUGU X GAA AGACUGGA | UCCAGUCUU UCAACACC |
| 994 | AGGUGUUG CUGAUGU X GAA AAGACUGG | CCAGUCUUU CAACACCU |
| 995 | GAGGUGUU CUGAUGU X GAA AAAGACUG | CAGUCUUUC AACACCUC |
| 1003 | CAUGCACG CUGAUGU X GAA AGGUGUUG | CAACACCUC CGUGCAUG |
| 1015 | CUUUUUCA CUGAUGU X GAA ACACAUGC | GCAUGUGUA UGAAAAAG |
| 1027 | CACUGAUG CUGAUGU X GAA AUCCUUUU | AAAAGGAUU CAUCAGUG |
| 1028 | ACACUGAU CUGAUGU X GAA AAUCCUUU | AAAGGAUUC AUCAGUGU |
| 1031 | UUCACACU CUGAUGU X GAA AUGAAUCC | GGAUUCAUC AGUGUGAA |
| 1044 | CUGCUUCC CUGAUGU X GAA AUGUUUCA | UGAAACAUC GGAAGCAG |
| 1084 | GCCGAUAG CUGAUGU X GAA ACCGUCUU | AAGACGGUC UAUCGGC |
| 1087 | ACAGCCGA CUGAUGU X GAA AGGACCGU | ACGGUCCUA UCGGCUGU |
| 1089 | GGACAGCC CUGAUGU X GAA AUAGGACC | GGUCCUAUC GGCUGUCC |
| 1096 | CUUUCAUG CUGAUGU X GAA ACAGCCGA | UCGGCUGUC CAUGAAAG |

Table VIII-continued

Mouse flt-1 VEGF Receptor-Hammerhead Ribozyme and Substrate Sequence

| nt. Position | HH Ribozyme | Substrate |
|---|---|---|
| 1114 | GGGAGGGG CUGAUGU X GAA AGGCCUUC | GAAGGCCUU CCCCUCCC |
| 1115 | GGGGAGGG CUGAUGU X GAA AAGGCCUU | AAGGCCUUC CCCUCCCC |
| 1120 | UUUCUGGG CUGAUGU X GAA AGGGGAAG | CUUCCCCUC CCCAGAAA |
| 1130 | AACCAUAC CUGAUGU X GAA AUUUCUGG | CCAGAAAUC GUAUGGUU |
| 1133 | UUUAACCA CUGAUGU X GAA ACGAUUUC | GAAAUCGUA UGGUUAAA |
| 1138 | CAUCUUUU CUGAUGU X GAA ACCAUACG | CGUAUGGUU AAAAGAUG |
| 1139 | CCAUCUUU CUGAUGU X GAA AACCAUAC | GUAUGGUUA AAAGAUGG |
| 1150 | UUGCAGGC CUGAUGU X GAA AGCCAUCU | AGAUGGCUC GCCUGCAA |
| 1162 | CAGACUUC CUGAUGU X GAA AUGUUGCA | UGCAACAUU GAAGUCUG |
| 1168 | AGCGAGCA CUGAUGU X GAA ACUUCAAU | AUUGAAGUC UGCUCGCU |
| 1173 | CAAAUAGC CUGAUGU X GAA AGCAGACU | AGUCUGCUC GCUAUUUG |
| 1177 | GUACCAAA CUGAUGU X GAA AGCGAGCA | UGCUCGCUA UUUGGUAC |
| 1179 | AUGUACCA CUGAUGU X GAA AUAGCGAG | CUCGCUAUU UGGUACAU |
| 1180 | CAUGUACC CUGAUGU X GAA AAUAGCGA | UCGCUAUUU GGUACAUG |
| 1184 | UAGCCAUG CUGAUGU X GAA ACCAAAUC | UAUUUGGUA CAUGGCUA |
| 1192 | UUAAUGAG CUGAUGU X GAA AGCCAUGU | ACAUGGCUA CUCAUUAA |
| 1195 | UAAUUAAU CUGAUGU X GAA AGUAGCCA | UGGCUACUC AUUAAUUA |
| 1198 | UGAUAAUU CUGAUGU X GAA AUGAGUAG | CUACUCAUU AAUUAUCA |
| 1199 | UUGAUAAU CUGAUGU X GAA AAUGAGUA | UACUCAUUA AUUAUCAA |
| 1202 | UCUUUGAU CUGAUGU X GAA AUUAAUGA | UCAUUAAUU AUCAAAGA |
| 1203 | AUCUUUGA CUGAUGU X GAA AAUUAAUG | CAUUAAUUA UCAAAGAU |
| 1205 | ACAUCUUU CUGAUGU X GAA AUAAUUAA | UUAAUUAUC AAAGAUGU |
| 1237 | AGAUCGUA CUGAUGU X GAA AGUCCCCU | AGGGGACUA UACGAUCU |
| 1239 | CAAGAUCG CUGAUGU X GAA AUAGUCCC | GGGACUAUA CGAUCUUG |
| 1244 | CCCAGCAA CUGAUGU X GAA AUCGUAUA | UAUACGAUC UUGCUGGG |
| 1246 | UGCCCAGC CUGAUGU X GAA AGAUCGUA | UACGAUCUU GCUGGGCA |
| 1256 | GACUGCUU CUGAUGU X GAA AUGCCCAG | CUGGGCAUA AAGCAGUC |
| 1264 | AUAGCCUU CUGAUGU X GAA ACUGCUUU | AAAGCAGUC AAGGCUAU |
| 1271 | UUUUUAAA CUGAUGU X GAA AGCCUUGA | UCAAGGCUA UUUAAAAA |
| 1273 | GGUUUUUA CUGAUGU X GAA AUAGCCUU | AAGGCUAUU UAAAAACC |
| 1274 | AGGUUUUU CUGAUGU X GAA AAUAGCCU | AGGCUAUUU AAAAACCU |
| 1275 | GAGGUUUU CUGAUGU X GAA AAAUAGCC | GGCUAUUUA AAAACCUC |
| 1283 | GUGGCAGU CUGAUGU X GAA AGGUUUUU | AAAAACCUC ACUGCCAC |
| 1293 | UACAAUGA CUGAUGU X GAA AGUGGCAG | CUGCCACUC UCAUUGUA |
| 1295 | UUUACAAU CUGAUGU X GAA AGAGUGGC | GCCACUCUC AUUGUAAA |
| 1298 | ACGUUUAC CUGAUGU X GAA AUGAGAGU | ACUCUCAUU GUAAACGU |
| 1301 | UUCACGUU CUGAUGU X GAA ACAAUGAG | CUCAUUGUA AACGUGAA |

Table VIII-continued

Mouse flt-1 VEGF Receptor-Hammerhead Ribozyme and Substrate Sequence

| nt. Position | HH Ribozyme | Substrate |
|---|---|---|
| 1314 | GUAGAUCU CUGAUGU X GAA AGGUUUCA | UGAAACCUC AGAUCUAC |
| 1319 | UUUUCGUA CUGAUGU X GAA AUCUGAGG | CCUCAGAUC UACGAAAA |
| 1321 | ACUUUUCG CUGAUGU X GAA AGAUCUGA | UCAGAUCUA CGAAAAGU |
| 1330 | AGGACACG CUGAUGU X GAA ACUUUUCG | CGAAAAGUC CGUGUCCU |
| 1336 | GAAGCGAG CUGAUGU X GAA ACACGGAC | GUCCGUGUC CUCGCUUC |
| 1339 | UUGGAAGC CUGAUGU X GAA AGGACACG | CGUGUCCUC GCUUCCAA |
| 1343 | GGGCUUGG CUGAUGU X GAA AGCGAGGA | UCCUCGCUU CCAAGCCC |
| 1344 | UGGGCUUG CUGAUGU X GAA AAGCGAGG | CCUCGCUUC CAAGCCCA |
| 1356 | CGGAUAGA CUGAUGU X GAA AGGUGGGC | GCCCACCUC UCUAUCCG |
| 1358 | AGCGGAUA CUGAUGU X GAA AGAGGUGG | CCACCUCUC UAUCCGCU |
| 1360 | CCAGCGGA CUGAUGU X GAA AGAGAGGU | ACCUCUCUA UCCGCUGG |
| 1362 | GCCCAGCG CUGAUGU X GAA AUAGAGAG | CUCUCUAUC CGCUGGGC |
| 1382 | CAAGUGAG CUGAUGU X GAA ACUUGUCU | AGACAAGUC CUCACUUG |
| 1385 | GUGCAAGU CUGAUGU X GAA AGGACUUG | CAAGUCCUC ACUUGCAC |
| 1389 | CACGGUGC CUGAUGU X GAA AGUGAGGA | UCCUCACUU GCACCGUG |
| 1399 | GGAUGCCA CUGAUGU X GAA ACACGGUG | CACCGUGUA UGGCAUCC |
| 1406 | GGCCGAGG CUGAUGU X GAA AUGCCAUA | UAUGGCAUC CCUCGGCC |
| 1410 | UGUUGGCC CUGAUGU X GAA AGGGAUGC | GCAUCCCUC GGCCAACA |
| 1421 | AGCCACGU CUGAUGU X GAA AUUGUUGG | CCAACAAUC ACGUGGCU |
| 1430 | GGGUGCCA CUGAUGU X GAA AGCCACGU | ACGUGGCUC UGGCACCC |
| 1443 | AUUGUGGU CUGAUGU X GAA ACAGGGGU | ACCCCUGUC ACCACAAU |
| 1452 | UUUGGAGU CUGAUGU X GAA AUUGUGGU | ACCACAAUC ACUCCAAA |
| 1456 | UUUCUUUG CUGAUGU X GAA AGUGAUUG | CAAUCACUC CAAAGAAA |
| 1468 | AGAAGUCA CUGAUGU X GAA ACCUUUCU | AGAAAGGUA UGACUUCU |
| 1474 | CAGUGCAG CUGAUGU X GAA AGUCAUAC | GUAUGACUU CUGCACUG |
| 1475 | UCAGUGCA CUGAUGU X GAA AAGUCAUA | UAUGACUUC UGCACUGA |
| 1495 | GGAUAAAG CUGAUGU X GAA AUUCUUCA | UGAAGAAUC CUUUAUCC |
| 1498 | CCAGGAUA CUGAUGU X GAA AGGAUUCU | AGAAUCCUU UAUCCUGG |
| 1499 | UCCAGGAU CUGAUGU X GAA AAGGAUUC | GAAUCCUUU AUCCUGGA |
| 1500 | AUCCAGGA CUGAUGU X GAA AAAGGAUU | AAUCCUUUA UCCUGGAU |
| 1502 | GGAUCCAG CUGAUGU X GAA AUAAAGGA | UCCUUUAUC CUGGAUCC |
| 1509 | GCUGCUGG CUGAUGU X GAA AUCCAGGA | UCCUGGAUC CCAGCAGC |
| 1522 | UGUUUCCU CUGAUGU X GAA AGUUGCUG | CAGCAAGUU AGGAAACA |
| 1523 | CUGUUUCC CUGAUGU X GAA AAGUUGCU | AGCAACUUA GGAAACAG |
| 1535 | AUGCUCUC CUGAUGU X GAA AUUCUGUU | AACAGAAUU GAGAGCAU |
| 1544 | CGCUGAGA CUGAUGU X GAA AUGCUCUC | GAGAGCAUC UCUCAGCG |

Table VIII-continued

Mouse flt-1 VEGF Receptor-Hammerhead Ribozyme and Substrate Sequence

| nt. Position | HH Ribozyme | Substrate |
|---|---|---|
| 1546 | UGCGCUGA CUGAUGU X GAA AGAUGCUC | AGACAUCUC UCAGCGCA |
| 1548 | CAUGCGCU CUGAUGU X GAA AGAGAUGC | GCAUCUCUC AGCGCAUG |
| 1562 | CCUUCUAU CUGAUGU X GAA ACCGUCAU | AUGACGGUC AUAGAAGG |
| 1565 | GUUCCUUC CUGAUGU X GAA AUGACCGU | ACGGUCAUA GAAGGAAC |
| 1578 | AACCGUCU CUGAUGU X GAA AUUUGUUC | GAACAAAUA AGACGGUU |
| 1586 | AAUGUGCU CUGAUGU X GAA ACCGUCUU | AAGACGGUU AGCACAUU |
| 1587 | CAAUGUGC CUGAUGU X GAA AACCGUCU | AGACGGUUA GCACAUUG |
| 1594 | CCACCACC CUGAUGU X GAA AUGUGCUA | UAGCACAUU GGUGGUGG |
| 1609 | GGGUCUGA CUGAUGU X GAA AGUCAGCC | GGCUGACUC UCAGACCC |
| 1611 | AGGGGUCU CUGAUGU X GAA AGAGUCAG | CUGACUCUC AGACCCCU |
| 1625 | CAGCUGUA CUGAUGU X GAA AUUCCAGG | CCUGGAAUC UACAGCUG |
| 1627 | GGCAGCUG CUGAUGU X GAA AGAUUCCA | UGGAAUCUA CAGCUGCC |
| 1642 | UUUUAUUG CUGAUGU X GAA AGGCCCGG | CCGGGCCUU CAAUAAAA |
| 1643 | AUUUUAUU CUGAUGU X GAA AAGGCCCG | CGGGCCUUC AAUAAAAU |
| 1647 | CCCUAUUU CUGAUGU X GAA AUUGAAGG | CCUUCAAUA AAAUAGGG |
| 1652 | ACAGUCCC CUGAUGU X GAA AUUUUAUU | AAUAAAAUA GGGACUGU |
| 1673 | UAAAAUUU CUGAUGU X GAA AUGUUUCU | AGAAACAUA AAAUUUUA |
| 1678 | UGACAUAA CUGAUGU X GAA AUUUUAUG | CAUAAAAUU UUAUGUCA |
| 1679 | GUGACAUA CUGAUGU X GAA AAUUUUAU | AUAAAAUUU UAUGUCAC |
| 1680 | UGUGACAU CUGAUGU X GAA AAAUUUUA | UAAAAUUUU AUGUCACA |
| 1681 | CUGUGACA CUGAUGU X GAA AAAAUUUU | AAAAUUUUA UGUCACAG |
| 1685 | ACAUCUGU CUGAUGU X GAA ACAUAAAA | UUUUAUGUC ACAGAUGU |
| 1705 | AAACGUGA CUGAUGU X GAA AGCCAUUC | GAAUGGCUU UCACGUUU |
| 1706 | GAAACGUG CUGAUGU X GAA AAGCCAUU | AAUGGCUUU CACGUUUC |
| 1707 | GGAAACGU CUGAUGU X GAA AAAGCCAU | AUGGCUUUC ACGUUUCC |
| 1712 | UCCAAGGA CUGAUGU X GAA ACGUGAAA | UUUCACGUU UCCUUGGA |
| 1713 | UUCCAAGG CUGAUGU X GAA AACGUGAA | UUCACGUUU CCUUGGAA |
| 1714 | UUUCCAAG CUGAUGU X GAA AAACGUGA | UCACGUUUC CUUGGAAA |
| 1717 | UCUUUCC CUGAUGU X GAA AGGAAACG | CGUUUCCUU GGAAAAGA |
| 1756 | CCACACAG CUGAUGU X GAA ACAGUUUC | GAAACUGUC CUGUGUGG |
| 1766 | AAUUUAUU CUGAUGU X GAA ACCACACA | UGUGUGGUC AAUAAAUU |
| 1770 | CAGGAAUU CUGAUGU X GAA AUUGACCA | UGGUCAAUA AAUUCCUG |
| 1774 | UGUACAGG CUGAUGU X GAA AUUUAUUG | CAAUAAAUU CCUGUACA |
| 1775 | CUGUACAG CUGAUGU X GAA AAUUUAUU | AAUAAAUUC CUGUACAG |
| 1780 | UGUCUCUG CUGAUGU X GAA ACAGGAAU | AUUCCUGUA CAGAGACA |
| 1790 | AUCCAGGU CUGAUGU X GAA AUGUCUCU | AGAGACAUU ACCUGGAU |
| 1791 | AAUCCAGG CUGAUGU X GAA AAUGUCUC | GAGACAUUA CCUGGAUU |

Table VIII-continued

Mouse flt-1 VEGF Receptor-Hammerhead Ribozyme and Substrate Sequence

| nt. Position | HH Ribozyme | Substrate |
|---|---|---|
| 1799 | GGUAGCAG CUGAUGU X GAA AUCCAGGU | ACCUGGAUU CUGCUACG |
| 1800 | CCGUAGCA CUGAUGU X GAA AAUCCAGG | CCUGGAUUC UGCUACGG |
| 1805 | ACUGUCCG CUGAUGU X GAA AGCAGAAU | AUUCUGCUA CGGACAGU |
| 1814 | CUGUUGUU CUGAUGU X GAA ACUGUCCG | CGGACAGUU AACAACAG |
| 1815 | UCUGUUGU CUGAUGU X GAA AACUGUCC | GGACAGUUA ACAACAGA |
| 1836 | GCUGAUAC CUGAUGU X GAA AUGGUGCA | UGCACCAUA GUAUCAGC |
| 1839 | CUUGCUGA CUGAUGU X GAA ACUAUGGU | ACCAUAGUA UCAGCAAG |
| 1841 | UGCUUGCU CUGAUGU X GAA AUACUAUG | CAUAGUAUC AGCAAGCA |
| 1866 | GUAAUCUU CUGAUGU X GAA AGUGGUGG | CCACCACUC AAGAUUAC |
| 1872 | GAUGGAGU CUGAUGU X GAA AUCUUGAG | CUCAAGAUU ACUCCAUC |
| 1873 | UGAUGGAG CUGAUGU X GAA AAUCUUGA | UCAAGAUUA CUCCAUCA |
| 1876 | GAGUGAUG CUGAUGU X GAA AGUAAUCU | AGAUUACUC CAUCACUC |
| 1880 | UUCAGAGU CUGAUGU X GAA AUGGAGUA | UACUCCAUC ACUCUGAA |
| 1884 | AAGGUUCA CUGAUGU X GAA AGUGAUGG | CCAUCACUC UGAACCUU |
| 1892 | UUGAUGAC CUGAUGU X GAA AGGUUCAG | CUGAACCUU GUCAUCAA |
| 1895 | UUCUUGAU CUGAUGU X GAA ACAAGGUU | AACCUUGUC AUCAAGAA |
| 1898 | ACGUUCUU CUGAUGU X GAA AUGACAAG | CUUGUCAUC AAGAACGU |
| 1909 | CUUCUAGA CUGAUGU X GAA ACACGUUC | GAACGUGUC UCUAGAAG |
| 1911 | GUCUUCUA CUGAUGU X GAA AGACACGU | ACGUGUCUC UAGAAGAC |
| 1913 | GAGUCUUC CUGAUGU X GAA AGAGACAC | GUGUCUCUA GAAGACUC |
| 1921 | AGGUGCCC CUGAUGU X GAA AGUCUUCU | AGAACACUC GGGCACCU |
| 1930 | UGCACGCA CUGAUGU X GAA AGGUGCCC | GGGCACCUA UGCGUGCA |
| 1952 | CCUGUGUA CUGAUGU X GAA AUGUUCCU | AGGAACAUA UACACAGG |
| 1954 | CCCCUGUG CUGAUGU X GAA AUAUGUUC | GAACAUAUA CACAGGGG |
| 1970 | UUCCGAAG CUGAUGU X GAA AUGUCUUC | GAAGACAUC UUCGGAA |
| 1973 | GUCUUCCG CUGAUGU X GAA AGGAUGUC | GACAUCCUU CGGAAGAC |
| 1974 | UGUCUUCC CUGAUGU X GAA AAGGAUGU | ACAUCCUUC GGAAGACA |
| 1988 | CUAACGAG CUGAUGU X GAA ACUUCUGU | ACAGAAGUU CUCGUUAG |
| 1989 | UCUAACGA CUGAUGU X GAA AACUUCUG | CAGAAGUUC UCGUUAGA |
| 1991 | UCUCUAAC CUGAUGU X GAA AGAACUUC | GAAGUUCUC GUUAGAGA |
| 1994 | GAAUCUCU CUGAUGU X GAA ACGAGAAC | GUUCUCGUU AGAGAUUC |
| 1995 | CGAAUCUC CUGAUGU X GAA AACGAGAA | UUCUCGUUA GAGAUUCG |
| 2001 | CGCUUCCG CUGAUGU X GAA AUCUCUAA | UUAGAGAUU CGGAAGCG |
| 2002 | GCGCUUCC CUGAUGU X GAA AAUCUCUA | UAGAGAUUC GGAAGCGC |
| 2021 | AGGUUUUG CUGAUGU X GAA AGCAGGUG | CACCUGCUU CAAAACCU |
| 2022 | GAGGUUUU CUGAUGU X GAA AAGCAGGU | ACCUGCUUC AAAACCUC |

Table VIII-continued

Mouse flt-1 VEGF Receptor-Hammerhead Ribozyme and Substrate Sequence

| nt. Position | HH Ribozyme | Substrate |
|---|---|---|
| 2030 | UAGUCACU CUGAUGU X GAA AGGUUUUG | CAAAACCUC AGUGACUA |
| 2038 | AGACCUCG CUGAUGU X GAA AGUCACUG | CAGUGACUA CGAGGUCU |
| 2045 | CUGAUGGA CUGAUGU X GAA ACCUCGUA | UACGAGGUC UCCAUCAG |
| 2047 | CACUGAUG CUGAUGU X GAA AGACCUCG | CGAGGUCUC CAUCAGUG |
| 2051 | GAGCCACU CUGAUGU X GAA AUGGAGAC | GUCUCCAUC AGUGGCUC |
| 2059 | AGGUCGUA CUGAUGU X GAA AGCCACUG | CAGUGGCUC UACGACCU |
| 2061 | UAAGGUCG CUGAUGU X GAA AGAGCCAC | GUGGCUCUA CGACCUUA |
| 2068 | GACAGUCU CUGAUGU X GAA AGGUCGUA | UACGACCUU AGACUGUC |
| 2069 | UGACAGUC CUGAUGU X GAA AAGGUCGU | ACGACCUUA GACUGUCA |
| 2076 | UCUAGCUU CUGAUGU X GAA ACAGUCUA | UAGACUGUC AAGCUAGA |
| 2082 | GACACCUC CUGAUGU X GAA AGCUUGAC | GUCAAGCUA GAGGUGUC |
| 2090 | GGCGCGGG CUGAUGU X GAA ACACCUGU | AGAGGUGUC CCCGCGCC |
| 2100 | AGUGAUCU CUGAUGU X GAA AGGCGCGG | CCGCGCCUC AGAUCACU |
| 2105 | AACCAAGU CUGAUGU X GAA AUCUGAGG | CCUCAGAUC ACUUGGUU |
| 2109 | UUUGAACC CUGAUGU X GAA AGUGAUCU | AGAUCACUU GGUUCAAA |
| 2113 | UGUUUUG CUGAUGU X GAA ACCAAGUG | CACUUGGUU CAAAAACA |
| 2114 | UUGUUUUU CUGAUGU X GAA AACCAAGU | ACUUGGUUC AAAAACAA |
| 2132 | UCUUGUUG CUGAUGU X GAA AUUUUGUG | CACAAAAUA CAACAAGA |
| 2150 | CCUAAAAU CUGAUGU X GAA AUUCCCGG | CCGGGAAUU AUUUUAGG |
| 2151 | UCCUAAAA CUGAUGU X GAA AAUUCCCG | CGGGAAUUA UUUUAGGA |
| 2153 | GGUCCUAA CUGAUGU X GAA AUAAUUCC | GGAAUUAUU UUAGGACC |
| 2154 | UGGUCCUA CUGAUGU X GAA AAUAAUUC | GAAUUAUUU UAGGACCA |
| 2155 | CUGGUCCU CUGAUGU X GAA AAAUAAUU | AAUUAUUUU AGGACCAG |
| 2156 | CCUGGUCC CUGAUGU X GAA AAAAUAAU | AUUAUUUUA GGACCAGG |
| 2179 | UUUCAAUA CUGAUGU X GAA ACAGCGUG | CACGCUGUU UAUUGAAA |
| 2180 | CUUUCAAU CUGAUGU X GAA AACAGCGU | ACGCUGUUU AUUGAAAG |
| 2181 | UCUUUCAA CUGAUGU X GAA AAACAGCG | CGCUGUUUA UUGAAAGA |
| 2183 | ACUCUUUC CUGAUGU X GAA AUAAACAG | CUGUUUAUU GAAAGAGU |
| 2192 | UCCUCUGU CUGAUGU X GAA ACUCUUUC | GAAAGAGUC ACAGAGGA |
| 2213 | CACCUAUA CUGAUGU X GAA ACACCCUC | GAGGGUGUC UAUAGGUG |
| 2215 | GGCACCUA CUGAUGU X GAA AGACACCC | GGGUGUCUA UAGGUGCC |
| 2217 | UCGGCACC CUGAUGU X GAA AUAGACAC | GUGUCUAUA GGUGCCGA |
| 2263 | CGGUGAGG CUGAUGU X GAA AGGCUGCG | CGCAGCCUA CCUCACCG |
| 2267 | UGCACGGU CUGAUGU X GAA AGGUAGGC | GCCUACCUC ACCGUGCA |
| 2284 | ACUUGUCU CUGAUGU X GAA AGGUUCCU | AGGAACCUC AGACAAGU |
| 2293 | CCAGGUUU CUGAUGU X GAA ACUUGUCU | AGACAAGUC AAACCUGG |
| 2309 | GUGAGCGU CUGAUGU X GAA AUCAGCUC | GAGCUGAUC ACGCUCAC |

Table VIII-continued

Mouse flt-1 VEGF Receptor-Hammerhead Ribozyme and Substrate Sequence

| nt. Position | HH Ribozyme | Substrate |
|---|---|---|
| 2315 | GUGCACGU CUGAUGU X GAA AGCGUGAU | AUCACGCUC ACGUGCAC |
| 2342 | AGCCAAAA CUGAUGU X GAA AGGGUCGC | GCGACCCUC UUUUGGCU |
| 2344 | GGAGCCAA CUGAUGU X GAA AGAGGGUC | GACCCUCUU UUGGCUCC |
| 2345 | AGGAGCCA CUGAUGU X GAA AAGAGGGU | ACCCUCUUU UGGCUCCU |
| 2346 | AAGGAGCC CUGAUGU X GAA AAAGAGGG | CCCUCUUUU GGCUCCUU |
| 2351 | GUUAGAAG CUGAUGU X GAA AGCCAAAA | UUUUGGCUC CUUCUAAC |
| 2354 | AGAGUUAG CUGAUGU X GAA AGGAGCCA | UGGCUCCUU CUAACUCU |
| 2355 | GAGAGUUA CUGAUGU X GAA AAGGAGCC | GGCUCCUUC UAACUCUC |
| 2357 | AAGAGAGU CUGAUGU X GAA AGAAGGAG | CUCCUUCUA ACUCUCUU |
| 2361 | GAUGAAGA CUGAUGU X GAA AGUUAGAA | UUCUAACUC UCUUCAUC |
| 2363 | CUGAUGAA CUGAUGU X GAA AGAGUUAG | CUAACUCUC UUCAUCAG |
| 2365 | UUCUGAUG CUGAUGU X GAA AGAGAGUU | AACUCUCUU CAUCAGAA |
| 2366 | UUUCUGAU CUGAUGU X GAA AAGAGAGU | ACUCUCUUC AUCAGAAA |
| 2369 | AGUUUCU CUGAUGU X GAA AUGAAGAG | CUCUUCAUC AGAAAACU |
| 2386 | CGGAAGAA CUGAUGU X GAA ACCGCUUC | GAAGCGGUC UUCUUCCG |
| 2388 | UUCGGAAG CUGAUGU X GAA AGACCGCU | AGCGGUCUU CUUCCGAA |
| 2389 | CUUCGGAA CUGAUGU X GAA AAGACCGC | GCGGUCUUC UUCCGAAG |
| 2391 | UACUUCGG CUGAUGU X GAA AGAAGACC | GGUCUUCUU CCGAAGUA |
| 2392 | UUACUUCG CUGAUGU X GAA AAGAAGAC | GUCUUCUUC CGAAGUAA |
| 2399 | UCUGUCUU CUGAUGU X GAA ACUUCGGA | UCCGAAGUA AAGACAGA |
| 2410 | UUGACAGG CUGAUGU X GAA AGUCUGUC | GACAGACUA CCUGUCAA |
| 2416 | UAAUGAUU CUGAUGU X GAA ACAGGUAG | CUACCUGUC AAUCAUUA |
| 2420 | UCCAUAAU CUGAUGU X GAA AUUGACAG | CUGUCAAUC AUUAUGGA |
| 2423 | GGGUCCAU CUGAUGU X GAA AUGAUUGA | UCAAUCAUU AUGGACCC |
| 2424 | UGGGUCCA CUGAUGU X GAA AAUGAUUG | CAAUCAUUA UGGACCCA |
| 2441 | UCCAGGGG CUGAUGU X GAA ACUUCAUC | GAUGAAGUU CCCCUGGA |
| 2442 | AUCCAGGG CUGAUGU X GAA AACUUCAU | AUGAAGUUC CCCUGGAU |
| 2473 | UGGCAUCA CUGAUGU X GAA AGGGCAGC | GCUGCCCUA UGAUGCCA |
| 2494 | CCCGUGCA CUGAUGU X GAA ACUCCCAC | GUGGGAGUU UGCACGGG |
| 2495 | UCCCGUGC CUGAUGU X GAA AACUCCCA | UGGGAGUUU GCACGGGA |
| 2516 | GAUUGCC CUGAUGU X GAA AGUUUCAG | CUGAAACUA GGCAAAUC |
| 2524 | UUCCGAGC CUGAUGU X GAA AUUUGCCU | AGGCAAAUC GCUCGGAA |
| 2528 | CCUCUUCC CUGAUGU X GAA AGCGAUUU | AAAUCGCUC GGAAGAGG |
| 2541 | UUUCCCAA CUGAUGU X GAA AGCCCCUC | GAGGGGCUU UUGGGAAA |
| 2542 | CUUUCCCA CUGAUGU X GAA AAGCCCCU | AGGGGCUUU UGGGAAAG |
| 2543 | ACUUUCCC CUGAUGU X GAA AAAGCCCC | GGGGCUUUU GGGAAAGU |

Table VIII-continued

Mouse flt-1 VEGF Receptor-Hammerhead Ribozyme and Substrate Sequence

| nt. Position | HH Ribozyme | Substrate |
|---|---|---|
| 2552 | GCUUGAAC CUGAUGU X GAA ACUUCCC | GGGAAAGUC GUUCAAGC |
| 2555 | GAGGCUUG CUGAUGU X GAA ACGACUUU | AAAGUCGUU CAAGCCUC |
| 2556 | AGAGGCUU CUGAUGU X GAA AACGACUU | AAGUCGUUC AAGCCUCU |
| 2563 | CAAAUGCA CUGAUGU X GAA AGGCUUGA | UCAAGCCUC UGCAUUUG |
| 2569 | UAAUGCCA CUGAUGU X GAA AUGCAGAG | CUCUGCAUU UGGCAUUA |
| 2570 | UUAAUGCC CUGAUGU X GAA AAUGCAGA | UCUGCAUUU GGCAUUAA |
| 2576 | GAUUUCUU CUGAUGU X GAA AUGCCAAA | UUUGGCAUU AAGAAAUC |
| 2577 | UGAUUUCU CUGAUGU X GAA AAUGCCAA | UUGGCAUUA AGAAAUCA |
| 2584 | AGGUGGGU CUGAUGU X GAA AUUUCUUA | UAAGAAAUC ACCCACCU |
| 2617 | CCUCUUUC CUGAUGU X GAA ACAUCUUC | GAAGAUGUU GAAAGAGG |
| 2644 | GAGCUUUG CUGAUGU X GAA ACUCACUG | CAGUGAGUA CAAAGCUC |
| 2652 | GGUCAUCA CUGAUGU X GAA AGCUUUGU | ACAAAGCUC UGAUGACC |
| 2666 | AAGAUCUU CUGAUGU X GAA AGUUCGGU | ACCGAACUC AAGAUCUU |
| 2672 | UGGGUCAA CUGAUGU X GAA AUCUUGAG | CUCAAGAUC UUGACCCA |
| 2674 | UGUGGGUC CUGAUGU X GAA AGAUCUUG | CAAGAUCUU GACCCACA |
| 2684 | UGAUGGCC CUGAUGU X GAA AUGUGGGU | ACCCACAUC GGCCAUCA |
| 2691 | AUUCAGAU CUGAUGU X GAA AUGGCCGA | AUGGCCAUC AUCUGAAU |
| 2694 | CACAUUCA CUGAUGU X GAA AUGAUGGC | GCCAUCAUC UGAAUGUG |
| 2705 | AGGAGGUU CUGAUGU X GAA ACCACAUU | AAUGUGGUU AACCUCCU |
| 2706 | CAGGAGGU CUGAUGU X GAA AACCACAU | AUGUGGUUA ACCUCCUG |
| 2711 | GCUCCCAG CUGAUGU X GAA AGGUUAAC | GUUAACCUC CUGGGAGC |
| 2742 | CACCAUCA CUGAUGU X GAA AGGCCCUC | GAGGGCCUC UGAUGGUG |
| 2753 | UAUCCAC CUGAUGU X GAA AUCACCAU | AUGGUGAUC GUGGAAUA |
| 2761 | AUUUGCAG CUGAUGU X GAA AUUCCACG | CGUGGAAUA CUGCAAAU |
| 2770 | GGUUUCCG CUGAUGU X GAA AUUUGCAG | CUGCAAAUA AGGAAACC |
| 2782 | GGUAGUUG CUGAUGU X GAA ACAGGUUU | AAACCUGUC CAACUACC |
| 2788 | UCUUGAGG CUGAUGU X GAA AGUUGGAC | GUCCAACUA CCUCAAGA |
| 2792 | UUGCUCUU CUGAUGU X GAA AGGUAGUU | AACUACCUC AAGAGCAA |
| 2809 | GACAGAAU CUGAUGU X GAA AGUCACGU | ACGUGACUU AUUCUGUC |
| 2810 | AGACAGAA CUGAUGU X GAA AAGUCACG | CGUGACUUA UUCUGUCU |
| 2812 | UGACACAG CUGAUGU X GAA AUAAGUCA | UGACUUAUU CUGUCUCA |
| 2813 | UUGAGACA CUGAUGU X GAA AAUAAGUC | GACUUAUUC UGUCUCAA |
| 2817 | CUUGUUGA CUGAUGU X GAA ACAGAAUA | UAUUCUGUC UCAACAAG |
| 2819 | UCCUUGUU CUGAUGU X GAA AGACAGAA | UUCUGUCUC AACAAGGA |
| 2836 | CCAUAUGC CUGAUGU X GAA AGGCUGCG | CGCAGCCUU GCAUAUGG |
| 2841 | GAGCUCCA CUGAUGU X GAA AUGCAAGG | CCUUGCAUA UGGAGCUC |
| 2849 | UCUUUCUU CUGAUGU X GAA AGCUCCAU | AUGGAGCUC AAGAAAGA |

Table VIII-continued

Mouse flt-1 VEGF Receptor-Hammerhead Ribozyme and Substrate Sequence

| nt. Position | HH Ribozyme | Substrate |
|---|---|---|
| 2900 | ACACUGUC CUGAUGU X GAA AGGCGGGG | CCCCGCCUA GACAGUGU |
| 2909 | GAGCUGCU CUGAUGU X GAA ACACUGUC | GACAGUGUC AGCAGCUC |
| 2917 | UGACACUU CUGAUGU X GAA AGCUGCUC | CAGCAGCUC AAGUGUCA |
| 2924 | GAGCUGGU CUGAUGU X GAA ACACUUGA | UCAAGUGUC ACCAGCUC |
| 2932 | GGAAGCUG CUGAUGU X GAA AGCUGGUG | CACCAGCUC CAGCUUCC |
| 2938 | CUUCAGGG CUGAUGU X GAA AGCUGGAG | CUCCAGCUU CCCUGAAG |
| 2939 | UCUUCAGG CUGAUGU X GAA AAGCUGGA | UCCAGCUUC CCUGAAGA |
| 2982 | CUCACUGU CUGAUGU X GAA AUCCUCGU | ACGAGGAUU ACAGUGAG |
| 2983 | UCUCACUG CUGAUGU X GAA AAUCCUCG | CGAGGAUUA CAGUGAGA |
| 2993 | UGCUUGGA CUGAUGU X GAA AUCUCACU | AGUGAGAUC UCCAAGCA |
| 2995 | GCUGCUUG CUGAUGU X GAA AGAUCUCA | UGAGAUCUC CAAGCAGC |
| 3008 | UCCAUGGU CUGAUGU X GAA AGGGGCUG | CAGCCCCUC ACCAUGGA |
| 3026 | CUGUAGGA CUGAUGU X GAA AUCAGGUC | GACCUGAUU UCCUACAG |
| 3027 | ACUGUAGG CUGAUGU X GAA AAUCAGGU | ACCUGAUUU CCUACAGU |
| 3028 | AACUGUAG CUGAUGU X GAA AAAUCAGG | CCUGAUUUC CUACAGUU |
| 3031 | GGAAACUG CUGAUGU X GAA AGGAAAUC | GAUUUCCUA CAGUUUCC |
| 3036 | CACUUGGA CUGAUGU X GAA ACUGUAGG | CCUACAGUU UCCAAGUG |
| 3037 | CCACUUGG CUGAUGU X GAA AACUGUAG | CUACAGUUU CCAAGUGG |
| 3038 | GCCACUUG CUGAUGU X GAA AAACUGUA | UACAGUUUC CAAGUGGC |
| 3061 | AGGACAGA CUGAUGU X GAA ACUCCAUG | CAUGGAGUU UCUGUCCU |
| 3062 | GAGGACAG CUGAUGU X GAA AACUCCAU | AUGGAGUUU CUGUCCUC |
| 3063 | GGAGGACA CUGAUGU X GAA AAACUCCA | UGGAGUUUC UGUCCUCC |
| 3067 | UUCUGGAG CUGAUGU X GAA ACAGAAAC | GUUUCUGUC CUCCAGAA |
| 3070 | ACUUUCUG CUGAUGU X GAA AGGACAGA | UCUGUCCUC CAGAAAGU |
| 3083 | UCCCGAUG CUGAUGU X GAA AUGCACUU | AAGUGCAUU CAUCGGGA |
| 3084 | GUCCCGAU CUGAUGU X GAA AAUGCACU | AGUGCAUUC AUCGGGAC |
| 3087 | CAGGUCCC CUGAUGU X GAA AUGAAUGC | GCAUUCAUC GGGACCUG |
| 3110 | GAUAAAAG CUGAUGU X GAA AUGUUUCU | AGAAACAUC CUUUUAUC |
| 3113 | UCAGAUAA CUGAUGU X GAA AGGAUGUU | AACAUCCUU UUAUCUGA |
| 3114 | CUCAGAUA CUGAUGU X GAA AAGGAUGU | ACAUCCUUU UAUCUGAG |
| 3115 | UCUCAGAU CUGAUGU X GAA AAAGGAUG | CAUCCUUUU AUCUGAGA |
| 3116 | UUCUCAGA CUGAUGU X GAA AAAAGGAU | AUCCUUUUA UCUGAGAA |
| 3118 | UGUUCUCA CUGAUGU X GAA AUAAAAGG | CCUUUUAUC UGAGAACA |
| 3140 | AAGUCGCA CUGAUGU X GAA AUCUUCAC | GUGAAGAUU AGCGACUU |
| 3141 | AAAGUCGC CUGAUGU X GAA AAUCUUCA | UGAAGAUUU GCGACUUU |
| 3148 | CCAGGCCA CUGAUGU X GAA AGUCGCAA | UUGCGACUU AGGCCUGG |

Table VIII-continued

Mouse flt-1 VEGF Receptor-Hammerhead Ribozyme and Substrate Sequence

| nt. Position | HH Ribozyme | Substrate |
|---|---|---|
| 3149 | GCCAGGCC CUGAUGU X GAA AAGUCGCA | UGCGACUUU GGCCUGGC |
| 3165 | CUUAUAAA CUGAUGU X GAA AUCCCGGG | CCCGGGAUA UUUAUAAG |
| 3167 | UUCUUAUA CUGAUGU X GAA AUAUCCCG | CGGGAUAUU UAUAAGAA |
| 3168 | GUUCUUAU CUGAUGU X GAA AAUAUCCC | GGGAUAUUU AUAAGAAC |
| 3169 | GGUUCUUA CUGAUGU X GAA AAAUAUCC | GGAUAUUUA UAAGAACC |
| 3171 | AGGGUUCU CUGAUGU X GAA AUAAAUAU | AUAUUUAUA AGAACCCU |
| 3183 | CCUCACAU CUGAUGU X GAA AUCAGGGU | ACCCUGAUU AUGUGAGG |
| 3184 | UCCUCACA CUGAUGU X GAA AUCAGGG | CCCUGAUUA UGUGAGGA |
| 3201 | AAGUCGAG CUGAUGU X GAA AUCUCCUC | GAGGAGAUA CUCGACUU |
| 3204 | GGGAAGUC CUGAUGU X GAA AGUAUCUC | GAGAUACUC GACUUCCC |
| 3209 | UUUAGGGG CUGAUGU X GAA AGUCGAGU | ACUCGACUU CCCCUAAA |
| 3210 | UUUUAGGG CUGAUGU X GAA AAGUCGAG | CUCGACUUC CCCUAAAA |
| 3215 | AUCCAUUU CUGAUGU X GAA AGGGGAAG | CUUCCCCUA AAAUGGAU |
| 3228 | GGAUUCAG CUGAUGU X GAA AGCCAUCC | GGAUGGCUC CUGAAUCC |
| 3235 | CAAAGAUG CUGAUGU X GAA AUUCAGGA | UCCUGAAUC CAUCUUUG |
| 3239 | UUGUCAAA CUGAUGU X GAA AUGGAUUC | GAAUCCAUC UUUGACAA |
| 3241 | CCUUGUCA CUGAUGU X GAA AGAUGGAU | AUCCAUCUU UGACAAGG |
| 3242 | ACCUUGUC CUGAUGU X GAA AAGAUGGA | UCCAUCUUU GACAAGGU |
| 3251 | GUGCUGUA CUGAUGU X GAA ACCUUGUC | GACAAGGUC UACAGCAC |
| 3253 | UGGUGCUG CUGAUGU X GAA AGACCUUG | CAAGGUCUA CAGCACCA |
| 3277 | CGCCAUAG CUGAUGU X GAA ACCACACA | UGUGUGGUC CUAUGGCG |
| 3280 | ACACGCCA CUGAUGU X GAA AGGACCAC | GUGGUCCUA UGGCGUGU |
| 3289 | CCCACAGC CUGAUGU X GAA ACACGCCA | UGGCGUGUU GCUGUGGG |
| 3302 | AAGGAGAA CUGAUGU X GAA AUCUCCCA | UGGGAGAUC UUCUCCUU |
| 3304 | CUAAGGAG CUGAUGU X GAA AGAUCUCC | GGAGAUCUU CUCCUUAG |
| 3305 | CCUAAGGA CUGAUGU X GAA AAGAUCUC | GAGAUCUUC UCCUUAGG |
| 3307 | CCCCUAAG CUGAUGU X GAA AGAAGAUC | GAUCUUCUC CUUAGGGG |
| 3310 | AACCCCCU CUGAUGU X GAA AGGAGAAG | CUUCUCCUU AGGGGUU |
| 3311 | GAACCCCC CUGAUGU X GAA AAGGAGAA | UUCUCCUUA GGGGUUC |
| 3318 | GUAUGGAG CUGAUGU X GAA ACCCCCUA | UAGGGGGUU CACCAUAC |
| 3319 | GGUAUGGA CUGAUGU X GAA AACCCCCU | AGGGGUUC UCCAUACC |
| 3321 | UGGGUAUG CUGAUGU X GAA AGAACCCC | GGGGUUCUC CAUACCCA |
| 3325 | CUCCUGGG CUGAUGU X GAA AUGGAGAA | UUCUCCAUA CCCAGGAG |
| 3352 | GGCUGCAG CUGAUGU X GAA AGUCUUCA | UGAAGACUU CUGCAGCC |
| 3353 | CGGCUGCA CUGAUGU X GAA AAGUCUUC | GAAGACUUC UGCAGCCG |
| 3397 | GUGUGGCA CUGAUGU X GAA ACUCCGGG | CCCGGAGUA UGCCACAC |
| 3413 | AUUUGGUA CUGAUGU X GAA AUUUACGG | CCUGAAAUC UACCAAAU |

Table VIII-continued

Mouse flt-1 VEGF Receptor-Hammerhead Ribozyme and Substrate Sequence

| nt. Position | HH Ribozyme | Substrate |
|---|---|---|
| 3415 | UGAUUUGG CUGAUGU X GAA AGAUUUCA | UGAAAUCUA CCAAAUCA |
| 3422 | UCCAACAU CUGAUGU X GAA AUUUGGUA | UACCAAAUC AUGUUGGA |
| 3427 | AGCAAUCC CUGAUGU X GAA ACAUGAUU | AAUCAUGUU GGAUUGCU |
| 3432 | GUGCCAGC CUGAUGU X GAA AUCCAACA | UGUUGGAUU GCUGGCAC |
| 3466 | GUUCAGCA CUGAUGU X GAA ACCGGGGC | GCCCCGGUU UGCUGAAC |
| 3467 | AGUUCAGC CUGAUGU X GAA AACCGGGG | CCCCGGUUU GCUGAACU |
| 3476 | UUCUCCAC CUGAUGU X GAA AGUUCAGC | GCUGAACUU GUGGAGAA |
| 3488 | AGGUCACC CUGAUGU X GAA AGUUUCUC | GAGAAACUU GGUGACCU |
| 3500 | UUGGCUUG CUGAUGU X GAA AGCAGGUC | GACCUGCUU CAAGCCAA |
| 3501 | GUUGGCUU CUGAUGU X GAA AAGCAGGU | ACCUGCUUC AAGCCAAC |
| 3512 | UCCUGUUG CUGAUGU X GAA ACGUUGGC | GCCAACGUC AACAGGA |
| 3531 | GGGGAUGU CUGAUGU X GAA AUCUUUCC | GGAAAGAUU ACAUCCCC |
| 3532 | GGGGGAUG CUGAUGU X GAA AAUCUUUC | GAAAGAUUA CAUCCCCC |
| 3536 | UUGAGGGG CUGAUGU X GAA AUGUAAUC | GAUUACAUC CCCCUCAA |
| 3542 | AUGGCAUU CUGAUGU X GAA AGGGGGAU | AUCCCCCUC AAUGCCAU |
| 3551 | CUAGUCAG CUGAUGU X GAA AUGGCAUU | AAUGCCAUA CUGACUAG |
| 3558 | ACUGUUUC CUGAUGU X GAA AGUCAGUA | UACUGACUA GAAACAGU |
| 3567 | UGUGAAGC CUGAUGU X GAA ACUGUUUC | GAAACAGUA GCUUCACA |
| 3571 | AGUAUGUG CUGAUGU X GAA ACGUACUG | CAGUAGCUU CACAUACU |
| 3572 | GAGUAUGU CUGAUGU X GAA AAGCUACU | AGUAGCUUC ACAUACUC |
| 3577 | GGGUCGAG CUGAUGU X GAA AUGUGAAG | CUUCACAUA CUCGACCC |
| 3580 | UGGGGGUC CUGAUGU X GAA AGUAUGUG | CACAUACUC GACCCCCA |
| 3592 | CCUCAGAG CUGAUGU X GAA AGGUGGGG | CCCCACCUU CUCUGAGG |
| 3593 | UCCUCAGA CUGAUGU X GAA AAGGUGGG | CCCACCUUC UCUGAGGA |
| 3595 | GGUCCUCA CUGAUGU X GAA AGAAGGUG | CACCUUCUC UGAGGACC |
| 3605 | UCCUUGAA CUGAUGU X GAA AGGUCCUC | GAGGACCUU UUCAAGGA |
| 3606 | GUCCUUGA CUGAUGU X GAA AAGGUCCU | AGGACCUUU UCAAGGAC |
| 3607 | CGUCCUUG CUGAUGU X GAA AAAGGUCC | GGACCUUUU CAAGGACG |
| 3608 | CCGUCCUU CUGAUGU X GAA AAAAGGUC | GACCUUUUC AAGGACGG |
| 3619 | GAUCUGCA CUGAUGU X GAA AGCCGUCC | GGACGGCUU UGCAGAUC |
| 3620 | GGAUCUGC CUGAUGU X GAA AAGCCGUC | GACGGCUUU GCAGAUCC |
| 3627 | AAAAUGUG CUGAUGU X GAA AUCUGCAA | UUGCAGAUC CACAUUUU |
| 3633 | GGAAUGAA CUGAUGU X GAA AUGUGGAU | AUCCACAUU UUCAUUCC |
| 3634 | CGGAAUGA CUGAUGU X GAA AAUGUGGA | UCCACAUUU UCAUUCCG |
| 3635 | CCGGAAUG CUGAUGU X GAA AAAUGUGG | CCACAUUUU CAUUCCGG |
| 3636 | UCCGGAAU CUGAUGU X GAA AAAAUGUG | CACAUUUUC AUUCCGGA |

Table VIII-continued

Mouse flt-1 VEGF Receptor-Hammerhead Ribozyme and Substrate Sequence

| nt. Position | HH Ribozyme | Substrate |
|---|---|---|
| 3639 | GCUUCCGG CUGAUGU X GAA AUGAAAAU | AUUUUCAUU CCGGAAGC |
| 3640 | AGCUUCCG CUGAUGU X GAA AAUGAAAA | UUUUCAUUC CGGAAGCU |
| 3649 | CAUCAUCA CUGAUGU X GAA AGCUUCCG | CGGAAGCUC UGAUGAUG |
| 3664 | CGUUUACA CUGAUGU X GAA AUCUCACA | UGUGAGAUA UGUAAACG |
| 3668 | AAAGCGUU CUGAUGU X GAA ACAUAUCU | AGAUAUGUA AACGCUUU |
| 3675 | GAAUUUGA CUGAUGU X GAA AGCGUUUA | UAAACGCUU UCAAAUUC |
| 3676 | UGAAUUUG CUGAUGU X GAA AAGCGUUU | AAACGCUUU CAAAUUCA |
| 3677 | AUGAAUUU CUGAUGU X GAA AAAGCGUU | AACGCUUUC AAAUUCAU |
| 3682 | GGCUCAUG CUGAUGU X GAA AUUUCAAA | UUUCAAAUU CAUGAGCC |
| 3683 | AGGCUCAU CUGAUGU X GAA AAUUUGAA | UUCAAAUUC AUGAGCCU |
| 3701 | AAGGUUUU CUGAUGU X GAA AUUCUUUC | GAAAGAAUC AAAACCUU |
| 3709 | GCUCCUCA CUGAUGU X GAA AGGUUUUG | CAAAACCUU UGAGGAGC |
| 3710 | AGCUCCUC CUGAUGU X GAA AAGGUUUU | AAAACCUUU GAGGAGCU |
| 3719 | UUCGGUGA CUGAUGU X GAA AGCUCCUC | GAGGAGCUU UCACCGAA |
| 3720 | GUUCGGUG CUGAUGU X GAA AAGCUCCU | AGGAGCUUU CACCGAAC |
| 3721 | AGUUCGGU CUGAUGU X GAA AAAGCUCC | GGAGCUUUC ACCGAACU |
| 3730 | UGGAGGUG CUGAUGU X GAA AGUUCGGU | ACCGAACUC CACCUCCA |
| 3736 | CAAACAUG CUGAUGU X GAA AGGUGGAG | CUCCACCUC CAUGUUUG |
| 3742 | AGUCCUCA CUGAUGU X GAA ACAUGGAG | CUCCAUGUU UGAGGACU |
| 3743 | UAGUCCUC CUGAUGU X GAA AACAUGAG | UCCAUGUUU GAGGACUA |
| 3751 | CCAGCUGA CUGAUGU X GAA AGUCCUCA | UGAGGACUA UCAGCUGG |
| 3753 | GUCCAGCU CUGAUGU X GAA AUAGUCCU | AGGACUAUC AGCUGGAC |
| 3765 | CAGAGUGC CUGAUGU X GAA AGUGUCCA | UGGACACUA GCACUCUG |
| 3771 | GCCCAGCA CUGAUGU X GAA AGUGCUAG | CUAGCACUC UGCUGGGC |
| 3781 | GCAAGGGG CUGAUGU X GAA AGCCCAGC | GCUGGGCUC CCCCUUGC |
| 3787 | GCUUCAGC CUGAUGU X GAA AGGGGGAG | CUCCCCCUU GCUGAAGC |
| 3799 | UCCAGGUG CUGAUGU X GAA ACCGCUUC | GAAGCGGUU CACCUGGA |
| 3800 | GUCCAGGU CUGAUGU X GAA AACCGCUU | AAGCGGUUC ACCUGGAC |
| 3829 | UCUUCAUG CUGAUGU X GAA AGGCCUUG | CAAGGCCUC CAUGAAGA |
| 3839 | CUCAAGUC CUGAUGU X GAA AUCUUCAU | AUGAAGAUA GACUUGAG |
| 3844 | CUAUUCUC CUGAUGU X GAA AGUCUAUC | GAUAGACUU GAGAAUAG |
| 3851 | UUACUCGC CUGAUGU X GAA AUUCUCAA | UUGAGAAUA GCGAGUAA |
| 3858 | CUUGCUUU CUGAUGU X GAA ACUCGCUA | UAGCGAGUA AAAGCAAG |
| 3878 | AGAUCGGA CUGAUGU X GAA AGUCCCGC | GCGGGACUU UCCGAUCU |
| 3879 | CAGAUCGG CUGAUGU X GAA AAGUCCCG | CGGGACUUU CCGAUCUG |
| 3880 | GCAGAUCG CUGAUGU X GAA AAAGUCCC | GGGACUUUC CGAUCUGC |
| 3885 | AUCGGAAA CUGAUGU X GAA AUCGGAAA | UUUCCGAUC UGCCGAGG |

Table VIII-continued

Mouse flt-1 VEGF Receptor-Hammerhead Ribozyme and Substrate Sequence

| nt. Position | HH Ribozyme | Substrate |
|---|---|---|
| 3901 | AGCUGGGC CUGAUGU X GAA AGCUGGGC | GCCCAGCUU CUGCUUCU |
| 3902 | AAGCUGGG CUGAUGU X GAA AAGCUGGG | CCCAGCUUC UGCUUCUC |
| 3907 | AGCUGGAG CUGAUGU X GAA AGCAGAAG | CUUCUGCUU CUCCAGCU |
| 3908 | CAGCUGGA CUGAUGU X GAA AAGCAGAA | UUCUGCUUC UCCAGCUG |
| 3910 | CACAGCUG CUGAUGU X GAA AGAAGCAG | CUGCUUCUC CAGCUGUG |
| 3926 | ACGGGCCU CUGAUGU X GAA AUGUGGCC | GGCCACAUC AGGCCCGU |
| 3949 | CCAGCUCA CUGAUGU X GAA AUUCAUCG | CGAUGAAUC UGAGCUGG |
| 3967 | AACAGCAG CUGAUGU X GAA ACUCCUUU | AAAGGAGUC CUGCUGUU |
| 3975 | GGGUGGAG CUGAUGU X GAA ACAGCAGG | CCUGCUGUU CUCCACCC |
| 3976 | GGGGUGGA CUGAUGU X GAA AACAGCAG | CUGCUGUUC UCCACCCC |
| 3978 | UGGGGGUG CUGAUGU X GAA AGAACAGC | GCUGUUCUC CACCCCCA |
| 3991 | CGGAGUUG CUGAUGU X GAA AGUCUGGG | CCCAGACUA CAACUCCG |
| 3997 | ACACCACG CUGAUGU X GAA AGUUGUAC | CUACAACUC CGUGGUGU |
| 4006 | AGGAGUAC CUGAUGU X GAA ACACCACG | CGUGGUGUU GUACUCCU |
| 4009 | GGGAGGAG CUGAUGU X GAA ACAACACC | GGUGUUGUA CUCCUCCC |
| 4012 | GCGGGGAG CUGAUGU X GAA AGUACAAC | GUUGUACUC CUCCCCGC |
| 4015 | CGGGCGGG CUGAUGU X GAA AGGAGUAC | GUACUCCUC CCCGCCCG |
| 4027 | AGAAGCUU CUGAUGU X GAA AGGCGGGC | GCCCGCCUA AAGCUUCU |
| 4033 | CUGGUGAG CUGAUGU X GAA AGCUUUAG | CUAAAGCUU CUCACCAG |
| 4034 | GCUGGUGA CUGAUGU X GAA AAGCUUUA | UAAAGCUUC UCACCAGC |
| 4036 | GGGCUGGU CUGAUGU X GAA AGAAGCUU | AAGCUUCUC ACCAGCCC |
| 4066 | AUGUAUAA CUGAUGU X GAA ACUGUCAG | CUGACAGUA UUAUACAU |
| 4068 | AGAUGUAU CUGAUGU X GAA AUACUGUC | GACAGUAUU AUACAUCU |
| 4069 | UAGAUGUA CUGAUGU X GAA AAUACUGU | ACAGUAUUA UACAUCUA |
| 4071 | CAUAGAUG CUGAUGU X GAA AUAAUACU | AGUAUUAUA CAUCUAUG |
| 4075 | AACUCAUA CUGAUGU X GAA AUGUAUAA | UUAUACAUC UAUGAGUU |
| 4077 | UAAACUCA CUGAUGU X GAA AGAUGUAU | AUACAUCUA UGAGUUUA |
| 4083 | UAGGUGUA CUGAUGU X GAA ACUCAUAG | CUAUGAGUU UACACCUA |
| 4084 | AUAGGUGU CUGAUGU X GAA AACUCAUA | UAUGAGUUU ACACCUAU |
| 4085 | AAUAGGUG CUGAUGU X GAA AAACUCAU | AUGUGUUUA CACCUAUU |
| 4091 | GAGCGGAA CUGAUGU X GAA AGGUGUAA | UUACACCUA UUCCGCUC |
| 4093 | UGGAGCGG CUGAUGU X GAA AUAGGUGU | ACACCUAUU CCGCUCCA |
| 4094 | GUGGAGCG CUGAUGU X GAA AAUAGGUG | CACCUAUUC CGCUCCAC |
| 4099 | CUCCUGUG CUGAUGU X GAA AGCGGAAU | AUUCCGCUC CACAGGAG |
| 4117 | GUCACGAA CUGAUGU X GAA AGCAGCUG | CAGCUGCUU UUCGUGAC |
| 4118 | GGUCACGA CUGAUGU X GAA AAGCAGCU | AGCUGCUUU UCGUGACC |

Table VIII-continued

Mouse flt-1 VEGF Receptor-Hammerhead Ribozyme and Substrate Sequence

| nt. Position | HH Ribozyme | Substrate |
|---|---|---|
| 4119 | AGGUCACG CUGAUGU X GAA AAAGCAGC | GCUGCUUUU CGUGACCU |
| 4120 | AAGGUCAC CUGAUGU X GAA AAAAGCAG | CUGCUUUUC GUGACCUU |
| 4128 | CACGAUUA CUGAUGU X GAA AGGUCACG | CGUGACCUU UAAUCGUG |
| 4129 | GACAGAUU CUGAUGU X GAA AAGGUCAC | GUGACCUUU AAUCGUGC |
| 4130 | AGCACGAU CUGAUGU X GAA AAAGGUCA | UGACCUUUA AUCGUGCU |
| 4133 | AAAAGCAC CUGAUGU X GAA AUUAAAGG | CCUUUAAUC GUGCUUUU |
| 4139 | AAACAAAA CUGAUGU X GAA AGCACGAU | AUCGUGCUU UUUUGUUU |
| 4140 | AAAACAAA CUGAUGU X GAA AAGCACGA | UCGUGCUUU UUUGUUUU |
| 4141 | AAAAACAA CUGAUGU X GAA AAAGCACG | CGUGCUUUU UUGUUUUU |
| 4142 | AAAAAACA CUGAUGU X GAA AAAAGCAC | GUGCUUUUU UGUUUUUU |
| 4143 | CAAAAAAC CUGAUGU X GAA AAAAAGCA | UGCUUUUUU GUUUUUUG |
| 4146 | AAACAAAA CUGAUGU X GAA ACAAAAAA | UUUUUUGUU UUUUGUUU |
| 4147 | AAAACAAA CUGAUGU X GAA AACAAAAA | UUUUUGUUU UUUGUUUU |
| 4148 | CAAAACAA CUGAUGU X GAA AAACAAAA | UUUUGUUUU UUGUUUUG |
| 4149 | ACAAAACA CUGAUGU X GAA AAAACAAA | UUUGUUUUU UGUUUUGU |
| 4150 | AACAAAAC CUGAUGU X GAA AAAAACAA | UUGUUUUUU GUUUUGUU |
| 4153 | ACAACAA CUGAUGU X GAA ACAAAAAA | UUUUUUGUU UUGUUUGU |
| 4154 | AACAAACA CUGAUGU X GAA AACAAAAA | UUUUUGUUU UGUUUGUU |
| 4155 | CAACAAAC CUGAUGU X GAA AAACAAAA | UUUUGUUUU GUUUGUUG |
| 4158 | CAACAACA CUGAUGU X GAA ACAAAACA | UGUUUUGUU UGUUGUUG |
| 4159 | GCAACAAC CUGAUGU X GAA AACAAAAC | GUUUUGUUU GUUGUUGC |
| 4162 | ACAGCAAC CUGAUGU X GAA ACAAACAA | UUGUUUGUU GUUGCUCU |
| 4165 | AAAACAGC CUGAUGU X GAA ACAACAAA | UUUGUUGUU GCUGUUUU |
| 4171 | UUAGUCAA CUGAUGU X GAA ACAGCAAC | GUUGCUGUU UUGACUAA |
| 4172 | GUUAGUCA CUGAUGU X GAA AACAGCAA | UUGCUGUUU UGACUAAC |
| 4173 | UGUUAGUC CUGAUGU X GAA AAACAGCA | UGCUGUUUU GACUAACA |
| 4178 | AUUCUUGU CUGAUGU X GAA AGUCAAAA | UUUUGACUA ACAAGAAU |
| 4189 | ACUGGGGU CUGAUGU X GAA ACAUUCUU | AAGAAUGUA ACCCCAGU |
| 4198 | ACGUCACU CUGAUGU X GAA ACUGGGGU | ACCCCAGUU AGUGACGU |
| 4199 | CACGUCAC CUGAUGU X GAA AACUGGGG | CCCCAGUUA GUGACGUG |
| 4216 | AACAAUAG CUGAUGU X GAA AUUCUUCA | UGAAGAAUA CUAUUGUU |
| 4219 | UCUAACAA CUGAUGU X GAA AGUAUUCU | AGAAUACUA UUGUUAGA |
| 4221 | UCUCUAAC CUGAUGU X GAA AUAGUAUU | AAUACUAUU GUUAGAGA |
| 4224 | AUUUCUCU CUGAUGU X GAA ACAAUAGU | ACUAUUGUU AGAGAAAU |
| 4225 | GAUUUCUC CUGAUGU X GAA AACAAUAG | CUAUUGUUA GAGAAAUC |
| 4233 | GCGGGGGG CUGAUGU X GAA AUUUCUCU | AGAGAAAUC CCCCCCGC |
| 4249 | GUUACCCU CUGAUGU X GAA AGGCUUUG | CAAAGCCUC AGGGUAAC |

Table VIII-continued

Mouse flt-1 VEGF Receptor-Hammerhead Ribozyme and Substrate Sequence

| nt. Position | HH Ribozyme | Substrate |
|---|---|---|
| 4255 | GUCCAGGU CUGAUGU X GAA ACCCUGAG | CUCAGGGUA ACCUGGAC |
| 4282 | GGUCGCCA CUGAUGU X GAA AGGCACCU | AGGUGCCUC UGGCGACC |
| 4323 | GCUGCAGG CUGAUGU X GAA AGGGUGGG | CCCACCCUC CCUGCAGC |
| 4341 | ACUGCCUC CUGAUGU X GAA AGUCCCAC | GUGGGACUA GAGGCAGU |
| 4350 | AAUGGGCU CUGAUGU X GAA ACUGCCUC | GAGGCAGUA AGCCCAUU |
| 4358 | CAUGAGCU CUGAUGU X GAA AUGGGCUU | AAGCCCAUU AGCUCAUG |
| 4359 | CCAUGAGC CUGAUGU X GAA AAUGGGCU | AGCCCAUUA GCUCAUGG |
| 4363 | GCAGCCAU CUGAUGU X GAA AGCUAAUG | CAUUAGCUC AUGGCUGC |
| 4387 | GAGAGACA CUGAUGU X GAA AGCAGGUC | GACCUGCUC UGUCUCUC |
| 4391 | AUAAGAGA CUGAUGU X GAA ACAGAGCA | UGCUCUGUC UCUCUUAU |
| 4393 | CCAUAAGA CUGAUGU X GAA AGACAGAG | CUCUGUCUC UCUUAUGG |
| 4395 | CUCCAUAA CUGAUGU X GAA AGAGACAG | CUGUCUCUC UUAUGGAG |
| 4397 | UCCUCCAU CUGAUGU X GAA AGAGAGAC | GUCUCUCUU AUGGAGGA |
| 4398 | UUCCUCCA CUGAUGU X GAA AAGAGAGA | UCUCUCUUA UGGAGGAA |
| 4445 | GCAUCCCA CUGAUGU X GAA AGCCUUUU | AAAAGGCUU UGGGAUGC |
| 4446 | CGCAUCCC CUGAUGU X GAA AAGCCUUU | AAAGGCUUU GGGAUGCG |
| 4456 | ACAGGACG CUGAUGU X GAA ACGCAUCC | GGAUGCGUC CGUCCUGU |
| 4460 | CUCCACAG CUGAUGU X GAA ACGGACGC | GCGUCCGUC CUGUGGAG |
| 4487 | GCAUAGCG CUGAUGU X GAA AGCCCCCU | AGGGGGCUC CGCUAUGC |
| 4492 | AAGUGGCA CUGAUGU X GAA AGCGGAGC | GCUCCGCUA UGCCACUU |
| 4500 | AGUCACUG CUGAUGU X GAA AGUGGCAU | AUGCCACUU CAGUGACU |
| 4501 | AAGUCACU CUGAUGU X GAA AAGUGGCA | UGCCACUUC AGUGACUU |
| 4509 | GGAGUGAG CUGAUGU X GAA AGUCACUG | CAGUGACUU CUCACUCC |
| 4510 | AGGAGUGA CUGAUGU X GAA AAGUCACU | AGUGACUUC UCACUCCU |
| 4512 | CCAGGAGU CUGAUGU X GAA AGAAGUCA | UGACUUCUC ACUCCUGG |
| 4516 | GAGGCCAG CUGAUGU X GAA AGUGAGAA | UUCUCACUC CUGGCCUC |
| 4524 | AAACAGCG CUGAUGU X GAA AGGCCAGG | CCUGGCCUC CGCUGUUU |
| 4531 | GGGCCCGA CUGAUGU X GAA ACAGCGGA | UCCGCUGUU UCGGGCCC |
| 4532 | GGGGCCCG CUGAUGU X GAA AACAGCGG | CCGCUGUUU CGGGCCCC |
| 4533 | GGGGGCCC CUGAUGU X GAA AAACAGCG | CGCUGUUUC GGGCCCCC |
| 4543 | CCUCUUGG CUGAUGU X GAA AGGGGGCC | GGCCCCCUU CCAAGAGG |
| 4544 | ACCUCUUG CUGAUGU X GAA AAGGGGGC | GCCCCCUUC CAAGAGGU |
| 4553 | UGCUCUGA CUGAUGU X GAA ACCUCUUG | CAAGAGGUA UCAGAGCA |
| 4555 | UCUGCUCU CUGAUGU X GAA AUACCUCU | AGAGGUAUC AGAGCAGA |
| 4577 | GUCUAGGA CUGAUGU X GAA ACGUCCCU | AGGGACGUU UCCUAGAC |
| 4578 | GGUCUAGG CUGAUGU X GAA AACGUCCC | GGGACGUUU CCUAGACC |

Table VIII-continued

Mouse flt-1 VEGF Receptor-Hammerhead Ribozyme and Substrate Sequence

| nt. Position | HH Ribozyme | Substrate |
|---|---|---|
| 4579 | UGGUCUAG CUGAUGU X GAA AAACGUCC | GGACGUUUC CUAGACCA |
| 4582 | CCCUGGUC CUGAUGU X GAA AGGAAACG | CGUUUCCUA GACCAGGG |
| 4598 | UUCCCGAG CUGAUGU X GAA ACAUGUGC | GCACAUGUU CUCGGGAA |
| 4599 | GUUCCCGA CUGAUGU X GAA AACAUGUG | CACAUGUUC UCGGGAAC |
| 4601 | UGGUUCCC CUGAUGU X GAA AGAACAUG | CAUGUUCUC GGGAACCA |
| 4614 | UUAAGAUU CUGAUGU X GAA ACUGUGGU | ACCACAGUU AAUCUUAA |
| 4615 | UUUAAGAU CUGAUGU X GAA AACUGUGG | CCACAGUUA AUCUUAAA |
| 4618 | AGAUUUAA CUGAUGU X GAA AUUAACUG | CAGUUAAUC UUAAAUCU |
| 4620 | AAAGAUUU CUGAUGU X GAA AGAUUAAC | GUUAAUCUU AAAUCUUU |
| 4621 | AAAAGAUU CUGAUGU X GAA AAGAUUAA | UUAAUCUUA AAUCUUUU |
| 4625 | CGGGAAAA CUGAUGU X GAA AUUUAAGA | UCUUAAAUC UUUUCCCG |
| 4627 | CCCGGGAA CUGAUGU X GAA AGAUUUAA | UUAAAUCUU UUCCCGGG |
| 4628 | UCCCGGGA CUGAUGU X GAA AAGAUUUA | UAAAUCUUU UCCCGGGA |
| 4629 | CUCCCGGG CUGAUGU X GAA AAAGAUUU | AAAUCUUUU CCCGGGAG |
| 4630 | ACUCCCGG CUGAUGU X GAA AAAAGAUU | AAUCUUUUC CCGGGAGU |
| 4639 | CAACAGAA CUGAUGU X GAA ACUCCCGG | CCGGGAGUC UUCUGUUG |
| 4641 | GACAACAG CUGAUGU X GAA AGACUCCC | GGGAGUCUU CUGUUGUC |
| 4642 | AGACAACA CUGAUGU X GAA AAGACUUC | GGAGUCUUC UGUUGUCU |
| 4646 | AAACAGAC CUGAUGU X GAA ACAGAAGA | UCUUCUGUU GUCUGUUU |
| 4649 | GGUAAACA CUGAUGU X GAA ACAACAGA | UCUGUUGUC UGUUUACC |
| 4653 | GGAUGGUA CUGAUGU X GAA ACAGACAA | UUGUCUGUU UACCAUCC |
| 4654 | UGGAUGGU CUGAUGU X GAA AACAGACA | UGUCUGUUU ACCAUCCA |
| 4655 | UUGGAUGG CUGAUGU X GAA AAACAGAC | GUCUGUUUA CCAUCCAA |
| 4660 | AUGCUUUG CUGAUGU X GAA AUGGUAAA | UUUACCAUC CAAAGCAU |
| 4669 | AUGUUAAA CUGAUGU X GAA AUGCUUUG | CAAAGCAUA UUUAACAU |
| 4671 | ACAUGUUA CUGAUGU X GAA AUAUGCUU | AAGCAUAUU UAACAUGU |
| 4672 | CACAUGUU CUGAUGU X GAA AAUAUGCU | AGCAUAUUU AACAUGUG |
| 4673 | ACACAUGU CUGAUGU X GAA AAAUAUGC | GCAUAUUUA ACAUGUGU |
| 4682 | CCCCCACU CUGAUGU X GAA ACACAUGU | ACAUGUGUC AGUGGGGG |
| 4698 | CAGAAGCC CUGAUGU X GAA AGCGCCAC | GUGGCGCUU GGCUUCUG |
| 4703 | GGCCUCAG CUGAUGU X GAA AGCCAAGC | GCUUGGCUU CUGAGGCC |
| 4704 | UGGCCUCA CUGAUGU X GAA AACGGAAG | CUUGGCUUC UGAGGCCA |
| 4720 | GAACUGAU CUGAUGU X GAA AUGGCUCU | AGAGCCAUC AUCAGUUC |
| 4723 | GAGGAACU CUGAUGU X GAA AUGAUGGC | GCCAUCAUC AGUUCCUC |
| 4727 | ACUAGAGG CUGAUGU X GAA ACUGAUGA | UCAUCAGUU CCUCUAGU |
| 4728 | CACUAGAG CUGAUGU X GAA AACUGAUG | CAUCAGUUC CUCUAGUG |
| 4731 | UCUCACUA CUGAUGU X GAA AGGAACUG | CAGUUCCUC UAGUGAGA |

Table VIII-continued

Mouse flt-1 VEGF Receptor-Hammerhead Ribozyme and Substrate Sequence

| nt. Position | HH Ribozyme | Substrate |
|---|---|---|
| 4733 | CAUCUCAC CUGAUGU X GAA AGAGGAAC | GUUCCUCUA GUGAGAUG |
| 4745 | AUGACCUC CUGAUGU X GAA AUGCAUCU | AGAUGCAUU GAGGUCAU |
| 4751 | UUGGGUAU CUGAUGU X GAA ACCUCAAU | AUUGAGGUC AUACCCAA |
| 4754 | AGCUUGGG CUGAUGU X GAA AUGACCUC | GAGGUCAUA CCCAAGCU |
| 4763 | AGGCCUGC CUGAUGU X GAA AGCUUGGG | CCCAAGCUU GCAGGCCU |
| 4777 | AGUAUGCG CUGAUGU X GAA AGGUCAGG | CCUGACCUU CGCAUACU |
| 4778 | CAGUAUGC CUGAUGU X GAA AAGGUCAG | CUGACCUUC GCAUACUG |
| 4783 | GUGAGCAG CUGAUGU X GAA AUGCGAAG | CUUCGCAUA CUGCUCAC |
| 4789 | CUCCCCGU CUGAUGU X GAA AGCAGUAU | AUACUGCUC ACGGGGAG |
| 4799 | GACCACUU CUGAUGU X GAA ACUCCCCG | CGGGGAGUU AAGUGGUC |
| 4800 | GGACCACU CUGAUGU X GAA AACUCCCC | GGGGAGUUA AGUGGUCC |
| 4807 | CCAAACUG CUGAUGU X GAA ACCACUUA | UAAGUGGUC CAGUUUGG |
| 4812 | CUAGGCCA CUGAUGU X GAA ACUGGACC | GGUCCAGUU UGGCCUAG |
| 4813 | ACUAGGCC CUGAUGU X GAA AACUGGAC | GUCCAGUUU GGCCUAGU |
| 4819 | AACCUUAC CUGAUGU X GAA AGGCCAAA | UUUGGCCUA GUAAGGUU |
| 4822 | GGCAACCU CUGAUGU X GAA ACUAGGCC | GGCCUAGUA AGGUUGCC |
| 4827 | CAGUAGGC CUGAUGU X GAA ACCUUACU | AGUAAGGUU GCCUACUG |
| 4832 | CCCAUCAG CUGAUGU X GAA AGGCAACC | GGUUGCCUA CUGAUGGG |
| 4843 | UGGCUUUU CUGAUGU X GAA AGCCCAUC | GAUGGGCUC AAAAGCCA |
| 4855 | CUGUUUAA CUGAUGU X GAA AUGUGGCU | AGCCACAUU UUAAACAG |
| 4856 | CCUGUUUA CUGAUGU X GAA AAUGUGGC | GCCACAUUU UAAACAGG |
| 4857 | ACCUGUUU CUGAUGU X GAA AAAUGUGG | CCACAUUUU AAACAGGU |
| 4858 | AACCUGUU CUGAUGU X GAA AAAAUGUG | CACAUUUUA AACAGGUU |
| 4866 | UGAGAUAA CUGAUGU X GAA ACCUGUUU | AAACAGGUU UUAUCUCA |
| 4867 | UUGAGAUA CUGAUGU X GAA AACCUGUU | AACAGGUUU UAUCUCAA |
| 4868 | CUUGAGAU CUGAUGU X GAA AAACCUGU | ACAGGUUUU AUCUCAAG |
| 4869 | ACUUGAGA CUGAUGU X GAA AAAACCUG | CAGGUUUUA UCUCAAGU |
| 4871 | AUACUUGA CUGAUGU X GAA AUAAAACC | GGUUUUAUC UCAAGUAU |
| 4873 | UAAUACUU CUGAUGU X GAA AGAUAAAA | UUUUAUCUC AAGUAUUA |
| 4878 | UAUAUUAA CUGAUGU X GAA ACUUGAGA | UCUCAAGUA UUAAUAUA |
| 4880 | UAUAUAUU CUGAUGU X GAA AUACUUGA | UCAAGUAUU AAUAUAUA |
| 4881 | CUAUAUAU CUGAUGU X GAA AAUACUUG | CAAGUAUUA AUAUAUAG |
| 4884 | UGUCUAUA CUGAUGU X GAA AUUAAUAC | GUAUUAAUA UAUAGACA |
| 4886 | CUUGUCUA CUGAUGU X GAA AUAUUAAU | AUUAAUAUA UAGACAAG |
| 4888 | GUCUUGUC CUGAUGU X GAA AUAUAUUA | UAAUAUAUA GACAAGAC |
| 4900 | UAAUGCAU CUGAUGU X GAA AGUGUCUU | AAGACACUU AUGCAUUA |

Table VIII-continued

Mouse flt-1 VEGF Receptor-Hammerhead Ribozyme and Substrate Sequence

| nt. Position | HH Ribozyme | Substrate |
|---|---|---|
| 4901 | AUAAUGCA CUGAUGU X GAA AAGUGUCU | AGACACUUA UGCAUUAU |
| 4907 | AACAGGAU CUGAUGU X GAA AUGCAUAA | UUAUGCAUU AUCCUGUU |
| 4908 | AAACAGGA CUGAUGU X GAA AAUGCAUA | UAUGCAUUA UCCGUUU |
| 4910 | UAAAACAG CUGAUGU X GAA AUAAUGCA | UGCAUUAUC CGUUUUA |
| 4915 | AUAUAUAA CUGAUGU X GAA ACAGGAUA | UAUCCUGUU UUAUAUAU |
| 4916 | GAUAUAUA CUGAUGU X GAA AACAGGAU | AUCCUGUUU UAUAUAUC |
| 4917 | GGAUAUAU CUGAUGU X GAA AAACAGGA | UCCUGUUUU AUAUAUCC |
| 4918 | UGGAUAUA CUGAUGU X GAA AAAACAGG | CCUGUUUUA UAUAUCCA |
| 4920 | AUUGGAUA CUGAUGU X GAA AUAAAACA | UGUUUUAUA UAUCCAAU |
| 4922 | UCAUUGGA CUGAUGU X GAA AUAUAAAA | UUUUAUAUA UCCAAUGA |
| 4924 | AUUCAUUG CUGAUGU X GAA AUAUAUAA | UUAUAUAUC CAAUGAAU |
| 4933 | CCCAGUUA CUGAUGU X GAA AUUCAUUG | CAAUGAAUA UAACUGGG |
| 4935 | GCCCCAGU CUGAUGU X GAA AUAUUCAU | AUGAAUAUA ACUGGGGC |
| 4948 | UGACUCUU CUGAUGU X GAA ACUCGCCC | GGGCGAGUU AAGAGUCA |
| 4949 | AUGACUCU CUGAUGU X GAA AACUCGCC | GGCGAGUUA AGAGUCAU |
| 4955 | UAGACCAU CUGAUGU X GAA ACUCUUAA | UUAAGAGUC AUGGUCUA |
| 4961 | CUUUUCUA CUGAUGU X GAA ACCAUGAC | GUCAUGGUC UAGAAAAG |
| 4963 | CCCUUUUC CUGAUGU X GAA AGACCAUG | CAUGGUCUA GAAAAGGG |
| 4974 | UACAGAGA CUGAUGU X GAA ACCCCUUU | AAAGGGGUU UCUCUGUA |
| 4975 | GUACAGAG CUGAUGU X GAA AACCCCUU | AAGGGGUUU CUCUGUAC |
| 4976 | GGUACAGA CUGAUGU X GAA AAACCCCU | AGGGGUUUC UCUGUACC |
| 4978 | UGGGUACA CUGAUGU X GAA AGAAACCC | GGGUUUCUC UGUACCCA |
| 4982 | GAUUUGGG CUGAUGU X GAA ACAGAGAA | UUCUCUGUA CCCAAAUC |
| 4990 | ACCAGCCC CUGAUGU X GAA AUUUGGGU | ACCCAAAUC GGGCUGGU |
| 4999 | CUUGGUCC CUGAUGU X GAA ACCAGCCC | GGGCUGGUU GGACCAAG |
| 5029 | GCUGGGAC CUGAUGU X GAA ACCACUCU | AGAGUGGUU GUCCCAGC |
| 5032 | AUAGCUGG CUGAUGU X GAA ACAACCAC | GUGGUUGUC CCAGCUAU |
| 5039 | AGUAACUA CUGAUGU X GAA AGCUGGGA | UCCCAGCUA UAGUUACU |
| 5041 | UUAGUAAC CUGAUGU X GAA AUAGCUGG | CCAGCUAUA GUUACUAA |
| 5044 | AGUUUAGU CUGAUGU X GAA ACUAUAGC | GCUAUAGUU ACUAAACU |
| 5045 | UAGUUUAG CUGAUGU X GAA AACUAUAG | CUAUAGUUA CUAAACUA |
| 5048 | GAGUAGUU CUGAUGU X GAA AGUAACUA | UAGUUACUA AACUACUC |
| 5053 | UGGGUGAG CUGAUGU X GAA AGUUUAGU | ACUAAACUA CUCACCCA |
| 5056 | CUUUGGGU CUGAUGU X GAA AGUAGUUU | AAACUACUC ACCCAAAG |
| 5066 | GAGGUCCC CUGAUGU X GAA ACUUUGGG | CCCAAAGUU GGGACCUC |
| 5074 | AAGCCAGU CUGAUGU X GAA AGGUCCCA | UGGGACCUC ACUGGCUU |
| 5082 | GUAAAGAG CUGAUGU X GAA AGCCAGUG | CACUGGCUU CUCUUUAC |

Table VIII-continued

Mouse flt-1 VEGF Receptor-Hammerhead Ribozyme and Substrate Sequence

| nt. Position | HH Ribozyme | Substrate |
|---|---|---|
| 5083 | AGUAAAGA CUGAUGU X GAA AAGCCAGU | ACUGGCUUC UCUUUACU |
| 5085 | GAAGUAAA CUGAUGU X GAA AGAAGCCA | UGGCUUCUC UUUACUUC |
| 5087 | AUGAAGUA CUGAUGU X GAA AGAGAAGC | GCUUCUCUU UACUUCAU |
| 5088 | GAUGAAGU CUGAUGU X GAA AAGAGAAG | CUUCUCUUU ACUUCAUC |
| 5089 | UGAUGAAG CUGAUGU X GAA AAAGAGAA | UUCUCUUUA CUUCAUCA |
| 5092 | CCAUGAUG CUGAUGU X GAA AGUAAAGA | UCUUUACUU CAUCAUGG |
| 5093 | UCCAUGAU CUGAUGU X GAA AAGUAAAG | CUUUACUUC AUCAUGGA |
| 5096 | AAAUCCAU CUGAUGU X GAA AUGAAGUA | UACUUCAUC AUGGAUUU |
| 5103 | GAUGGUGA CUGAUGU X GAA AUCCAUGA | UCAUGGAUU UCACCAUC |
| 5104 | GGAUGGUG CUGAUGU X GAA AAUCCAUG | CAUGGAUUU CACCAUCC |
| 5105 | GGGAUGGU CUGAUGU X GAA AAAUCCAU | AUGGAUUUC ACCAUCCC |
| 5111 | UGCCUUGG CUGAUGU X GAA AUGGUGAA | UUCACCAUC CCAAGGCA |
| 5122 | UCCUCUCA CUGAUGU X GAA ACUGCCUU | AAGGCAGUC UGAGAGGA |
| 5134 | AUACUCUU CUGAUGU X GAA AGCUCCUC | GAGGAGCUA AAGAGUAU |
| 5141 | UGGGCUGA CUGAUGU X GAA ACUCUUUA | UAAAGAGUA UCAGCCCA |
| 5143 | UAUGGGCU CUGAUGU X GAA AUACUCUU | AAGAGUAUC AGCCCAUA |
| 5151 | UUAAUAAA CUGAUGU X GAA AUGGGCUG | CAGCCCAUA UUUAUUAA |
| 5153 | GCUUAAUA CUGAUGU X GAA AUAUGGGC | GCCCAUAUU UAUUAAGC |
| 5154 | UGCUUAAU CUGAUGU X GAA AAUAUGGG | CCCAUAUUU AUUAAGCA |
| 5155 | GUGCUUAA CUGAUGU X GAA AAAUAUGG | CCAUAUUUA UUAAGCAC |
| 5157 | AAGUGCUU CUGAUGU X GAA AUAAAUAU | AUAUUUAUU AAGCACUU |
| 5158 | AAAGUGCU CUGAUGU X GAA AAUAAAUA | UAUUUAUUA AGCACUUU |
| 5165 | GGAGCAUA CUGAUGU X GAA AGUGCUUA | UAAGCACUU UAUGCUCC |
| 5166 | AGGAGCAU CUGAUGU X GAA AAGUGCUU | AAGCACUUU AUGCUCCU |
| 5167 | AAGGAGCA CUGAUGU X GAA AAAGUGCU | AGCACUUUA UGCUCCUU |
| 5172 | GUGCCAAG CUGAUGU X GAA AGCAUAAA | UUUAUGCUC CUUGGCAC |
| 5175 | GCUGUGCC CUGAUGU X GAA AGGAGCAU | AUGCUCCUU GGCACAGC |
| 5195 | GCAUAAAU CUGAUGU X GAA ACACAUCA | UGAUGUGUA AUUUAUGC |
| 5198 | CUUGCAUA CUGAUGU X GAA AUUACACA | UGUGUAAUU UAUGCAAG |
| 5199 | GCUUGCAU CUGAUGU X GAA AAUUACAC | GUGUAAUUU AUGCUUGC |
| 5200 | AGCUUGCA CUGAUGU X GAA AAAUUACA | UGUAAUUUA UGCAAGCU |
| 5209 | UGGAGAGG CUGAUGU X GAA AGCUUGCA | UGCAAGCUC CUCUCCA |
| 5213 | UAGCUGGA CUGAUGU X GAA AGGGAGCU | AGCUCCCUC UCCAGCUA |
| 5215 | CCUAGCUG CUGAUGU X GAA AGAGGGAG | CUCCCUCUC CAGCUAGG |
| 5221 | CUGAGUCC CUGAUGU X GAA AGCUGGAG | CUCCAGCUA GGACUCAG |
| 5227 | AAUAUCCU CUGAUGU X GAA AGUCCUAG | CUAGGACUC AGGAUAUU |

Table VIII-continued

Mouse flt-1 VEGF Receptor-Hammerhead Ribozyme and Substrate Sequence

| nt. Position | HH Ribozyme | Substrate |
|---|---|---|
| 5233 | UUGACUAA CUGAUGU X GAA AUCCUGAG | CUCAGGAUA UUAGUCAA |
| 5235 | CAUUGACU CUGAUGU X GAA AUAUCCUG | CAGGAUAUU AGUCAAUG |
| 5236 | UCAUUGAC CUGAUGU X GAA AAUAUCCU | AGGAUAUUA GUCAAUGA |
| 5239 | GGCUCAUU CUGAUGU X GAA ACUAAUAU | AUAUUAGUC AAUGAGCC |
| 5250 | UUCCUUUU CUGAUGU X GAA AUGGCUCA | UGAGCCAUC AAAAGGAA |
| 5273 | AAAUAAGA CUGAUGU X GAA AGGUUUUU | AAAAACCUA UCUUAUUU |
| 5275 | GAAAAUAA CUGAUGU X GAA AUAGGUUU | AAACCUAUC UUAUUUUC |
| 5277 | AUGAAAAU CUGAUGU X GAA AGAUAGGU | ACCUAUCUU AUUUUCAU |
| 5278 | GAUGAAAA CUGAUGU X GAA AAGAUAGG | CCUAUCUUA UUUUCAUC |
| 5280 | CAGAUGAA CUGAUGU X GAA AUAAGAUA | UAUCUUAUU UUCAUCUG |
| 5281 | ACAGAUGA CUGAUGU X GAA AAUAAGAU | AUCUUAUUU UCAUCUGU |
| 5282 | AACAGAUG CUGAUGU X GAA AAAUAAGA | UCUUAUUUU CAUCUGUU |
| 5283 | AAACAGAU CUGAUGU X GAA AAAAUAAG | CUUAUUUUC AUCUGUUU |
| 5286 | AUGAAACA CUGAUGU X GAA AUGAAAAU | AUUUUCAUC UGUUUCAU |
| 5290 | AGGUAUGA CUGAUGU X GAA ACAGAUGA | UCAUCUGUU UCAUACCU |
| 5291 | AAGGUAUG CUGAUGU X GAA AACAGAUG | CAUCUGUUU CAUACCUU |
| 5292 | CAAGGUAU CUGAUGU X GAA AAACAGAU | AUCUGUUUC AUACCUUG |
| 5295 | AGACAAGG CUGAUGU X GAA AUGAAACA | UGUUUCAUA CCUUGUCU |
| 5299 | CCCCAGAC CUGAUGU X GAA AGGUAUGA | UCAUACCUU GUCUGGGG |
| 5302 | AGACCCCA CUGAUGU X GAA ACAAGGUA | UACCUUGUC UGGGGUCU |
| 5309 | CGUCAUUA CUGAUGU X GAA ACCCCAGA | UCUGGGGUC UAAUGACG |
| 5311 | AUCGUCAU CUGAUGU X GAA AGACCCCA | UGGGGUCUA AUGACGAU |
| 5331 | CCCAUGUC CUGAUGU X GAA ACCCUGUU | AACAGGGUA GACAUGGG |
| 5350 | CCCUUUUC CUGAUGU X GAA ACCCUGUC | GACAGGGUA GAAAAGGG |
| 5367 | ACCCCAAA CUGAUGU X GAA AGCGGGCA | UGCCCGCUC UUUGGGGU |
| 5369 | AGACCCCA CUGAUGU X GAA AGAGCGGG | CCCGCUCUU UGGGGUCU |
| 5370 | UAGACCCC CUGAUGU X GAA AAGAGCGG | CCGCUCUUU GGGGUCUA |
| 5376 | CAUCUCUA CUGAUGU X GAA ACCCCAAA | UUUGGGGUC UAGAGAUG |
| 5378 | CUCAUCUC CUGAUGU X GAA AGACCCCA | UGGGGUCUA GAGAUGAG |
| 5395 | AUUUUAGA CUGAUGU X GAA ACCCAGGG | CCCUGGGUC UCUAAAAU |
| 5397 | CCAUUUUA CUGAUGU X GAA AGACCCAG | CUGGGUCUC UAAAAUGG |
| 5399 | AGCCAUUU CUGAUGU X GAA AGAGACCC | GGGUCUCUA AAAUGGCU |
| 5408 | UUCUAAGA CUGAUGU X GAA AGCCAUUU | AAAUGGCUC UCUUAGAA |
| 5410 | ACUUCUAA CUGAUGU X GAA AGAGCCAU | AUGGCUCUC UUAGAAGU |
| 5412 | CAACUUCU CUGAUGU X GAA AGAGAGCC | GGCUCUCUU AGAAGUUG |
| 5413 | ACAACUUC CUGAUGU X GAA AAGUGUGC | GCUCUCUUA GAAGUUGU |
| 5419 | GCACAUAC CUGAUGU X GAA ACUUCUAA | UUAGAAGUU GUAUGUGC |

Table VIII-continued

Mouse flt-1 VEGF Receptor-Hammerhead Ribozyme and Substrate Sequence

| nt. Position | HH Ribozyme | Substrate |
|---|---|---|
| 5422 | UUUGCACA CUGAUGU X GAA ACAACUUC | GAAGUUGUA UGUGCAAA |
| 5432 | CAGACCAU CUGAUGU X GAA AUUUGCAC | GUGCAAAUU AUGGUCUG |
| 5433 | ACAGACCA CUGAUGU X GAA AAUUUGCA | UGCAAAUUA UGGUCUGU |
| 5438 | AGCACACA CUGAUGU X GAA ACCAUAAU | AUUAUGGUC UGUGUGCU |
| 5447 | CACGACCU CUGAUGU X GAA AGCACACA | UGUGUGCUU AGGUCGUG |
| 5448 | GCACGACC CUGAUGU X GAA AAGCACAC | GUGUGCUUA GGUCGUGC |
| 5452 | GUGUGCAC CUGAUGU X GAA ACCUAAGC | GCUUAGGUC GUGCACAC |
| 5475 | CCAGCUGU CUGAUGU X GAA ACCGGCUC | GAGCCGGUC ACAGCUGG |
| 5497 | AAAGCAGC CUGAUGU X GAA AUUCAUCG | CGAUGAAUA GCUGCUUU |
| 5504 | CUCUCCCA CUGAUGU X GAA AGCAGCUA | UAGCUGCUU UGGGAGAG |
| 5505 | GCUCUCCC CUGAUGU X GAA AAGCAGCU | AGCUGCUUU GGGAGAGC |
| 5524 | UAAGUGGC CUGAUGU X GAA AGCAUGCU | AGCAUGCUA GCCACUUA |
| 5531 | AGAGAAUU CUGAUGU X GAA AGUGGCUA | UAGCCACUU AAUUCUCU |
| 5532 | CAGAGAAU CUGAUGU X GAA AAGUGGCU | AGCCACUUA AUUCUCUG |
| 5535 | GCUCAGAG CUGAUGU X GAA AUUAAGUG | CACUUAAUU CUCUGACC |
| 5536 | CGGUCAGA CUGAUGU X GAA AAUUAAGU | ACUUAAUUC UCUGACCG |
| 5538 | CCCGGUCA CUGAUGU X GAA AGAAUUAA | UUAAUUCUC UGACCGGG |
| 5554 | GUACCCAU CUGAUGU X GAA AUGCUGGC | GCCAGCAUC AUGGGUAC |
| 5561 | GGAGCAGG CUGAUGU X GAA ACCCAUGA | UCAUGGGUA CCUGCUCC |
| 5568 | ACACAGGG CUGAUGU X GAA AGCAGGUA | UACCUGCUC CCCUGUGU |
| 5577 | GGAUGGGG CUGAUGU X GAA ACACAGGG | CCCUGUGUA CCCCAUCC |
| 5584 | ACCUUAAG CUGAUGU X GAA AUGGGGUA | UACCCCAUC CUUAAGGU |
| 5587 | AAAACCUU CUGAUGU X GAA AGGAUGGG | CCCAUCCUU AAGGUUUU |
| 5588 | GAAAACCU CUGAUGU X GAA AAGGAUGG | CCAUCCUUA AGGUUUUC |
| 5593 | AGACAGAA CUGAUGU X GAA ACCUUAAG | CUUAAGGUU UUCUGUCU |
| 5594 | CAGACAGA CUGAUGU X GAA AACCUUAA | UUAAGGUUU UCUGUCUG |
| 5595 | UCAGACAG CUGAUGU X GAA AAACCUUA | UAAGGUUUU CUGUCUGA |
| 5596 | AUCAGACA CUGAUGU X GAA AAAACCUU | AAGGUUUUC UGUCUGAU |
| 5600 | UCUCAUCA CUGAUGU X GAA ACAGAAAA | UUUUCUGUC UGAUGAGA |
| 5627 | UCAGUGGG CUGAUGU X GAA AUUGCACU | AGUGCAAUC CCACUGA |
| 5660 | UGCACCAA CUGAUGU X GAA AGCCACAG | CUGUGGCUC UUGGUGCA |
| 5662 | AGUGCACC CUGAUGU X GAA AGAGCCAC | GUGGCUCUU GGUGCACU |
| 5671 | UGGCUGGU CUGAUGU X GAA AGUGCACC | GGUGCACUC ACCAGCCA |
| 5685 | UACUUGUC CUGAUGU X GAA AGUCCUGG | CCAGGACUA GACAAGUA |
| 5693 | CCCUUUCC CUGAUGU X GAA ACUUGUCU | AGACAAGUA GGAAAGGG |
| 5704 | GUGGCUAG CUGAUGU X GAA AGCCCUUU | AAAGGGCUU CUAGCCAC |

Table VIII-continued

Mouse flt-1 VEGF Receptor-Hammerhead Ribozyme and Substrate Sequence

| nt. Position | HH Ribozyme | Substrate |
|---|---|---|
| 5705 | UGUGGCUA CUGAUGU X GAA AAGCCCUU | AAGGGCUUC UAGCCACA |
| 5707 | AGUGUGGC CUGAUGU X GAA AGAAGCCC | GGGCUUCUA GCCACACU |
| 5731 | CCCUACCU CUGAUGU X GAA AUUUUCUU | AAGAAAAUC AGGUAGGG |
| 5736 | GCCAGCCC CUGAUGU X GAA ACCUGAUU | AAUCAGGUA GGGCUGGC |
| 5754 | UGGACAAA CUGAUGU X GAA AUGUCUUU | AAAGACAUC UUUGUCCA |
| 5756 | AAUGGACA CUGAUGU X GAA AGAUGUCU | AGACAUCUU UGUCCAUU |
| 5757 | GAAUGGAC CUGAUGU X GAA AAGAUGUC | GACAUCUUU GUCCAUUC |
| 5760 | UGCGAAUG CUGAUGU X GAA ACAAAGAU | AUCUUUGUC CAUUCGCA |
| 5764 | CUUUUGCG CUGAUGU X GAA AUGGACAA | UUGUCCAUU CGCAAAAG |
| 5765 | GCUUUUGC CUGAUGU X GAA AAUGGACA | UGUCCAUUC GCAAAAGC |
| 5775 | GCCGACAA CUGAUGU X GAA AGCUUUUG | CAAAAGCUC UUGUCGGC |
| 5777 | CAGCCGAC CUGAUGU X GAA AGAGCUUU | AAAGCUCUU GUCGGCUG |
| 5780 | CUGCAGCC CUGAUGU X GAA ACAAGAGC | GCUGUUGUC GGCUGCAG |
| 5794 | GCCUGACU CUGAUGU X GAA ACACACUG | CAGUGUGUA AGUCAGGC |
| 5798 | CAUCGCCU CUGAUGU X GAA ACUUACAC | GUGUAAGUC AGGCGAUG |
| 5818 | UUCUCUGG CUGAUGU X GAA AGCCUGUC | CAGAGGCUA CCAGAGAA |
| 5852 | GGAUGAGA CUGAUGU X GAA ACCUCAGG | CCUGAGGUU UCUCAUCC |
| 5853 | UGGAUGAG CUGAUGU X GAA AACCUCAG | CUGAGGUUU CUCAUCCA |
| 5854 | CUGGAUGA CUGAUGU X GAA AAACCUCA | UGAGGUUUC UCAUCCAG |
| 5856 | AUCUGGAU CUGAUGU X GAA AGAAACCU | AGGUUUCUC AUCCAGAU |
| 5859 | GAUAUCUG CUGAUGU X GAA AUGAGAAA | UUUCUCAUC CAGAUAUC |
| 5865 | UUGCUGGA CUGAUGU X GAA AUCUGGAU | AUCCAGAUA UCCAGCAA |
| 5867 | AAUUGCUG CUGAUGU X GAA AUAUCUGG | CCAGAUAUC CAGCAAUU |
| 5875 | CACCCCCC CUGAUGU X GAA AUUGCUGG | CCAGCAAUU GGGGGGUG |
| 5896 | GGACCAUC CUGAUGU X GAA AUGGUCUU | AAGACCAUA GAUGGUCC |
| 5903 | UAAUACAG CUGAUGU X GAA ACCAUCUA | UAGAUGGUC CUGUAUUA |
| 5908 | AGGAAUAA CUGAUGU X GAA ACAGGACC | GGUCCUGUA UUAUUCCG |
| 5910 | AUCGGAAU CUGAUGU X GAA AUACAGGA | UCCUGUAUU AUUCCGAU |
| 5911 | AAUCGGAA CUGAUGU X GAA AAUACAGG | CCUGUAUUA UUCCGAUU |
| 5913 | AAAAUCGG CUGAUGU X GAA AUAAUACA | UGUAUUAUU CCGAUUUU |
| 5914 | UAAAAUCG CUGAUGU X GAA AAUAAUAC | GUAUUAUUC CGAUUUUA |
| 5919 | AUUAUUAA CUGAUGU X GAA AUCGGAAU | AUUCCGAUU UUAAUAAU |
| 5920 | GAUUAUUA CUGAUGU X GAA AAUCGGAA | UUCCGAUUU UAAUAAUC |
| 5921 | AGAUUAUU CUGAUGU X GAA AAAUCGGA | UCCGAUUUU AAUAAUCU |
| 5922 | UAGAUUAU CUGAUGU X GAA AAAAUCGG | CCGAUUUUA AUAAUCUA |
| 5925 | AAUUAGAU CUGAUGU X GAA AUUAAAAU | AUUUUAAUA AUCUAAUU |
| 5928 | ACGAAUUA CUGAUGU X GAA AUUAUUAA | UUAAUAAUC UAAUUCGU |

Table VIII-continued

Mouse flt-1 VEGF Receptor-Hammerhead Ribozyme and Substrate Sequence

| nt. Position | HH Ribozyme | Substrate |
|---|---|---|
| 5930 | UCACGAAU CUGAUGU X GAA AGAUUAUU | AAUAAUCUA AUUCGUGA |
| 5933 | UGAUCACG CUGAUGU X GAA AUUAGAUU | AAUCUAAUU CGUGAUCA |
| 5934 | AUGAUCAC CUGAUGU X GAA AAUUAGAU | AUCUAAUUC GUGAUCAU |
| 5940 | CUCUUAAU CUGAUGU X GAA AUCACGAA | UUCGUGAUC AUUAAGAG |
| 5943 | AGUCUCUU CUGAUGU X GAA AUGAUCAC | GUGAUCAUU AAGAGACU |
| 5944 | AAGUCUCU CUGAUGU X GAA AAUGAUCA | UGAUCAUUA AGAGACUU |
| 5952 | AUUUACUA CUGAUGU X GAA AGUCUCUU | AAGAGACUU UAGUAAAU |
| 5953 | CAUUUACU CUGAUGU X GAA AAGUCUCU | AGAGACUUU AGUAAAUG |
| 5954 | ACAUUUAC CUGAUGU X GAA AAAGUCUC | GAGACUUUA GUAAAUGU |
| 5957 | GGGACAUU CUGAUGU X GAA ACUAAAGU | ACUUUAGUA AAUGUCCC |
| 5963 | GGAAAAGG CUGAUGU X GAA ACAUUUAC | GUAAAUGUC CCUUUUCC |
| 5967 | UGUGGGAA CUGAUGU X GAA AGGGACAU | AUGUCCCUU UUCCCACA |
| 5968 | UUGUGGGA CUGAUGU X GAA AAGGGACA | UGUCCCUUU UCCCACAA |
| 5969 | UUUGUGGG CUGAUGU X GAA AAAGGGAC | GUCCCUUUU CCCACAAA |
| 5970 | UUUUGUGG CUGAUGU X GAA AAAAGGGA | UCCCUUUUC CCACAAAA |
| 5981 | CUUUUCUU CUGAUGU X GAA ACUUUUGU | ACAAAAGUA AAGAAAAG |
| 5992 | AAUCCCGA CUGAUGU X GAA AGCUUUUC | GAAAAGCUA UCGGGAUU |
| 5994 | AGAAUCCC CUGAUGU X GAA AUAGCUUU | AAAGCUAUC GGGAUUCU |
| 6000 | AACCAGAG CUGAUGU X GAA AUCCCGAU | AUCGGGAUU CUCUGGUU |
| 6001 | GAACCAGA CUGAUGU X GAA AAUCCCGA | UCGGGAUUC UCUGGUUC |
| 6003 | CAGAACCA CUGAUGU X GAA AGAAUCCC | GGGAUUCUC UGGUUCUG |
| 6008 | UUAAGCAG CUGAUGU X GAA ACCAGAGA | UCUCUGGUU CUGCUUAA |
| 6009 | UUUAAGCA CUGAUGU X GAA AACCAGAG | CUCUGGUUC UGCUUAAA |
| 6014 | AAGUCUUU CUGAUGU X GAA AGCAGAAC | GUUCUGCUU AAAGACUU |
| 6015 | UAAGUCUU CUGAUGU X GAA AAGCAGAA | UUCUGCUUA AAGACUUA |
| 6022 | CCAAAGCU CUGAUGU X GAA AGUCUUUA | UAAAGACUU AGCUUUGG |
| 6023 | UCCAAAGC CUGAUGU X GAA AAGUCUUU | AAAGACUUA GCUUUGGA |
| 6027 | AGGCUCCA CUGAUGU X GAA AGCUAAGU | ACUUAGCUU UGGAGCCU |
| 6028 | UAGGCUCC CUGAUGU X GAA AAGCUAAG | CUUAGCUUU GGAGCCUA |
| 6036 | AACUUUCA CUGAUGU X GAA AGGCUCCA | UGGAGCCUA UGAAAGUU |
| 6044 | GGCUGAUC CUGAUGU X GAA ACUUUCAU | AUGAAAGUU GAUCAGCC |

Where "X" represents stem II region of a HH ribozyme (Hertel et al., 1992 Nucleic Acids Res. 20 3252). The length of stem II may be ≥ 2 base-pairs.

TABLE IX

Mouse flt1 VEGF Receptor-Hairpin Ribozyme and Substrate Sequence

| nt. Position | HP Ribozyme | Substrate |
|---|---|---|
| 33 | GUCCCAGC AGAA GACCAU ACCAGAGAAACACACGUUGUGGUACAUUACCUGGUA | AUGGUCA GCU GCUGGGAC |
| 36 | GGUGUCCC AGAA CCUGAC ACCAGAGAAACACACGUUGUGGUACAUUACCUGGUA | GUCAGCU GCU GGGACACC |
| 50 | UAAGGCAA AGAA GCGGUG ACCAGAGAAACACACGUUGUGGUACAUUACCUGGUA | CACCGCG GUC UUGCCUUA |
| 67 | GACACCCG AGAA GCGCGU ACCAGAGAAACACACGUUGUGGUACAUUACCUGGUA | ACGCGCU GCU CGGGUGUC |
| 79 | CUGUGAGA AGAA GACACC ACCAGAGAAACACACGUUGUGGUACAUUACCUGGUA | GGUCUCU GCU UCUCACAG |
| 166 | GAAAGAGA AGAA GGCCUG ACCAGAGAAACACACGUUGUGGUACAUUACCUGGUA | CAGGCCA GAC UCUCUUUC |
| 197 | CAUGAGUG AGAA GCCUCC ACCAGAGAAACACACGUUGUGGUACAUUACCUGGUA | GGAGGCA GCC CACUCAUG |
| 214 | CGGUCGUG AGAA GAGACC ACCAGAGAAACACACGUUGUGGUACAUUACCUGGUA | GGUCUCU GCC CACGACCG |
| 266 | CUCCCACA AGAA GAUGGG ACCAGAGAAACACACGUUGUGGUACAUUACCUGGUA | CCCAUCG GCC UGUGGGAG |
| 487 | GGAUGAUG AGAA GUCUUC ACCAGAGAAACACACGUUGUGGUACAUUACCUGGUA | GAAGACA GCU CAUCAUCC |
| 501 | CGUCACCC AGAA GGGGAU ACCAGAGAAACACACGUUGUGGUACAUUACCUGGUA | AUCCCCU GCC GGGUGACG |
| 566 | CUUUGCCC AGAA GGGGUA ACCAGAGAAACACACGUUGUGGUACAUUACCUGGUA | UACCCCU GAU GGGCAAAG |
| 640 | CGCAGUUC AGAA GUCCUA ACCAGAGAAACACACGUUGUGGUACAUUACCUGGUA | UAGGACU GCU GAACUGCG |
| 691 | GCCGAUGG AGAA GAUAGU ACCAGAGAAACACACGUUGUGGUACAUUACCUGGUA | ACUAUCU GAC CCAUCGGC |
| 703 | UUGUAUUG AGAA GCCGAU ACCAGAGAAACACACGUUGUGGUACAUUACCUGGUA | AUCGGCA GAC CAAUACAA |
| 736 | CUGGGCUC AGAA GGCGUA ACCAGAGAAACACACGUUGUGGUACAUUACCUGGUA | UACGCCC GCC GAGCCCAG |
| 754 | GCCCGUGG AGAA GUCUCA ACCAGAGAAACACACGUUGUGGUACAUUACCUGGUA | UGAGACU GCU CCACGGGC |
| 766 | GGACAAGA AGAA GCCCGU ACCAGAGAAACACACGUUGUGGUACAUUACCUGGUA | ACGGGCA GAC UCUUGUCC |
| 871 | UCCGGUCA AGAA GCUGCC ACCAGAGAAACACACGUUGUGGUACAUUACCUGGUA | GGCAGCG GAU UGACCGGA |
| 960 | CUUCACGC AGAA GGUGUA ACCAGAGAAACACACGUUGUGGUACAUUACCUGGUA | UACACCU GUC GCGUGAAG |
| 988 | UGUUGAAA AGAA GGAACG ACCAGAGAAACACACGUUGUGGUACAUUACCUGGUA | CGUUCCA GUC UUUCAACA |
| 1051 | CCUGCACC AGAA GCUUCC ACCAGAGAAACACACGUUGUGGUACAUUACCUGGUA | GGAAGCA GCC GGUGCAGG |
| 1081 | GCCGAUAG AGAA GUCUUC ACCAGAGAAACACACGUUGUGGUACAUUACCUGGUA | GAAGACG GUC CUAUCGGC |
| 1090 | UCAUGGAC AGAA GAUAGG ACCAGAGAAACACACGUUGUGGUACAUUACCUGGUA | CCUAUCG GCU GUCCAUGA |
| 1093 | CUUUCAUG AGAA GCCGAU ACCAGAGAAACACACGUUGUGGUACAUUACCUGGUA | AUCGGCU GUC CAUGAAAG |
| 1169 | AAAUAGCG AGAA GACUUC ACCAGAGAAACACACGUUGUGGUACAUUACCUGGUA | GAAGUCU GCU CGCUAUUU |
| 1315 | UUUCGUAG AGAA GAGGUU ACCAGAGAAACACACGUUGUGGUACAUUACCUGGUA | AACCUCA GAU CUACGAAA |
| 1363 | UGCUGCCC AGAA GAUAGA ACCAGAGAAACACACGUUGUGGUACAUUACCUGGUA | UCUAUCC GCU GGGCAGCA |
| 1604 | GUCUGAGA AGAA GCCACC ACCAGAGAAACACACGUUGUGGUACAUUACCUGGUA | GGUGGCU GAC UCUCAGAC |
| 1612 | UUCCAGGG AGAA GAGAGU ACCAGAGAAACACACGUUGUGGUACAUUACCUGGUA | ACUCUCA GAC CCCUGGAA |
| 1629 | GGCCCGGC AGAA GUAGAU ACCAGAGAAACACACGUUGUGGUACAUUACCUGGUA | AUCUACA GCU GCCGGGCC |
| 1632 | GAAGGCCC AGAA GCUGUA ACCAGAGAAACACACGUUGUGGUACAUUACCUGGUA | UACAGCU GCC GGGCCUUC |
| 1688 | UUCGGCAC AGAA GUGACA ACCAGAGAAACACACGUUGUGGUACAUUACCUGGUA | UGUCACA GAU GUGCCGAA |
| 1730 | UCUCCUUC AGAA GGCAUC ACCAGAGAAACACACGUUGUGGUACAUUACCUGGUA | GAUGCCA GCC GAAGGAGA |
| 1753 | CCACACAG AGAA GUUUCA ACCAGAGAAACACACGUUGUGGUACAUUACCUGGUA | UGAAACU GUC CUGUGUGG |
| 2017 | GGuUUUGA AGAA GGUGUG ACCAGAGAAACACACGUUGUGGUACAUUACCUGGUA | CACACCU GCU UCAAAACC |
| 2101 | ACCAAGUG AGAA GAGGCG ACCAGAGAAACACACGUUGUGGUACAUUACCUGGUA | CGCCUCA GAU CACUUGGU |

TABLE IX-continued

Mouse flt1 VEGF Receptor-Hairpin Ribozyme and Substrate Sequence

| nt. Position | HP Ribozyme | Substrate |
|---|---|---|
| 2176 | UUUCAAUA AGAA GCGUGC ACCAGAGAAACACACGUUGUGGUACAUUACCUGGUA | GCACGCU GUU UAUUGAAA |
| 2258 | GUGAGGUA AGAA GCGCUU ACCAGAGAAACACACGUUGUGGUACAUUACCUGGUA | AAGCGCA GCC UACCUCAC |
| 2305 | UGAGCGUG AGAA GCUCCA ACCAGAGAAACACACGUUGUGGUACAUUACCUGGUA | UGGAGCU GAU CACGCUCA |
| 2383 | CGGAAGAA AGAA GCUUCA ACCAGAGAAACACACGUUGUGGUACAUUACCUGGUA | UGAAGCG GUC UUCUUCCG |
| 2405 | GACAGGUA AGAA GUCUUU ACCAGAGAAACACACGUUGUGGUACAUUACCUGGUA | AAAGACA GAC UACCUGUC |
| 2432 | GGAACUUC AGAA GGGUCC ACCAGAGAAACACACGUUGUGGUACAUUACCUGGUA | GGACCCA GAU GAAGUUCC |
| 2464 | CAUAGGGC AGAA GUUCAC ACCAGAGAAACACACGUUGUGGUACAUUACCUGGUA | GUGAACG GCU GCCCUAUG |
| 2467 | CAUCAUAG AGAA GCCGUU ACCAGAGAAACACACCUUGUGGUACAUUACCUGGUA | AACGGCU GCC CUAUGAUG |
| 2592 | CACAGUCC AGAA GGUGGG ACCAGAGAAACACACGUUGUGGUACAUUACCUGGUA | CCCACCU GCC GGACUGUG |
| 2596 | CAGCCACA AGAA GGCAGG ACCAGAGAAACACACGUUGUGGUACAUUACCUGGUA | CCUGCCG GAC UGUGGGUG |
| 2653 | GUUCGGUC AGAA GAGCUU ACCAGAGAAACACACGUUGUGGUACAUUACCUGGUA | AAGCUCU GAU GACCGAAC |
| 2743 | CGAUCACC AGAA GAGGCC ACCAGAGAAACACACGUUGUGGUACAUUACCUGGUA | GGCCUCU GAU GGUGAUCG |
| 2779 | GGUAGUUG AGAA GGUUUC ACCAGAGAAACACACGUUGUGGUACAUUACCUGGUA | GAAACCU GUC CAACUACC |
| 2814 | CUUGUUGA AGAA GAAUAA ACCAGAGAAACACACGUUGUGGUACAUUACCUGGUA | UUAUUCU GUC UCAACAAG |
| 2831 | AUAUGCAA AGAA GCGUCC ACCAGAGAAACACACGUUGUGGUACAUUACCUGGUA | GGACGCA GCC UUGCAUAU |
| 2895 | ACUGUCUA AGAA GGGCUU ACCAGAGAAACACACGUUGUGGUACAUUACCUGGUA | AAGCCCC GCC UAGACAGU |
| 2913 | GACACUUG AGAA GCUGAC ACCAGAGAAACACACGUUGUGGUACAUUACCUGGUA | GUCAGCA GCU CAAGUGUC |
| 2928 | GAAGCUGG AGAA GGUGAC ACCAGAGAAACACACGUUGUGGUACAUUACCUGGUA | GUCACCA GCU CCAGCUUC |
| 2934 | UUCAGGGA AGAA GGAGCU ACCAGAGAAACACACGUUGUGGUACAUUACCUGGUA | AGCUCCA GCU UCCCUGAA |
| 3001 | UGGUGAGG AGAA GCUUGG ACCAGAGAAACACACGUUGUGGUACAUUACCUGGUA | CCAAGCA GCC CCUCACCA |
| 3022 | UGUAGGAA AGAA GGUCUU ACCAGAGAAACACACGUUGUGGUACAUUACCUGGUA | AAGACCU GAU UUCCUACA |
| 3033 | CACUUGGA AGAA GUAGGA ACCAGAGAAACACACGUUGUGGUACAUUACCUGGUA | UCCUACA GUU UCCAAGUG |
| 3064 | UUCUGGAG AGAA GAAACU ACCAGAGAAACACACGUUGUGGUACAUUACCUGGUA | AGUUUCU GUC CUCCAGAA |
| 3179 | CUCACAUA AGAA GGGUUC ACCAGAGAAACACACGUUGUGGUACAUUACCUGGUA | GAACCCU GAU UAUGUGAG |
| 3357 | CUUCAGGC AGAA GCAGAA ACCAGAGAAACACACGUUGUGGUACAUUACCUGGUA | UUCUGCA GCC GCCUGAAG |
| 3360 | UUCCUUCA AGAA GCUGCA ACCAGAGAAACACACGUUGUGGUACAUUACCUGGUA | UGCAGCC GCC UGAAGGAA |
| 3379 | GGGUUCUC AGAA GCAUGC ACCAGAGAAACACACGUUGUGGUACAUUACCUGGUA | GCAUGCG GAU GAGAACCC |
| 3463 | GUUCAGCA AGAA GGGGCC ACCAGAGAAACACACGUUGUGGUACAUUACCUGGUA | GGCCCCG GUU UGCUGAAC |
| 3496 | UGGCUUGA AGAA GGUCAC ACCAGAGAAACACACGUUGUGGUACAUUACCUGGUA | GUGACCU GCU UCAAGCCA |
| 3553 | UGUUUCUA AGAA GUAUGG ACCAGAGAAACACACGUUGUGGUACAUUACCUGGUA | CCAUACU GAC UAGAAACA |
| 3615 | AUCUGCAA AGAA GUCCUU ACCAGAGAAACACACGUUGUGGUACAUUACCUGGUA | AAGGACG GCU UUGCAGAU |
| 3623 | AAAUGUGG AGAA GCAAAG ACCAGAGAAACACACGUUGUGGUACAUUACCUGGUA | CUUUGCA GAU CCACAUUU |
| 3650 | CUCACAUC AGAA GAGCUU ACCAGAGAAACACACGUUGUGGUACAUUACCUGGUA | AAGCUCU GAU GAUGUGAG |
| 3754 | UAGUGUCC AGAA GAUAGU ACCAGAGAAACACACGUUGUGGUACAUUACCUGGUA | ACUAUCA GCU GGACACUA |
| 3772 | GGGAGCCC AGAA GAGUGC ACCAGAGAAACACACGUUGUGGUACAUUACCUGGUA | GCACUCU GCU GGGCUCCC |
| 3796 | UCCAGGUG AGAA GCUUCA ACCAGAGAAACACACGUUGUGGUACAUUACCUGGUA | UGAAGCG GUU CACCUGGA |
| 3881 | CUCGGCAG AGAA GAAAGU ACCAGAGAAACACACGUUGUGGUACAUUACCUGGUA | ACUUUCC GAU CUGCCGAG |

TABLE IX-continued

Mouse flt1 VEGF Receptor-Hairpin Ribozyme and Substrate Sequence

| nt. Position | HP Ribozyme | Substrate |
|---|---|---|
| 3886 | UGGGCCUC AGAA GAUCGG ACCAGAGAAACACACGUUGUGGUACAUUACCUGGUA | CCGAUCU GCC GAGGCCCA |
| 3897 | GAAGCAGA AGAA GGGCCU ACCAGAGAAACACACGUUGUGGUACAUUACCUGGUA | AGGCCCA GCU UCUGCUUC |
| 3903 | GCUGGAGA AGAA GAAGCU ACCAGAGAAACACACGUUGUGGUACAUUACCUGGUA | AGCUUCU GCU UCUCCAGC |
| 3912 | GUGGCCAC AGAA GGAGAA ACCAGAGAAACACACGUUGUGGUACAUUACCUGGUA | UUCUCCA GCU GUGGCCAC |
| 3969 | UGGAGAAC AGAA GGACUC ACCAGAGAAACACACGUUGUGGUACAUUACCUGGUA | GAGUCCU GCC GUUCUCCA |
| 3972 | GGGUGGAG AGAA GCAGGA ACCAGAGAAACACACGUUGUGGUACAUUACCUGGUA | UCCUGCU GUU CUCCACCC |
| 3986 | GAGUUGUA AGAA GGGGGU ACCAGAGAAACACACGUUGUGGUACAUUACCUGGUA | ACCCCCA GAC UACAACUC |
| 4018 | UUUAGGCG AGAA GGGAGG ACCAGAGAAACACACGUUGUGGUACAUUACCUGGUA | CCUCCCC GCC CGCCUAAA |
| 4022 | AAGCUUUA AGAA GGCGGG ACCAGAGAAACACACGUUGUGGUACAUUACCUGGUA | CCCGCCC GCC UAAAGCCU |
| 4040 | GUUGUCGG AGAA GGUGAG ACCAGAGAAACACACGUUGUGGUACAUUACCUGGUA | CUCACCA GCC CCGACAAC |
| 4053 | CUGUCAGG AGAA GGUUGU ACCAGAGAAACACACGUUGUGGUACAUUACCUGGUA | ACAACCA GCC CCUGACAG |
| 4095 | UCCUGUGG AGAA GAAUAG ACCAGAGAAACACACGUUGUGGUACAUUACCUGGUA | CUAUUCC GCU CCACAGGA |
| 4110 | CGAAAGC AGAA GGCUCC ACCAGAGAAACACACGUUGUGGUACAUUACCUGGUA | GGAGCCA GCU GCUUUUCG |
| 4113 | UCACGAAA AGAA GCUGGC ACCAGAGAAACACACGUUGUGGUACAUUACCUGGUA | GCCAGCU GGU UUUCGUGA |
| 4168 | UUAGUCAA AGAA GCAACA ACCAGAGAAACACACGUUGUGGUACAUUACCUGGUA | UGUUGCU GUU UUGACUAA |
| 4290 | GGUGGCG AGAA GUCGCC ACCAGAGAAACACACGUUGUGGUACAUUACCUGGUA | CGCGACC GCC CGCCCACC |
| 4294 | GGCCGGUG AGAA GGCGGU ACCAGAGAAACACACGUUGUGGUACAUUACCUGGUA | ACCGCCC GCC CACCGGCC |
| 4329 | AGUCCCAC AGAA GCAGGG ACCAGAGAAACACACGUUGUGGUACAUUACCUGGUA | CCCUGCA GCU GUGGGACU |
| 4378 | CAGAGCAG AGAA GUGCAU ACCAGAGAAACACACGUUGUGGUACAUUACCUGGUA | AUGCACU GAC CUGCUCUG |
| 4383 | AGAGACAG AGAA GGUCAG ACCAGAGAAACACACCUUGUGGUACAUUACCUGGUA | CUGACCU GCU CUGUCUCU |
| 4388 | AUAAGAGA AGAA GAGCAG ACCAGAGAAACACACGUUGUGGUACAUUACCUGGUA | CUGCUCU GUC UCUCUUAU |
| 4457 | CUCCACAG AGAA GACGCA ACCAGAGAAACACACGUUGUGGUACAUUACCUGGUA | UGCGUCC GUC CUGUGGAG |
| 4525 | CCCGAAAC AGAA GACGCC ACCAGAGAAACACACGUUGUGGUACAUUACCUGGUA | GGCCUCC GCU GUUUCGGG |
| 4528 | GGGCCCGA AGAA GCGGAG ACCAGAGAAACACACGUUGUGGUACAUUACCUGGUA | CUCCGCU GUU UCGGGCCC |
| 4643 | AAACAGAC AGAA GAAGAC ACCAGAGAAACACACGUUGUGGUACAUUACCUGGUA | GUCUUCU GUU GUCUGUUU |
| 4650 | GGAUGGUA AGAA GACAAC ACCAGAGAAACACACGUUGUGGUACAUUACCUGGUA | GUUGUCU GUU UACCAUCC |
| 4724 | ACUAGAGG AGAA GAUGAU ACCAGAGAAACACACGUUGUGGUACAUUACCUGGUA | AUCAUCA GUU CCUCUAGU |
| 4771 | AUGCGAAG AGAA GGCCUG ACCAGAGAAACACACGUUGUGGUACAUUACCUGGUA | CAGGCCU GAC CUUCGCAU |
| 4785 | UCCCCGUG AGAA GUAUGC ACCAGAGAAACACACGUUGUGGUACAUUACCUGGUA | GCAUACU GCU CACGGGGA |
| 4809 | CUAGGCCA AGAA GGACCA ACCAGAGAAACACACGUUGUGGUACAUUACCUGGUA | UGGUCCA GUU UGGCCUAG |
| 4834 | UUGAGCCC AGAA GUAGGC ACCAGAGAAACACACGUUGUGGUACAUUACCUGGUA | GCCUACU GAU GGGCUCAA |
| 4912 | AUAUAUAA AGAA GGAUAA ACCAGAGAAACACACGUUGUGGUACAUUACCUGGUA | UUAUCCU GUU UUAUAUAU |
| 5119 | UCCUCUCA AGAA GCCUUG ACCAGAGAAACACACGUUGUGGUACAUUACCUGGUA | CAAGGCA GUC UGAGAGGA |
| 5144 | UAAAUAUG AGAA GAUACU ACCAGAGAAACACACGUUGUGGUACAUUACCUGGUA | AGUAUCA GCC CAUAUUUA |
| 5287 | AGGUAUGA AGAA GAUGAA ACCAGAGAAACACACGUUGUGGUACAUUACCUGGUA | UUCAUCU GUU UCAUACCU |
| 5363 | CCCCAAAG AGAA GGCACC ACCAGAGAAACACACGUUGUGGUACAUUACCUGGUA | GGUGCCC GCU CUUUGGGG |
| 5462 | CCGGCUCC AGAA GGUGUG ACCAGAGAAACACACGUUGUGGUACAUUACCUGGUA | CACACCU GCC GGAGCCGG |

TABLE IX-continued

Mouse flt1 VEGF Receptor-Hairpin Ribozyme and Substrate Sequence

| nt. Position | HP Ribozyme | Substrate |
|---|---|---|
| 5478 | GUCUGCCC AGAA GUGACC ACCAGAGAAACACACGUUGUGGUACAUUACCUGGUA | GGUCACA GCU CGGCAGAC |
| 5486 | UAUUCAUC AGAA GCCCAG ACCAGAGAAACACACGUUGUGGUACAUUACCUGGUA | CUGGGCA GAC GAUGAAUA |
| 5500 | UCUCCCAA AGAA GCUAUU ACCAGAGAAACACACGUUGUGGUACAUUACCUGGUA | AAUAGCU GCU UUGGGAGA |
| 5539 | CUGGCCCG AGAA GAGAAU ACCAGAGAAACACACGUUGUGGUACAUUACCUGGUA | AUUCUCU GAC CGGGCCAG |
| 5564 | CACAGGGG AGAA GGUACC ACCAGAGAAACACACGUUGUGGUACAUUACCUGGUA | GGUACCU GCU CCCCUGUG |
| 5597 | UCUCAUCA AGAA GAAAAC ACCAGAGAAACACACGUUGUGGUACAUUACCUGGUA | GUUUUCU GUC UGAUGAGA |
| 5601 | CCAGUCUC AGAA GACAGA ACCAGAGAAACACACGUUGUGGUACAUUACCUGGUA | UCUGUCU GAU GAGACUGG |
| 5639 | GGGCUGCA AGAA GUCUCA ACCAGAGAAACACACGUUGUGGUACAUUACCUGGUA | UGAGACA GCC UGCAGCCC |
| 5646 | CCACAGUG AGAA GCAGGC ACCAGAGAAACACACGUUGUGGUACAUUACCUGGUA | GCCUGCA GCC CACUGUGG |
| 5781 | CACACUGC AGAA GACAAG ACCAGAGAAACACACGUUGUGGUACAUUACCUGGUA | CUUGUCG GCU GCAGUGUG |
| 5829 | CUGUUCUC AGAA GUUUCU ACCAGAGAAACACACGUUGUGGUACAUUACCUGGUA | AGAAACG GAU GAGAACAG |
| 5842 | AAACCUCA AGAA GCUGUU ACCAGAGAAACACACGUUGUGGUACAUUACCUGGUA | AACAGCA GCC UGAGGUUU |
| 5915 | UUAUUAAA AGAA GAAUAA ACCAGAGAAACACACGUUGUGGUACAUUACCUGGUA | UUAUCC GAU UUUAAUAA |
| 6010 | AGUCUUUA AGAA GAACCA ACCAGAGAAACACACGUUGUGGUACAUUACCUGGUA | UGGUUCU GCU UAAAGACU |

TABLE X

Homologous Hammerhead Ribozyme Target Sites Between Human flt-1 and KDR RNA

| nt. Position | flt-1 Target Sequence | nt. Position | KDR Target Sequence |
|---|---|---|---|
| 3388 | CCGGGAU A UUUAUAA | 3151 | CCGGGAU A UUUAUAA |
| 2174 | AAUGUAU A CACAGGG | 3069 | AgUGUAU c CACAGGG |
| 2990 | UGCAAAU A UGGAAAU | 2756 | UGCAAAU u UGGAAAc |
| 2693 | CUCCCUU A UGAUGCC | 2459 | CUgCCUU A UGAUGCC |
| 2981 | GUUGAAU A CUGCAAA | 2747 | GUgGAAU u CUGCAAA |
| 1359 | UAUGGUU A AAAGAUG | 2097 | UgUGGUU u AAAGAUa |
| 3390 | GGGAUAU U UAUAAGA | 3153 | GGGAUAU U UAUAAAg |
| 3391 | GGAUAUU U AUAAGAA | 3154 | GGAUAUU U AUAAAgA |
| 2925 | ACGUGGU U AACCUGC | 2691 | AuGUGGU c AACCUuC |
| 7140 | UAUUUCU A GUCAUGA | 2340 | UACUUCU u GUCAUCA |
| 1785 | CAAUAAU A GAAGGAA | 1515 | CucUAAU u GAAGGAA |
| 2731 | GAGACUU A AACUGGG | 768 | UUGACUU c AACUGGG |
| 3974 | GAUGACU A CCAGGGC | 1466 | GAgGACU u CCAGGGa |
| 6590 | UUAAUGU A GAAAGAA | 2603 | aaAAUGU u GAAAGAA |
| 6705 | GCCAUUU A UGACAAA | 3227 | aCaAUUU u UGACAgA |
| 974 | GUCAAAU U ACUUAGA | 147 | uUCAAAU U ACUUgCA |
| 1872 | AUAAAGU U GGGACUG | 1602 | ACAAAGU c GGGAgaG |
| 2333 | ACUUGGU U UAAAAAC | 1088 | AaaUGGU a UAAAAAU |
| 2775 | AAGUGGU U CAAGCAU | 1745 | AcaUGGU a CAAGCuU |
| 3533 | UUCUCCU U AGGUGGG | 3296 | UUuUCCU U AGGUGcu |
| 3534 | UCUCCUU A GGUGGGU | 3297 | UuUCCUU A GGUGcuU |
| 3625 | GUACUCU A CUCCUGA | 4054 | GagUCU c CUCCUGu |
| 1814 | AGCACCU U GGUUGUG | 1059 | AGuACCU U GGUUacc |
| 2744 | GGCAAAU C ACUUGGA | 147 | uuCAAAU u ACUUGcA |
| 2783 | CAAGCAU C AGCAUUU | 796 | gAAGCAU C AGCAUaa |
| 3613 | GAGAGCU C CUGAGUA | 2968 | GgaAGCU C CUGAagA |
| 4052 | AAGGCCU C CCUCAAG | 1923 | ucuGCCU u GCUCAAG |
| 5305 | UCUCCAU A UCAAAAC | 456 | ggUCCAU u UCAAAuC |
| 7158 | AUGUAUU U UGUAUAC | 631 | gUcUAUU a UGUAcAu |
| 1836 | CUAGAAU U UCUGGAA | 1007 | aUgGAAU c UCUGGUg |
| 2565 | CUCUCUU C UGGCUCC | 2328 | uguUCUU C UGGCUaC |
| 4250 | CUGUACU C CACCCCA | 3388 | UUaUACU a CACCagA |
| 7124 | ACAUGGU U UGGUCCU | 3778 | cagUGGU a UGGUuCU |
| 436 | AUGGUCU U UGCCUGA | 1337 | AcGGUCU a UGCCauu |
| 2234 | GCACCAU A CCUCCUG | 1344 | augCCAU u CCUCCcc |
| 2763 | GGGCUUU U GGAAAAG | 990 | uuGCUUU U GGAAguG |

TABLE X-continued

Homologous Hammerhead Ribozyme Target Sites Between Human flt-1 and KDR RNA

| nt. Position | flt-1 Target Sequence | nt. Position | KDR Target Sequence |
|---|---|---|---|
| 4229 | CCAGACU A CAACUCG | 767 | auuGACU u CAACUgG |
| 5301 | GUUUUCU C CAUAUCA | 3307 | ugcUUCU C CAUAUCc |
| 6015 | AGAAUGU A UGCCUCU | 1917 | AcuAUGU c UGCCUug |
| 6095 | AUUCCCU A GUGAGCC | 1438 | AUaCCCU u GUGAaga |
| 6236 | UGUUGUU C CUCUUCU | 76 | UagUGUU u CUCUUga |
| 5962 | GCUUCCU U UUAUCCA | 3099 | auaUCCU c UUAUCgg |
| 7629 | UAUAUAU U CUCUGCU | 3096 | gAAAUAU c CUCUuaU |

Lowercase letters are used to represent sequence variance between flt-1 and KDR RNA

TABLE XI 2.5 μmol RNA Synthesis Cycle

| Reagent | Equivalents | Amount | Wait Time* |
|---|---|---|---|
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

Other embodiments are within the following claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6346398B1). An electronic copy of the "Sequence Listing" will also be available from the USPTO upon request and payment of the fee set forth in 37 CFR 1.19(b)(3).

What is claimed is:

1. A nucleic acid molecule which specifically inhibits the synthesis, expression and/or stability of an mRNA encoding flt-1 receptor of human or mouse vascular endothelial growth factor, wherein said nucleic acid molecule is an enzymatic nucleic acid molecule or an antisense nucleic acid molecule.

2. The nucleic acid of claim 1, wherein said nucleic acid molecule is an enzymatic nucleic acid molecule.

3. The nucleic acid molecule of claim 2, wherein said enzymatic nucleic acid molecule comprises binding arms containing sequence complementary to a substrate nucleotide base sequence to any one of SEQ ID NOS; 1481–1482, 1493, 1574, 1664, 1669, 1838, 1847, 1913, 1933, 1974, 1984, 1997, 1999, 2000, 2025, 2130, 2382, or 2394.

4. The nucleic acid molecule of claims 2, wherein said nucleic acid molecule is in a hammerhead motif.

5. The nucleic acid molecule of claim 2, wherein said nucleic acid molecule is in a hairpin, hepatitis Delta virus, group I intron, VS nucleic acid or RNase P nucleic acid motif.

6. A method of cleaving RNA of flt-1 gene comprising the step of contacting said RNA with the enzymatic nucleic acid molecule of claim 3, under conditions suitable for the cleavage of said RNA.

7. The method claim 6, wherein said enzymatic nucleic acid molecule is in a hammerhead motif.

8. The method of claim 6, wherein said enzymatic nucleic acid molecule comprises between 12 and 100 bases complementary to the RNA of flt-1 gene.

9. The method of claim 6, wherein said enzymatic nucleic acid molecule comprises between 14 and 24 bases complementary to the RNA of flt-1 gene.

10. The nucleic acid molecule of claim 1, wherein said nucleic acid molecule comprises between 12 and 100 bases complementary to the RNA encoding the flt-1 receptor.

11. The nucleic acid molecule of claim 10, wherein said nucleic acid molecule comprises between 14 and 24 bases complementary to the RNA encoding the flt-1 receptor.

12. A mammalian cell including a nucleic acid molecule of claim 1, wherein said mammalian cell is not a living human.

13. The mammalian cell of claim 12, wherein said mammalian cell is a human cell.

14. An expression vector comprising nucleic acid sequence encoding the nucleic acid molecule of claim 1, in a manner which allows expression and/or delivery of that nucleic acid molecule within a mammalian cell.

15. The expression vector of claim 14, wherein said nucleic acid molecule is an enzymatic nucleic acid.

16. A mammalian cell including an expression vector of claim 11, wherein said mammalian cell is not a living human.

17. The mammalian cell of claim 16, wherein said mammalian cell is a human cell.

18. The nucleic acid molecule of claim 1, wherein said nucleic acid molecule is an antisense nucleic acid molecule.

19. The nucleic acid molecule of claim 18, wherein said antisense nucleic acid molecule contains sequence complementary to the substrate nucleotide base sequence selected from the group consisting of: 1481–1482, 1493, 1574, 1664, 1669, 1838, 1847, 1913, 1933, 1974, 1984, 1997, 1999, 2000, 2025, 2130, 2382, or 2394.

20. An expression vector comprising nucleic acid sequence encoding the antisense nucleic acid molecule of claim 18, in a manner which allows expression and/or delivery of that antisense nucleic acid molecule within a mammalian cell.

21. A mammalian cell including the expression vector of claim 20, wherein said mammalian cell is not a living human.

22. The mammalian cell of claim 21, wherein said mammalian cell is a human cell.

23. An enzymatic nucleic acid molecule comprising any ribozyme sequence selected from the group consisting of: SEQ ID NOS: 50–51, 62, 143, 233, 238, 407, 416–417, 482, 502, 543, 553, 566, 568–569, 574, 594, 699, 951, and 963.

* * * * *

UNITED STATES PATENT AND TRADEMARK OFFICE
CERTIFICATE OF CORRECTION

PATENT NO. : 6,346,398 B1  Page 1 of 1
DATED : February 12, 2002
INVENTOR(S) : Pamela Pavco, James McSwiggen, Daniel Stinchcomb and Jaime Escobedo It is certified that error appears in the above-identified patent and that said Letters Patent is hereby corrected as shown below:

<u>Title page,</u>
Item [73], after "Boulder, CO (US)", please add -- Chiron Corporation, Emeryville, CA (US) --

Signed and Sealed this

Twelfth Day of November, 2002

Attest:

Attesting Officer

JAMES E. ROGAN
*Director of the United States Patent and Trademark Office*